US006087485A

United States Patent [19]
Brooks-Wilson et al.

[11] Patent Number: 6,087,485
[45] Date of Patent: Jul. 11, 2000

[54] ASTHMA RELATED GENES

[75] Inventors: Angela R. Brooks-Wilson, San Diego; Alan Buckler, Cardiff; Lon Cardon; Alisoun H. Carey, both of San Diego; Margaret Galvin, Encinitas; Andrew Miller; Michael North, both of San Diego, all of Calif.

[73] Assignee: AxyS Pharmaceuticals, Inc., South San Francisco, Calif.

[21] Appl. No.: 09/009,913

[22] Filed: Jan. 21, 1998

Related U.S. Application Data

[60] Provisional application No. 60/035,663, Jan. 21, 1997, and provisional application No. 60/051,432, Jul. 1, 1997.

[51] Int. Cl.[7] .................................................. C07H 21/04
[52] U.S. Cl. ........................................ 536/23.5; 536/23.1
[58] Field of Search ................................ 536/23.1, 23.5; 435/6, 252.33

[56] References Cited

PUBLICATIONS

Hillier et al. EST Accession No. AA133068, 469 base pairs, Nov. 1996.
Hillier et al. EST Accession No. AA132792, 457 base pairs, Nov. 1996.
Takeda, J. EST Accession No. D82303, 448 base pairs, Aug. 1996.
Takeda, J. EST Accession No. D82445, 390 base pairs, Aug. 1996.
Hillier et al. EST Accession No. H39906, 472 base pairs, Aug. 1996.
Caraballo, L.R., et al., "HLA Halotype Segregation In Families With Allergic Asthma,"*Tissue Antigens* (1990) vol. 35:182–186.
Cookson, William et al., "Linkage Between Immunolobulin E Responses Underlying Asthma and Rhinitis and Chromosome 11q," *The Lancet* (Jun. 10, 1989) vol. i:1292–1294.
Daniels, Susan et al., "A Genome–Wide Search For Quantitative Trait Loci Underlying Asthma," *Nature* (Sep. 19, 1996) vol. 383:247–250.
Hill, M.R., et al., "A New Variant of the β Subunit of the High–Affinity Receptor for Immunoglobulin E (FceR1–βE237G): Associations With Measures of Atopy and Bronchial Hyper–Responsiveness," *Human Molecular Genetics* (1996) vol. 5, No. (7):959–962.
Hill M.R., et al., "FceR1–β Polymorphism and Risk of Atopy in a General Population Sample," *British Medical Journal* (Sep. 23, 1995) vol. 311, No. (7008):775–779.
Hizawa, N. et al., "Lack of Linkage Between Atopy and Locus 11q13," *Clinical and Experimental Allergy* (1992) vol. 22:1065–1069.
Lander, Eric S., et al., "Genetic Dissection of Complex Traits," *Science* (Sep. 30, 1994) vol. 265:2037–2048.
Lawrence, S. et al., "Genetic Analysis of Atopy and Asthma as Quantitative Traits and Ordered Polychotomies," *Ann. Hum. Genet.* (1994) vol.58:359–368.

Lympany, P. et al., "Genetics Analysis of the Linkage Between Chromosome 11q and Atopy," *Clinical and Experimental Allergy* (1992) vol. 22:1085–1092.
Marsh, David G. et al., "Linkage Analysis of IL4 and Other Chromosome 5q31.1 Markers and Total Serum Immunoglobulin E Concentrations," vol. 264:1152–1156.
Meyers, D.A et al., "Evidence for a Locus Regulating Total Serum 1gE Levels Mapping to Chromosome 5," *Genomics* vol. 23:464–470.
Meyers et al., "A Genome–Wide Search for Asthma Susceptibility Loci In Ethnically Diverse Populations," *American Journal of Human Genetics* (Oct. 1996) vol. 59, No. (4):A228.
Moffatt, M.F. et al., "Genetic Linkage of T–Cell Receptor α/δ Complex To Specific 1gE Responses,"*The Lancet* (Jun. 25, 1994) vol. 343:1597–1600.
Moss, Richard B., "Allergic Etiology and Immunology of Asthma", *Annals of Allergy* (Dec. (Part II) 1989) vol. 63:566–577.
Postma, Dirkje, et al., "Genetic Susceptibility to Asthma—Bronchial Hyperresponsiveness Coinherited With A Major Gene for Atopy," *The New England Journal of Medicine* (Oct. 5, 1995) vol. 333, No. (14):894–900.
Reed, P.W., et al., "Chromosome–Specfic Microsatellite Sets for Fluorescence–Based, Semi–Automated Genome Mapping," *Nature Genetics* (Jul. 1994) vol. 7:390–395.
Rich, S.S., et al., "Genetic Analysis of Atopy in Three Large Kindreds: No Evidence of Linkage to D11S97," *Clinical and Experimental Allergy* (1992) vol. 22:1070–1076.
Risch, Neil, "A Note on Multiple Testing Procedures In Linkage Analysis," *Am. J. Hum. Genet.* (1991) vol. 48:1058–1064.
Sanford, A.J., et al., "A Genetic Map of Cromosome 11q, Including the Atopy Locus," *Eur J Hum Genet* (1995) vol. 3:188–194.
Schwengel, Deborah et al., "Comparison of Fluorescence–Based Semi–automated Genotyping of Multiple Microsatellite Loci with Autoradiographic Techniques," *Genomics* (1994) vol. 22::46–54.
Shirakawa, Taro et al., "Association Between Atopy and Variants of the β Subunit of the High–Affinity Immunoglobulin E Receptor," *Nature Genetics* (Jun 1994) vol. 7:125–130.

(List continued on next page.)

*Primary Examiner*—Remy Yucel
*Attorney, Agent, or Firm*—Pamela J. Sherwood; Paul A. Borden; Bozicevic, Field & Francis LLP

[57] ABSTRACT

A genetic locus associated with asthma is identified. The genes within the locus, ASTH1I and ASTH1J, and the regulatory sequences of the locus are characterized. The genes are used to produce the encoded proteins; in screening for compositions that modulate the expression or function of ASTH1 proteins; and in studying associated physiological pathways. The DNA is further used as a diagnostic for genetic predisposition to asthma.

7 Claims, 1 Drawing Sheet

OTHER PUBLICATIONS

Smith, Laurie et al., "Bronchial Hyperreactivity Revisited," *Annals of Allergy, Asthma & Immunology* (1995) vol. 74:454–470.

Song, Zhimin et al., "Polymorphic Nucleotides Within the Human IL–4 Promoter That Mediate Overexpression of the Gene," *The Journal of Immunology* (1996) vol. 156:424–429.

Van Herwerden, Lynne et al., "Linkage of High–Affinity 1gE Receptor Gene With Bronchial Hyperreactivity, Even in Absence of Atopy," *The Lancet* (Nov. 11, 1995) vol. 346:1262–1265.

Xu, J., et al., "Evidence for Two Unlinked Loci Regulating Total Serum 1gE Levels," *Am. J. Hum. Genet.* (1995) vol. 57:425–430.

Young, R.P., et al., "Confirmation of Genetic Linkage Between Atopic 1gE Responses and Chromosomes 11q13", *J Med Genet* (1992) vol. 29:236–238.

Zamel, N., et al., "Asthma on Tristan Da Cunha: Looking for the Genetic Link," *American Journal of Respiratory and Critical Care Medicine* (1996) vol. 153:1902–1906.

Genbank Accession No. AA149006.

Genbank Accession No. AA055327.

Genbank Accession No. AA055924.

Genbank Accession No. T64537.

Genbank Accession No. T656960.

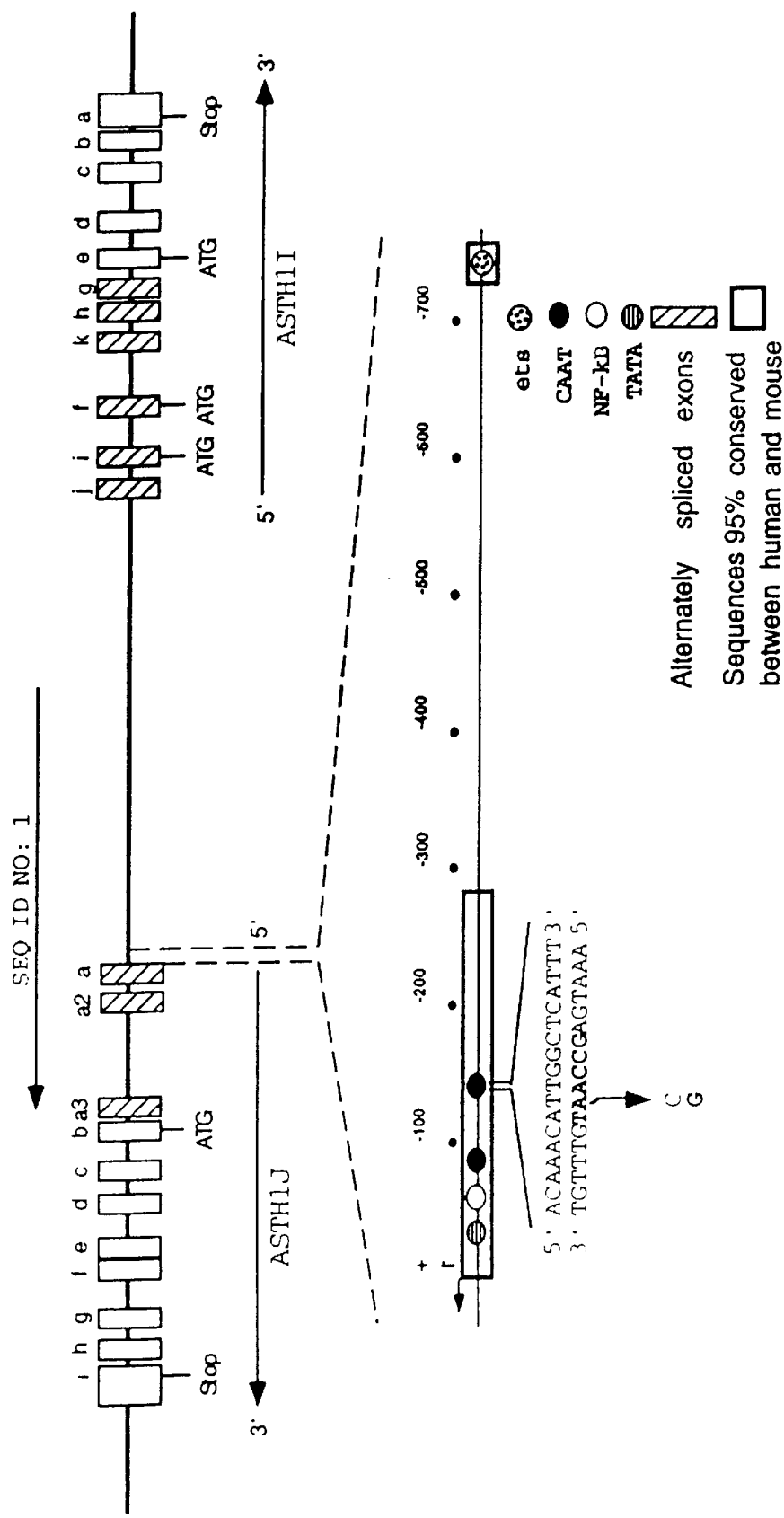
FIGURE 1: GENOMIC STRUCTURE OF THE ASTH1I AND ASTH1J GENES

ASTHMA RELATED GENES

CROSS-REFERENCE TO RELATED APPLICATIONS

This application claims benefit of priority under 35 U.S.C. §119(e) to U.S. Provisional Patent Application Ser. No. 60/035,663, filed Jan. 21, 1997, and to U.S. Provisional Patent Application Ser. No. 60/051,432, filed Jul. 1, 1997, the contents of which are hereby incorporated in their entirety.

Asthma is a disease of reversible bronchial obstruction, characterized by airway inflammation, epithelial damage, airway smooth muscle hypertrophy and bronchial hyperreactivity. Many asthma symptoms can be controlled by medical intervention, but incidence of asthma-related death and severe illness continue to rise in the United States. The approximately 4,800 deaths in 1989 marked a 46 percent increase since 1980. As many as 12 million people in the United States have asthma, up 66 percent since 1980, and annually, the disease's medical and indirect costs are estimated at over $6 billion.

Two common subdivisions of asthma are atopic (allergic, or extrinsic) asthma and non-atopic (intrinsic) asthma. Atopy is characterized by a predisposition to raise an IgE antibody response to common environmental antigens. In atopic asthma, asthma symptoms and evidence of allergy, such as a positive skin test to common allergens, are both present. Non-atopic asthma may be defined as reversible airflow limitation in the absence of allergies.

The smooth muscle surrounding the bronchi are able to rapidly alter airway diameter in response to stimuli. When the response is excessive, it is termed bronchial hyperreactivity, a characteristic of asthma thought to have a heritable component. Studies have demonstrated a genetic predisposition to asthma by showing, for example, a greater concordance for this trait among monozygotic twins than among dizygotic twins. The genetics of asthma is complex, however, and shows no simple pattern of inheritance. Environment also plays a role in asthma development, for example, children of smokers are more likely to develop asthma than are children of non-smokers.

In recent years thousands of human genes have been cloned. In many cases, gene discovery has been based on prior knowledge about the corresponding protein, such as amino acid sequence, immunological reactivity, etc. This approach has been very successful, but is limited in some important ways. One limitation is that genes in these cases are identified based on knowledge of molecular level protein properties. For a large number of important human genes, however, there is little or no biochemical data concerning the encoded product. For example, genes that predispose to human diseases, such as cystic fibrosis, Huntington's disease, etc. are of interest because of their phenotypic effect. Biochemical characterization of such genes may be secondary to genetic characterization.

A solution to this impasse has been found in combining classical genetic mapping with the ability to identify genes and, if necessary, to sequence large regions of chromosomes. Population and family studies enable genes associated with a trait of interest to be localized to a relatively small region of a chromosome. At this point, physical mapping can be used to identify candidate genes, and various molecular biology techniques used to pick out mutated genes in affected individuals. This "top-down" approach to gene discovery has been termed positional cloning, because genes are identified based on position in the genome.

Positional cloning is now being applied to complex genetic diseases, which affect a greater fraction of humanity than do the more simple and usually rarer single gene disorders. Such studies must take into account the contribution of both environmental and genetic factors to the development of disease, and must allow for contributions to the genetic component by more than one, and potentially many, genes. The clinical importance of asthma makes it of considerable interest to characterize genes that underlie a genetic predisposition to this disease. Positional cloning provides an approach to this goal.

Relevant Literature

The symptoms and biology of asthma are reviewed in Chanez et al. (1994) *Odyssey* 1:24–33. A review of bronchial hyperreactivity may be found in Smith and McFadden (1995) *Ann. Allergy. Asthma and Immunol.* 74:454. Moss (1989) *Annals of Allergy* 63:566 review the allergic etiology and immunology of asthma.

The genetic dissection of complex traits is discussed in Lander and Schork (1994) *Science* 265:2037–2048. Genetic mapping of candidate genes for atopy and/or bronchial hyperreactivity is described in Postma et al. (1995) *N.E.J.M.* 333:894; Marsh et al. (1994) *Science* 264:1152; and Meyers et al. (1994) *Genomics* 23:464. Lawrence et al. (1994) *Ann. Hum. Genet.* 58:359 discuss an approach to the genetic analysis of atopy and asthma. Genetic linkage between the alpha subunit of the T cell receptor and IgE reactions has been noted by Moffat et al. (1994) *The Lancet* 343:1597. Caraballo and Hernandez (1990) *Tissue Antigens* 35:182 noted an association between HLA alleles and allergic asthma. Evidence of linkage of atopy to markers on chromosome 11q has been seen in some British asthma families (Cookson et al. (1989) *Lancet i:*1292–1295; Young et al. (1991) *J. Med. Genet.* 29:236, but not in other British families (Lympany et al. (1992) *Clin. Exp. Allergy* 22:1085–1092) or in families from Minnesota or Japan (Rich et al. (1992) *Clin. Exp. Allergy* 22:1070–1076; and Hizawa et al. (1992) *Clin. Exp. Allergy* 22:1065).

The association of a polymorphism for the FcεRI-β gene and risk of atopy is described in Hill et al. (1995) *B.M.J.* 311:776; Hill and Cookson (1996) *Human Mol. Genet.* 5:959; and Shirakawa et al. (1994) *Nature Genetics* 7:125; an association of FcεRI-β with bronchial hyperreactivity is described in van Herwerden (1995) *The Lancet* 346:1262.

Collections of polymorphic markers from throughout the human genome have been tested for linkage to asthma, described in Meyers et al. (1996) *Am. J. Hum. Genet.* 59:A228 and Daniels et al. (1996) Nature 383:247–250. No linkage to human chromosome 11p was detected in these studies.

SUMMARY OF THE INVENTION

Human genes associated with a genetic predisposition to asthma are provided. The genes, herein termed ASTH1I and ASTH1J, are located close to each other on human chromosome 11p, have similar patterns of expression, and common sequence motifs. The nucleic acid compositions are used to produce the encoded proteins, which may be employed for functional studies, as a therapeutic, and in studying associated physiological pathways. The nucleic acid compositions and antibodies specific for the protein are useful as diagnostics to identify a hereditary predisposition to asthma.

BRIEF DESCRIPTION OF THE DRAWINGS

FIG. 1: Genomic organization of the ASTH1I and ASTH1J genes. The sizes of the exons are not to scale.

Alternative exons are hatched. The direction of transcription is indicated below each gene.

DESCRIPTION OF THE SPECIFIC EMBODIMENTS

The provided ASTH1 genes and fragments thereof, encoded protein, ASTH1 genomic regulatory regions, and anti-ASTH1 antibodies are useful in the identification of individuals predisposed to development of asthma, and for the modulation of gene activity in vivo for prophylactic and therapeutic purposes. The encoded ASTH1 protein is useful as an immunogen to raise specific antibodies, in drug screening for compositions that mimic or modulate ASTH1 activity or expression, including altered forms of ASTH1 protein, and as a therapeutic.

Asthma, as defined herein, is reversible airflow limitation in a patient over a period of time. The disease is characterized by increased airway responsiveness to a variety of stimuli, and airway inflammation. A patient diagnosed as asthmatic will generally have multiple indications over time, including wheezing, asthmatic attacks, and a positive response to methacholine challenge, i.e. a $PC_{20}$ on methacholine challenge of less than about 4 mg/ml. Guidelines for diagnosis may be found in the *National Asthma Education Program Expert Panel. Guidelines for diagnosis and management of asthma*. National Institutes of Health, 1991; Pub. #91-3042. Atopy, respiratory infection and environmental predisposing factors may also be present, but are not necessary elements of an asthma diagnosis. Asthma conditions strictly related to atopy are referred to as atopic asthma.

The human ASTH1I and ASTH1J gene sequences are provided, as are the genomic sequences 5' to ASTH1J. The major sequences of interest provided in the sequence listing are as follows:

| | | |
|---|---|---|
| ASTH1J 5' Genomic Region | DNA | (SEQ ID NO:1) |
| ASTH1J alt1 | cDNA | (SEQ ID NO:2) |
| ASTH1J alt2 | cDNA | (SEQ ID NO:3) |
| ASTH1J alt3 | cDNA | (SEQ ID NO:4) |
| ASTH1J protein | protein | (SEQ ID NO:5) |
| ASTH1l alt1 | cDNA | (SEQ ID NO:6) |
| ASTH1l alt1 protein | protein | (SEQ ID NO:7) |
| ASTH1l alt2 | cDNA | (SEQ ID NO:8) |
| ASTH1l alt2 protein | protein | (SEQ ID NO:9) |
| ASTH1l alt3 | cDNA | (SEQ ID NO:10) |
| ASTH1l alt3 protein | protein | (SEQ ID NO:11) |
| CAAT box "A" form | DNA | (SEQ ID NO:12) |
| CAAT box "G" form | DNA | (SEQ ID NO:13) |
| ASTH1J 5' promoter region | DNA | (SEQ ID NO:14) |
| Mouse asth1j | cDNA | (SEQ ID NO:338) |
| Mouse asth1j | protein | (SEQ ID NO:339) |
| Polymorphisms | DNA | (SEQ ID NO:16–159) |
| Microsatellite flanking sequences | DNA | (SEQ ID NO:160–281) |
| Microsatellite repeats | DNA | (SEQ ID NO:282–292) |
| Intron-Exon boundaries | DNA | (SEQ ID NO:293–335) |

The ASTH1 locus has been mapped to human chromosome 11p. The traits for a positive response to methacholine challenge and a clinical history of asthma were shown to be genetically linked in a genome scan of the population of Tristan da Cunha, a single large extended family with a high incidence of asthma (discussed in Zamel et al. (1996) *Am. J. Respir. Crit. Care Med.* 153:1902–1906). The linkage finding was replicated in a set of Canadian asthmatic families. The region of strongest linkage was the marker D11S907 on the short arm of chromosome 11. Additional markers were identified from the four megabase region surrounding D11S907 from public databases and by original cloning of new polymorphic microsatellite markers. Refinement of the region of interest was obtained by genotyping new markers in the studied populations, and applying the transmission disequilibrium test (TDT), which reflects the level of association between marker alleles and disease status. TDT curves were superimposed on the physical map. Molecular genetic techniques for gene identification were applied to the region of interest. A one megabase genomic region was sequenced to high accuracy, and the resulting data used for the sequence-based prediction of genes and determination of the intron/exon structure of genes in the region.

Nucleic Acid Compositions

ASTH1I produces a 2.8 kb mRNA expressed at high levels in trachea and prostate, and at lower levels in lung and kidney and possibly other tissues. ASTH1I cDNA clones have also been identified in prostate, testis and lung libraries. Sequence polymorphisms are shown in Table 3. ASTH1I has at least three alternate forms denoted as alt1, alt2, and alt3. The alternative splicing and start codons give the three forms of ASTH1I proteins different amino termini. The ASTH1I proteins, alt1, alt2 and alt3 are 265, 255 and 164 amino acids in length, respectively.

A domain of the ASTH1I and ASTH1J proteins is similar in sequence to transcription factors of the ets family. The ets family is a group of transcription factors that activate genes involved in a variety of immunological and other processes. The family members most similar to ASTH1I and ASTH1J are: ETS1, ETS2, ESX, ELF, ELK1, TEL, NET, SAP-1, NERF and FLI. The ASTH1I and ASTH1J proteins show similarity to each other. Over the ets domain they are 66% similar (ie. have amino acids with similar properties in the same positions) and 46% identical to each other. All forms of ASTH1I and ASTH1J have a helix turn helix motif, characteristic of some transcription factors, located near the carboxy terminal end of the protein.

ASTH1J produces an approximately 6 kb mRNA expressed at high levels in the trachea, prostate and pancreas and at lower levels in colon, small intestine, lung and stomach. ASTH1J has at least three forms, consisting of the alt1, alt2 and alt3 forms. The open reading frame is identical for the three forms, which differ only in the 5' UTR. The protein encoded by ASTH1J is 300 amino acids in length.

Mouse coding region sequence of asth1j is provided in SEQ ID NO:326, and the amino acid sequence is provided in SEQ ID NO:327. The mouse and human proteins have 88.4% identity throughout their length. The match in the ets domain is 100%. The mouse cDNA was identified by hybridization of a full-length human cDNA to a mouse lung cDNA library (Stratagene).

The term "ASTH1 genes" is herein used generically to designate ASTH1I and ASTH1J genes and their alternate forms. The two genes lie in opposite orientations on a native chromosome, with the 5' regulatory sequences between them. Part of the genomic sequence between the two coding regions is provided as SEQ ID NO:1. The term "ASTH1 locus" is used herein to refer to the two genes in all alternate forms and the genomic sequence that lies between the two genes. Alternate forms include splicing variants, and polymorphisms in the sequence. Specific polymorphic sequences are provided in SEQ ID NOs:16–159. For some purposes the previously known EST sequences described herein may be excluded from the sequences defined as the ASTH1 locus.

The DNA sequence encoding ASTH1 may be cDNA or genomic DNA or a fragment thereof. The term "ASTH1 gene" shall be intended to mean the open reading frame encoding specific ASTH1 polypeptides, introns, as well as adjacent 5' and 3' non-coding nucleotide sequences involved in the regulation of expression, up to about 1 kb beyond the coding region, but possibly further in either direction. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the ASTH1 protein.

The genomic ASTH1 sequence has non-contiguous open reading frames, where introns interrupt the protein coding regions. A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

Genomic regions of interest include the non-transcribed sequences 5' to ASTH1J, as provided in SEQ ID NO:1. This region of DNA contains the native promoter elements that direct expression of the linked ASTH1J gene. Usually a promoter region will have at least about 140 nt of sequence located 5' to the ASTH1 gene and further comprising a TATA box and CMT box motif sequence (SEQ ID NO:14, nt. 597–736). The promoter region may further comprise a consensus ets binding motif, (C/A)GGA(A/T) (SEQ ID NO:14, nt 1–5). A region of particular interest, containing the ets binding motif, TATA box and CAAT box motifs 5' to the ASTH1J gene, is provided in SEQ ID NO:14. The position of SEQ ID NO:14 within the larger sequence is SEQ ID NO:1, nt 60359–61095. The promoter sequence may comprise polymorphisms within the CAAT box region, for example those shown in SEQ ID NO:12 and SEQ ID NO:13, which have been shown to affect the function of the promoter. The promoter region of interest may extend 5' to SEQ ID NO:14 within the larger sequence, e.g. SEQ ID NO:1, nt 59000–61095; SEQ ID NO:1, nt 5700–61095, etc.

The sequence of this 5' region, and further 5' upstream sequences and 3' downstream sequences, may be utilized for promoter elements, including enhancer binding sites, that provide for expression in tissues where ASTH1J is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease. See, for example, SEQ ID NO:12 and 13. Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol Med* 1: 194–205; Mortlock et al. (1996) *Genome Res.* 6: 327–33; and Joulin and Richard-Foy (1995) *Eur J Biochem* 232: 620–626.

The regulatory sequences may be used to identify cis acting sequences required for transcriptional or translational regulation of ASTH1 expression, especially in different tissues or stages of development, and to identify cis acting sequences and trans acting factors that regulate or mediate ASTH1 expression. Such transcription or translational control regions may be operably linked to a ASTH1 gene in order to promote expression of wild type or altered ASTH1 or other proteins of interest in cultured cells, or in embryonic, fetal or adult tissues, and for gene therapy.

The nucleic acid compositions of the subject invention may encode all or a part of the subject polypeptides. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The ASTH1 genes are isolated and obtained in substantial purity, generally as other than an intact mammalian chromosome. Usually, the DNA will be obtained substantially free of other nucleic acid sequences that do not include an ASTH1 sequence or fragment thereof, generally being at least about 50%, usually at least about 90% pure and are typically "recombinant", i.e. flanked by one or more nucleotides with which it is not normally associated on a naturally occurring chromosome.

The DNA sequences are used in a variety of ways. They may be used as probes for identifying ASTH1 related genes. Mammalian homologs have substantial sequence similarity to the subject sequences, i.e. at least 75%, usually at least 90%, more usually at least 95% sequence identity with the nucleotide sequence of the subject DNA sequence. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) *J Mol Biol* 215:403–10.

Nucleic acids having sequence similarity are detected by hybridization under low stringency conditions, for example, at 50° C. and 10×SSC (0. 9 M saline/0.09 M sodium citrate) and remain bound when subjected to washing at 55° C. in 1×SSC. Sequence identity may be determined by hybridization under stringent conditions, for example, at 50° C. or higher and 0.1×SSC (9 mM saline/0.9 mM sodium citrate). By using probes, particularly labeled probes of DNA sequences, one can isolate homologous or related genes. The source of homologous genes may be any species, e.g. primate species, particularly human; rodents, such as rats and mice, canines, felines, bovines, ovines, equines, yeast, Drosophila, Caenhorabditis, etc.

The DNA may also be used to identify expression of the gene in a biological specimen. The manner in which one probes cells for the presence of particular nucleotide sequences, as genomic DNA or RNA, is well established in the literature and does not require elaboration here. mRNA is isolated from a cell sample. mRNA may be amplified by RT-PCR, using reverse transcriptase to form a complementary DNA strand, followed by polymerase chain reaction amplification using primers specific for the subject DNA sequences. Alternatively, mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of ASTH1 gene expression in the sample.

The subject nucleic acid sequences may be modified for a number of purposes, particularly where they will be used intracellularly, for example, by being joined to a nucleic acid cleaving agent, e.g. a chelated metal ion, such as iron or chromium for cleavage of the gene; or the like.

The sequence of the ASTH1 locus, including flanking promoter regions and coding regions, may be mutated in various ways known in the art to generate targeted changes in promoter strength, sequence of the encoded protein, etc. The DNA sequence or product of such a mutation will be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used. Such mutated genes may be used to study structure-function relationships of ASTH1 polypeptides, or to alter properties of the protein that affect its function or regulation. For example, constitutively active transcription factors, or a dominant negatively active protein that binds to the ASTH1 DNA target site without activating transcription, may be created in this manner.

Techniques for in vitro mutagenesis of cloned genes are known. Examples of protocols for scanning mutations may be found in Gustin et al., *Biotechniques* 14:22 (1993); Barany, Gene 37:111–23 (1985); Colicelli et al., *Mol Gen Genet* 199:537–9 (1985); and Prentki et al., *Gene* 29:303–13 (1984). Methods for site specific mutagenesis can be found in Sambrook et al., *Molecular Cloning. A Laboratory Manual*, CSH Press 1989, pp. 15.3–15.108; Weiner et al., *Gene* 126:35–41 (1993); Sayers et al., *Biotechniques* 13:592–6 (1992); Jones and Winistorfer, *Biotechniques* 12:528–30 (1992); Barton et al., *Nucleic Acids Res* 18:7349–55 (1990); Marotti and Tomich, *Gene Anal Tech* 6:67–70 (1989); and *Zhu Anal Biochem* 177:120–4 (1989).

Synthesis of ASTH1 Proteins

The subject gene may be employed for synthesis of a complete ASTH1 protein, or polypeptide fragments thereof, particularly fragments corresponding to functional domains; binding sites; etc.; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, or cells of a higher organism such as vertebrates, particularly mammals, e.g. COS 7 cells, may be used as the expression host cells. In many situations, it may be desirable to express the ASTH1 gene in mammalian cells, where the ASTH1 gene will benefit from native folding and post-translational modifications. Small peptides can also be synthesized in the laboratory.

With the availability of the polypeptides in large amounts, by employing an expression host, the polypeptides may be isolated and purified in accordance with conventional ways. A lysate may be prepared of the expression host and the lysate purified using HPLC, exclusion chromatography, gel electrophoresis, affinity chromatography, or other purification technique. The purified polypeptide will generally be at least about 80% pure, preferably at least about 90% pure, and may be up to and including 100% pure. Pure is intended to mean free of other proteins, as well as cellular debris.

The polypeptide is used for the production of antibodies, where short fragments provide for antibodies specific for the particular polypeptide, and larger fragments or the entire protein allow for the production of antibodies over the surface of the polypeptide. Antibodies may be raised to the wild-type or variant forms of ASTH1. Antibodies may be raised to isolated peptides corresponding to these domains, or to the native protein, e.g. by immunization with cells expressing ASTH1, immunization with liposomes having ASTH1 inserted in the membrane, etc.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

Detection of ASTH1 Associated Asthma

Diagnosis of ASTH1 associated asthma is performed by protein, DNA or RNA sequence and/or hybridization analysis of any convenient sample from a patient, e.g. biopsy material, blood sample, scrapings from cheek, etc. A nucleic acid sample from a patient having asthma that may be associated with ASTH1, is analyzed for the presence of a predisposing polymorphism in ASTH1. A typical patient genotype will have at least one predisposing mutation on at least one chromosome. The presence of a polymorphic ASTH1 sequence that affects the activity or expression of the gene product, and confers an increased susceptibility to asthma is considered a predisposing polymorphism. Individuals are screened by analyzing their DNA or mRNA for the presence of a predisposing polymorphism, as compared to an asthma neutral sequence. Specific sequences of interest include any polymorphism that leads to clinical bronchial hyperreactivity or is otherwise associated with asthma, including, but not limited to, insertions, substitutions and deletions in the coding region sequence, intron sequences that affect splicing, or promoter or enhancer sequences that affect the activity and expression of the protein. Examples of specific ASTH1 polymorphisms in asthma patients are listed in Tables 3–8.

The CAAT box polymorphism of SEQ ID NO:12 and 13 (which is located within SEQ ID NO:14) is of particular interest. The "G" form, SEQ ID NO:13, can be associated with a propensity to develop bronchial hyperreactivity or asthma. Other polymorphisms in the surrounding region affect this association. It has been found that substitution of "G" for "A" results in decreased binding of nuclear proteins to the DNA motif.

The effect of an ASTH1 predisposing polymorphism may be modulated by the patient genotype in other genes related to asthma and atopy, including, but not limited to, the Fcε receptor, Class I and Class II HLA antigens, T cell receptor and immunoglobulin genes, cytokines and cytokine receptors, and the like.

Screening may also be based on the functional or antigenic characteristics of the protein. Immunoassays designed to detect predisposing polymorphisms in ASTH1 proteins may be used in screening. Where many diverse mutations lead to a particular disease phenotype, functional protein assays have proven to be effective screening tools.

Biochemical studies may be performed to determine whether a candidate sequence polymorphism in the ASTH1 coding region or control regions is associated with disease. For example, a change in the promoter or enhancer sequence that affects expression of ASTH1 may result in predisposition to asthma. Expression levels of a candidate variant allele are compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like. The activity of the encoded ASTH1 protein may be determined by comparison with the wild-type protein.

A number of methods are available for analyzing nucleic acids for the presence of a specific sequence. Where large amounts of DNA are available, genomic DNA is used directly. Alternatively, the region of interest is cloned into a suitable vector and grown in sufficient quantity for analysis. Cells that express ASTH1 genes, such as trachea cells, may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985) Science 239:487, and a review of current techniques may be found in Sambrook, et al. Molecular Cloning: A Laboratory Manual, CSH Press 1989, pp.14.2–14.33. Amplification may also be used to determine whether a polymorphism is present, by using a primer that is specific for the polymorphism. Alternatively, various methods are known in the art that utilize oligonucleotide ligation as a means of detecting polymorphisms, for examples see Riley et al. (1990) N.A.R. 18:2887–2890; and Delahunty et al. (1996) Am. J. Hum. Genet. 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, 35S, $^3$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a neutral ASTH1 sequence. Hybridization with the variant sequence may also be used to determine its presence, by Southern blots, dot blots, etc. The hybridization pattern of a control and variant sequence to an array of oligonucleotide probes immobilised on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

The hybridization pattern of a control and variant sequence to an array of oligonucleotide probes immobilised on a solid support, as described in U.S. Pat. No. 5,445,934, or in WO95135505, may be used as a means of detecting the presence of variant sequences. In one embodiment of the invention, an array of oligonucleotides are provided, where discrete positions on the array are complementary to at least a portion of mRNA or genomic DNA of the ASTH1 locus. Such an array may comprise a series of oligonucleotides, each of which can specifically hybridize to a nucleic acid, e.g. mRNA, cDNA, genomic DNA, etc. from the ASTH1 locus.

An array may include all or a subset of the polymorphisms listed in Table 3 (SEQ ID NOs:16–126). One or both polymorphic forms may be present in the array, for example the polymorphism of SEQ ID NO:12 and 13 may be represented by either, or both, of the listed sequences. Usually such an array will include at least 2 different polymorphic sequences, i.e. polymorphisms located at unique positions within the locus, usually at least about 5, more usually at least about 10, and may include as many as 50 to 100 different polymorphisms. The oligonucleotide sequence on the array will usually be at least about 12 nt in length, may be the length of the provided polymorphic sequences, or may extend into the flanking regions to generate fragments of 100 to 200 nt in length. For examples of arrays, see Hacia et al. (1996) *Nature Genetics* 14:441–447; Lockhart et al. (1996) *Nature Biotechnol.* 14:1675–1680; and De Risi et al. (1996) *Nature Genetics* 14:457–460.

Antibodies specific for ASTH1 polymorphisms may be used in screening immunoassays. A reduction or increase in neutral ASTH1 and/or presence of asthma associated polymorphisms is indicative that asthma is ASTH1-associated. A sample is taken from a patient suspected of having ASTH1-associated asthma. Samples, as used herein, include biological fluids such as tracheal lavage, blood, cerebrospinal fluid, tears, saliva, lymph, dialysis fluid and the like; organ or tissue culture derived fluids; and fluids extracted from physiological tissues. Also included in the term are derivatives and fractions of such fluids. Biopsy samples are of particular interest, e.g. trachea scrapings, etc. The number of cells in a sample will generally be at least about 101, usually at least 104 more usually at least about $10^5$. The cells may be dissociated, in the case of solid tissues, or tissue sections may be analyzed. Alternatively a lysate of the cells may be prepared.

Diagnosis may be performed by a number of methods. The different methods all determine the absence or presence or altered amounts of normal or abnormal ASTH1 in patient cells suspected of having a predisposing polymorphism in ASTH1. For example, detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and ASTH1 in a lysate. Measuring the concentration of ASTH1 binding in a sample or fraction thereof may be accomplished by a variety of specific assays. A conventional sandwich type assay may be used. For example, a sandwich assay may first attach ASTH1-specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Patient sample lysates are then added to separately assayable supports (for example, separate wells of a microtiter plate) containing antibodies. Preferably, a series of standards, containing known concentrations of normal and/or abnormal ASTH1 is assayed in parallel with the samples or aliquots thereof to serve as controls. Preferably, each sample and standard will be added to multiple wells so that mean values can be obtained for each. The incubation time should be sufficient for binding, generally, from about 0.1 to 3 hr is sufficient. After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample.

After washing, a solution containing a second antibody is applied. The antibody will bind ASTH1 with sufficient specificity such that it can be distinguished from other components present. The second antibodies may be labeled to facilitate direct, or indirect quantification of binding. Examples of labels that permit direct measurement of second receptor binding include radiolabels, such as $^3$H or $^{125}$I, fluorescers, dyes, beads, chemilumninescers, colloidal particles, and the like. Examples of labels which permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for ASTH1 as desired, conveniently using a labeling method as described for the sandwich assay.

Other diagnostic assays of interest are based on the functional properties of ASTH1 proteins. Such assays are particularly useful where a large number of different sequence changes lead to a common phenotype, ie. altered protein function leading to bronchial hyperreactivity. For example, a functional assay may be based on the transcriptional changes mediated by ASTH1 gene products. Other assays may, for example, detect conformational changes, size changes resulting from insertions, deletions or truncations, or changes in the subcellular localization of ASTH1 proteins.

In a protein truncation test, PCR fragments amplified from the ASTH1 gene or its transcript are used as templates for in vivo transcription/translation reactions to generate protein products. Separation by gel electrophoresis is performed to determine whether the polymorphic gene encodes a truncated protein, where truncations may be associated with a loss of function.

Diagnostic screening may also be performed for polymorphisms that are genetically linked to a predisposition for bronchial hyperreactivity, particularly through the use of microsatellite markers or single nucleotide polymorphisms. Frequently the microsatellite polymorphism itself is not phenotypically expressed, but is linked to sequences that result in a disease predisposition. However, in some cases the microsatellite sequence itself may affect gene expression. Microsatellite linkage analysis may be performed alone, or in combination with direct detection of polymorphisms, as described above. The use of microsatellite markers for genotyping is well documented. For examples, see Mansfield et al. (1994) Genomics 24:225–233; Ziegle et al. (1992) Genomics 14:1026–1031; Dib et al., supra.

Microsatellite loci that are useful in the subject methods have the general formula:

$$U(R)_nU',$$

where U and U' are non-repetitive flanking sequences that uniquely identify the particular locus, R is a repeat motif, and n is the number of repeats. The repeat motif is at least 2 nucleotides in length, up to 7, usually 2–4 nucleotides in length. Repeats can be simple or complex. The flanking sequences U and U' uniquely identify the microsatellite locus within the human genome. U and U' are at least about 18 nucleotides in length, and may extend several hundred bases up to about 1 kb on either side of the repeat. Within U and U', sequences are selected for amplification primers. The exact composition of the primer sequences are not critical to the invention, but they must hybridize to the flanking sequences U and U', respectively, under stringent conditions. Criteria for selection of amplification primers are as previously discussed. To maximize the resolution of size differences at the locus, it is preferable to chose a primer sequence that is close to the repeat sequence, such that the total amplification product is between 100–500 nucleotides in length.

The number of repeats at a specific locus, n, is polymorphic in a population, thereby generating individual differences in the length of DNA that lies between the amplification primers. The number will vary from at least 1 repeat to as many as about 100 repeats or more.

The primers are used to amplify the region of genomic DNA that contains the repeats. Conveniently, a detectable label will be included in the amplification reaction, as previously described. Multiplex amplification may be performed in which several sets of primers are combined in the same reaction tube. This is particularly advantageous when limited amounts of sample DNA are available for analysis. Conveniently, each of the sets of primers is labeled with a different fluorochrome.

After amplification, the products are size fractionated. Fractionation may be performed by gel electrophoresis, particularly denaturing acrylamide or agarose gels. A convenient system uses denaturing polyacrylamide gels in combination with an automated DNA sequencer, see Hunkapillar et al. (1991) Science 254:59–74. The automated sequencer is particularly useful with multiplex amplification or pooled products of separate PCR reactions. Capillary electrophoresis may also be used for fractionation. A review of capillary electrophoresis may be found in Landers, et al. (1993) BioTechniques 14:98–111. The size of the amplification product is proportional to the number of repeats (n) that are present at the locus specified by the primers. The size will be polymorphic in the population, and is therefore an allelic marker for that locus.

A number of markers in the region of the ASTH1 locus have been identified, and are listed in Table 1 in the Experimental section (SEQ ID NOs:160–273). Of particular interest for diagnostic purposes is the marker D11S2008, in which individuals having alleles C or F at this locus, particularly in combination with the CAAT box polymorphism and other polymorphisms, are predisposed to develop bronchial hyperreactivity or asthma. The association of D11 S2008 alleles is as follows:

| Allele | Association with asthma | Number of TATC repeats relative to allele C (SEQ ID NO:15) |
|---|---|---|
| A | no | −2 |
| B | no | −1 |
| C | yes | equivalent |
| D | no | +1 |
| E | no | +2 |
| F | yes | +3 |
| G | no | +4 |
| H | no | +5 |

A DNA sequence of interest for diagnosis comprises the D11S2008 primer sequences shown in Table 1 (SEQ ID NO:242 and 243), flanking one or three repeats of SEQ ID NO-15.

Other microsatellite markers of interest for diagnostic purposes are CA39_2; 774F; 774J; 774O; L19PENTA1; 65P14TE1; AFM205YG5; D11S907; D11S4200; 774N; CA11–11; 774L; AFM283WH9; ASMI14 and D11S1900 (primer sequences are provided in Table 1, the repeats are provided in Table 1 B).

Regulation of ASTH1 Expression

The ASTH1 genes are useful for analysis of ASTH1 expression, e.g. in determining developmental and tissue specific patterns of expression, and for modulating expression in vitro and in vivo. The regulatory region of SEQ ID NO:1 may also be used to investigate analysis of ASTH1 expression. Vectors useful for introduction of the gene include plasmids and viral vectors. Of particular interest are retroviral-based vectors, e.g. Moloney murine leukemia virus and modified human immunodeficiency virus; adenovirus vectors, etc. that are maintained transiently or stably in mammalian cells. A wide variety of vectors can be employed for transfection and/or integration of the gene into the genome of the cells. Alternatively, micro-injection may be employed, fusion, or the like for introduction of genes into a suitable host cell. See, for example, Dhawan et al. (1991) Science 254:1509–1512 and Smith et al. (1990) Molecular and Cellular Biology 3268–3271.

Administration of vectors to the lungs is of particular interest. Frequently such methods utilize liposomal formulations, as described in Eastman et al. (1997) *Hum Gene Ther* 8:765–773; Oudrhiri et al. (1997) *P.N.A.S.* 94:1651–1656; McDonald et al. (1997) *Hum Gene Ther* 8:411–422.

The expression vector will have a transcriptional initiation region oriented to produce functional mRNA. The native transcriptional initiation region, e.g. SEQ ID NO:14, or an exogenous transcriptional initiation region may be employed. The promoter may be introduced by recombinant methods in vitro, or as the result of homologous integration of the sequence into a chromosome. Many strong promoters are known in the art, including the β-actin promoter, SV40 early and late promoters, human cytomegalovirus promoter, retroviral LTRs, methallothionein responsive element (MRE), tetracycline-inducible promoter constructs, etc.

Expression vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

Antisense molecules are used to down-regulate expression of ASTH1 in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnoloay* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-0'-5'-S-phosphorothioate, 3'-S-5'-0-phosphorothioate, 3'-CH2-5'-0-phosphonate and 3'-NH-5'-0-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995) *Nucl. Acids Res* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) *Appl Biochem Biotechnol* 54:43–56.

Therapeutic Use of ASTH1 Protein

A host may be treated with intact ASTH1 protein, or an active fragment thereof to modulate or reduce bronchial hyperactivity. Desirably, the peptides will not induce an immune response, particularly an antibody response. Xenogeneic analogs may be screened for their ability to provide a therapeutic effect without raising an immune response. The protein or peptides may also be administered to in vitro cell cultures.

Various methods for administration may be employed. The polypeptide formulation may be given orally, or may be injected intravascularly, subcutaneously, peritoneally, etc. Methods of administration by inhalation are well-known in the art. The dosage of the therapeutic formulation will vary widely, depending upon the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc. to maintain an effective dosage level. In many cases, oral administration will require a higher dose than if administered intravenously. The amide bonds, as well as the amino and carboxy termini, may be modified for greater stability on oral administration.

The subject peptides may be prepared as formulations at a pharmacologically effective dose in pharmaceutically acceptable media, for example normal saline, PBS, etc. The additives may include bactericidal agents, stabilizers, buffers, or the like. In order to enhance the half-life of the subject peptide or subject peptide conjugates, the peptides may be encapsulated, introduced into the lumen of liposomes, prepared as a colloid, or another conventional technique may be employed that provides for an extended lifetime of the peptides.

The peptides may be administered as a combination therapy with other pharmacologically active agents. The additional drugs may be administered separately or in conjunction with the peptide compositions, and may be included in the same formulation.

Models for Asthma

The subject nucleic acids can be used to generate genetically modified non-human animals or site specific gene modifications in cell lines. The term "transgenic" is intended to encompass genetically modified animals having a deletion or other knock-out of ASTH1 gene activity, having an exogenous ASTH1 gene that is stably transmitted in the host cells, or having an exogenous ASTH1 promoter operably linked to a reporter gene. Transgenic animals may be made through homologous recombination, where the ASTH1 locus is altered. Alternatively, a nucleic acid construct is randomly integrated into the genome. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

A "knock-out" animal is genetically manipulated to substantially reduce, or eliminate endogenous ASTH1 function. Different approaches may be used to achieve the "knock-out". A chromosomal deletion of all or part of the native ASTH1 homolog may be induced. Deletions of the non-coding regions, particularly the promoter region, 3' regulatory sequences, enhancers, or deletions of gene that activate expression of ASTH1 genes. A functional knock-out may also be achieved by the introduction of an anti-sense construct that blocks expression of the native ASTH1 genes (for example, see Li and Cohen (1996) Cell 85:319–329).

Transgenic animals may be made having exogenous ASTH1 genes. The exogenous gene is usually either from a different species than the animal host, or is otherwise altered in its coding or non-coding sequence. The introduced gene may be a wild-type gene, naturally occurring polymorphism, or a genetically manipulated sequence, for example those previously described with deletions, substitutions or insertions in the coding or non-coding regions. The introduced sequence may encode an ASTH1 polypeptide, or may utilize the ASTH1 promoter operably linked to a reporter gene. Where the introduced gene is a coding sequence, it usually operably linked to a promoter, which may be constitutive or inducible, and other regulatory sequences required for expression in the host animal.

Specific constructs of interest, but are not limited to, include anti-sense ASTH1, which will block ASTH1 expression, expression of dominant negative ASTH1 mutations, and over-expression of a ASTH1 gene. A detectable marker, such as lac Z may be introduced into the ASTH1 locus, where upregulation of ASTH1 expression will result in an easily detected change in phenotype. Constructs utilizing the ASTH1 promoter region, e.g. SEQ ID NO:1; SEQ ID NO:14, in combination with a reporter gene or with the coding region of ASTH1J or ASTH1I are also of interest.

The modified cells or animals are useful in the study of ASTH1 function and regulation. Animals may be used in functional studies, drug screening, etc., e.g. to determine the effect of a candidate drug on asthma. A series of small deletions and/or substitutions may be made in the ASTH1 gene to determine the role of different exons in DNA binding, transcriptional regulation, etc. By providing expression of ASTH1 protein in cells in which it is otherwise not normally produced, one can induce changes in cell behavior. These animals are also useful for exploring models of inheritance of asthma, e.g. dominant v. recessive; relative effects of different alleles and synergistic effects between ASTH1I and ASTH1J and other asthma genes elsewhere in the genome.

DNA constructs for homologous recombination will comprise at least a portion of the ASTH1 gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) Methods in Enzymology 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture.

Investigation of genetic function may utilize non-mammalian models, particularly using those organisms that are biologically and genetically well-characterized, such as C. elegans, D. melanogaster and S. cerevisiae. For example, transposon (Tc1) insertions in the nematode homolog of an ASTH1 gene or promoter region may be made. The subject gene sequences may be used to knock-out or to complement defined genetic lesions in order to determine the physiological and biochemical pathways involved in ASTH1 function. A number of human genes have been shown to complement mutations in lower eukaryotes.

Drug screening may be performed in combination with the subject animal models. Many mammalian genes have homologs in yeast and lower animals. The study of such homologs' physiological role and interactions with other proteins can facilitate understanding of biological function. In addition to model systems based on genetic complementation, yeast has been shown to be a powerful tool for studying protein-protein interactions through the two hybrid system described in Chien et al. (1991) *P.N.A.S.* 88:9578–9582. Two-hybrid system analysis is of particular interest for exploring transcriptional activation by ASTH1 proteins.

Drug Screening Assays

By providing for the production of large amounts of ASTH1 protein, one can identify ligands or substrates that bind to, modulate or mimic the action of ASTH1. Areas of investigation are the development of asthma treatments. Drug screening identifies agents that provide a replacement or enhancement for ASTH1 function in affected cells. Conversely, agents that reverse or inhibit ASTH1 function may stimulate bronchial reactivity. Of particular interest are screening assays for agents that have a low toxicity for human cells. A wide variety of assays may be used for this purpose, including labeled in vitro protein-protein binding assays, protein-DNA binding assays, electrophoretic mobility shift assays, immunoassays for protein binding, and the like. The purified protein may also be used for determination of three-dimensional crystal structure, which can be used for modeling intermolecular interactions, transcriptional regulation, etc.

The term "agent" as used herein describes any molecule, e.g. protein or pharmaceutical, with the capability of altering or mimicking the physiological function of ASTH1. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Other assays of interest detect agents that mimic ASTH1 function. For example, candidate agents are added to a cell that lacks functional ASTH1, and screened for the ability to reproduce ASTH1 in a functional assay.

The compounds having the desired pharmacological activity may be administered in a physiologically acceptable carrier to a host for treatment of asthma attributable to a defect in ASTH1 function. The compounds may also be used to enhance ASTH1 function. The therapeutic agents may be administered in a variety of ways, orally, topically, parenterally e.g. subcutaneously, intraperitoneally, by viral infection, intravascularly, etc. Inhaled treatments are of particular interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Pharmacogenetics

Pharmacogenetics is the linkage between an individual's genotype and that individual's ability to metabolize or react to a therapeutic agent. Differences in metabolism or target sensitivity can lead to severe toxicity or therapeutic failure by altering the relation between bioactive dose and blood concentration of the drug. In the past few years, numerous studies have established good relationships between polymorphisms in metabolic enzymes or drug targets, and both response and toxicity. These relationships can be used to individualize therapeutic dose administration.

Genotyping of polymorphic alleles is used to evaluate whether an individual will respond well to a particular therapeutic regimen. The polymorphic sequences are also used in drug screening assays, to determine the dose and specificity of a candidate therapeutic agent. A candidate ASTH1 polymorphism is screened with a target therapy to determine whether there is an influence on the effectiveness in treating asthma. Drug screening assays are performed as described above. Typically two or more different sequence polymorphisms are tested for response to a therapy.

Drugs currently used to treat asthma include beta 2-agonists, glucocorticoids, theophylline, cromones, and anticholinergic agents. For acute, severe asthma, the inhaled beta 2-agonists are the most effective bronchodilators. Short-acting forms give rapid relief; long-acting agents provide sustained relief and help nocturnal asthma. First-line therapy for chronic asthma is inhaled glucocorticoids, the only currently available agents that reduce airway inflammation. Theophylline is a bronchodilator that is useful for severe and nocturnal asthma, but recent studies suggest that it may also have an immunomodulatory effect. Cromones work best for patients who have mild asthma: they have few adverse effects, but their activity is brief, so they must be given frequently. Cysteinil leukotrienes are important mediators of asthma, and inhibition of their effects may represent a potential breakthrough in the therapy of allergic rhinitis and asthma.

Where a particular sequence polymorphism correlates with differential drug effectiveness, diagnostic screening may be performed. Diagnostic methods have been described in detail in a preceding section. The presence of a particular polymorphism is detected, and used to develop an effective therapeutic strategy for the affected individual.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Materials and Methods
Asthma families for genetic mapping studies

Asthma phenotype measurements and blood samples were obtained from the inhabitants of Tristan da Cunha, an isolated island in the South Atlantic, and from asthma families in Toronto, Canada (see Zamel et al., (1996) supra.) The 282 inhabitants of Tristan da Cunha form a single large extended family descended from 28 original founders. Settlement of Tristan da Cunha occurred beginning in 1817 with soldiers who remained behind when a British garrison was withdrawn from the island, followed by the survivors of several shipwrecks. In 1827 five women from St. Helena, one with children, emigrated to Tristan da Cunha and married island men. One of these women is said to have been asthmatic, and could be the origin of a genetic founder effect for asthma in this population. Inbreeding has resulted in kinship resemblances of at least first cousin levels for all individuals.

The Tristan da Cunha family pedigrees were ascertained through review of baptismal, marriage and medical records, as well as reliably accurate historical records of the early inhabitants (Zamel (1995) Can. Respir. J. 2:18). The prevalence of asthma on Tristan da Cunha is high; 23% had a definitive diagnosis of asthma.

The Toronto cohort included 59 small families having at least one affected individual. These were ascertained based on the following criteria: (i) an affected proband; (ii) availability of at least one sibling of the proband, either affected or unaffected; (iii) at least one living parent from whom DNA could be obtained. A set of 156 "triad" families consisting of an affected proband and his or her parents were also collected. Signed consent forms were obtained from each individual prior to commencement of phenotyping and blood sample collection. The Toronto patients were mainly of mixed European ancestry.

Clinical characterization

A standardized questionnaire based on that of the American Thoracic Society (American Lung Association recommended respiratory diseases questionnaire for use with adults and children in epidemiology research. 1978. *American Review of Respiratory Disease* 118(2):7–53) was used to record the presence of respiratory symptoms such as cough, sputum and wheezing; the presence of other chest disorders including recent upper respiratory tract infection, allergic history; asthmatic attacks including onset, offset, confirmation by a physician, prevalence, severity and precipitating factors; other illnesses and smoking history; and all medications used within the previous 3 months. A physician-confirmed asthmatic attack was the principal criterion for a diagnosis of asthma.

Skin atopy was determined by skin prick tests to common allergens: *A. fumigatus*, Cladosporium, Alternaia, egg, milk, wheat, tree, dog, grass, horse, house dust, cat, feathers, house dust mite *D. fadnae*, and house dust mite *D. pteronyssinus*. Atopy testing of Toronto subjects omitted *D. pteronyssinus* and added cockroach and ragweed allergens. Saline and histamine controls were also performed (Bencard Laboratories, Mississauga, Ontario). Antihistamines were withdrawn for at least 48 hours prior to testing. Wheal diameters were corrected by subtraction of the saline control wheal diameter, and a corrected wheal size of >3 mm recorded 10 min after application was considered a positive response.

Airway responsiveness was assessed by a methacholine challenge test in those subjects with a baseline FEV1 (forced exhalation volume in one second) >70% of predicted (Crapo et al. (1981) *Am. Rev. Respir. Dis.* 123:659). Methacholine challenge response was determined using the tidal breathing method (Cockcroft et al. (1977) *Clin. Allergy* 7:235). Doubling doses of methacholine from 0.03 to 16 mg/ml were administered using a Wright nebulizer at 4-min intervals to measure the provocative concentration of methacholine producing a 20% fall in FEV1 (PC20). If FEV1 was <70% of predicted, a bronchodilator response to 400 mg salbutamol aerosol was used to determine airway responsiveness. Both methacholine challenges and bronchodilator responses were measured using a computerized bronchial challenge system (S&M Instrument Co. Inc., Doyleston, Pa.) consisting of a software package and interface board installed in a Toshiba T1850C laptop computer and connected to a flow sensor (RS232FS). The power source for instruments used on Tristan da Cunha has been described (Zamel et al. (1996) supra.) Increased airway responsiveness was defined as a PC20<4.0 mg/ml or a >15% improvement in FEV1 15 min postbronchodilator. Participants were asked to withhold bronchodilators at least 8 h before testing; inhaled or systemic steroids were maintained at the usual dosage. Subjects with a history of an upper respiratory tract infection within a month of testing were rechallenged at a later date.

Genotyping

PCR primer pairs were synthesized using Applied Biosystems 394 automated oligo synthesizer. The forward primer of each pair was labeled with either FAM, HEX, or TET phosphoramidites (Applied Biosystems). No oligo purification step was performed.

Genomic DNA was extracted from whole blood. PCR was performed using PTC100 thermocyclers (MJ Research). Reactions contained 10 mM Tris-HCl, pH 8.3; 1.5–3.0 mM $MgCl_2$; 50 mM KCl; 0.01% gelatin; 250 μM each dGTP, dATP, dTTP, dCTP; 20 μM each PCR primer; 20 ng genomic DNA; and 0.75 U Taq Polymerase (Perkin Elmer Cetus) in a final volume of 20 μl. Reactions were performed in 96 well polypropylene microtiter plates (Robbins Scientific) with an initial 94° C., 3 min. denaturation followed by 35 cycles of 30 sec. at 94° C., 30 sec. at the annealing temp., and 30 sec. at 72° C., with a final 2 min. extension at 72° C. following the last cycle. Dye label, annealing temperature, and final magnesium concentration were specific to the individual marker.

Dye label intensity and quantity of PCR product (as assessed on agarose gels) were used to determine the amount to be pooled for each marker locus. The pooled products were precipitated and the product pellets mixed with 0.4 μl Genescan 500 Tamra size standard, 2 μl formamide, and 1 μl ABI loading dye. Plates of PCR product pools were heated to 80° C. for 5 minutes and immediately placed on ice prior to gel loading.

PCR products were electrophoresed on denaturing 6% polyacrylamide gels at a constant 1000 volts using ABI 373a instruments. Peak detection, sizing, and stutter band filtering were achieved using Genescan 1.2 and Genotyper 1.1 software (Applied Biosystems). Genotype data were subsequently submitted to quality control and consistency checks (Hall et al. (1996) *Genome Res.* 6:781).

Genotyping of 'saturation' markers in the ASTH1 region was done by the method described above with several exceptions. In most cases, the unlabeled primer of each pair was modified with the sequence GTTTCTT at the 5' end (Smith et al. 1995 *Genome Res.* 5:312). Amplitaq Gold (Perkin Elmer Cetus) and buffer D (2.5 mM $MgCl_2$, 33.5 mM Tris-HCl pH 8.0, 8.3 mM $(NH_4)_2SO_4$, 25 mM KCl, 85 μg/ml BSA) were used in the PCR. A 'touchdown' amplification profile was employed in which the annealing temperature began at 66° C. and decreased one degree per cycle to a final 20 cycles at 56° C. Products were run on 4.25% polyacrylamide gels using ABI 377 instruments. The data was processed with Genescan 2.1 and Genotyper 1.1 software.

The Genome Scan

A genome scan was performed in the population of Tristan da Cunha using 274 polymorphic microsatellite markers chosen from among those developed at Oxford (Reed et al. (1994) *Nature Genetics* 7:390), Genethon (Dib et al. (1996) *Nature* 380:152) and the Cooperative Human Linkage Center (CHLC, Murray et al. (1994) *Science* 265:2049). Markers with heterozygosity values of 0.75 or greater were selected to cover all the human chromosomes, as well as for ease of genotyping and size of PCR product for multiplexing of markers on gels. Fifteen multiplexed sets were used to provide a ladder of PCR products in each of three dyes when separated by size. Published distances were used initially to estimate map resolution. More accurate genetic distances were calculated using the study population as the data was generated. The 274 markers gave an average 14 cM interval for the genome scan.

Linkage analysis

Parametric linkage analyses of marker data were conducted using the methods of Haseman and Elston (1972) *Behav. Genet.* 2:3, and FASTLINK (Schaffer et al. (1996) *Hum. Hered.* 46:226), assuming a dominant mode of transmission with incomplete penetrance. Linkage to three primary phenotypes including asthma diagnosis (history), airway responsiveness (PC20<4 mg/ml for methacholine challenge) and atopy (one or more skin-prick test which yielded a wheal diameter >3 mm) and combinations of these, were tested.

Small scale yeast artificial chromosome (YAC) DNA preparation

Small scale isolation of YAC DNA for STS mapping was done by a procedure which uses glass beads and physical shearing to damage the yeast cell wall (Scherer and Tsui (1991) *Cloning and analysis of large DNA molecules*, In Advanced Techniques in Chromosome Research. (K. W. Adolph, ed.) pp. 33–72. Marcel Dekker, Inc. New York, Basel, Hong Kong.)

YAC block prep and pulsed field gel electrophoresis (PFGE)

A 50 ml culture of each YAC was grown in 2× AHC at 30° C. The cells were pelleted by centrifugation and washed twice in sterile water. After resuspension of the cells in 4 ml of SCEM (1 M sorbitol, 0.1 M sodium citrate (pH 5.8), 10 mM EDTA, 30 mM β-mercaptoethanol), 5 ml of 1.2% low melting temperature agarose in SCEM was added, mixed, pipetted into 100 ml plug molds and allowed to solidify.

Plugs were incubated overnight in 50 ml of SCEM containing 30 U/ml lyticase (Sigma). Plugs were rinsed 3 times in TE (10 mM Tris pH 8.0, 1 mM EDTA) and incubated twice for 12 hours each at 50° C. in lysis solution (0.5 M EDTA, pH 8.0; 1% w/v sodium lauryl sarcosine; 0.5 mg/ml proteinase K). They were washed 5 times with TE and stored in 0.5 M EDTA (pH 8.0) at 4° C.

YACs and yeast chromosomes were separated on pulsed field gels using a CHEF Mapper (BIO-RAD) and according to methods supplied by the manufacturer, then transferred to nitrocellulose. YACs which comigrated with yeast chromosomes were visualized by hybridization of the blot with radiolabelled YAC vector sequences (Scherer and Tsui (1991) supra.)

Hybridization of YAC DNA to bacterial artificial chromosome (BAC) and cosmid grids Size-purified YAC DNA was prepared by pulsed field gel electrophoresis on a low melting temperature Seaplaque GTG agarose (FMC) gel, purified by GeneClean (BIO101) and radiolabeled for 30 mins with $^{32}$P-dCTP using the Prime-It II kit (Stratagene). 50 μl of water was added and unincorporated nucleotide was removed by Quick Spin Column (Boehringer Mannheim). 23 μl of 11.2 mg/ml human placental DNA (Sigma) and 36 μl of 0.5 M $Na_2HPO_4$, pH 6.0 were added to the approximately 150 μl of eluant. The probe was boiled for 5 mins and incubated at 65° C. for exactly 3 hours, then added to the prehybridized gridded BAC (Shizuya et al. (1992) *Proc. Natl. Acad. Sci.* 89:8794; purchased from Research Genetics) or chromosome 11 cosmid [Resource Center/Primary Database of the German Human Genome Project, Berlin; Lehrach et al. (1990), In Davies, K. E. and Tilghman, S. M. (eds.), *Genome Analysis* Volume 1: Genetic and Physical Mapping. Cold Spring Harbor Laboratory Press, Cold Spring Harbor, pp. 39–81] filters in dextran sulfate hybridization mix (10% dextran sulfate, 1% SDS, 1 M NaCl). Hybridizations were at 65° C. for 12–48 hours, followed by 2 washes at room temperature in 2× SSC for 10 mins each, and 3 washes at 65° C. in 0.2× SSC, 0.2% SDS for 20 mins each.

Metaphase fluorescence in situ hybridization (FISH) and direct visual in situ hybridisation (DIRVISH)

Metaphase FISH was carried out by standard methods (Heng and Tsui (1994) FISH detection on DAPI banded chromosomes. In *Methods of Molecular Biology: In Situ Hybridisation Protocols* (K. H. A. Choo, ed.) pp. 35–49. Human Press, Clifton, N.J.). High resolution FISH, or DIRVISH, was used to map the relative positions of two or more clones on genomic DNA. The protocol used was as described by Parra and Windle (1993) *Nature Genet.* 5:17. Briefly, slides containing stretched DNA were prepared by adding 2 $\mu$l of a suspension of normal human lymphoblast cells at one end of a glass slide and allowing to dry. 8 $\mu$l lysis buffer (0.5% SDS, 50 mM EDTA, 200 mM Tris-HCL, pH 7.4) was added and the slide incubated at room temperature for 5 minutes. The slide was tilted so that the DNA ran down the slide, then dried. The DNA was fixed by adding 400 $\mu$l 3:1 methanol/acetic acid. Probes were labeled either with biotin or with digoxygenin by standard nick translation (Rigby et al. (1977) *J. Mol. Biol.* 113:237). Hybridization and detections were carried out using standard fluorescence in situ hybridization techniques (Heng and Tsui (1994) supra.). Results were visualised using a Mikrophot SA microscope (Nikon) equipped with a CCD camera (Photometrics). Images were recorded using Smartcapture software (Vysis).

Gap filling

Clones flanking gaps in the map were end cloned by digestion with enzymes that do not cut the respective vector sequences (NsiI for BAC clones and XbaI for PAC clones), followed by religation and transformation into competent DH5$\alpha$. Clones which produced two end fragments and plasmid vector upon digestion with NotI and NsiI or XbaI were sequenced. Gaps in the tiling path were filled by screening a gridded BAC library with the end clone probes or by screening DNA pools of a human genomic PAC library (Ioannou et al. (1994) *Nature Genetics* 6:84; licensed from Health Research, Inc.) by PCR using primers designed from end clone sequences.

Direct cDNA selection

Direct cDNA selection (Lovett et al., (1991) *Proc. Natl. Acad. Sci.* 88:9628) was carried out using cDNA derived from both adult whole lung tissue and fetal whole lung tissue (Clontech). 5 $\mu$g of Poly(A)+ RNA was converted to double stranded cDNA using the Superscript Choice System for cDNA synthesis and the supplied protocol (Gibco BRL). First strand priming was achieved by both oligo(dT) and random hexamers. The resulting cDNA was split into 2 equal aliquots and digested with either MboI or TaqI prior to the addition of specific linker primers. Linker primers for MboI-digested DNA were as described by Morgan et a/. (1992) *Nucleic Acid Res.* 20:5173. Linker primers for TaqI-digested DNA were a modification of these: (SEQ ID NO:336) Taq1a: 5'-CGAGAATTCACTCGAGCATCAGG; (SEQ ID NO:337) Taq1b: 5'-CCTGATGCTCGAGTGAATTCT. The modified cDNA was ethanol precipitated and resuspended in 200 $\mu$l of H$_2$O. 1 $\mu$l of cDNA was amplified with the linker primer MboI b in a 100 $\mu$l PCR reaction. The resulting cDNA products, approximately 1 $\mu$g, were blocked with 1 $\mu$g of COT1 DNA (Gibco BRL) for 4 hours at 60oC in 120 mM NaPO$_4$ buffer, pH 7.0.

Approximately 1 $\mu$g of the appropriate genomic clones was biotinylated using the BioNick Labeling System (Gibco BRL). Unincorporated biotin was removed by spin column chromatography. Approximately 100 ng of biotinylated genomic DNA was denatured and allowed to hybridize to 1 $\mu$g of blocked cDNA in a total volume of 20 $\mu$l in 120 mM NaPO$_4$ for 60 hours at 60oC under mineral oil. After hybridization, the biotinylated DNA was captured on streptavidin-coated magnetic beads (Dynal) in 100 $\mu$l of binding buffer (1 M NaCl, 10 mM Tris, pH 7.4, 1 mM EDTA) for 20 minutes at room temperature with constant rotation. Two 15 minute washes at room temperature with 500 $\mu$l of 1× SSC/0.1% SDS were followed by four washes for 20 minutes at 65° C. with 500 ul of 0.1× SSC/0.1% SDS with constant rotation. After each wash, the beads were collected on the side of the tube using magnet separation and the supernatant was removed with a pipette. Following the last wash, the beads were briefly rinsed once with wash solution prior to eluting the bound cDNA with 50 $\mu$l of 0.1 M NaOH for 10 minutes at room temperature. The supernatant was removed and neutralized with 50 $\mu$l 1 M Tris pH 7.4. The primary selected cDNA was desalted using a Sephadex G-50 column (Boehringer Mannheim). PCR was performed on 1, 2, 5, and 10 $\mu$l of eluate with MboI b primers. Amplified products were analyzed on a 1.4% agarose gel. The reaction with the cleanest bands and least background was scaled up to produce approximately 1 $\mu$g of primary selected cDNA. This amplified primary selected cDNA was blocked with 1 $\mu$g of COT1 at 60° C. for 1 hour followed by a second round of hybridization to 100 ng of the appropriate genomic DNA under the same conditions as the first round of selection. Washing of the bound cDNA, elution, and PCR of the selected cDNA was identical to the first round. 1 $\mu$l of PCR amplified secondary selected cDNA was cloned using the TA cloning system according to the manufacturers protocol (Invitrogen). Colonies were picked into 96-well microtiter plates and grown overnight prior to sequencing.

Exon Trapping

Exon trapping was performed by the method of Buckler et al. (1991, *Proc. Natl. Acad. Sci. USA* 88:4005) with modifications described in Church et al., (1994) *Nature Genetics* 6:98. Each BAC clone of the minimal set of clones required to the cover the ASTH1 region (i.e. the tiling path) was subject to exon trapping separately. Briefly, restriction fragments (PstI or BamHI/BgIII) of each cosmid were shotgun subcloned into PstI- or BamHI-digested and phosphatase-treated psPL3B which had been modified as in Burns et al. (1995) *Gene* 161:183 (GIBCO BRL). Ligations were electroporated into ElectroMax HB101 cells (Gibco BRL) and plated on 20 cm diameter LB ampicillin plates. DNA was prepared from plates with >2000 colonies by collection of the bacteria in LB ampicillin liquid and plasmid DNA purification by a standard alkaline lysis protocol (Sambrook et al. (1989) sLipra.) 5 $\mu$g of DNA from each plasmid pool preparation were electroporated into Cos 7 cells (ATCC) and RNA harvested using TRIZOL (Gibco BRL) after 48 hours of growth. RT-PCR products were digested with BstXI prior to a second PCR amplification. Products were cloned into pAMP10 (Gibco BRL) and transformed into DH5 cells (Gibco BRL). 96 colonies per BAC were picked and analyzed for insert size by PCR.

Northern blot hybridisation

Northern hybridisation was performed using Multiple Tissue Northern (MTN) blots (Clontech). DNA probes were radioactively labeled by random priming [Feinberg and Vogelstein (1984) *Anal. Biochem.* 137:266] using the Prime-It II kit (Stratagene). Hybridizations were performed in ExpressHyb hybridisation solution (Clontech) according to the manufacturer's recommendations. Filters were exposed to autoradiographic film overnight or for 3 days.

cDNA library screening

Phage cDNA libraries were plated and screened with radiolabeled probes (exon trapping or cDNA selection products amplified by PCR from plasmids containing these sequences) by standard methods (Sambrook et al. (1989) supra.)

Rapid amplification of cDNA ends (RACE)

RACE libraries were constructed using polyA+ RNA and the Marathon cDNA amplification kit (Clontech). Nested RACE primer sets were designed for each cDNA or potential gene fragment (trapped exon, predicted exon, conserved fragment, etc). The RACE libraries were tested by PCR using one primer pair for each potential gene fragment; the two strongly positive libraries were chosen for RACE experiments.

Genomic sequencing

DNA from cosmid, PAC, and BAC clones was prepared using Qiagen DNA prep kits and further purified by CsCl gradient. DNA was sonicated and DNA fragments were repaired using nuclease BAL-31 and T4 DNA polymerase. DNA fragments of 0.8–2.2 kb were size-fractionated by agarose gel electrophoresis and ligated into pUC9 vector. Inserts of the plasmid clones were amplified by PCR and sequenced using standard ABI dye-primer chemistry.

ABI sample file data was reanalyzed using Phred (Phil Green, University of Washington) for base calling and quality analysis. Sequence assembly of reanalyzed sequence data was accomplished using Phrap (Phil Green, University of Washington). Physical gaps between assembled contigs and unjoined but overlapping contigs were identified by inspection of the assembled data using GFP (licensed from Baylor College of Medicine) and Consed (Phil Green, University of Washington). Material for sequence data generation across gaps was obtained by PCR amplification. Low coverage regions were resequenced using dye-primer and dye-terminator chemistries (ABI). Final base-perfect editing (to >99% accuracy) was accomplished using Consed.

Single stranded conformational polymorphism (SSCP) analysis

PCR primers flanking each exon of the ASTH1I and ASTH1J genes, or more than one primer pair for large exons, were designed from genomic sequence generated using Primer (publicly available from the Whitehead Institute for Biomedical Research) or Oligo 4.0 (licensed from National Biosciences). Radioactive SSCP was performed by the method of Orita et al. (1989, Proc. Natl. Acad. Sci. 86:2766). Briefly, radioactively labeled PCR products between 150 and 300 bp and spanning exons of the ASTH1I and ASTH1J genes were generated from a set of asthma patient and control genomic template DNAs, by incorporating $\alpha$-$^{32}$P dCTP in the PCR. PCR reactions (20 $\mu$l) included 1× reaction buffer, 100 $\mu$M dNTPs, 1 $\mu$M each forward and reverse primer, and 1 unit Taq DNA polymerase (Perkin-Elmer) and 1 $\mu$Ci $\alpha$-$^{32}$P dCTP. A brief denaturation at 94° C. was followed by 30–32 cycles of: 94° C. for 30 sec, 30 sec at the annealling temperature, and 72° C. for 30 sec; followed by 5 mins at 72°. Radiolabeled PCR products were diluted 1:20 in water, mixed with an equal volume of denaturing loading dye (95% formamide, 0.25% bromophenol blue), and denatured for 10 minutes at 80° C. immediately prior to electrophoresis. 0.5× MDE (FMC) gels with and without 8% glycerol in 1× TBE were run at 8–12 Wafts for 16–20 hours at room temperature. Dried gels were exposed to autoradiographic film (Kodak XAR) for 1–2 days at −80° C. PCR products from individuals carrying SSCP variants were subcloned into the PCR2.1 or pZeroBlunt plasmid vector (Invitrogen). Inserts of the plasmid clones were amplified by PCR and sequenced using standard ABI dye-primer chemistry to determine the nature of the sequence variant responsible for the conformational changes detected by SSCP.

Fluorescent SSCP was carried out according to the recommended ABI protocol (ABI User Bulletin entitled 'Multi Color Fluorescent SSCP'). Unlabeled PCR primers were used to amplify genomic DNA segments containing different exons of the ASTH1I or ASTH1J genes, in patient or control DNA. Nested fluorescently labeled (TET, FAM or HEX) primers were then used to amplify smaller products, 150 to 300 bp containing the exon or region of interest. Amplification was done using a 'touchdown' PCR protocol, in which the annealing temperature decreased from 57° C. to 42° C., and Amplitaq Gold polymerase (Perkin Elmer, Cetus). In most cases the fluorescently labeled primers were identical in sequence to those used for conventional radioactive SSCP. The fluorescent PCR products were diluted and mixed with denaturing agents, GeneScan size standard (Genescan 500 labelled with Tamra) and Blue dextran dye. Samples were heated at 90° C. and quick chilled on ice prior to loading on 6.5% standard or 0.5× MDE (manufacturer) polyacrylamide gels containing 2.5% glycerol and run using externally temperature controlled modified ABI 377 instruments. Gels were run at 1240 V and 20° C. for 7–9 hrs and analyzed using GeneScan software (ABI).

Comparative (heterozygote detection) sequencing

Unlabeled PCR primers were used to amplify genomic DNA segments containing different exons of the ASTH1I or ASTH1J genes, from patient or control DNAs. A set of nested PCR primers was then used to reamplify the fragment. Unincorporated primers were removed from the PCR product by Centricon-100 column (Amicon), or by Centricon-30 column for products less than 130 bp. The nested primers and dye terminator sequencing chemistry (ABI PRISM dye terminator cycle sequencing ready reaction kit) were then used to cycle sequence the exon and flanking region. Volumes were scaled down to 5 $\mu$l and 10% DMSO added to increase peak height uniformity. Sequences were compared between samples and heterozygous positions detected by visual inspection of chromatograms and using Sequence Navigator (licensed from ABI).

For some exons, PCR products were also compared by subcloning and sequencing, and comparison of sequences for ten or more clones.

Results

Genome scanning and linkage analysis

A genome scan was performed using polymorphic microsatellite markers from throughout the human genome, and DNA isolated from blood samples drawn from the inhabitants of Tristan da Cunha. Linkage analysis, an established statistical method used to map the locations of genes and markers relative to other markers, was applied to verify the marker orders and relative distances between markers on all human chromosomes, in the Tristan da Cunha population. Linkage analysis can detect cosegregation of a marker with disease, and was used as a means to detect genes influencing the development of asthma in this population. The most highly significant linkage in the genome scan (p=0.0001 for history of asthma and p=0.0009 for methacholine challenge) was obtained at D11S907, a marker on the short arm of chromosome 11. This significant linkage result indicated that a gene influencing predisposition to asthma in the Tristan da Cunha population was located near D11S907.

Replication of this finding was obtained in a collection of asthma families from Toronto, in which D11S907 and several nearby markers were tested for linkage. The significant linkage seen (p=0.001 for history of asthma and p=0.05 for methacholine challenge) supported the mapping of an asthma gene near D11S907 and indicated that the gene was likely to be relevant in the more diverse outbred Toronto group as well as in the inbred population of Tristan da Cunha.

The approximate genetic location of the ASTH1 gene in the Tristan da Cunha population was confirmed by genotyping and analyzing data from several markers near D11 S907, spaced at intervals no greater than 5 cM across a possible linked region of about 30 cM. Sib-pair and affected pedigree member linkage analyses of these markers yielded confirmatory evidence for linkage and refined the genetic interval.

Physical mapping at ASTH1: YAC contig construction

Yeast artificial chromosome (YAC) clones were derived from the CEPH megaYAC library (Cohen et al. 1993 *Nature* 366:698). Individual YAC addresses were obtained from a public physical map of CEPH megaYAC STS (sequence tagged site; Olson et al. (1989) *Science* 245:1434) mapping data maintained by the Whitehead Institute and accessible through the world wide web (Cohen et al. 1993. supra.; http://www-genome.wi.mit.edu/cgi-bin/contig/phys_map). YAC clones spanning or overlapping other YACs containing D11S907 were chosen for map construction; STSs mapping to these YACs were used for map and clone verification. Some YACs annotated in the public database as being chimeric were excluded from the analyses. Multiple colonies of each YAC, obtained from a freshly streaked plate inoculated from the CEPH megaYAC library masterplate, were scored using STS markers from the ASTH1 region. These markers included polymorphic microsatellite repeats, expressed sequence tags (ESTS) and STSs. Comparison of STS mapping data for each clone with the public map allowed choice of the individual clone which retained the greatest number of ASTH1 region STSs, and was therefore least likely to be deleted. YAC addresses for which clones differed in STS content were interpreted to be prone to deletion; those for which a subset of clones contained no ASTH1 region STSs were presumed to be contaminated with yeast cells containing a YAC from another region of the genome. Chimerism of the chosen clones was assessed by metaphase fluorescent in situ hybridization (FISH). Their sizes were determined by pulsed field gel electrophoresis (PFGE), Southern blotting and hybridization with a YAC vector probe. The PFGE analyses also showed that no YAC clone chosen contained more than one yeast artificial chromosome.

An STS map based on assuming the least number of deletions in the YAC clones was generated. The STS marker order was in agreement with that of the Whitehead map. The STS retention pattern of individual YACs, however, was slightly different from that of the public data. In general, the chosen clones were positive for a greater number ASTH1 region markers, showing that the data set was likely to have fewer false negatives than the public map. Non-chimeric YAC clones spanning the region of greatest interest were chosen for use as hybridization probes for the identification of smaller BAC, PAC, P1 or cosmid clones from the region.

Conversion to a plasmid-based clone map

The YAC map at ASTH1 provided continuous coverage of a 4 Mb region, the central 1 Mb of which was of greatest interest. YAC clones comprising a minimal tiling path of this region were chosen, and the size purified artificial chromosomes were used as hybridization probes to identify BAC and cosmid clones. Gridded filters of a 3x human genomic BAC library and of a human chromosome 11-specific cosmid library were hybridized with radiolabeled purified YAC. Clones corresponding to the grid coordinates of the positives were streaked to colony purity, and filters gridded with four clones of each BAC or cosmid. These secondary filters were hybridized with size-purified YAC DNAS. A proportion of both the BACs and cosmids were found to be non-clonal by these analyses. A positively hybridizing clone of each was chosen for further analysis.

The BAC and cosmid clones were STS mapped to establish overlaps between the clones. The BACs were further localized by DIRVISH. BACs which did not contain an STS marker were mapped in pairwise fashion by simultaneous two-color DIRVISH with another BAC. The map produced had three gaps which were subsequently filled by end cloning and hybridization of the end clones to a human genomic PAC library. Genetic refinement of the ASTH1 region had occurred concurrently with mapping, rendering it unnecessary to extend the BAC-contigged region. Mapping data was recorded in ACeDB (Eeckman and Durbin (1995) *Methods Cell Biol.* 48:583).

Genomic sequencing and gene prediction

A minimal tiling path of BAC and cosmid clones was chosen for genomic sequencing. Over 1 Mb of genomic sequence was generated at ASTH1. On average, sequencing was done to 12x coverage (12 times redundancy in sequences). Marker order was verified relative to the STS map.

BLAST searches (Altschul et al. (1990) supra.) were performed to identify sequences in public databases that were related to those in the ASTH1 region. Sequence-based gene prediction was done with the GRAIL [Roberts (1991) *Science* 254:805] and Geneparser [Snyder and Stormo (1993) *Nucleic Acids Res.* 21: 607] programs. Genomic sequence and feature data was stored in ACeBD.

Development of new microsatellite markers for genetic refinement of the ASTH1 region Additional informative polymorphic markers were important for the genetic refinement of the ASTH1 region. 'Saturation' cloning of every microsatellite in the 1 Mb region surrounding D11S907 was performed. Plasmid libraries were constructed from PFGE purified DNA from each YAC, prescreened with a primer from each known microsatellite marker, then screened with radiolabeled (CA)15 or a pool of trinucleotide and tetranucleotide repeat oligonucleotides. The plasmid inserts were sequenced, the set of sequences compared with those of the known microsatellite markers in the region, using Power assembler (ABI) or Sequencher (Alsbyte). Primer pairs flanking each novel microsatellite repeat were designed, and the heterozygosity of each new marker was tested by Batched Analysis of Genotypes (BAGs; LeDuc et al., 1995, *PCR Methods and Applications* 4:331). Additional microsatellites were found by analysis of the genomic sequence in AceDB. Table 1 lists all the microsatellite markers used for genotyping in the ASTH1 region and their repeat type, source and primers. Table 1B lists some repeat sequences.

TABLE 1

Polymorphic microsatellite markers in the ASTH1 region

| SEQ ID | MARKER | PRIMER 1 |
|---|---|---|
| 160. | 11O5GT1 | CTGCTGTGGACGAATAGG |
| 161. | | TCAATATAATCTTGCTTAACTTGG |
| 162. | 139C7GT1 | GACCTGTTTGGGTTGATTTCAG |
| 163. | | GTTTCTTACAGTGTCTTGCTATCACATCACC |
| 164. | 171L24AT1 | GAGGACTGGCAGTACCAAGTAAAC |
| 165. | | GTTTCTTTGGTTCATTCTAAGATGGCTGG |
| 166. | 253E6GT1 | GCTGAGGCAGGAGAAAAGACAAG |
| 167. | | GTTTCTTCATGCAAAGGTCAGGAGGTAGG |
| 168. | 253E6TE1 | GTTGCTTCCAGACGAGGTACATG |
| 169. | | GTTTCTTCAATGGCTCCACAAACATCTCTG |
| 170. | 253E6TR1 | AGGTTTAGGGGACAGGGTTTGG |
| 171. | | GTTTCTTTCCTGGCTAACACGGTGAAATC |
| 172. | 65P14 | GTTTCTTATTGCCTCCTCCCAAAATTC |
| 173. | | AGAGGCCACTGGAAGACGAA |
| 174. | 65P14GT1 | AACTGGAGTCAGGCAAAACGTG |
| 175. | | GTTTCTTTGGCTGGTAAGGAAAGAAACCAC |
| 176. | 65P14TE1 | GGCTAGGTTCATAAACTCTGTGCTG |
| 177. | | GTTTCTTGATTGTTTGAGATCCTTGACCCAG |
| 178. | 65P14TE2 | GCCGAAATCACAACACTGCATC |
| 179. | | GTTTCTTGATTCTGCTCTTACTCTTGCCCC |
| 180. | 65P14TR1 | GTAATAGAACCAAAGGGCTGAGAC |
| 181. | | GTTTCTTCGGAGTCAGACCTTACATTGTTGAG |
| 182. | 774F | ATCTCCCTGCTACCCACCTT |
| 183. | | GTTTCTTGTTTTCAGTGAGTTTCTGTTGGG |
| 184. | 774J | GTGTGCCAAACAACATTTGC |
| 185. | | GTTTCTTCAAGCCATCAAGCTAGAGTGG |
| 186. | 774L | GGGCTTTTAAACCCTTATTTAACC |
| 187. | | GTTTCTTAGGTGATCTCAGAGCCACTCA |
| 188. | 774N | AGGGCAGGTGGGAACTTACT |
| 189. | | GTTTCTTTGGAGTCAGTTGAGCTTTCTACC |
| 190. | 774O | TGAACTTGCCTACCTCCCAG |
| 191. | | GTTTCTTAGCATATATCCTTACACAAGCACA |
| 192. | 774T | CATGGTTCCAAAGGCAAGTT |
| 193. | | GTTTCTTTTGAGGCTGAATGAGCTGTG |
| 194. | 86J5AT2 | ACAGGTGGGAAGACTGAATGTC |
| 195. | | GTTTCTTGCAGTACACATCACATGACCTTG |
| 196. | 86J5CA1 | GAAATAGGCGGAAACTGGTTC |
| 197. | | GTTTCTTCGTTGTGGTTGTTCAGAAAGG |
| 198. | 86J5GT1 | GGTCAAGTGTTCAGAACGCATC |
| 199. | | GTTTCTTGCAGGGATTATGCTAGGTCTGTAG |
| 200. | 86J5GT2 | AGCACTTCTGAGGAAGGGACAC |
| 201. | | GTTTCTTAGGGCAGGCAGACATACAAAC |
| 202. | 86J5TE1 | GCCAATGTGTTCCTAGAGCGAC |
| 203. | | GTTTCTTTTAAAGGGGTAGGGTGTCACC |
| 204. | 8E.PENTA1 | GGAAGGGAAAAGGACAAGGTTTTG |
| 205. | | GTTTCTTAGCAAGAGCACTGGTGTAGGAGTC |
| 206. | 8E04DO5 | GCTTTTCAAGCACTTGTCTC |
| 207. | | TGGGATTGTGACTTACCATG |
| 208. | 8O16GT1 | ACTTGGTGTCTTATAGAAAGGTG |
| 209. | | GTTTCTTAGCTGTGTTTGCTGCATC |
| 210. | 8O16GT2 | AGATGTGTGATGAGATGCAG |
| 211. | | GTTTCTTCAAATAGTGCAACAAACCC |
| 212. | AFM198YB10(G) | TGTCATTCTGAAAGTGCTTCC |
| 213. | | GTTTCTTCTGTAACTAACGATCTGTAGTGGTG |
| 214. | AFM205YG5(G) | TATCAAGGTAATATAGTAGCCACGG |
| 215. | | AGGTCTTTCATGCAGAGTGG |
| 216. | AFM206XB2(G) | ATTGCCAAAACTTGGAAGC |
| 217. | | AGGTGACATATCAAGACCCTG |
| 218. | AFM283WH9(G) | TTGTCAACGAAGCCCAC |
| 219. | | GTTTCTTGCAAGATTGTGTGTATGGATG |
| 220. | AFM324YH5(G) | GCTCTCTATGTGTTTGGGTG |
| 221. | | AAGAGTACGCTAGTGGATGG |
| 222. | AFMA154ZD1(G) | TCCATTAGACCCAGAAAGG |
| 223. | | GTTTCTTCACCAGGCTGAGATGTTACT |
| 224. | ASMI14 | AATCGTTCCTTATCAGGTAATTTGG |
| 225. | | GTTTCTTCAAAGAAAGCAATTCCATCATAACA |
| 226. | ASMI14T | GCATTTGTTGAAGCAAGCGG |
| 227. | | CTTTGTTCCTTGGCTGATGG |
| 228. | CA11_11 | AATAGTACCAGACACACGTG |
| 229. | | CAATGGTTCACAGCCCTTTT |
| 230. | CA39_2 | AGCCTGGGAGACAGAGTGAG |
| 231. | | GTTTCTTGCACTTTTTGGGGAAGGTG |
| 232. | CD59(L) | GTTCCTCCCTTCCCTCTCC |
| 233. | | GTTTCTTTCAGGGACTGGATTGTAG |
| 234. | D11S1301(U) | GTGTTCTTTATGTGTAGTTC |

TABLE 1-continued

Polymorphic microsatellite markers in the ASTH1 region

| SEQ ID | MARKER | PRIMER 1 |
|---|---|---|
| 235. |  | GTTTCTTGGCAACAGAGTGAGACTCA |
| 236. | D11S1751(G) | GTGACATCCAGTGTTGGGAG |
| 237. |  | GTTTCTTCCTAAGCAAGCAAGCAATCA |
| 238. | D11S1776(G) | AAAGGCAATTGGTGGACA |
| 239. |  | GTTTCTTTTCAATCCTTGATGCAAAGT |
| 240. | D11S1900(U) | GGTGACAGAGCAAGATTTCG |
| 241. |  | GTTTCTTGTAGAGTTGAGGGAGCAGC |
| 242. | D11S2008/D11S1392 (C) | CATCCATCTCATCCCATCAT |
| 243. |  | GTTTCTTTTCACCCTACTGCCAACTTC |
| 244. | D11S2014(C) | CCGCCATTTTAGAGAGCATA |
| 245. |  | GTTTCTTTTCTGGGACAATTGGTAGGA |
| 246. | D11S4300(G) | TTTGTGTTATTATTTCAGGTGC |
| 247. |  | GTTTCTTGTTTTTTGTTTCA GTTTAGGAAC |
| 248. | D11S907(G) | CATACCCAAATCGTTCTCTTCCTC |
| 249. |  | GTTTCTTGGAAAAGCAAAG GCATCGTAGAG |
| 250. | D11S935(G) | TACTAACCAAAAGAGTTGGGG |
| 251. |  | CTATCATTCAGAAAATGTTGGC |
| 252. | GATA-P18492(C) | GTATGGCAGTAGAGGGCATG |
| 253. |  | AAGGTTACATTTCAAGAAATAAAGT |
| 254. | GATA-P6915(C) | CTGTTCAGGCCTCAATATATACC |
| 255. |  | AAGAGGATAGGTGGGGTTTG |
| 256. | L19CA3 | CCTCCCACCTAGACACAAT |
| 257. |  | ATATGATCTTTGCATCCCTG |
| 258. | L19PENTA1 | AAGAAAGACCTGGAAGGAAT |
| 259. |  | AAACAGCAAAACCTCATCTC |
| 260. | L19TETRA5 | CCACCACTTATTACCTGCAT |
| 261. |  | TGAATGAATGAATGAACGAA |
| 262. | LMP2 | AACTGTGATTGTGCCACTGCACTC |
| 263. |  | GTTTCTTCACCGCCTTTATCCCTCAAATG |
| 264. | LMP3 | GATGGGTGGAGGGCAGTTAAAG |
| 265. |  | GTCAAGCAACTTGTCCAAGGCTAC |
| 266. | LMP4 | CAGGCTATCAGTTTCCTTTGGAG |
| 267. |  | GGCAGGTAATACTGGAGAATTAGG |
| 268. | LMP7 | GACGGATCTCAGAGCCACTC |
| 269. |  | GTTTCTTAAAAGATAAGGGCTTTTAAACC |
| 270. | T18_5 | AGTTTCACAGCTTGTTATGG |
| 271. |  | GGTTGATGAAGTGAGACTTT |
| 272. | T29_9 | ATGGTGGATGCATCCTGTG |
| 273. |  | GTTTCTTGTATTGACTCCTCCTCTGC |
| 274. | 774L | CAGTAAACAT |
| 275. |  | TGTTGAGTGG |
| 276. | 774N | TCTCCTCAATGTGCATGT |
| 277. |  | ATTCTACATA |
| 278. | ASMI4 | GTGTTTGCAT |
| 279. |  | ACAAGTTGGC |
| 280. | CA11_11 | TAGTACCAGA |
| 281. |  | TACATCCAAGAAAA |

The source of marker was Sequana Therapeutics, Inc. unless a letter in parenthesis is indicated after the name, where G = Genethon; L = Nothen and Dewald (1995) Clin.Genet. 47:165; U = the Utah genome center, see: The Utah Marker Development Group (1995) Am.J.Hum.Genet. 57:619; c = the cooperative Human Lineage Center.

TABLE 1B

| SEQ | Marker | Repeat and flanking sequence |
|---|---|---|
| 282. | CA39_2 | GAGACTCTGA(CA)nAATATATATA |
| 283. | 774F | TGTTGATCGC(CA)nAACCAAAATC |
| 284. | 774J | AATGCATGTA(TG)2TATA(TG)nGTGTGGTATG(TG)3TACATATG CG |
| 285. | 774O | CCTCCCAGAA(CA)n ATCATGATAA |
| 286. | L19PENTA1 | AGACAGTCTCAAAAAAT(ATTTT)nAAAGAAAAAGCTGGATAAAT |
| 287. | 65P14TE1 | AACTAGCTTTAAGAAAATAAGAAGAAAAAGAAAGAAG(AAAG)2TAA G(AAAG)nAGAAAGAAAAG(AAAG)nAAAAG(AAAG)nAGGAATGAT TGAC |
| 288. | 65P14 | CGCGCACATA(CA)nCCCTTTCTCT |
| 289. | 774L | CAGTAAACAT(CA)n TGTTGAGTGG |
| 290. | 774N | TCTCCTCAATGTGCATGT (GTGC)2 ATGA (GTGC)2 (AC)n |

TABLE 1B-continued

| SEQ | Marker | Repeat and flanking sequence |
|---|---|---|
| 291. | ASMI14 | ATTCTACATA GTGTTTGCAT (GT)n T (GT)3 ACAAGTTGGC |
| 292. | CA11_11 1234567890 | TAGTACCAGA (CA)2 CG(TG)2 (CA)2 GGCAAGCG (CA)n C (CA)2 TACATCCAAGAAAA |

Genetic refinement of the ASTH1 region

The microsatellite markers isolated from YACs from the ASTH1 region were genotyped in both the Tristan da Cunha and Toronto cohorts. Genetic refinement of the ASTH1 region was accomplished by applying the transmission/disequilibrium test (TDT; Spielman et al. (1993) *Am. J. Hum. Genet.* 52:506) to genetic data from the Tristan and Toronto populations, at markers throughout the ASTH1 region. The TDT statistic reflects the level of association between a marker allele and disease status. A multipoint version of the TDT test controls for variability in heterozygosities between loci, and results in a smoother regional TDT curve than would a plot of single locus TDT data. Significance of a TDT value is determined by means of the $\chi^2$ test; A $\chi^2$ value of 3.84 or greater is considered statistically significant at a probability level of 0.05.

The Toronto TDT peak is located at marker D11S2008 ($\chi^2$=11.6, p <0.0001). The marker allele in disequilibrium is fairly rare (freq=6%), representing the fourth most common allele at this marker. The relative risk of affection vs. normal for this allele is 5.25. This is also the peak marker for linkage and linkage disequilibrium in Tristan da Cunha, indicating that the ASTH1 gene is very close to this marker. The markers defining the limits of linkage disequilibrium were D11 S907 and 65P14TE1. The physical size of the refined region is approximately 100 kb.

A significant TDT test reflects the tendency of alleles of markers located near a disease locus (also said to be in "linkage disequilibrium" with the disease) to segregate with the disease locus, while alleles of markers located further from the disease locus segregate independently of affection status. An expectation that derives from this is that a population for which a disease gene (ie a disease predisposing polymorphism) was recently introduced would show statistically significant TDT over a larger region surrounding the gene than would a population in which the mutant gene had been segregating for a greater length of time. In the latter case, time would have allowed more opportunity for markers in the vicinity of the disease gene to recombine with it. This expectation is fulfilled in our populations. The Tristan da Cunha population, founded only 10 generations ago, shows a broader TDT curve than does the set of Toronto families, which are mixed European in derivation and thus represent an older and more diverse, less recently established population.

Gene isolation and characterization

The tiling path of BACs, cosmids and PAC clones was subjected to exon trapping and cDNA selection to isolate sequences derived from ASTH1 region genes. Exon trap clones were isolated on the basis of size and ability to cross-hybridize. Approximately 300 putatively non-identical clones were sequenced. cDNA selection was performed with adult and fetal lung RNA using pools of tiling path clones. The cDNA selection clones were sequenced and the sequences assembled with those of the exon trap clones. Representative exon trapping clones spanning each assembly were chosen, and arranged as "masterplates" (96-well microtitre dishes) of clones. Exon trap masterplate clones and cDNA selection clones were subjected to expression studies.

Human multi-tissue Northern blots were probed with PCR products of masterplate clones. In some cases, exon trapping clones did not detect RNA species, either because they did not represent expressed sequences, or represented genes with very restricted patterns of expression, or due to small size of the exon probe.

Masterplate clones detecting discrete RNA species on Northern blots were used to screen lambda phage based cDNA libraries chosen on the basis of the expression pattern of the clone. The sequences of the cDNAs were determined by end sequencing and sequence walking. cDNAs were also isolated, or extended, by 5' and 3' rapid amplification of cDNA ends (RACE). In most cases, 5' RACE was necessary to obtain the 5' end of the cDNA.

ASTH1I and ASTH1J were detected by exon trapping. ASTH1I exons detected a 2.8 kb mRNA expressed at high levels in trachea and prostate, and at lower levels in lung and kidney. ASTH1I exons were used as probes to screen prostate, lung and testis cDNA libraries; positive clones were obtained from each of these libraries. Isolation of a ASTH1I cDNA clone from testis demonstrates that this gene is expressed in this tissue, and possibly others, at a level not detectable by Northern blot analysis.

ASTH1J exons detected a 6.0 kb mRNA expressed at high levels in the trachea, prostate and pancreas and at lower levels in colon, small intestine, lung and stomach. Pancreas and prostate libraries were screened with exon clones from ASTH1J. cDNA clone end sequences were assembled using Sequencher (Alsbyte) with the sequences of the exon trapped clones, producing sequence contigs used to design sequence walking and RACE primers. The additional sequences produced by these methods were assembled with the original sequences to produce longer contigs of cDNA sequences. It was evident from the sequence assemblies that both ASTH1I and ASTH1J are alternatively spliced and/or have alternative transcription start sites at their 5' ends, since not all clones of either gene contained the same 5' sequence.

ASTH1J has three splice forms consisting of the alt1 form, found in prostate and lung cDNA clones, and in which the exons (illustrated in FIG. 1) are found in the order: 5' a, b, c, d, e, f, g, h, i 3'. A second form, alt2, in which the exon order is: 5' a2, b, c, d, e, f, g, h, i 3' was seen in a pancreas cDNA clone. A third form, alt3, contains an alternate exon, a3, between exons a2 and b. The start codon is within exon b, so that the open reading frame is identical for the three forms, which differ only in the 5' UTR. The ASTH1J cDNAs shown as SEQ ID NO:2 (form alt1); SEQ ID NO:3 (form alt2); SEQ ID NO:4 (form alt3) are 5427, 5510 and 5667 bp in length, respectively. The sequence of the entire protein coding region and alternate 5' UTRs are provided. The 3' terminus, where the polyA tail is added, varies by 7 bp between clones. The provided sequences are the longest of these variants. The encoded protein product is provided as SEQ ID NO:5.

ASTH1I was seen in three isoforms denoted as alt1, alt2, and alt3. The exons of ASTH1I and ASTH1J were given letter designations before the directionality of the cDNA was known, the order is different for the two genes. In the alt1 form of ASTH1I, exons are in the following order: 5' i, f, e, d, c, b, a 3'. In the alt2 form of ASTH1I, an alternative 5' exon, j, substitutes for exon i, with the following exon arrangement: 5' j, f, e, d, c, b, a 3'. The alt3 form of the gene has the exon order: 5' f, k, h, g, e, d, c, b, a 3'. The alternative splicing and start codons in each of exons i, f and e give the three forms of ASTH1I protein different amino termini. The common stop codon is located in exon a, which also contains a long 3' UTR. Two polyadenylation signals are present in the 3' UTR; some cDNA clones end with a polyA tract just after the first polyA signal and for others the polyA tract is at the end of the sequence shown. Since the sequences shown for the alt1, alt2, and alt3 forms of ASTH1I (2428 bp-2280 bp and 2498 bp; respectively) are close to the estimated Northern blot transcript size of 2.8 kb, these sequences are essentially full length.

EST matches

The nucleotide sequences of the alt1, alt2 and alt3 forms of ASTH1J and the alt1, alt2 and alt3 forms of ASTH1I were used in BLAST searches against dbEST in order to identify EST sequences representing these genes. Perfect or near perfect matches were taken to represent sequence identity rather than relatedness. Accession numbers T65960, T64537, AA055924 and AA055327 represent the forward and reverse sequences of two clones which together span the last 546 bp (excluding the polyA tail) of the 3' UTR of ASTH1I. No ESTs spanned any part of the coding region of this gene. One colon cDNA clone (accession number AA149006) spanned 402 bp including the last 21 bp of the ASTH1J coding region and part of the 3' UTR.

Intron/exon structure determination

The genomic organization of genes in the ASTH1 region was determined by comparison by BLAST of cDNA sequences to the genomic sequence of the region. The genomic sequence of the ASH1I region 5' to and overlapping ASTH1J, is provided in SEQ ID NO:1. Genomic structure of the ASTH1I and ASTH1J genes is shown in FIG. 1; the intron/exon junction sequences are in Table 2.

TABLE 2

Genomic organization of the ASTH1I and ASTH1J genes. *Exonic sequences are upper case, flanking sequences lower case.

| SEQ NO | Exon | Size of exon (bp) | Sequences at the ends of and flanking the exons of ASTH1I and ASTH1J* |
|---|---|---|---|
| ASTH1I | | | |
| 293. | i | >214 | ggaggctgagCAGGGGTGCC... |
| 294. | | | ...ACTCCCACAGgtacctgcag |
| 295. | j | >66 | ...CTGCCCTCACgtaagcgcct |
| 296. | f | 125 | gctgttgagGGTAATGTTG... |
| 297. | | | ...CATCAGACAGgtgcgtaca |
| 298. | k | 226 | ggctggtgagGAGGGGCTGA... |
| 299. | | | ...CGCTCTGTGGgtgagcttca |
| 300. | h | 93 | tgtggaatagCCCAATTACA... |
| 301. | | | ...AGGGTGCTGAgtgagtagta |
| 302. | g | 79 | ttcttttcagGCCCTCGTGT... |
| 303. | | | ...TGCTGACCCGgtatggtggt |
| 304. | e | 232 | tttggtgcagCCTGTGACTC... |
| 305. | | | ...CGCACACAAGgtcagtgttc |
| 306. | d | 51 | tctttcccagGTTACTCCTT... |
| 307. | | | ...ATCAAAGACTgtaagtaacc |
| 308. | c | 69 | tctatttcagATGCTGATTC... |
| 309. | | | ...AGTAGAACAAgtaagtgcag |

TABLE 2-continued

Genomic organization of the ASTH1I and ASTH1J genes. *Exonic sequences are upper case, flanking sequences lower case.

| SEQ NO | Exon | Size of exon (bp) | Sequences at the ends of and flanking the exons of ASTH1I and ASTH1J* |
|---|---|---|---|
| 310. | b | 196 | ttttcaaaagGCCTCCAAAG... |
| 311. | | | ...GAGCCCTGAGgtaagttaat |
| 312. | a | 1522 | gcttttcagATACTACTAT... |
| 313. | | | ...TAACATGTTCaactgtctgt |
| 314. | a | 146 | tgttatatgcATTTATCTTC... |
| 315. | | | ...GGTAAATGAGgtaagtcctg |
| 316. | a2 | 229 | tcttgttaagATCGCTCTCT... |
| 317. | | | ...CCTTGCCCAGgttctcttaa |
| 318. | a3 | 157 | gcaatcgcacCTGCACACCC... |
| 319. | | | ...ACTGCCCATTtctggtaaag |
| 320. | b | 100 | cccctaacagATCATGATTC... |
| 321. | | | ...ACGTGCAATGgtaagagggc |
| 322. | c | 246 | tgttttgcagTTTCCAGTGG... |
| 323. | | | ...AAGTGGAACGgtgactctct |
| 324. | d | 63 | tccttcacagGCCAGTGCAG... |
| 325. | | | ...GAACAAACTGgtg agtagta |
| 326. | e | 69 | tttttttgtagAGCCTTCCAT... |
| 327. | | | ...AGCACAGTAGgtaactaact |
| 328. | f | 69 | atggccacagATTTGTTGGA... |
| 329. | | | ...CTTCCTGTTGgtaagctgtc |
| 330. | g | 63 | ttctccttagCAGAGTCACC... |
| 331. | | | ...AAAAAGCACAgtaagttggc |
| 332. | h | 196 | ttttcatcagACCCGAGAGG... |
| 333. | | | ...GAGCTATGAGgtgaggagtt |
| 334. | i | 4457 | tttgttacagATATTACTAC... |
| 335. | | | ...AGCCTGGAAAtgcgtgtttc |

The deduced ASTH1I and ASTH1J proteins

The protein encoded by ASTH1J (SEQ ID NO:5) is 300 amino acids in length. A BLASTP search of the protein sequence against the public nonredundant sequence database (NCBI) revealed similarity to one protein domain of transcription factors of the ets family. The ets family, named for the E26 oncoprotein which originally defined this type of transcription factor, is a group of transcription factors which activate genes involved in a variety of immunological and other processes, or implicated in cancer. The family members most similar to ASTH1I and ASTH1J are: ETS1, ESX, ETS2, ELF, ELK1, TEL, NET, SAP-1, NERF and FLI. Secondary structure analysis and comparison of the protein sequence to the crystal structure of the human ETS1-DNA complex (Werner et al. (1995) Cell 83:761) confirmed that it has a winged helix turn helix motif characteristic of some DNA binding proteins which are transcription factors.

Multiple sequence alignment of ASTH1I, ASTH1J, and other ETS-domain proteins detected a second, N-terminal domain shared by ASTH1I, ASTH1J and some, but not all, ETS-domain proteins. Conservation of this motif have been observed (Tei et al. (1992) Proc. Natl. Acad. Sci. USA 89: 6856–6860), and its involvement in protein self-association have been documented for TEL, an ETS-domain protein, upon its fusion with platelet-derived growth factor β receptor (Carrol et al. (1996) Proc. Natl. Acad. Sci. USA 93:14845–14850). Alignment of the N-terminal conserved domain in the ETS proteins was converted into a generalized sequence profile to scan the protein databases using the Smith-Waterman algorithm. This search revealed that the N-terminal domain in ASTH1I, ASTH1J and other ETS-domain proteins belongs to the SAM-domain family (Schultz et al. (1997) Protein Science 6:249–253). SAM domains are found in diverse developmental proteins where they are thought to mediate protein-protein interactions. Thus, both ASTH1I and ASTH1J are predicted to contain two conserved modules, the N-terminal protein interaction domain (SAM-domain) and the C-terminal DNA-binding domain (ETS-domain). The sequence segments between these two domains is predicted to have elongated, non-globular structure and may be hinges between the two functional domains in ASTH1I and ASTH1J.

The ASTH1I alt1 (SEQ ID NO:7), alt2 (SEQ ID NO:9) and alt3 (SEQ ID NO:11) forms are 265, 255 and 164 amino acids in length, respectively, and differ at their 5' ends. The ASTH1 and ASTH1J proteins show similarity to each other in the ets domain and between ASTH1J exon c and ASTH1I exon e. They are more related to each other than to other proteins. Over the ets domain they are 66% similar (ie. have amino acids with similar properties in the same positions) and 46% identical to each other. All three forms of ASTH1I have the helix turn helix motif located near the carboxy terminal end of the protein.

The alternate forms of the ASTH1I protein may differ in function in critical ways. The activity of ets transcription factors can be affected by the presence of independently folding protein structural motifs which interact with the ets protein binding domain (helix loop helix). The differing 5' ends of the ASTH1I proteins may help modulate activity of the proteins in a tissue-specific manner.

Polymorphism analysis of ASTH1I and ASTH1J

Affected and unaffected individuals from the Toronto cohort were used to determine sequence variants, as were approximately 25 controls derived from populations not selected for asthma. Affected and unaffected individuals from the Tristan da Cunha population were also chosen; the set to be assayed was also selected to represent all the major haplotypes for the ASTH1 region in that population. This ensured that all chromosome types for Tristan were included in the analysis.

Polymorphism analysis was accomplished by three techniques: comparative (heterozygote detection) sequencing, radioactive SSCP and fluorescent SSCP. Polymorphisms found by SSCP were sequenced to determine the exact sequence change involved.

PCR and sequencing primers were designed from genomic sequence flanking each exon of the coding region and 5' UTRs of ASTH1I and ASTH1J. For fluorescent SSCP, the forward and reverse PCR primers were labeled with different dyes to allow visualization of both strands of the PCR product. In general, a variant seen in one strand of the product was also apparent in the other strand. For comparative sequencing, heterozygotes were also detected in sequences from both DNA strands.

Polymorphisms associated with the ASTH1I locus are listed in Table 3. The sequence flanking each variant is shown. Polymorphisms were also deduced from comparison of sequences from multiple independent cDNA clones spanning the same region of the transcripts, and comparison with genomic DNA sequence. The polymorphisms in the long 3' UTR regions of these genes were found by this method. One polymorphism in each gene is associated with an amino acid change in the protein sequence. An alanine/valine difference in exon c of ASTH1J is a conservative amino acid change. A serine/cysteine variant in exon g of ASTH1I is not a conservative change, but would be found only in the alt3 form of the protein.

The polymorphisms in the ASTH1I and J transcribed regions were genotyped in the whole Tristan da Cunha and Toronto populations, as well as in a larger sample of non-asthma selected controls, by high throughput methods such as OLA (oligonucleotide ligation assay; Tobe et al. (1996) *Nucl. Acids Res.* 24:3728) or Taqman (Holland et al. (1992) Clin. Chem. 38: 462), or by PCR and restriction enzyme digestion. The population-wide data were used in a statistical analysis for significant differences in the frequencies of ASTH1I or ASTH1J alleles between asthmatics and non-asthmatics.

TABLE 3

POLYMORPHISMS IN THE ASTH1I AND ASTH1J GENES.

| SEQ | Polymorphism Location ASTH1I Transcribed region | Sequence |
|---|---|---|
| 16. | EXON B (+)170 | ACAGAATGACRTATGAAAAGT |
| 17. | INTRON D (+)15 | GTAACCAAGCKCAAGCCACCC |
| 18. | INTRON F (+)24 | AAGGAGCCCAYCTGAGTGCAG |
| 19. | EXON G (+)62 ser→cys | CGTTCCATCTSTGCTCTGTGC |
| 20. | EXON H (+)77 | AGCGCCTCGGYTGGCTGAGGG |
| 21. | EXON A 3' UTR (+)1176 | TGTATTCAAGYGCTATAACAC |
| 22. | EXON I (+)76 | CACTGAGAAGCCC/-ACAGGCCTGT |
| 23. | EXON I (+)86 | CCCACAGGCCWGTCCCTCCAA |
| 24. | INTRON J (+)93 | CGTCCATCTCYAGCTCCAGGG |
|  | ASTH1J Transcribed region |  |
| 25. | EXON A 5' UTR (+)38 | GACTTGATAAYGCCCGTGGTG |
| 26. | EXON A 5' UTR (+)39 | ACTTGATAACRCCCGTGGTGC |
| 27. | EXON A 5' UTR (+)99 | CTCCCCTCCAWGAGCCACAGC |
| 28. | INTRON A (+) 224/225 | ATTTCCTGCATT/-GTCTGGACTT |
| 29. | INTRON A (+)48 | ATCCAAACACYTGAGTGGAAA |
| 30. | EXON A3 (+)28 | AGTTTCCTCARTGCGGGAGCT |
| 31. | EXON C (+)158 | GCGAGCACCTYTGCAGCATGA |
| 32. | EXON C (+)190 ala→val | TTCACCCGGGYGGCAGGGACG |
| 33. | INTRON D (-)36/37 | CTGGGGAAAA(GA)/TGATCGCTGAC |
| 34. | INTRON F (-)22 | GTCAATTAAAYGGCTCTCATT |
| 35. | INTRON G (=)27 | TAGATCATTCRTAACCTGCCT |
| 36. | EXON I (3' UTR) (+)22 | AAAGAGAAATWCTGGAGCGTG |
| 37. | EXON I (3' UTR) (+)220 | ATGAGGGGAAMAAGAAACTAC |
| 38. | EXON I (3' UTR) (+)475 | TTTTGTATGTKACATGATTTA |
| 39. | EXON I (3' UTR) (+)871 | AGCTTGGTTCYTTTTTGCTCC |
| 40. | EXON I (3' UTR) (+)1084 | TTGACACCAGRAACCCCCCAG |
|  | 5' to ASTH1J |  |
| 41. | CAAT box -165 | AAATGAGCCARTGTTTGTAAT |

| | | |
|---|---|---|
| 42. | 5PW1J_P01+399 | ATCCATTTTGYATTCCTCATT |
| 43. | 5PW1J_P01+1604 | CTGGAGCTCARACCAGACAGC |
| 44. | 5PW1J_P02+1382 | GCCAGTGCAGSCATCATTACC |
| 45. | 5PW1J_P03+128 | AGTTCAAATCRTAATTTTTAT |
| 46. | 5PW1J_P03+556 | TCATCAGAATYTAAATCTCCC |
| 47. | 5PW1J_P03+712 | GGAGATTCAGA/-TGAAGCAAGA |
| 48. | 5PW1J_P03+781 | TTTTTCCACAYCCAGCCTGGC |
| 49. | 5PW1J_P03+791 | CCCAGCCTGGYGAACCCTGGC |
| 50. | 5PW1J_P03+820 | CTCTTCATCAYGGTCAAATAC |
| 51. | 5PW1J_P03+1530 | CAACTTGCTGYCAAAGTGCTG |
| 52. | 5PW1J_P03+1605 | TACTATGTGCYAGATACTAAG |
| 53. | 5PW1J_P04+542/543 | ATGCCACTTTRRACAACTTGAG |
| 54. | 5PW1J_P04+973 | CGCATGCCTGKAAAGAAGAGA |
| 55. | 5PW1J_P04+1079 | GGATAAGCACMAGTGAGCCTG |
| 56. | 5PW1J_P04+1153 | AAAGCCAGACRGCAACTTGTG |
| 57. | 5PW1J_P04+1430 | TCTCAAAAAGRGTGATAGGAG |
| 58. | 5PW1J_P05+334 | TCTGAATCCTSTCTCCTCCTT |
| 59. | 5PW1J_P05+749 | TAGAACCAGGWTGTGGGACCA |
| 60. | 5PW1J_P05+915 | TTCTTGTGTCRGGCGCAAAAC |
| 61. | 5PW1J_P06+529 | AACCAACATGRAGAAACCCCA |
| 62. | 5PW1J_P06+1290 | AATAAACTATRGTTCACCTAG |
| 63. | 5PW1J_P06+1573 | ACATATTTGTRTCTCATATGA |
| 64. | 5PW1J_P06+1661 | CAAAGCAGTTYCTAATAATCC |
| 65. | 5PW1J_P07+335 | AGATCCTAACYGGGGCCTCCT |
| 66. | 5PW1J_P07+731 | CTCTTTCTCTYTGCTTCCTCC |
| 67. | 5PW1J_P07+1024 | TTAGGAATCCWCAAATATGTA |
| 68. | 5PW1J_P07+1610 | GTCTGACTCCRCCTCCCTCAT |
| 69. | 5PW1J_P08+398 | GAATCACATCRTGAGAAATGT |
| 70. | 5PW1J_P08+439 | AATTCAATCCYTCACAGACTT |
| 71. | 5PW1J_P08+580 | GTGTAGCCAGRGTTGCTAATT |
| 72. | 5PW1J_P08+762 | CCTAGAAATASCCAAGGGCAC |
| 73. | 5PW1J_P08+952 | AAATTCTCATRCCTCACCCTC |
| 74. | 5PW1J_P08+1172 | TCCCACCCCTRTCACCTTCAT |
| 75. | 5PW1J_P08+1393 | CCTCATTCTCRGAAGCCAACA |
| 76. | 5PW1J_P08+1433 | GAAGAGCCGTYCAGTCCCTTT |
| 77. | 5PW1J_P08+1670 | TCCATAGGCTYTTTATTTGGC |
| 78. | 5PW1J_P08+1730 | TCGTTTAGTAYACAGGCTTTG |
| 79. | 5PW1J_P09+59 | GCCTCAGTTGYCCCAGCTATA |
| 80. | 5PW1J_P09+145 | AGCAAAATGCWCTATGCACTG |
| 81. | 5PW1J_P09+892 | GTGTCCTGAC(TTGCACTCCAC)/- ACACTGCCTG |
| 82. | 5PW1J_P10+1070 | ATCAGATAACRCCTACACTTA |
| 83. | 5PW1J_P10+1511 | TCTCTCTTCTSCCTGCCCTGT |
| 84. | 5PW1J_P09+1132 | TGGACACAGGKAGGGGAATAT |
| 85. | 5PW1J_P09+1688 | TGTCACTTGCRCATACAAGGC |
| 86. | 5PW1J_P09+1900 | ATCATCAGATYAGCCCAGAAT |
| 87. | 5PW1J W1R1-1060 | TCAACAGAGARAGTTAATGGT |
| 88. | 5PW1J W1R1-1831 | AGCAATAATGYTTCCCTTTTC |
| 89. | 5PW1J W1R1-2355 | TCTAGCTTTTYTGTGTTTTTT |
| 90. | 5PW1J W1R1-3160 | GATTCCTTAAYGCTTGATACT |
| 91. | 5PW1J W1R1-3787 | CCTCCTCCAGYACCAAAGTGG |
| 92. | W1J_CD+24 | ATGGCCACAGRTCAAATCCTG |
| 93. | W1J_CA+564 5' to ASTH1I | ACTGAGTGTTYATGCCAATTT |
| 94. | WI_CL+94 | GACAAGCCCTRTCTGACACAC |
| 95. | WI_CN+134 | TGAAAAGCCTYCTTGCTGCCT |
| 96. | WI_CQ-28 | TCCTGGAGTTYCTTTGCTCCC |
| 97. | WI_CQ+39 | GATTCCAAATWAACTAAAGAT |
| 98. | P14-16+191662 | GACCTCAAGTCRTCCACCCGCC |
| 99. | P14-16+192592 | AACAAATACTMCCCGCAACCC |
| 100. | P14-16+192762 | ATTTTTTTTTT/-AAGGAAAATA |
| 101. | P14-16+195066 | AAATTTCCCCMAAACAAGCAG |
| 102. | P14-16+196590 | GAGAAAGGGTRTGTGTGTGTG |
| 103. | P14-16+196617 | GTGTGTGTGT-/GTGTATGTGCGCGTG |
| 104. | P14-16+196902 | ATCGGGAACCYCATACCCCAA |
| 105. | P14-16+198040 | TTTGTTTCGCMATGAGGTACG |
| 106. | P14-16+198240 | TGAGGGTGTTSTGGGCTGGAC |
| 107. | P14-16+198840 | TCTTCATTGGYATCTGAATGT |
| 108. | P14-16+200120 | GCGAGCACCTYTGCAGCATGA |
| 109. | P14-16+200617 | AACCCCCCCCMCACACACACA |
| 110. | J5-16+4454 | TCAGTGCTCTSTAATCAGTCA |
| 111. | J5-16+4825 | TCTTTGTGAAA-/(GA)AATTAGTCTG* |
| 112. | J5-16+5426 | GCTGCCCTGASAGCTGGGCCA |
| 113. | J5-16+5623 | CCTTCTGATCYTTGTTTGCTG |
| 114. | J5-16+7386 | GGAACACTGAKTCTTGATTAG |
| 115. | J5-16+7904 | TAGGCTTCTCYTGATAATTGA |
| 116. | J5-16+8055 | TCTTAAAATAMTTGGCTTGTA |
| 117. | J5-16+10595 | TAGATCATTARTAACCTGCCT |
| 118. | J5-16+11140 | ATGAGGGAAMAAGAAACTAC |
| 119. | J5-16+12004 | TTGACACCAGRAACCCCCCAG |
| 120. | J5-16+12219 | TGTTTTAAATRTTAGGGACAA |
| 121. | J5-16+12303 | GTAAGCATAGYAATGTAGCAG |

| | | |
|---|---|---|
| 122. | J5-16+13504 | GGCTCTTTCT<u>K</u>CAACCTTTCC |
| 123. | J5-16+14120 | GACCCAGGTT<u>R</u>TGAGTTTTCC |
| 124. | ASTH1I, exon B +169 | GACAGAATGA<u>Y</u>ATATGAAAAG |
| 125. | ASTH1I, exon I +69 | TGTGTGACAC<u>Y</u>GAGAAGCCCA |
| 126. | ASTH1J, exon C +56 | AGTACTGGAC<u>M</u>AAGTACCAGG |
| 127. | 5' ASTH1J, WI_Cg -9 ASTH1J Intron A | CCTGGGAGCA<u>R</u>GTATTGCATT |
| 128. | WIJ_Ia01 +39 | AGATTTGAGG<u>Y</u>CTCAGGTCCC |
| 129. | WIJ_Ia01 +140 | TGTCAATGTC<u>R</u>CATGATAAGC |
| 130. | WIJ_Ia01 +678 | TTGCCCCAGT<u>K</u>TTCTCCGGGC |
| 131. | WIJ_Ia01 +855 | TATGAGCAGC<u>R</u>TAGGGAGTGG |
| 132. | WIJ_Ia01 +929 | AGTTGACTGA(<u>AAAA</u>)/-<u>T</u>AAATAAGAC |
| 133. | WIJ_Ia 03 +362 | ATTCAAATAG<u>S</u>CTCTAGAAAC |
| 134. | WIJ_Ia 03 +918 | CCCAGAATTT<u>M</u>ATATCCATTC |
| 135. | WIJ_Ia 03 +943 | TGACCCAACA<u>R</u>AAACTCACTG |
| 136. | WIJ_Ia 03 +1569 | CCAGAATATA<u>W</u>CATCAGCCCT |
| 137. | WIJ_Ia 03 +1580 | CATCAGCCCT<u>W</u>CTGAGGAGAT |
| 138. | WIJ_Ia 02 +435 | CCAGAACAGA<u>Y</u>TTTATTCTGT |
| 139. | WIJ_Ia 02 +583 | TTCAGCCATC<u>Y</u>TTCCAGTTGT |
| 140. | WIJ_Ia 02 +643 | TCACTAACTC<u>W</u>AAAACGACAT |
| 141. | WIJ_Ia 02 +648 | AACTCAAAAA<u>Y</u>GACATCCTCC |
| 142. | WIJ_Ia 02 +1048 | GAACTGCACA<u>R</u>GTTGCACACT |
| 143. | WIJ_Ia 02 +1061 | TTGTTCCATG<u>S</u>ACTACCTCCT |
| 144. | WIJ_Ia 02 +1142 | ACAGCAGGCA<u>Y</u>TCAACAAATT |
| 145. | WIJ_Ia 04 +410 | TTATTTTTGG<u>S</u>TTTGTTTTAA |
| 146. | WIJ_Ia 04 +1056 | TAGGCTGTTC<u>Y</u>CTGCCATCAC |
| 147. | WIJ_Ia 05 +1484 | GTGCTCTGGG<u>M</u>CACACAGCTC |
| 148. | WIJ_Ia 05 +1103 | AGACCCGATA<u>R</u>GAGCTCCTTC |
| 149. | WIJ_Ia 05 +1823 | CATCTTGCGC<u>R</u>GTCATGTAAG |
| 150. | WIJ_Ia 05 +1852 | CAGCACAGCT<u>R</u>TTCCCTCAAA |
| 151. | WIJ_Ia 05 +1906 | TTTGGAAACA<u>Y</u>GGTGAAGTAT |
| 152. | WIJ_Ia 05 +1913 | ACACGGTGAA<u>R</u>TATTGTCTCC |
| 153. | WIJ_Ia 06 +794 | AAAAGTGGAT<u>M</u>CTCTGCAAAC |
| 154. | WIJ_Ia 06 +814 | CTTCAAATGC<u>R</u>GCTATTAAAG |
| 155. | WIJ_Ia 06 +1197 | CCTGGGAGCA<u>Y</u>GGTAAATCAG |
| 156. | WIJ_Ia 06 +1231 | TGAAAATGTC<u>R</u>CTTTCTCACCT |
| 157. | WIJ_Ia 06 +1256 | CCTGATATTT<u>R</u>CCAACAAGAA |
| 158. | WIJ_Ia 06 +1535 | AAAGGGTTAG<u>Y</u>TTGTCCCCTT |
| 159. | WI_Caa +163 | TGAAAATAAAA<u>S</u>ACAATTTTTT |

The sequences are listed with the variant residues represented by the appropriate single letter designation, i.e. A or G is shown by "R". The variant residues are underlined. Where the polymorphism is a deletion, the underlined residues are underlined, and the alternative form shownas a "-".
<sup>a</sup>Where intron 'a' is the intron 3' to exon 'a', etc.
<sup>b</sup>Position numbers correspond to the position within the intron or exon, with nucleotide +1 being the 5'-most base of the exon or the intron. Alternatively, negative numbers denote the number of bases from the 3' end of an intron.
<sup>c</sup>Position in cDNA = position # for the exon a form of ASTH1J or the exon i form of ASTH1I.
<sup>d</sup>Exonic sequences are uppercase, intronic sequences lower case.
UTR = untranslated region. N/A = not applicable.

Cross-species sequence conservation

Cross-species sequence conservation can reveal the presence of functionally important areas of sequence within a larger region. Approximately 90 kb of sequence lie between ASTH1I and ASTH1J, which are transcribed in opposite directions (FIG. 1). The transcriptional orientation of these genes may allow coordinate regulation of their expression. The expression patterns of these genes are similar but not identical. Sequences found 5' to genes are critical for expression. To search for regulatory or other important regions, the genomic sequence between ASTH1I and ASTH1J, was examined and plasmid clones derived from genomic sequencing experiments chosen for cross-species hybridization experiments. The criterion for probe choice was a lack of repeat elements such as Alu or LINEs. Inserts from these clones were used as probes on Southern blots of EcoRI-digested human, mouse and pig or cow genomic DNA. Probes that produced discrete bands in more than one species were considered conserved.

Conserved probes clustered in four locations. One region was located 5' to ASTH1I and spanned exon j of this gene. A second conserved region was located 5' to ASTH1J, spanning approximately 10 kb and beginning 6 kb 5' to ASTH1J exon a (and is within SEQ ID NO:1). Two other clusters of conserved probes were noted in the region between ASTH1I and J. They are approximately 10 and 6 kb in length.

Promoters, enhancers and other important control regions are generally found near the 5' ends of genes or within introns. Methods of identifying and characterizing such regions include: luciferase assays, chloramphenicol acetyl transferase (CAT) assays, gel shift assays, DNAseI protection assays (footprinting), methylation interference assays, DNAseI hypersensitivity assays to detect functionally relevant chromatin-ree regions, other types of chemical protection assays, transgenic mice with putative promoter regions linked to a reporter gene such as β-galactosidase, etc. Such studies define the promoters and other critical control regions of ASTH1I and ASTH1J and establish the functional significance of the evolutionarily conserved sequences between these genes.

Discussion

The ASTH1 locus is associated with asthma and bronchial hyperreactivity. ASTH1I and ASTH1J are transcription factors expressed in trachea, lung and several other tissues. The main site of their effect upon asthma may therefore be in trachea and lung tissues. Since ets family genes are transcription factors, a function for ASTH1I and ASTH1J is activation of transcription of particular sets of genes within cells of the trachea and lung. Cytokines are extracellular signalling proteins important in inflammation, a common feature of asthma. Several ets family transcription factors activate expression of cytokines or cytokine receptors in response to their own activation by upstream signals. ELF, for example, activates IL-2, IL-3, IL-2 receptor α and GM-CSF, factors involved in signaling between cell types important in asthma. NET activates transcription of the IL-1 receptor antagonist gene. ETS1 activates the T cell receptor α gene, which has been linked to atopic asthma in some families (Moffatt et al. (1994) supra.)

Activation of genes involved in inflammation by other members of the ets family suggest that the effect of these ASTH1 genes on development of asthma is exerted through influencing cytokine or receptor expression in trachea and/or lung. Cytokines are produced by structural cells within the airway, including epithelial cells, endothelial cells and fibroblasts, bringing about recruitment of inflammatory cells into the airway.

A model for the role of ASTH1I and ASTH1J in asthma that is consistent with the phenotype linked to ASTH1, the expression pattern of these genes, the nature of the ASTH1I/J genes, and the known function of similar genes is that aberrant function of ASTH1I and/or ASTH1J in trachea or lung leads to altered expression of factors involved in the inflammatory process, leading to chronic inflammation and asthma.

Functional analysis of a ASTH1J promoter sequence variant and location of the ASTH1J promoter Primer extension analyses performed using total RNA isolated from both bronchial and prostate epithelial cells have revealed one major and five minor transcription start sites for ASTH1J. The major site accounts for more than 90% of ASTH1J gene transcriptional initiation. None of these sites are found when the primer extension analysis is performed using mRNA isolated from human lung fibroblasts that do not express ASTH1J.

Identification of the ASTH1J transcriptional start site has allowed the localization of a putative TATA box (TTTAAAA) between positions −24 and −30 (24 to 30 bp 5' to the transcription start site). Although the sequence is not that of a typical TATA box, it conforms to the consensus sequence (TATAMA) for TATA box protein binding as compared with 389 TATA elements (Transfac database: http://transfac.gbf-braunschweig.de/, ID: V$TATA_01).

Analysis of the CAAT box "G" polymorphism by gel shift assay

Binding of nuclear proteins to a polymorphism in the GCCAAT motif (GCCAAT or GCCAGT) found at position −140 (140 bp 5' to the transcription start of ASTH1J as defined by primer extension experiments, previously referred to as "−165 bp"), has been assessed using electrophoretic mobility shift assays. These experiments clearly showed a remarkable difference when binding of nuclear proteins to radioactively-labelled double stranded oligonucleotides containing the normal "A" vs the mutant "G" nucleotide was examined. A specific set of nuclear proteins was able to bind to the normal oligonucleotide, but did not bind to the "G" oligonucleotide. The specificity of the DNA binding complexes was further addressed by competition with either normal or mutant unlabeled oligonucleotides. Addition of increasing amounts of normal unlabeled oligonucleotide effectively competed binding of nuclear proteins to the labeled normal oligonucleotide, while the addition of increasing amounts of unlabelled "G" oligonucleotide did not.

The GCCAAT cis-element is found in many promoters at various locations relative to genes, as well as in distal enhancer elements. There is no known correlation between location of these elements and activity. Both positive and negative regulatory trans-acting factors are known to bind this class of cis element. These factors can be grouped into the NF-1 and C/EBP families.

The nuclear factor-1 (NF-1) family of transcription factors comprises a large group of eukaryotic DNA binding proteins. Diversity within this gene family is contributed by multiple genes (including: NF-1A, NF-1B, NF-1C and NF-1X), differential splicing and heterodimerization.

Transcription factor C/EBP (CCAAT-enhancer binding protein) is a heat stable, sequence-specific DNA binding protein first purified from rat liver nuclei. C/EBP binds DNA through a bipartite structural motif and appears to function exclusively in terminally differentiated, growth arrested cells. C/EBPα was originally described as NF-IL-6; it is induced by IL-6 in liver, where it is the major C/EBP binding component. Three more recently described members of this gene family, designated CRP 1, C/EBP β and C/EBP δ, exhibit similar DNA binding specificities and affinities to C/EBP α. Furthermore, C/EBP β and C/EBP δ readily form heterodimers with each other as well as with C/EBP α.

Members of the C/EBP family of transcription factors, but not members of the NF-1 family, bind to the ASTH1J promoter region, as determined by the use of commercially available antibodies (Santa Cruz Biotechnologies, Santa Cruz, Calif.) that recognize all NF-1 and C/EBP family members known to date, in electrophoretic mobility shift assays.

Fabricating a DNA array of polymorphic sequences

DNA array: is made by spotting DNA fragments onto glass microscope slides which are pretreated with poly-L-lysine. Spotting onto the array is accomplished by a robotic arrayer. The DNA is cross-linked to the glass by ultraviolet irradiation, and the free poly-L-lysine groups are blocked by treatment with 0.05% succinic anhydride, 50% 1-methyl-2-pyrrolidinone and 50% borate buffer.

The spots on the array are oligonucleotides synthesized on an ABI automated synthesizer. Each spot is one of the alternative polymorphic sequences indicated in Tables 3 to 8. For each pair of polymorphisms, both forms are included. Subsets include (1) the ASTH1J polymorphisms of Table 3, (2) the ASTH1I polymorphisms of Table 3; and (3) the polymorphisms of Table 4. Some internal standards and negative control spots including non-polymorphic coding region sequences and bacterial controls are included.

Genomic DNA from patient samples is isolated, amplified and subsequently labeled with fluorescent nucleotides as follows: isolated DNA is added to a standard PCR reaction containing primers (100 pmoles each), 250 uM nucleotides, and 5 Units of Taq polymerase (Perkin Elmer). In addition, fluorescent nucleotides (Cy3-dUTP (green fluorescence) or Cy5-dUTP (red fluorescence), sold by Amersham) are added to a final concentration of 60 uM. The reaction is carried out in a Perkin Elmer thermocycler (PE9600) for 30 cycles using the following cycle profile: 92° C. for 30 seconds, 58° C. for 30 seconds, and 72° C. for 2 minutes. Unincorporated fluorescent nucleotides are removed by size exclusion chromatography (Microcon-30 concentration devices, sold by Amicon).

Buffer replacement, removal of small nucleotides and primers and sample concentration is accomplished by ultrafiltration over an Amicon microconcentrator-30 (mwco=30,000 Da) with three changes of 0.45 ml TE. The sample is reduced to 5 μl and supplemented with 1.4 μl 20× SSC and 5 μg yeast tRNA. Particles are removed from this mixture by filtration through a pre-wetted 0.45μ microspin filter (Ultrafree-MC, Millipore, Bedford, Mass.). SDS is added to a 0.28% final concentration. The fluorescently-labeled cDNA mixture is then heated to 98° C. for 2 min., quickly cooled and applied to the DNA array on a microscope slide. Hybridization proceeds under a coverslip, and the slide assembly is kept in a humidified chamber at 65° C. for 15 hours.

The slide is washed briefly in 1× SSC and 0.03% SDS, followed by a wash in 0.06% SSC. The slide is kept in a humidified chamber until fluorescence scanning was done.

Fluorescence scanning and data acquisition. Fluorescence scanning is set for 20 microns/pixel and two readings are taken per pixel. Data for channel 1 is set to collect fluorescence from Cy3 with excitation at 520 nm and emission at 550–600 nm. Channel 2 collects signals excited at 647 nm and emitted at 660–705 nm, appropriate for Cy5. No neutral density filters are applied to the signal from either channel, and the photomultiplier tube gain is set to 5. Fine adjustments are then made to the photomultiplier gain so that signals collected from the two spots are equivalent.

Construction of an asth1J Transgenic Mouse

Isolation of mouse asth1-J genomic fragment:

Phage MW1-J was isolated by screening a mouse 129Sv genomic phage library (Stratagene) with the 443 bp BamHI-SmaI fragment from the 5' region of the human asth1-J cDNA clone PA1001A as probe. The 23 kb insert in MW1-J was sequenced.

Assembly of asth1-Jexb targeting construct:

A 2.65 kb Sacd fragment (bp7115-bp9765) from MW1-J was isolated, cloned into the SacI site of pUC19, isolated from the resultant plasmid as an EcoRI-XbaI fragment, inserted into the EcoRI-XbaI sites of pBluescriptII KS+ (Stratagene), and the 2.5 kb XhoI-MluI fragment isolated. A 5.4 kb HindIII fragment (bp11515-bp16909) was isolated from MW1-J, inserted into the HindIII site of pBluescriptII KS+, reisolated as a XhoI-NotI fragment, inserted into the XhoI-NotI sites of PPNT, and the 9.5 kb XhoI-MluI fragment isolated. The two XhoI-MluI fragments were ligated together to produce the final targeting construct plasmid, asth1exb. Asth1exb was linearized by digestion with NotI and purified by CsCl banding.

Identification of targeted ES clones:

Approximately 10 million RW4 ES cells (Genome Systems) were electroporated with 20 μg of linearized asth1exb and grown on mitomycin C inactivated MEFs (Mouse Embryo Fibroblasts) in ES cell medium (DMEM+ 15% fetal bovine serum+1000U/ml LIF (Life Technologies)) and 400 μg/ml G418. After 24–48 hrs, the cells were refed with ES cell medium. After 7–10 days in selection culture approximately 200 colonies were picked, trypsinized, grown in 96 well microtiter plates, and expanded in duplicate 24 well microtiter plates. Cells from one set of plates were trypsinized, resuspended in freezing medium (Joyner, A., ed., Gene Targeting, A Practical Approach. 1993. Oxford University Press), and stored at −85° C. Genomic DNA was isolated from the other set of plates by standard methods (Joyner, supra.) Approximately 10 μg of genomic DNA per clone were digested with NdeI and screened by southern blotting using a 100 bp fragment (bp6164-bp6260) as probe. A banding pattern consistent with targeted replacement by homologous recombination at the asth1-J locus was detected in 10 of 113 clones screened.

Production of asth1-J knockout mice:

Two of the targeted clones, cl#117 and cl#58, were expanded and injected into C57BL/6 blastocysts according to standard methods (Joyner, supra). High percentage male chimeric founder mice (as ascertained by extent of agouti coat color contribution) were bred to A/J and C57BL/6 female mice. Germline transmission was ascertained by chinchilla or albino coat color offspring from A/J outcrosses and by agouti coat color offsprint from C57BL/6 outcrosses. The NdeI southern blot assay employed for ES cell screening was used to identify germline offspring carrying the targeted allele of Asth1-J. Germline offspring from both A/J and C57BL/6 outcrosses were identified and bred with A/J or C57BL/6 mates respectively.

Mice heterozygous for the Asth1-J targeted allele are interbred to obtain mice homozygous for the asth1-J targeted allele. Homozygotes are identified by NdeI Southern blot screening described above. The germline offspring of the chimeric founders are 50% A/J or C57BL6 and 50% 129SvJ in genetic background. Subsequent generations of back-crossing with wild type A/J or C57BL/6 mates will result in halving of the 129SvJ contribution to the background. The percentage A/J or C57BL/6 background is calculated for each homozygous mouse from its breeding history.

Molecular and cellular analysis of homozygous mice

Various tissues of homozygotes, heterozygotes and wild type littermates at various stages of development from embryonic stages to mature adults are isolated and processed to obtain RNA and protein. Northern and western expression analyses as well as in situ hybridizations and immunohistochemical analyses are performed using cDNA probes and polyclonal and/or monoclonal antibodies specific for asth1-J protein.

Phenotypic analysis of homozygous mice:

A/J, C57BL/6, wild type, heterozygous and homozygous mice in both A/J and C57BL/6 backgrounds at varying stages of development are assessed for gross pathology and overt behavioral phenotypic differences such as weight, breeding performance, alertness and activity level, etc.

Metacholine challenge tests are performed according to published protocols (De Sanctis et al. (1995). Quantitative Locus Analysis of Airway Hyperresponsiveness in A/J and C57BL/6J mice. *Nat. Genet.* 11:150–154.).

Targeting at asth1-J exon C:

Assembly of exon C targeting construct:

A 3.2 kb HindIII-XbaI fragment (bp11515-bp14752) from MW1-J was isolated, cloned into the HindIII-XbaI site of pUC19, isolated from the resultant plasmid as a KpnI-XbaI fragment, inserted into the KpnI-XbaI sites of pBluescriptII KS+ (Stratagene), and the 4.5 kb RsrII-MluI fragment isolated. A 3.4 kb HindIII fragment (bp17217–bp20622) was isolated from MW1-J, inserted into the HindIII site of pBluescriptII KS+, reisolated as a XhoI-NotI fragment, inserted into the XhoI-NotI sites of pPNT, and the 9.5 kb RsrII-MluI fragment isolated. The two RsrII-MluI fragments were ligated together to produce the final targeting construct plasmid, Asth1exc. Asth1exc was linearized by digestion with NotI and purified by CsCI banding.

Identification of targeted ES clones:

Approximately 10 million RW4 ES cells (Genome Systems) were electroporated with 20μg of linearized asth1exc and grown on mitomycin C inactivated MEFs (Mouse Embryo Fibroblasts) in ES cell medium (DMEM+ 15% fetal bovine serum+1000U/ml LIF (Life Technologies)) and 400 μg/mI G418. After 24–48 hrs, the cells were refed with ES cell medium. After 7–10 days in selection culture approximately 200 colonies were picked, trypsinized, grown in 96 well microtiter plates, and expanded in duplicate 24 well microtiter plates. Cells from one set of plates were trypsinized, resuspended in freezing medium (Joyner, supra), and stored at −85 C. Genomic DNA was isolated from the other set of plates by standard methods (Joyner, supra). Approximately 10 μg of genomic DNA per clone were digested with NcoI and screened by southern blotting using a 518 bp fragment (bp8043–bp8560) as probe. A banding pattern consistent with targeted replacement by homologous recombination at the Asth1-J locus was detected in 3 of 46 clones screened.

Targeted clones are injected into blastocysts and high percentage chimeras bred to A/J and C57BL/6 mates analogously to that done for asth1-Jexb knockout mice. Heterozygote, homozygote and wild type littermates are obtained and analyzed analogously to that done for asth1-Jexb knockout mice.

The data presented above demonstrate that ASTH1I and ASTH1J are novel human genes linked to a history of clinical asthma and bronchial hyperreactivity in two asthma cohorts, the population of Tristan da Cunha and a set of Canadian asthma families. A TDT curve in the ASTH1 region indicates that ASTH1I and ASTH1J are located in the region most highly associated with disease. The genes have been characterized and their genetic structure determined.

Full length cDNA sequence for three isoforms of ASTH1I and three isoforms of ASTH1J are reported. The genes are novel members of the ets family of transcription factors, which have been implicated in the activation of a variety of genes including the TCRa gene and cytokine genes known to be important in the aetiology of asthma. Polymorphisms in the ASTH1I and ASTH1J genes are described. These polymorphisms are useful in the presymptomatic diagnosis of asthma susceptibility, and in the confirmation of diagnosis of asthma and of asthma subtypes.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid molecule other than a naturally occurring chromosome comprising a sequence which encodes a mammalian ASTH1 protein.

2. An isolated nucleic acid molecule according to claim 1, wherein said mammalian ASTH1 protein is selected from the group consisting of SEQ ID NO:5, and SEQ ID NO:339.

3. An isolated nucleic acid molecule according to claim 2, wherein said nucleic acid comprises the nucleotide sequence of SEQ ID NO:2.

4. An isolated nucleic acid molecule according to claim 2, wherein said nucleic acid comprises the nucleotide sequence of SEQ ID NO:3.

5. An isolated nucleic acid molecule according to claim 2, wherein said nucleic acid comprises the nucleotide sequence of SEQ ID NO:4.

6. A cell comprising a nucleic acid according to claim 1.

7. An isolated nucleic acid molecule other than a naturally occurring chromosome comprising a sequence which hybridizes under stringent conditions to the nucleotide sequence of SEQ ID. NO: 1 and which encodes a mammalian ASTHIJ protein.

* * * * *

```
SEQUENCE LISTING (1) GENERAL INFORMATION:

(iii) NUMBER OF SEQUENCES: 339

(2) INFORMATION FOR SEQ ID NO:1:

(i) SEQUENCE CHARACTERISTICS:
        (A) LENGTH: 72928 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:1:

GCACTTTTTG GGGAAGGTGG AAGAATAAAA GTAAGGGAGG TGTGCTGAGA CTTCAATTTT      60

AATATCTTAT TTCTTAGGTT GAGTGTTACA CAGGCATTTG TAATCATATA TACTTTTGTA    120

CACTTGAAAT ATATATATTT GTGTGTGTGT GTGTGTGTGT GTCAGAGTCT CACTCTGTCT    180

CCCAGGCTGG AGTGCAGTGG TGTGATCTTG GCTCATTGCA ACCTCCACCT CCCAGGTTCA    240

AGAGCTTTTT GTGCCTCCAT CTCCTGAGTA GCTGAGACTA CAGGCAAGCA CCACCACACC    300

GGCTAATTTT TGTATTTTTA GTAGAGATGG GGTTTCACCA TGTTGCCCAG GCTGGTCTCA    360

AATTCCTGGC CTCAAGTGAT CCAGTCACCT TGGCCTCCCA AAGTGCTGGA ATTACAGGCG    420

TGAGCCACCA TGCCCGGTCT GAAATATTTC AAAATGTAAA AAAGCTAAAC CCAAATCCAG    480

ATGTCTACTT TCAAGGTGCT CACAGGTCAG ATCTAGGATT ATTGCTACTA ACTGATATTT    540

ATTATCCCAG CACCAGCATG TTTGGCTGTG TGTCATGGGT AAGTTACTCA CCTTCTCTGC    600

GACAGTGTCA TCATTGTAAA ATAGGGATAA AAGAGTTTAG ACCTTGCAGA GTCCTTCAGA    660

TTAAAGGAGA TAATCAGTAC GTGGCACTGA GTACCTGCAA TATATTAAGT GGTGTGTGCT    720

CAGAGATATG ATCACATACA GTATCTTGGA TCTGCCCAGC AACTCTATGA AGATGAGGAA    780

ACAGACTCAG GCAGGTCAGA GCCAGAACAT AATGTTTCTG GAATTTGAAC GTAAACGTTC    840
```

```
CCCTTTCTCT TATCCAGGCT GAGTGCTAAA GGAATTGTAA AAATGGAATT TGCCTGTTGC    900

CTGCATCTCC CTCTCTTTTT CTTCCTCTGT GTCCTCTGAA TATCTAGCAC CAGTGGGACT    960

TTACAGTGTT GGCCTCAATG CTGTAGGGTG CTGTGTGCAC ACTTGTCTTC AGCTCCCTGA   1020

GTTAGCAGAG CATTGCCCCA ACTCTGCCCT CTGGCCAGCT CATGTGCCTT ACAACTTTCT   1080

GTTGCCAGAA GAGAGCCCTG CTCATTCTCT AGACTCAACC AACAAAAGCT GCCTACCATT   1140

TTCAGAATGC CAGTGGGCAG TGAGAAGTGC AGAGCTTGTG TCCTGAGCTT GGCAGCCATC   1200

TTGCTTGGTG TTAACAAAGA GTAATTAAGT GATCTCATAA AACTCAGTGG TGGAGGTTGT   1260

GGTTCAGAGC AAGCTGGGTC AATGCCAAGG CTACTTTGGC TTCATCTGGT CCATAGCCCC   1320

ACATTTCTCT TCTGATGGTT CAGTTCCGGG AATGAGAACC AGTCTGAGTG TAAGAAGACT   1380

TGGGTTTGAA TCTGTCTCCT CCAATCACTA GCTGACCTTA GAAAAGTGAC TTAACCTCCC   1440

GAGCTGCTAT TTCCTCATCT TAAATGGTGA TAGTAATCTT TCCTTACCTT AAGGTTGTTG   1500

AGCAGCTTAA ATAATATAAT GAGTTGAAAG CTTTTTGTAT GATCTGTTAT TAGGAGTCCA   1560

GATAGTGTTT TATAAACAAG AGGATAAAAA AAAAAAAAAA AAAAAAAACA GGATTCTGAA   1620

GGCTGGACTC ATTGCATTCC TTGCAAACTA CCCACTGAGC CCCAACTCTT CCGTCAGCTC   1680

AAAGTCACTT CTCAGAGCAA ACCAGATTGT CCTGAACCCA GCACTTGCCA ACATCTCCTC   1740

CTCTTCCCTG ATGAAAACTC TGGGCTGGAG TTGTGGTGGG TGAGGGGAAG GCAGGATAAA   1800

TCAAAAATTG ATGTTTTAAG AAAACTATGG TATTCTTGGA TGCAAAGGCA TGAGAATGAT   1860

ACCTTAGACT TTGGGGCTTG GGGAAAAGGG TGGGGGGTGG CGAGGGATAA AAGACTACAC   1920

ATTGGGTTTA GTGGACACTG CTCGGGTTAT GGGTGCACCA AAATCTCAGA AATCACCACT   1980

AAAGAACTGA TTCAGGTAAC CAAACACCAC CTGTTCCCCA AAAACCTATT GAAATAAAAA   2040

CAGAAAATTA AAAAAAGAA AACCTATGGT ATTCTTGGAA GAAGCACAGT GGTGAAGTGG   2100

AGTAGACACA GATGTGGAAG TGATGTGAAC TTTGGTAAGT TGCTGAGCCT CTGAGGATGA   2160

TTTCCCTCAT CTGTCAATCA GGAACAAAA TCCCTTACTT GTACAATGAG TATTATAAAG   2220

ATCAATTCAG ATGACGCATG TAAAGATGCA ATGTGGGACT GGTAGGTAGT AAGCATCCCA   2280

TAAATGGCAG CTATTAATAA GTAATAATCA CCGAGTGGTG GGCTGCCTTT CATGAAAACA   2340

TTCCCAGCAA GCTGCTCTTC TGTCGGCTCA AAGTCACTTC TCAGAGTAAA TGAGATTGGC   2400

CAGTTCTTTC TTTTCCAAGGC TTTTCTGGAT ATTCATTTGT CCCAGATTTC TCCTGTATAC   2460

AAAGCTCAGG AGTGAGGACC CCCACAGTGG GGCTTGCACA AGGATAGCCT TGGGGGGCTT   2520

TTTCTAAGAG CTATGACTTT GAATGCTCTC TTCATCGATG CTGACAGATG AGGGCTGATG   2580

GAAGTGGTCA TGTTTTAAAA TGTCTGATGT CCAGAAACAC AGAGATGTGT ACGCAAAACA   2640

TTCATTCATT CAAGATGGAA TTAGTGCCCC AGACACAGAG GCAGGGGATA AATAGCAAAC   2700

AAGGCTTGAT TCCTGCCTTC ATAGAGCTTA CTGTCTTGTA GGGGAAACAT GAGTAAATTC   2760

AGCAGAGTAA GGGCTCTAAT TGGGTAAATG GGGGCTAGGC TGCCTGTGTC CTTGGGGTGG   2820

TGGGAAGGCT GCTGATCTGG GGTGCCAGAA GACCTGAGTT TTGATGCAGG CTCTGTGACT   2880

TTGAGCAGGT CGTTTCCAAC TTCTGAGCTT CCATTTCCCT AGCTGAAAAT GGGGCTTGC   2940

CATACTCGAT GCTGTACTCT ATGAGTCTTT GCAGCTCTGT CATCTTTTT TCTTTTGGTC   3000

ACTCAGAGAC TCCAGGATTG GGAGAACAAC CTGCATTCTG ATTTAAAGTG TGAATCTAAT   3060

AATTTCAAAA AGAAAGGGAC TAAAAGGGAC AAACTTGTTT CTGTTTATTT TCCATCCTTC   3120

TTTGGGGAAG TGTAACATTT GAAATCAAAT TCTCATTGGC TTAGCCAATG TGTAGACTTC   3180
```

-continued

```
GAGGGGAAAT TCTCACTGCC CAGAGAAGTG ACTAAAAATG ACCATTACAG CCAAAAAGAG   3240

AAGTTTTTTT TTTTTTAAAA TCTGTGCTCT ACAGATGGAT GAAGTGCTGC TGCACATGGA   3300

CAGAGTGGAT CTGGACATTC TGCATGAGCC CAGGGATCCT GAGAATGGAT TGGCTGAGCA   3360

TAGACAGGGT GACCTATCGA TGTTCACTGT GGTCCTGATC TATGTGGCCT CTTCCTAAGG   3420

GAAGATTTTT CTTAAGGTTG TTTCCTTTCT CAGCAGATAT TTGTGAAGAA ACTGTATCTG   3480

TAGTCTCATT TTGTCCTTAT AATGACCCTG ATGGATGGGA GGTAGAGGGA TGATGATCAG   3540

TAAGAGCTGG GAAAGCACCA GGAACTAGCA AGAGCAGGAC ACCTTTTCCA CCACTAGGTA   3600

AATGGACCTA GTGACTGCTG GCACCGTGGG TGAGGGACT GCCTGGCAGG AGCTGTGGCC   3660

GTAGCTAGGG GATTACAGCT ACGGCCACAA CTCTGGCCCT GTACGGAGGG AGTGGGGGAA   3720

ATAAAGAGTT CATATCACTC CCCTCTTTCC CTGGAGTCTC CTGCTGGTAC CTTGCATTGG   3780

CTGAGTCTAA CTGGAAGCCA GAGGGCAAAG GAGGTACCCT TTCCAGCTCT GCAATTCTCT   3840

TCAGACAGGG CTGGGATTTC TGGAGAGAAT TTGCAGAATC AGAAAGCAGA GCTTTCCAAT   3900

CAATGCCAAG CAAGAGACTC TGCAGACTCT CATAGCCTTG GGACCTGAGA AACCAGGTAT   3960

CCAGTGAGCA GTCACTTAAG CCTGTTCACC TGGCCCTCTC TTACTTTCTC TCCTATAGCA   4020

GCAGCAAAGG AGCGATGGGC CGAAGGGACT TGCTGGGTAG AAGTGGACCC ACATTCTAAA   4080

AAGGAATGGA AGAGAAACCT GATTTCTTTG ACTCGCCCTG TCCCTGAAGA TGAGGGGCAG   4140

GCACAGACCA GCCCTCTCCA GAAAGACAAA TATATTCTTC CATTCATGGG AGGGGTAGTA   4200

GAGACTAACA TTTGTTAAGT ATCTATTACA TGGGGGGTAT GGAGGTAGGC CCTTTGTGTG   4260

TGTTGCCTCT TTTAATCCTT TGGTGATCAA CTCATGAAAA TAAACAGCTC CAGAGCCAGC   4320

TGTCTTTGGA GGGTGTAGGC AGGCCCGGCT CTGGAAACC TGGTGACACT GACCTAGTTT   4380

GACTTCCAAA TCTTCTCTCT TCTTCGATTC TGGTGAGCCC CACTCTAGCC CCATAGTATG   4440

TATGGCCAAG CACCCAGATA CTGCTTCCAT CAGGAGGAAA TAACATACCT GATGAATTTC   4500

TTCACTCAAG GTGTTAGGAG CTTAATGTGT TTCCCCCGCC CCCCGCACCA AGAGAATTTG   4560

TGTTTTCCAA GACAGTCAGA GAGTGGGTGG TGCTGAACTC AAAGGAGTGA ATCACTAATA   4620

GTGGAATCCC AGGCATTCAG GGAGGTCCTA TTTCTGGGGT GGGTTCCTTC CTGACACTTC   4680

ATTTTCTACA AAGGTGGCAG CCACCTATTG CTCCAGAAA GGAGGCTGTC CCTGTGGGTG   4740

TGGTGACGGT GGGAAAGGAG AGGCACCTGC AGGCTGAAGC CAAGATCACC TGATTTTCAA   4800

AACCAAATCT GTCCCTACAA AGGAGAAGTG GCTTAAAAAT CCACACAGCC TCCCGAGTGG   4860

AGGGAAGAAT TCCCTCTCCT CTCTGGAACA GGGTTCCCTT CACCCAGAAC ACGGTGCTGT   4920

TGTTATGCAA TGTCCCTGTT GGCAAAGATA TTTGAGCCCC TTGTTTTCAG GTCTGTGTCA   4980

TTTCCAAGAA AGAGCTGTGG CCTTTGAGTA GGACTGGGCT CCTGAATAGG GTCCCTGGTG   5040

CCAAATGAGG GAGCCAAGAA AAGGCAGAGA AGAGGAAAGT CCTGACTTTT ACATGAAGAT   5100

GAGACAGCCA GCCCTGTGGC AGCCAGATGG CAGTCCTGTT GCTCTGTAGT GGCCTTGGGG   5160

TCAGACTAGG GGCAGAGCTG GGCTGAAGGC AGGAAGGCCA GGACAAGACA GGTGAGAAGG   5220

GCAAAGTCTC CTGTAACCTG GTGAGAAAAT GTGGGCTAAG CCATTCTCAT CTGGAGCTGA   5280

AGGCTTGGTG GAGAATGGCC CTCAACATTC AAGTTCACAC CCATGGATTT ATAAAAGGCA   5340

GGGCTGGGGG GAAAGGTTTT TCCCATTATA CTTAATAACA TTATCAACAA CAATAATCAC   5400

TACTATCATT TATTGAGCAT TGACTCAAAA GACAGTCCTT TTATGAAAAT TATTTACTTA   5460

AATCCTTACA AAGCTTCTAT TCATTCACCC AACACATATT TATTGAGTTC CTACTATGAG   5520

CCAGGCATTA TTCTAGGTGC TTAATTTAGA TCAAGGGACA AGACAGACAA AATCCCTGTT   5580
```

```
CTGGTGGCAG GGCTACTACA TGCAATTAAC AGCACACAAC TCTAGGGGGA GCCACATACA   5640

TGGGCCACCT TATGAATGGT GTGCCCTGAG GTTAAGCATC CTGGCAGCCC CTTTCTGTGA   5700

CATTTGCATT CTAGTGAAGG GAGTCTAATA CCAATGAAGT AGATGTCATT ATCCCCTGAC   5760

TACAGTTTAG GAAACAGAGA CACATAGGAA TTAAGTAACT TGCTGAGTTT TTCAGCCAAA   5820

AATGACTGAC CCATGATTTA TACTGAAGTC AGTCCTTGCA ATTCACCTGT GCCACGTACT   5880

TGCCTTTCTC TCCCTGGTGG GCACAGGGAA GAGGGAGTAG CCAGGCTGGC CAGATGAGTG   5940

CTGGGCTGGC TGGCCCAGTA GAGGCACCAT GTCCTGACTG GGTGGACAAA GACTGGGTAG   6000

GAGGTAACAG AGAATCCCTT GGTGAGTCTA ACTTAGCTAT AAGAAGGCTT GCTGAGAGCA   6060

GCTGCCTCCA TGCAGAGGGT GGGGTGACCG GCCTTTAATC CTTCCCAGCT GAGGATTTAG   6120

TCAAAGAAGC TTGTCTCTGG GGATAGCCTA TGGTCTTGAA GGGCCTGAGT TAGCTATTAG   6180

TTCACCCATT TATTTAACAT TCATTCATTA TTTTTAAAAA ATTTCCTAGC TATGTTTGGG   6240

GGCAGAGAAG TGGGTCCAGA GACCTAGAGG TTTGCAAGGG TAGCTTCTAA ACTCCTTTGG   6300

TTCAGAACAG AATAGAAAGT GTCCTCGGGT GACCTTGGGT CTGCTTCCCA AGCAAATTGA   6360

GCATACGCAG CCAGAACAAA GACTGCACTC TACTCTAGTG AGCTCAGCCT GCTAGGCTTG   6420

GATCTAGATT TTATAGCAAT AAGCTTGGAG TCTCACCTTT GGGTCAGACA GAGTACTACC   6480

CCAGACATGA GGTAGGGAGA GCCTAGTCTA TATTCCTCTG CCTTTGTCCA AGCCTGCTTT   6540

GTCCTTCCTC TTGACGAGGA ATAAAGATGG CTTCTGGGTG TGCATCCCCT TCCTTCTTCC   6600

ACCTGCAGAT GTACCTGTTT GTGTGCAGTG GGCTTCTGAG TCCTGGGCAG GGATGCCAGA   6660

GACCGCAAGC CAGATGCTTG GGATGCCAAT CCTTGGGACT TGAGGAGAA AGAGAGGTTC   6720

TGAGGGGCAT CTGTCTATGG CACAGAGTCA AATGGAACAC ATGGAAGTCC CTTAGAAGGC   6780

TGGTATCTAA GTGTTGGCCA CACAATGTCC GTTCTTCCTC CATTATTTGA ATTTCTCCTT   6840

CTCTATCCTT CTATCTTTCT TGGCACCTTG AGCCAGGTCT GGGGTGAGAG AAGGGATGGT   6900

GTAGGTGAAT TAGTGGTAGT TATTGGAGGA AGGCAATAAA CCCAGAAAAA GTGTCACGTG   6960

ACTTCTTTCT TGGGCCCAGT GTGACGCTTC TAGTTAGGCT AACGTGGGTC TTGGGACTGT   7020

TCCTGAGATT TTGTGGAAAA CTCTTTGTAT TTGTGCTGGT AACAGAAGGA AACCAGAGTT   7080

AGGGCTGGTG GGATGAAGCA GTGGGAACAC TGATTTCTCC TTTTTTTCAG ATTCAGGGAT   7140

TTCTGTCAGA GACATCCGTG GGGGAGGGAT GGGATTGGGA GTGAGGAGAA TCCCTTTCCT   7200

CTCCTCTCAC CATCTGGTGG TCCCCGTGCC CACGCACCAG CTCGTTGGAT GGACATTTTG   7260

ATTCCCTTAA GATGTACATT CTTCAAATCA TTGTTTGTCA TTAGCTCCCT GGAGAAAATG   7320

GAGGGGCTGA GATATTAGTG AGAAAACATA AAGTTAATTG GGTGATGGAG ACTGGGAGAA   7380

GGGGAATGTT AGAAGAAAGT GAGCGAGGTC TGCTAAAAGT GAACTTTATC TTCTTCTCAA   7440

TTTTGCCTAA GACTCGTGTT GCCTGGGCAG TCTCTTTTTG GAAGAGAAAT TTTCATGACA   7500

GTTTGGGCCA GAGATGGCAA ATAAATGCCT GACATGGTTG CTGCCAGCCC CTGTCTCCCG   7560

ACACGTTCAC AAGGGTGCAC ACCACTTCTC CTCTCTGTGA CCATAGACTC AGACCCATTG   7620

CAATCCAGCA TCCTGCATGG CCCCATTGGT CAGAGTTGAC ATTTGCAATG AAGCTGCTTC   7680

CCTATGCCTG GTTAGGCCTT TTGCTATGAA TTCTCTGGAG TTAACTATTT CCAAGGGGCT   7740

CCAACTTATT CTTGTGATTT CCACGGGATT TGGAGCCCCA GAAGACAATC CCATGTGGAT   7800

TCACAAAATG CCCTCTAAAT TTGATGGCTG TCAGTGCATA CTAAGTATGA CTGACTCACT   7860

GGTATCTGTT TCCTCCGCTG ACACAGCTGG TTCTTAGGCT CGGCAGGAGT TTGGGCTGAG   7920
```

```
ACCTCTCATT GCTCTATATT CCCTCTGTTA CTAATGAGGT GTTGTTCCTT AATTACTAGG     7980

TGCTGGATAC TAGAATTGCT TTTCTTTGTT TCAGGGGATT TAGCAAAGGG CTTATAAATA     8040

TTTCTTGTGT CTGGCATGAA CTACCTGATT TTTTTATTCT TCAGGTCACT GAGCTGGCAA     8100

TAAAGGCAAC TCAAAGTTAG CTGGGAATCA GAATGAAGGG GGACTAGGAA AAGTGATGCC     8160

TAGAACACCA ACAGGTGTGG GATCATCTTC ATTGTACCTT TCAGAGCCTA AGATATAAGT     8220

CCTCTGGATA CTCTCTGCTT GTTTATTTAA AGGAAAAAAT AATCAGAATG TGGGAGAAAT     8280

GGGTGCTTTG GGTAATTTCA TATTCTAATT GATGAACGTG TATGAAATTA TAATATTAAA     8340

CCACTACTAG CCCTTGCCGT AAAAAACTAT TCCAAAATAG CTGAGTCTAA GTTTCCTGCC     8400

TCAGTGTGTC CCACCTCTTG CGCTTGAGTC CTTAATGATC CAGAGTTTCA AGTCCCCAGT     8460

GCCCTAATCT TGAAAAGCAG AAACTTTAGA AGTTTGCTGA AGTTTATTAG TTGGCTATAC     8520

GATCCATCAA GAAATTGACT TTTTTGGATT AAATTCAAGA TAGTTTTTAA AAAATCAGAA     8580

GTTTCTTTAT CATGAAAGCT AAAAAAATAA TTGAAGGTAG AGGCTAGTTG GAATCCCAGT     8640

TAATAGATGG ATTTCTTCCT TCTTGAAGAA ACTTGTGTCC AAGGGCAAAC TGAATCCTGG     8700

TGGTCTATGC TGGCCACATT CAGCAAAAAA TGGCCCGAGG TTTTGATGGT TATCATTCTC     8760

AAAACTGTTC CTGCCAACAC ACTCTGATCC CAGGAGGTTA CCTGACCTTT ATAAGGCTCA     8820

GTTTCCTCCC CTGTAAAATG GGCAGGGTAA TCAAGCTAGG CAAAATATTT AACCTAAGTG     8880

AGGAAATTGT GCTATTAGTG CCCTGAAAAA CATGTAGAAA GACATTAGAC ATTATTTTAT     8940

TTAATATCAT GTTGAACTTA GTTTTTAAAA AGAAGACCTA TTGGATTTTC CAAGAACAAC     9000

TAAACTGATT CCTTGTAGAC AGTTAGAGA ATACAGAAAA TTAGAAATAG GAAAAAAGCA      9060

AAACAAAACA AAAACCATCA AACAAAGTCT ACGCAAATAC AGTTTCTCTT AACTTTTGGT     9120

TTATTTCCTT CTAGTCATTT TTTAGGTGCA TTTTTAAATT GTGGTAAAAT ATATGTAATG     9180

TAGAATTTAC CATTGTAGCC ATTTTTAAGT GTAGAGTTCA GTGGCATTAA GTACATTTAT     9240

ATTGCCGTGC AACCATCACC ACCATCTATC TCCAGATTTT ATAACCCCAG ACTGAAACTC     9300

CATATCCATT AAATGATAAC TCCCCATTCC CCTCTCCCTA CCCTGGTGAC CACCATTTTA     9360

CTTTCTGTTT TTATGAATTT GACTTTCTTG GCGCCTCTTA TAAGTGGGAT CATTTTTAGT     9420

TGTTTTTATA ATCGGTTTCC TTCCTTTAAA AATATGAATG GAGCCTAATG AATATTGAAT     9480

TTAGTGTACT GGTTTCTTTG AACATTTCAG CATCATAAAC ATGTTTTTGT ATTCTACATT     9540

CTTCTTGTAT TGCTATATTC TCTATAGGAA TTTTTTTTTT TTTTTTGACA GAGTCTCACT     9600

CTGTTGCCCA GGCTGGAGTG CAGTGGCACA ATTTCAGCTC ACTGCAACCT CCGCCTACTG     9660

GGTTCAAATG ATTCTCCTGC CTCAGCCTCC CAAGTAGCTG GGACCAGAGG TGCATGCCAC     9720

CATGCCTGGC TAATTTTTGC ATTTTTAGTA GAGATGGGGT TTCATCATGT TGGCCAGGCT     9780

GGTCTTGAAC TCCTGACCTC AGGTGATCCG CCCACCTTGG CCTCCCAAAG TGCTGGAATT     9840

ACAGGTGTGA GCCATTGGCC CCAGCCTTGA ACATCATTTT TAATGGCTGA AGATTATAGA     9900

ATCCAGTGGG TGTGCCATCC ATTATTAGTA TTCTGTTGTT TCCAAATATT TGCTGTTTTA     9960

AACAGTGTTG TGAAAACATA TTTTTGTGTT GAACTTTTAT CATATTGAGA GGCACTTCCT    10020

CTGTGCAGAA TCAAGAAATT AATTACCGGT TTATAAGGAA TGTGAACCTT TCAGGCTCAT    10080

AATCTGTATT ACCAAATGGT TAGGAAAAAA ATGTTCAGAA GGTGCCATTC ACAGATGGAG    10140

TGGGCTTCCA CCAGGGGCTG TGAAGCTCTA ATCTCAAAGG ATGTTGACTA CTGGTAGGGC    10200

TGATTCAAGT ATTAGATATC TAGGAAGGGT GGGAAGGGCA GAGAAGCTTC CAAAATTCCT    10260

ATGTAGGAGA GGCATAGGGG TGCTGATCTC TTCATAAGGG GTGACGGGAA TTTTCCTTGA    10320
```

-continued

```
AACAGCATGT GCAGATCAAG CACTGTTCTT TCCTTTAGAG TGTGTGTTTA TTTGGGGCGA   10380
CTTGGAGGGT TGCTAATTGA GATTATGGGG AATCTAAAGC CACACCCCAA ACCGCCCCTT   10440
GGTTCCCCTA CCTGGGGGAG AGTTGACACT AGTCAAACCT CTCCCATCTC TGAGATTTTG   10500
TGAATCTAGG ACTCTTGCCA CTGCACAGAC TCCAGCTGGA CCCAGGGACT CCAGCTTCTC   10560
ACATCACCCT GGCTCATCCA TAACTCTCTT TTGTTTCATC TCAAACATCA CTGAGAGATG   10620
GCTGCCTCTT CTCCCTTCCT AGGAAAGCCC ATGTCACAAT AAGCGCGCCT GTGCTTCTCA   10680
TCAGTGCTTT CCTGGTAGCA CCACCTGACA AACACTGCTC GCGGCTGCCT TCAGCTGCTC   10740
TCCAAGAAGA CGTCATAACC ACAAGAGATC TGAATCAGCC CATTTTTTCC CCTGTGGCAC   10800
TGTGTGCTTT GGCTGCCTGG CCAGAAAGCT GGGACTGTAT TTACCTATCA TTTTGATACT   10860
ATCTTGGGGT GTAATTGGAA TTGAGCTCTT AGTGTGGAAA TTCTTACTCA GAACACAAAG   10920
GATTGAAGAG TGCTTGGAGG CTGAACTCTG GAAGGACTCT TCCCTGAGGC CTCTTGGCAT   10980
CTGGCTCTTG TTTCTTGGAG CGGTGGTATG GCCCACAGGT GGGTGTTTCC TTTGGGAGCA   11040
ATTTCTTGCT TTTTCAGTAG CTCTGGGCTG TCATCGAGCC CACTGTTCCT TGTCTTCTCT   11100
GCACTGTTTA GTGATGATGT AGGTGAATTG CTCCACAGTT TAATTCCAGT GGTAGAGCAG   11160
TCACCATTTG TTGGTTTCTT TTTCTTATGG GAACTCTGGT CTGCATCTCA CTGTGTTTCC   11220
CTTGAACGTG TCTGGGGTCC TCCAAACAGC TTCGTGTCCC TCTGAGTGCG ACACTCAGA    11280
TTCTAACTCA GATTCTAAGT CAATGGTCTC AGCCTTTAGA ACCGCAGGAG GCCAGGCGCG   11340
GTGACTCACG CCTGTAATCC CAGGACTTTG GGAGGCCTAC GCGGGTGGAT CACCTAAGGT   11400
CAGGAGTTCG AGACCAGCCT GGCCAACACA GTGAAACCCC ATCTCTACTA AAAATACAAA   11460
AATTAGCCAG ATGTGGTGGC ATGTGCCTGT AATCCCGGCT ACTCAGGAGG CTGAGGCAGA   11520
GGCAGGAGAA TCGCTTGAAC ACGGGAGGTG GAGGTTGCAG TGAGCCGAGA TTGTGAGATT   11580
GTGCCATTGC ACTCTAGCCT GGGCAACAGA GTGAGACTCC ATCTCAAAAA AAAAAAAAA    11640
AAAAAAAAAA AGAACCACAG GAGGGAGAGA TCATATATGA CCCCGTATGT GTGAAAAGTC   11700
CTATCATTGC TACCCACACC AACAATATTA GTGGAAAAAT GTCTTCAAAG GACATTCGAT   11760
TCAATGATAC ATGAGATTTG CTTCCTTCCT TAATTTTTCC CTGTACAGCT ATATAATGAT   11820
TTTTTCAATC AGATCCTCTT TTCCCCCTAT TAATTGTATT TATAGGATGA GATTGATTCT   11880
AACACAATAG CAAATGATGT ATGCACATTT AACACATTTC GTGAAGGCAG GAAAGGGCAC   11940
ACTATAAATT CTGTGAAATC CACATTAGAT CATGCCTCTC CTTTCTCAGT TGGGAGGTGG   12000
GCTCTGACAG TGCTCAAGAG AAAAAAAAAT CAAGTTGTGA CAGTTTAAAA AATATTTTAA   12060
ATATTAAACT ATTTATTATG GAACTTAAAA CATACACAGA AGTTGGCAGA ATAACATCAT   12120
GTACCCTAAA TATCTATCTC CAAACCTCAA CAGTGATCAA CCTGTGGTCA GTTCTGCCTC   12180
TTCTGGTTCC CATCTGCTCT CTGACTTCAG TTTATTTTGA AGCATGTCTC AGACATCTTG   12240
TGACTTCAGT ATTGCACGAT GTATGTCCTA AACGTAAGCA TTCCCTTTAA AACATGTATC   12300
TACTTTTTAA ATGAAGAACA ATTAGGTGCA TTTTCATAAG GGTTTTAGAA AGGGAAGAAA   12360
CTGTATTTCT TTAATTTAAA AATGTATCAG ACAACTAATC CATGTTTACT GTTTCTAACA   12420
CGGATACCAT AATAATAGGA TCATTCTATT ATACATAGAC TAGTGAGATC AATTTGTCAG   12480
ATAAACTTAG AAGGGCCATT AAGAAAGTTA TGTCATAATT TTTGTCACTT GCTGAAACCA   12540
AGACTTTAAT TCTGCAGAAC ATCATACCAG GATTCACAAT TGTATACACT GATTGTGTTT   12600
GTCCAGAGGT AATCTCAGAT CCACTGTATA TAATTTTCCA TTTGCCTAGC TATGGGGTTG   12660
```

```
GACACGTCAG TTTTTTCCAG ACCAAGGGTC TCCTAGCTTT TTTTTTATTT TTATTTTTAT  12720

TTTTTGAGAC AGAGTCTCTG TTGCCTGTGC TGGAGTACAC TGGTGCGATC TCGGCTCACT  12780

GCACCCTCCA CCTCTCAGAT TCAAGTGATT CTTGTGTCTC AGCCTCCTGA GTTGTAGGTG  12840

GGACTACAGG CACCTGCCAC CATGCCTGGA TTTTTTTTTT GTTTTTTTGT ATCTTAGTA   12900

GAGATGGAGT TTTGCCATGT TGGCCAGGCT GGTCTTGACC TCTTGATCTT AGAAGATCTG  12960

CCCACCTTGG CCTCCCAAAG CTGGGATTAC AGGCATGAGC CACTGTGCCC AGCCTCCTAG  13020

CTGTTTTGGC TGCACACTTC TATCCGTAGA TAATTAAGCA TGTACCCTTA CTATTTTCCG  13080

CAATATAAAT TATTTACTTA TAAATTACAT TATGTACTCT ATCACACTGG TAAATTAAGT  13140

ATATTATAAA ACAGAAACTA AAAGTATGAA GTGAGAATTA AAAATGAATA GCAATTCTAA  13200

TATCTTCATC TTCCCCTCAG TGGATCCTCC TGTACATACT CCAATTTGCA GACCACTGGA  13260

GGAGGCTGTA GGAGGCAATA TTATATCCCA GTGAGGTGTG TGGGTTGTAA AGCCGAACAG  13320

CCTGAGTCCA CATCCCAGCT CCACCACTCC TTAGTTCTGT GACTTGGAAA CATCACTTAA  13380

CCTCTCTGAA TCTATCTTCT CACCTGTAAT ATGAGGGCAT TAACCCCTTA CAGGTTATTG  13440

TAAGGTTTCT TACACTGTGC CTGTGGTAAG CATCAATACA TTTTAGCCAA TAATAACAGT  13500

AATGATAATA ACACATTCCT AGAGGGCTGG GATGGATCTA GATTTTTCTT CCCCTTTTAG  13560

TGGAAGACCA CAGCATGATG CATGAATTTA CATTTCCTCA GACATTCTGG TGCTGATGAA  13620

GGTAAAGATG GTGAGGCTGC GATGATGGTT TCAGGGATGG GTGTGTTGGG CGTGATGAAT  13680

AGCATGATGC ATATTGTCAC TCATTTAGTT TATCTGCACT GATGATGATG CTGATTATAT  13740

GATGACTGTT ACAGGGATGG TCACATTGTG GGTGATGAAT ATGACCAGAA AGGGAAGACT  13800

TTCACAGTTC CTACCCGAAC TACAACATCG ATATTTTCAT TTGTCTTTCC TAGGAACTCT  13860

TACCTTAATC ACCTGACCAA TATGCTGACG ACTAACATGT TGCGCCCTGC CTTTCTTCCG  13920

GGCCTCTCTG CCTTGCTGAT CTGTTTTGCT GGTGTGCCCT CCACTGTGCT CTTGGGTCTT  13980

TGTCTCTCGG TAAAGCCTAG TACTGTGGTT GCTGTACACA AAACCTGTAG ATGATTAAGA  14040

TCTCTGTTCA CTGCAGGGCC ATTCATCTCC CAGCAACTAT TTTATCCTTA AGTCAAGAGA  14100

CTTGCCTCTC AGCCCCTGGG GACCATGGAA AGAGTGCTAG AAACCTACAG AGTATGACCC  14160

TTTGTAGCCT TATGCAAGAA GTGACCTGTG TCTTTCCTGT CATGAGAGAG GACAGACATT  14220

GCAGGAATCA AACGCATAAC ACTAGTGCAA AACTGGGGAT AATGCCCAAA CCTGGTTAGG  14280

CAGGGGCGCC TGGAACATGC TTGTCCAGGA AATCTTCCAC TCAGTTCTGC TGCCTCCATG  14340

TCCCAGATGA TCACAGAAGC CTCCTGAGAA GGGTTGAATC CCCCGTCGCC TGGGGATCCC  14400

AAGAAAGCTG CAGAGGAAAG ACTTTCTCTT CCAAGATCAG AACAAAGGAC GGTTAGCATT  14460

GTGCCCAGTA GTGCCAAAAG GTAAGGTTGG GTTAAAATAA GAATTTGCCT TAAGCTCTTT  14520

TCCCGGGGGC TTGTTTTTTT CATTAACCTT GTTGGCTGGA CTTTAGGGAA GTATGCACCA  14580

TCTTCTCCAG AAGTGCTTCA GATTTTATAT TTTTAAGAAA TTCAAGAGTC TGAGTTAGGC  14640

ACTTTAATGT AACCTCCCCA AAGCTTTTGT TCCAGGAATT GACTTGGGGA TTAATCTGTT  14700

TAGCAAATTC TGACACAGAG GCATCTCATA ACCTTTTATT TTTTCTACAG ACCACATTGT  14760

ATCTACCTGG GATGTTTTGA AAATGAACAG TGACACCTAA GAATGTATAC TTATCTCTTC  14820

ATGCCAATTC TCCAAACTGG ATGTTGCCCA TGTCTCAAAA TTACTTGCCT CCAATTTTAG  14880

GGCATAAAGT GTGAGATTCT GTAGCATGAG ATCATATGCT CTTAAAATAC TAAGTATATA  14940

TAAATTATCC CTTAGCATCT TTAACATGCA TTTTTTTTTT GTAGAGACAG TATCTCTACA  15000

AAAAAATCTC TCTGTATTGC TCAGGCTGGT CTTGAAATCC TGGGCTCAAG AGATCTTCCC  15060
```

```
ATCTCGGCTT CCCAAAATGC TAGAATTACA GGCATGAGTC TCCACACCTG GCCTAACATG   15120

AAATATTCTT TAACAGTATT CTTTAGGATA ATATATTATT CTATAGATTT GAAATAATTT   15180

ATCAGTTCTA TACTTAATTA TAAATACTCT TGGGAATAAA ACATACTTAT CTAATAAGCA   15240

AACAGTCGTG CTATTCCAAA CAATTTGGGA TTGCCTTTCC AAGCATTTTT TGGGGGTTTC   15300

TTCAACTGAT TGAGAGACCC CCGGCCGGGG AAGAGAAAGA GAATTTGATT TGTGACACTG   15360

ATGGAATGGA CTACAACCTT TTGGTGGTGA CTCTACTGGG GACTTGTCAC AGAGCTTATT   15420

TTCTAAACAG ATGTGAAAAA TGAAAGTCAG GCTGCTGTCT GGTTGGTAAG ATAAAGCTTT   15480

CATTAATACT TGGCAGCATT ATTTTAGCTA AAGTGTCAGA TCAAACGCCC ACATTATCAC   15540

CTCCCCTTCC TGATTCCAAC CGCCCATGAT AGAAAAGAAA TAAAAGACTA GGAATAGGTC   15600

CATCAACTGG TGAATGGCTA AACAAAATGA GGTATATACA TACAATAGAT GGTTATTGAA   15660

TCACAGTAGG GAATGAAGTA CTGATACATG CTACAATATA GATGATCGTC ATAAACATCA   15720

TGCTACGTGA AAGAGGCCAG ATGCAAAAAT GTCACATATT ATATGATTCT ACTTATTTGA   15780

AAAACTCAAA GTAGGCAAAT CCATAGAGAC AGAAAGCAGA CTGGTAGTTT CCCAGTGCTG   15840

GGGAGAAGGC AGACAGGGAA GTGACTGCTT AATGAGTATG AAGTTTCCTT TTGGGATGAT   15900

GAAAATGTCT TGGGACTTAG ATAGAAGTGA TGGTTGCACA ACACTGTGAA TGTAGTAATT   15960

GCCATGGAGA TGTACACCTC AAAATGGCTA AAATGAATTC TATGTTATGT GAATTTTACC   16020

TGAATTTAAA GAAGAGTAGA AACAAACACC AAGAAAAAGG GAGGAAAGGA GGCATTATTG   16080

AACAAGACAT TTCAACAAGT TTTGGAATAT GGAAAATATA CGGAGAAGTG GCAACTGACT   16140

TACCAGAGTG GCAGAAGAAA TAGTCTATGT GAGTGTGGGG AATGGGGTGG ATGTGGAACC   16200

AGTGAGAAAT AAGCCGCTTT ACTGGGAAGA ACTACAGAAA GACTGAGGCT TGGACGCAGC   16260

TTGTGCTACT ACAGGTAGCA GTAAACAGGG GGATTTGTTG AACTTCAGAA TATAGAGAAT   16320

TTTGATGTAA GAGGTTTTTT TTTTCTCGTC TCAAACCAGG AGACTTTTTT TGTTCTCTAG   16380

GTGAGGGAGA TCTAGAGACA GCCAAGTACA GGGTGCAGTA TCATCTAGAA AATAAAGAAG   16440

AGGTTTGAGT CTGCAGGTGA GACTCCTGCT CTCTTCCTGG AATGCTGGCA GCCAGGCTTA   16500

GATCAGCCTC TCTGCCCTGC TCCAGGCAGA AGATGGAAAG ATCCCTTTCT GGAGAAACTG   16560

ACTCATCCAA GAGATAACAG CTCATATTCT TACTTTTTAG AGCTCTCCAG TAAAATGCAG   16620

CTCAACACTT GATCAGTTTC CAGCGATGAC CCCTGATCAG GCCCTCACTA CGAACCTCTG   16680

GGTTTTAATT GGTTATTTAG TATCTCAATT TTAAAGATCA AAGACAGGAT CGCTTTTGAG   16740

GAAACTTCCA ACTTTAATGA AAGAATTTAA AAAAAAAAAG GAAAAAAAAC CTGATAGTGT   16800

AAAGAGCAGA GAAATGGCAG GGAAATGAAA ATTAAGTTAA AAAACAGAAA CTTTTATATA   16860

ATTCTAATCC TTTGCAGAGA TAAAAAAATA CATTGCATAC CTAAAACAAG TACAAGTTGC   16920

CATGGAAACA GATTCATTAG TGAAGAGGAA AGAGATCTTG GAAATTAAAG ACATAAAAGA   16980

CAAAATAAAA ATTAAAAAAA TTAAACAGAA TTTAGAACAT AATGTTGAAA TGAGAGAACT   17040

TTAGATCTCA AAAACAACAG AGAATCAACC CAGGAGATTG TGTGTGACTA AAGAAGTCTC   17100

AGAAAGAGAA TAGAGGAAAG GAAGGAATAT TATAAGAAAA GTTTCAAGAA TAAAAGGTCA   17160

TGGGCCTCCA GACTGATAAA AATCCATCTT GTACCCAGAA AAAATTGACT TTTCAAGAAC   17220

TGAATCAGAA CCTATCCTGT GAAATGTTAG GACAAGTAGA TCCTAAAATC TTCCAGAGGG   17280

AATCCATTCA AAGGCCTTGA ATGGCATTAG ACTTCTCCAT ATCAATACTG GATGGTGAAA   17340

GAAAAGAGC AATACCTTAA ACTTGCTAAA AGAAAATGAT TTTTAACTAG AATTCAATTT   17400
```

-continued

```
CCATCTCAAT TAAAAAACCC ACTGTAAAGA AAAAATTCAA ATCTTCTCAG GCATATAATA   17460
ACTCTAAAAT TCTACCTCCT GTGCACCTAA TTTTGGCAAG TATCTCAGGA AGATACACTT   17520
TGCTAGAACA AGGACATAGT TTAAGAAAGT GGAAGAAATC AGATCTGGGA ATCAGGGGAT   17580
CACATGATAC AGAGGCACAG CCAGAGGGAT CCCAGGGAGA GCATGTCCAG TGTGACAAGG   17640
AGTGGACAGC TTCAGAAGGG ACAGCACCAG GGGAAAAAAC AAAATGAATA TCTGATTGGC   17700
ATAAACATTT GGAAAGTAGT ATTAAAAATG TGTGTAACAG GTGTGTTGTT ACATTTGCCA   17760
AAAAAGAGCA AAAGGGAAAA AAAACCCCAA GCAGATGAAA AGTAAAGAAG GCAATGGTTA   17820
ACTACTGGAA AAACAAAAAA CAATATTCAA GAAAGGAAAC GAAATCATGG TATACTTCTT   17880
GACTAATGGG TGAAAAATGA AGATGTACAT AGTTATTAAA ATGCAAACAT TGATTATTGA   17940
GTTAACCCAA AGTTGTGACA TTTGGAAGCA CGGGTAGGCA CAGTGGGGTG TAAGAGACCT   18000
AAATCCTCAC TTACCGTAAT GTTTAAAAAA TTGCCATGTC AAAGAATAGC AGCATATCAT   18060
ATTATTTAGA AATATGGATG CAAATGCCAG AAGAAAAATT AAAGGAAGTG AAAAATGTTT   18120
TCCTCTAGGA ATAGGACAGG GGACGTAATA GGGAACAGAT ATTCTGCATT ATCTCAATTA   18180
ATTCTCACAA CTGTGACTGA AGCTCTTTTG CTCTCCTTGT TTTGCAGATG AGCAAACTCA   18240
CAGAGGGATG CAACTTGCCT AGGATCGTAT AGCCAGCAGC TCATGAGTGT GGAATGGGGA   18300
TTCAAATAAG GTCTAGGAGA CTCCAAAATC CATGTGCTTA ACCATGAAGT TTTACTACCC   18360
CTTCTCTGCT TCTTCATTAA GTATTTTTAG TGCCTAATTG CCCATGCTCT CTGCCAGGTG   18420
CAGTAAAGGA GGATTACACA GGTGCAATAT GAGCCATGAC TCTTGTTGAA ATCAGCACGT   18480
CAAAAATAAG GCTAATGAGC ACGTGAAAAG ATGCTCAACA TCACTAATCA TTAGGGAAAT   18540
GCAAAACTGC ATTAAAATAT CACCTCATAT ACATTAGGAT GGCTACTATG AAAAAAACCA   18600
GAAAATAACA AATATTGGCA AGGATGTGGA ATAACTGGAA CACTCATGCA CTGTTGGTGG   18660
GAATGTAAAA TGGTGCAGCT GCTGTGGAAA ACAGTATGAT GGCTCTTAAA AAAATTTTAA   18720
AAAAATAGAT TTCTCATATA ATTCTGCAAT TCCATTCCTG GATATATACC CCAAAGAATG   18780
GAGAAAACAG GATCCTGGAG AGATGTTTGT ATACCCATGT TCATAGCAGC ATTATTCACA   18840
ATAGCTAACA TCTGGCAGAA CCCAATGAAT GAGTGGATAA ACAAAATGTA GTATATACAC   18900
ACAATGGGAT ATTAGTCTTA AAAGGAAGG AAATTCTGAC ACATGCCACA ACATGGAGGT   18960
GCCTTGAGGA CATTATGCTA AGTGAAATAA AGCCAGTCAC AAAAGGACAA ATATTATATG   19020
ATTCCATTTA TATAAGCTAC TTAGAGTGGT CAAATTCATA GAGACAGAAA GTAGAATGGT   19080
GGTTGCCGGG GATGTAAAGG TGGGCATTTC TCAAAAAACT GAGAAATACA GAAAAATAAA   19140
AATCACTCAC TGTTTGCCAC ACTTCTACCC TGGTTCTTTT TAAATCTATT TTTCTTACTC   19200
AAAGAAATAC ATGTTTATAG TTTAAACATT CAAATAGTAC TACAGGTTCG TAATAAACAA   19260
GAGCGGTCCA ACTCCCCTCC TCCTAGCCCT GTGCTCCAGT CCTTTCAGAT GTTGTTTCTG   19320
GTCTTTGTAT TTCTCAATAA CATGCCTAAA TGTATTTTCT GGCTCCTTGT ATTGTTTATT   19380
TATTATTTGT TGAGTTTATT GCTATGAAAA ATAGAGATTA GATCACTTAC AGGGTCTTCC   19440
TGACACCGTG CTCACCTTCC CCACCTATAT GTACAATTCA CCTTCCCTGT CCTCATGGAA   19500
ATAATATTAC TCTTTTAGTT AAGTCACAGG TCAGTATTTA TGTTATGATT ATGTAAATAT   19560
TGTTTATGTA ATGTGCTAGG GCTACTTTTT TTTTCTTTAA TTCCTTATCC TCCTTCACCC   19620
TCACCACCCA ACCCCAATCT CATCCTGGAG TTCACAGTTA TCTCATTTTT CCTTTGCTTG   19680
GTTTTCTAAA ATCTATCTCC TGGCTCTTTC TCCAACTCTT CTCTCAGTAA GATAGTTTCT   19740
CAGCTCTACC TTTTCCCCTT GTTGACATTG CTCCAGAGCC CTTCAACCTG CTCAGGTGGC   19800
```

```
TATTCTGCTT GGTCACTCAC TTGTCCTCCT AGGTTTTCTT ATCTCCATCA TCTTGGGGAT   19860

TCTGGTCTCC AATTTCCTGT GTTAGACCAA CTGTGTCCTG GATCCCATAT CTTTCTGTCT   19920

CTTAGTTTAT TTCTTTGCTT TGATTGAACA TACTACCTAT GACATTTCTG AGAAACAATG   19980

AAAGAGAAAT GATTTTTTGA GTTGTGGGAT GAATATTAAA GTCACTACCC GGGAAGGATC   20040

ATTGTGCCTC TATCTGTATG AGGGATTCCC CTTGCACTTC TCAACCATAG ACAGCTCTGT   20100

TCTGTCTCTT GAGCTCTTGG TGAACCCATC CCCCAGGACA ACATTTCTAT GTGTCTTGGT   20160

CTGGCACAAG GTGACTACCT ATTCCCAGCA AATGCCAATC AACACCTGTC TTAATAATAC   20220

CTTAGCTTCA ACACCCAAGG TTTAAGTTGC ATTAATCACT TAATAAAGAA ACCTTCACAA   20280

ATGCTAATTA CTAACCTAGT CCTTAAACCA TACTCATTTA AAGAGGTGGC ATCTTAGAAG   20340

TTACAGTGTT TATAGTCATT CAACAAACAT TTATTGTCAG CCATATAGAA GACACCATGC   20400

AAGGGCTTTA CATGGGTTAT CCAATGTAGT CCTCATGAAG GTCCTGTGAA GTGGAATTA    20460

TTGCCATTTG TGAATGAGTT TCAGAGAGAT AAAACTTCTC CAGCCATTCA TTCAACACAT   20520

TTACTGAGTA TCTACTATGT GCTAGAAAAT GAGGATACCG CAGGGGGCAG AGGCACATGT   20580

CCCTGACCTC TTGGAGTTTC TAGTCTAGCC TAGTCTGTTT CCAAGGGTAA CAGATATTAA   20640

ATAAATAATT TCACAAATAG TCTATTAAAT ACATTTGAGA CAAGTGTCAT GAAAAAGAAG   20700

TACAAGATGC TATGGGAATG TATAAAGGCC ATAAGCTGTC CTAGTCTGGG GCTCAGAGGT   20760

GGTTTTTCTG AAGCAGTGCA TTAAGTCTGC AGGATAAGGA AGAGTCAGCC AGATGAAATG   20820

AAGTCTAAGG TTGGAGAGAG GGAGGGAACA GCATGAGCAA AGGCTCAGGG GCAGGAAGGG   20880

GCTTTGCATA TACGAAGAAC TGAAAGGCCA ATGCGGCTGG AACAAAGAAT GGAATGGTGT   20940

GGCATAAAGT GCAGCAGGGA CCGGGTCAGG GAGAAGACCA TAAAGCATTT GTGCACGCTG   21000

TTAAAGAATC TGTATGCAAC CTTGGTGGAC GTGGGAGACA TGACTGCTGA ACTTGAAGCG   21060

CATCCCTGGA GATGGGGATA AATGGAGGGA TGCGGGATGT GTGAAGCAAG AGGCTTGTTC   21120

ATGGTCAGAA CCGGCATCTG AACCCAGCTC TCATGACAAG TCTGCTGCTC TTTTTGGTAC   21180

ACAAAACCCG TTTCTTTCTC TGTGTGAGAA TGAACAAGGT GCCTGCACAT TTTTCTGTCC   21240

CAGTGCAGTG TTTGAGGATG CTAAGTTACA CCCCAACAGC TGTGCAAAAT CTGTTTCTCT   21300

CTTGTGTAGT GATGGAGGCT ATACATTGTG TTGTGAAAGG TGTCACTCAT TTGGGAAATT   21360

AGAACAAAAC ATAGTCATTG CCTTTAACAG CACACAGCCT AATAGAGGCA ATAGGAATGT   21420

AAACAGGGTC CCAAGCCAAA ACTTAACATG AGCAAGTTAT AGAATCATAT ACAATTCTTA   21480

GGGTCATAAT TCTAGGGCTA CATGTTTTGA CTGTTTGACC ACACTATATG CAGCAGTATC   21540

GTTAATGGTC CTGGATCTAG GCAGCATTTT CCGAAGTAGA CTTAAAATAA CATCACTCTT   21600

AGACTGGTCT GATTCTCTGT TTTGGCTAGA AATTGTGTTC CTCAAGAATA ATAACACATT   21660

TAAAATCATC CTTATTTTTT AAGTTCAGAT ATTCTGCTAA ATCATTGATC TCCATGAATT   21720

CATTGGTCAA TGTTTTAAAA CTTTCTCACA AACGGGCTTA TTGGAAATGG AGGCAGAAAA   21780

TAAGGTGTTC AATAATATGA CCACATGGTC TAAATTTCCT ACAATACGCT TAGTTTACAT   21840

GTGCAACACC TTTGTCAGAC ATATACCCAA TTTTGGTTTG AAAATAGCAT TTACTTCCCA   21900

GGAGTGGTGT GTAGGAACTT AAGGGTCCTA GTATGTATGT CTCTAGTGGA AACTTTGGGG   21960

TTCAGTTTGA AAAGGCAGTG TATCTCATGT GGATCCCTGT GATTCTCAGG GATTCTATAC   22020

TAGGCAGTCC CTTGTGGATG CCTGGGGAAG TCGGGCTGTG ATCCTTACAG ACCTTCTCTG   22080

AGCTGCCATA CAGATGGGGC AGAGGGTGAA TGATGGAAAA AGAACAAATG TTGCTGATGG   22140
```

```
TCCATGATTC GTCCGCAAAT ATTGTAAAAC CCTGTACTAC CTGGCTGATG CTTTAACAAA 22200

ATAGCTTCAG GGACATTAAA AAAGTAGTGT TTCCTGGTGT GCTGGTAAAT ATTTATTGAT 22260

ACAAAGATTG TGTAATCACA ATTTAAAATA TACAGTACTC TTGATTGTAA ATTCCTTATA 22320

ACCAATTGAT CCCCACAGAA TGCTCTTGTT GACTTTTGTT TGAGGCTCTT GTATCTATAG 22380

TGTATCCAAT CTATTATTGC AATTGATGGA CAAGTGCCAT TCTGATAAGA ATGTGGGCTG 22440

AGATTTCCCT TTATGTTAAT GAGTAAGAAG AAAGGGAAAC AGCAGAGCTA GACACTGGGC 22500

CTTCAATCGT TTGTTAACAA CACGAGCAAC CTTTTTGTTG AACTGGATAA TAGTTTTTGA 22560

ATACTGGAAG AATATTTCCT CAGTCTTTTT CTGTTATTCA CCATGCATTG GCTACAGTCA 22620

CATTTTAGAA TTTAACCTGC ATTATTAGCA TTTCTCCATC ACTTTTTATA AGTCTAGACT 22680

GGGGATTATT AAACTGTGGT CTAGGGGCCA TATCTGGTCC CCTGACCTGT TTTCGTACAT 22740

AAAGTTTTCT GGAACACAAC CATGTCCACT AGTTTTATAT ATTGTATATG GCTGCTTTTG 22800

TATTACAATA GCAGAAGCAG AGTCGAGTAG GTTGGACAGA GATTTAATGG ACGCAAAGTC 22860

AAAATTATTT AATATCTGGC CTTTTGCAAA ATAAGATTTA CCAAGCCTTG GTCTGGGTGG 22920

TCAACAAAAC AATAAATCAA GCCTTGATCT GTAGTGTCTG CCAATTTCCA TGGTGTAAAT 22980

ACTCCCATCA TGGCCAATTT CTATCTACCA ACATGACACA GCAAAACATA GAGTTGGGAA 23040

GAGATGTGTA AAGTACACCG TTATAGAGTA TTCTCACTCT ATAGCTACAG TGGCTATAAA 23100

TAACTTCCAG AGCATAGACA ATAGTAAAAT GTAGTCATAA TTAAGAACTG GTAAGTTTTG 23160

AGTGTTTATT ACCTTTGTTT CTAAATACAA TTTATTTAAT TTTAAGTTTA TATTTTAATT 23220

TCGAATAATG GCTGGGTTTA ACAAGTGGTT TGCAAAATCT CTGAGAACTT AACAATCAGT 23280

TATCATGAGT TGGCACTATT GCTTTCCTTT GGTGCCCAGC TGTCTTCTTT TTTCAGCCAT 23340

TTCCCTGTCT CCAGGAGATA ATCCTTTTTT TTCTTCTCAG CCTGTCTGCT TCCCAAAGTA 23400

TCCTTTGTTC TTTTCATGGC CCTCTGGCTA CGCAGGGACC CCACTTTTTG CCAAACTAAT 23460

CTTTTAAAAC ATATGTCCCA CAGAGTACCA TTCCCTTTCA TCTGCTTCCC ATCAATACTC 23520

TTATTTCTAC AATAGGGTTG ATACCAAATG GCCAGCAACA ATTTGTAATA AGCTGTAAAT 23580

GATTAATGGC CTGGAAACAC TTGCATTTTA AAAAAGGAG TCTTGTTGAC CAAAGGTTA 23640

TAGGGTTTGA ATGTCTGGCA ACATTGCAGG TGTGAGGAAC GTCTTTGGAA TTCCTAGTTC 23700

CCCCCAAAAG GTTACTGTCT TCTTCAGTGA CAAACAACCA ACCCAAGCGT GTACCCTGAT 23760

GCTCCTCATT ACCCCTCAAA ACTTTTTCCT TTTCAATCTT TTTAGTTTTA GCTCTTTATT 23820

TCCCCTCCAC TTTCATTCCT TATTTAAACC TCTCAATTGT AACTGAAGCA GATGTTATAT 23880

GGACTTGGGG AAAGGGATCA AGAAATCATT CAGTTGTTTG TGCTTATCTA GAACTGTCAG 23940

CCCCTGAATT GTGTGGTCTT GGCTGGCATC TGAGCACACC TGGTGCATCA GCAGAATCAG 24000

TGTTCTCTCA GTTCCTGGTT GGCTCTACTG TCTGGCACCA TTCGGCTGTT TGTACTTATC 24060

TGGAACTGCC AATGGGAAGA TCACATGGTC ATTGAGAAAC CGCACCCTGA AGAGATGGCT 24120

AAAAGCCTGG AGGGCATGCC CATCACAGCC TTGCCGGGAG TGTGAAAGGT GGTGTGAAGA 24180

CCCTGGGGCT CACAGGACTC CCTCACCATG GGCACAGTG TAAGAAGGTC CACGGTGAAA 24240

ATGCAGTAGG AGGCAGTTAC ATCAGGCTCT GGATCGATGA TATCAAGGAA CAACCCAGGC 24300

TGAAGGAAAA GGCGTTTGTG TTTCAGGAAA GATGTATTGA GCCTCATCCA TGCTCCAGAC 24360

TTTGTTTAGG CCCTGGGTTA CAGCATGGAA TGGAATGAAA CCCCTGTTCT TTAGTTTCTT 24420

ACATGTTGAG TGGGTGAGAC AGAAAGCAGC AATATGGTAA AGAGGGGGA ACAGGGGAAG 24480

AATGGTAGGA GATCAAGTTA GAGAGGGGAA TGGGCTAGAT CATGGAGCAA CCGGGGCAAG 24540
```

```
ATGTCAAGCC CTTGGAAGGT TTTGAGCAAG AGAGTGTTAT GTTCTGACTT ACGTCTTGAA 24600

ACACTCTAGT TGCTGTACAA GGAGACCAGG TCAGAGGCTA TTGCAGTTGT CCAGGTGAAG 24660

GTGGCCAGGT AGCGATGGAG GATGAGAAGT AGAAAATTCT GTGAAGGCAG AGCTGACAGG 24720

ATTTACAGAT GGATTGGCTC ATGAGAGGAA AAGAGGGACT CACGGATGAT GCCAAAGTTT 24780

TTGACCTGAG AAACTGGAAG AATGGAATTT CCACTTACTA TGATGGGAGA GGTTGTGAAA 24840

GGATGACTTA GGGGTTGGAG AAAACCAGGA GTTTGGATAT GGGCCTTAGA TATTGCCATG 24900

CAGATGTTGA GTAGACAGCT GCACATATGA GTTGGGAGTG CAGAGGGAGA GGCTGGGGTT 24960

CTGGGTATCA GTATATGAAT CATCTGTGTC CACATGGCAT TTAAAGGCAT GAGACCAGGT 25020

GACCCCCCTT ATAGAAAGAT TAGATCCAAA AGAGTAGTGG TCTGAGGACT GGGCTTTAGG 25080

CCCTGATGCT CAGAGGTGAG GACCCAGGAA AGGAGACACA GAGAATCCTC TTTGTCAGAG 25140

CATTACAAAA GGGCTATTTG GAAATAGTTC AGGTGGTGAC TGGGTGAAAA GCCCTTCGAA 25200

CAGCCTCAAG GACCCAGGCT GGTGGACTGC TGGCTGAGTC CTGTTGTGCC TCAGAGGATA 25260

TTGTAATATT TGGAAAAATT TCTCCAAGTC AAATTTAAAT TAACATGAAT GTCATATGGC 25320

TTTTTGGTAC GTCCTACAGT CAAGCAAATA ACAATTGGAT AGGGTAGCTG CAGGAAGACT 25380

GGGTGTCTCT ACAGTGGTCA AGTTGGAAGA ACAAAGAATG AGTGATTGAT CTTTTGCTAC 25440

TCCCCAAGGG GAGAAGCCAC TGATAGCTTC CTTGGAAGCA CTTTGTACCT CACCTGCCCC 25500

AGAGTAGATT AAATATTAAG TTTCCTCCCT TCTTTCAAGT CCTAGTGCTG CCATTGATAG 25560

TGCTGTGACT TCAGGAAAGT TGCTTAACTT TTCCAAACCT CTATTTCCTC ATTACTAATG 25620

AGTAATAATT CCCACCATAG GGTGTTTATA AAGATTAAAT AATTTTAAAT ATGTTGAAGC 25680

ATGTAGTGAA CTGCAAAGCA ATATGCAAAT ATAAGAGGTG GAAATGACTA TGCCTATAAT 25740

TACGTGGCTC AATTTACACA ATAATAGATT TTCACACTTT GCATAAATAA TGAGGGTTTT 25800

TATACTCAAG TCACTGAACT TACTATCTTC AGGATCCAAA ATCCCCAAAC AGAAGGCATC 25860

CCCTACTGTT AGCTCAAATA GCTCTTGCTG GTTTAGAGAG TTAATGCAAG CCCCACTGCC 25920

TCCTGAGCTG GAAACATGAA ACAGAAGTTT CAGTTCCCTA ATCAATCCAT TCTTTCTTCC 25980

TCTGGCTTCT GATAGGCCTC CTCCTTATCT TTGTAAACCC TGTAGCTGGT TGCTAGTTGA 26040

AAGTGCCTCT GATCTCCCTC TTCTGCCTCC CATGATGTTG ATAAAAAGCA CGAGGGCACA 26100

TGCAGGATGA AAACGATCGT GGTCCTGCCA GCCTGAATTA TTAAAGCATT TCAGTCCTAA 26160

GTATGAGGTG TGTATATGTT GGGGTGTGGA GTGAGTTGTG GAGATGAGAG ACAGCTGAAT 26220

TACATAAAGT TGAAGATCTC TGAGTTCTAG TCTTGAAATT CACAAGCCAT CTCTATACAA 26280

TAGTTCCGTT ACTCAGTAAA GTAAAAGCAT TGGATCTAAG CTTTAAGGAC CCTTCTAGTT 26340

CTTTCTGATT GGAATTCTGT GACTTCATCT TTTGTGGGTT AGAAACTCAT CACTCTGTCC 26400

AGTTATTTCT ATATTATGCC ACCAGATGGC AATGTTTCCT TAACCCCAAA GAAAGTTTTC 26460

ATTCTGGTAA AAAGTCAAGT TTTGTTGCCA ACTTTTCCCC CTCTGAACGT GCAAAAGAAT 26520

GATTTTCCGA AGCTGTGGAG GAAAGAAAGA ACTCTCCTTC TGAACATCTC AGGTGGTTTA 26580

TGCTGGAAAC AGACAGGACC CTGTTTAGAG AAGATCTCTC TTTTCTTCGT GGACTGGGAA 26640

CTCCAGTTGG AATGATGTCT CCTGTGATTG CGTATGGTGG GAGGTGGGAG ATGTTGGAAT 26700

TGGCGTGTCC TCAGGAGGCT TGGGGGTGGG GGAGATGTGC CCTAGCTGGT GGGCCTGCAT 26760

GAGCCCTGCA AAACTCTGAC TTATAGAGGG GCATCAGATG CCAAGTTTTA CCAGACCATG 26820

CAGAACTAGG AATTGCCAGA TGCACTCATA GGGCAGCTAA AATGGTCCTG GCAGAATCAG 26880
```

-continued

```
ACTCTTTCGC TCATAAAGGT CAGAGACGCA AGAAAGTGAC ATAAAGTCCA GCCCTTTTCT 26940
TGTGCAGATG GGGAAATTGA GGCCTAGAGC AGGTCAGCTG TCCTGATTCT ATCTCCTTGC 27000
CAAGTTACTT TGTATTTAAA CATTTCAAGT AGACTTTTCA ATCATCTCAT CTTGCTGTGT 27060
TCAGCTAGCG CACCTTGTTA AGCCTGTTGG CCTCCGGGCC TGCCAAGCCC CTGCATCTAT 27120
ACACACCAGG GCATGCTGCA TGCGCTCAGT GAGACTTCAA CAGCTGACTG ATTCGTTCAA 27180
ACCTATCAAA CAGCAGACTT AGCTAGTTGG GGAGAAAAGT CATTTAAAGT AATTGCTTAT 27240
TAATCTGCAA AACAAGTCTC ATAGCAGGTT TTTATTTTAT TTTATTTTAT TTTTTTGCTT 27300
TTAACAACGA TATAATAACA ACAAACATTT GTTTAGTGTT TCCTGTGGAC CAGGCTCTGT 27360
GTTAAGCACT TAACATCACT ATATCATGCA CTTTTGCTAA TAAAGCTGTG AAATAGTTAT 27420
TACTATTTCT GCTTTACAGC TGCAACAGAG ACTCAGAGAG GTTAGGTAAC TTGCCCCAGG 27480
TCACAGAGCT GGAAGGAGCA GAGCCAATAT TCACACCCTG ATTTGCGTAA TTCCAGATTT 27540
GATCTTCTAG CTTCTATGCT GTGCTGCCTC TTCATGACAG TTTTTCTCAT GTACAGGATC 27600
TGATGCAGAA ACTTATCGGA GTTTCTTACC GGAGCACCAG TCACCTCTCA TCATTTTCCT 27660
GTTTTGACGT GAAGGCTCAG TGATAGTGAG CAGGCTCAGG GTCTACAGAG TTGGTGATAT 27720
CAGCATCACA CAGGACATTC AGAATGTTGA CTCCAGGGAT GTTGAGAGAT ACTCCTGCAC 27780
AAAGCTGCCA GCACCCGTGT CCAAGAAACA CTCAGAATCT AGGTCTCCTT GTATATTTTC 27840
CCCACTACCT GCAAAGGTAA AGAGGAACAG GCAGTGCTGG GACCGAGGGA GCGACAGTCC 27900
TAATGGAAGC TAGTGTGTTG AGAGTCTCCT CTGTGTCATG CTCTGAGCGA CATGTTTTAT 27960
ATGCACGATC TCATTTAGAC CTTGTGACAG CATGTTGTAG CAAGGACCCC ATCATCACAG 28020
GGGGCAAATG TCTGCAGTGC AGAAAGTCGT CCTGAAGAAA TGGATGTCAG ATAAAAACAG 28080
TCTTCATAAA TCAATGATCC TGTTTTACCT CAAAAGTGCA TGAAATGGAA ATGGAAATAT 28140
CTTGTGAAGA TGTAGACAAA TGACGGTCAT TGCCCAGAGC AGTAGTTACT GTCAGAAAAA 28200
GAGATAAGGA TTTCCAGTCT GACAGACTGG ATTCCTGGCT CAACACCACC CCCTTCTAAC 28260
CATGTGACCT TGGGCAAATT ACCTAACCTT TTCTGAGTCT CAATTTCCTC ATCTTCCAAA 28320
AGGGGATAAT ATCATATATG TTCCAAGATT GCTGTGAGTA TTAAATGAGA TGATGTATGT 28380
AAAGTACCTG GCCAGCAGTT TCTGGCACAT AGTAAGTATT CAATAAAGAC TAATGGTGGA 28440
GATGAGTATA GGGGCTACTA ATGCCCATCC TTACTCCAGA GACTTCTTTC TGACCATCAT 28500
GAGGCACTTT TGAATATCTA AACCCATTTA AAGCCCACTT TTCTCTATGG CTGGCCATTT 28560
CTGCCTATTG ACAGCTAATT TGCCTCATCC TACAGGACAC CTTCCATGTT TCCCCAGACT 28620
CCAGAAATCA GGTATTAAAT TATCAGGGCT TCAGGAGCCA TGGTCTATGA TGAGTTTACT 28680
ACCTGTGCCC AATAAATGTT TAAGAAATAA ATAAGAGCCA ATATAACTAT AAAGACCAAG 28740
AGCCAAAATA AGTCTCTTTG CTTGCGCTTT AGATCTTAAG AGTCCTTTAT ATTCAAGCTG 28800
CTCAGAGTCA AACGTGTGCC TAATAAACAT TCTACAAAGG TCCTGGCGTG GTGTGACCAA 28860
AGGAAGAGAG AGGGCTCCAG TGTCTGTCAC TGGGAGACCA GATGGACAGC CACGTGGGGC 28920
AGGGCCACTG GTGCCACATG TCCAGGTCTG TTAAGCCCTA TGAAAGACAC TTGAGTCAAA 28980
ATGTATTTCT ATCTAAGAAA GAAGACTATA AATGGAAAAG GGAGAGGGGA GAAGACCTCT 29040
CAAGGGCATC TCCCTCTAGA AGTAGAGATT GTGAATCTGC AGCAGAAAGG TTTTAAACAA 29100
GGGATAGCAG AATGCCTGGA TGGTGTTCTA GTGCCTGAAT GGAAAAAGGC CACAATGACC 29160
AACAAATCCC ACCTACATCC GCCTTCCTCG CTGCCTGAAA TCCCACCATT AGGATTTTTT 29220
TCCTTTTGGG TTAGCAACCA AGAAAGAGTA AAGTCTGGAA GACTCTTATT CCACATCTTC 29280
```

```
ACTTTGCAGC GCCTCTTTTT TTTTTTTTTT TTGAGATAGA GTCTTGCTCT GTCACCCAGG 29340
CTGGAGTGCA GTGATGCGAT CTCAGCTCAC TGCAAGCTCT GCTTCCTGGG TTCACATCAT 29400
TCTCGTGCTT CAGCCTCCCG AGTAGCTGGG ACTACAGGCA CCTGCCACCA CTCCCAGCTA 29460
TTTTTTTTTG TATTTTTAGT GGAGACAGGG TTTCACCGTG TTAGCCAGGA TGGTCTTGAC 29520
CTCATGATCC GTCCGCCTTG GCCTCCCAAA GTGCTGGGAT TACCACCTCT TCTTAATTAC 29580
AAACATAAAC AAAAACTAAC AACTTTCTAG TTTTTTCTTT TTCTTTTTTT TTAAATTACA 29640
AAAGAGATCC ATATTCGTCA GAGAATAATT GGAAAAAAGA GATAAGCAAA ATCAGAAAAA 29700
TAAATTCAGC CTGTAATCAC CCAGAGATAA CAATTATTAA AATTTAGGTA TTCACTTTGT 29760
TATTTCCTTT TATAACAAAA CTTTTTTTTC TTGTGAAATT TAATAGAATA CAATTGAACT 29820
ATTTTTTCCT TTATGGTTAA TGATTCTTGT TTCTTATTTA GGAAATCATT TCCTGAGTCA 29880
TAAAGAATTC TCTCATATTT TCTTCTAAAG CTTTATACAG TTTTGCCCTT CAAATAAGGT 29940
TAATAACCCA CCTAGAATTG ATTTCTGTGT ATGGCATGCA GTAGAGACAA GTTCTACTTT 30000
TTTCTCTCAA ATGAATATTC AGTTGGACCA AGGCTGTCCT TTCTCCACTA CTTTGCAGTT 30060
TCACTTTTTG TTGAAAAATC AATTGTTCAT ACATGGGTAG ATCTCTTTCT GGGCACTCTT 30120
GGAGTCTATT GGTCTGTCTA TAAGTTGAAC AGGATCAGAC AGGCTGTGCT TTGTTTCAGG 30180
TAACAAAGAA CCCCAACATC TCACTGATGA ATACACTAAA GTCATTTTTG TTTTCCATTG 30240
GCAGTTCACT TCTGATGCAG GAGATGCATC AGGGCAATCG CCCTTTGCAA GGTGAAGTGT 30300
CTGCACCATT GGAAGTACTC TCCATCCAGG GGAGAGAGAC TGGAAATGGT CCATGAGGTT 30360
TTCATCGACC CAGAATGAAA GCATCACCCA TCATTCCCTT CTTGTTACAG CCTATTTGTC 30420
AGAACCAGTC AGAGTTCCAC CCACCTGCAA AAGGTTGTGA CGTGCTGTTT GCGATTTGCC 30480
TGGAAGGAGG GAATACCCAG ATACAGGAAA ATGCTAGTGA CGTGCACTTC CATCTAACTA 30540
TCTTTGAATG AAAATGACAG TCTTAATTAC TGCAGTAAGA TAAGCAGACT CTATACCTGG 30600
TAGAGCAAGT CCTCTTACCC CATTTCTTCT TCAAGAAGGT CTTGGCTAGT TTGGAACCTT 30660
GGCAATCCCA TATAAACTTT AGAAAATGCT AGTTAAGTTC TTTAAAAATC CTGCTGAGAC 30720
TTTTATTGAA TCCATAGCTT CATTTAGAGA GAGCTGACAT TTAAATTAGG GAGTGCTCCA 30780
AGCCACTAAC ATAGAATTTC TCTCTTTTAC TCCAGGTCTT CTTTAATTTC TCTCGAGTGT 30840
TTTGTAATGT TTTGCGCAAA GTTCTTGCAC ATCTTTTGAT AGATTTCCCC CTAGGTTTTG 30900
GATATTTTA AGATGCTAGT GTAAATGTTA TTGCTATATA TTTTTCATTT TACAAATATA 30960
TGTGTTTAGT ATATAGAAAT TTAATTCATG TTTCTGTATT GACTTTATTG AGTAACCTTA 31020
TGAAACTTTC TTAAATTCTA AAAATTATCC ACAGCTTCCC ATAGATTTTC TATGTAGGTA 31080
ATAACATAAT CCACAAAAAT GACACTTCAA TTTTTTCCTT TCTGTTTCTT ATGTCTTTAT 31140
TTCTCTTTCT TGCATTTCCC ATGTGGGGTC CCTAGACACT GTTGAATAGA TGTCGTGATA 31200
GTGAGCATCC CTGTTCTGTA CACAGCCTCG AAAGGAAAAT TTTCAGAGTT TTGTTTTAAA 31260
CAATCTGGTT GTTATAGGTT TTATTGTAGC AGCTCTTCAC CAGATTACCT GCATGTTTTC 31320
TTTTTTCTAG TTTCTAAGAC TTTTAATCCA TTAATGAGTG GATGTTGAAT TTTAACAAAT 31380
GCTTGTCTCT GCATGTATTG AAATGACTAT ATGACTTTTC CCCAATTGAT CTGTTAAGTT 31440
GGTAAATTAC ACTGATATTC CAAAGTTAAA GCAATTTTTA CACTGGCACC CTCAAGTAAG 31500
CCAAATTTGG ACATGATGTA TTTTTAAATA TATATTGCTG GTGTTGGCCT GTTAATATTT 31560
TATTTAGAAT TGTTGAGCCT ATGTTCAAGA ATAAAATTGG CTTGTGATTT TCCTTCACAT 31620
```

```
                                    -continued
ACTGTTCATA TTGGGTTTTG GTATCAAGAT TACTCAAGCC TCACAAAATA ACATAGGGAG  31680

TCTCATTTTT TCTATTTTCT GGAAGAGTTT GCATAAGTGT GGCATTATAT CTTCTTTATC  31740

TCATAAAATT TGCTTGAGCC ATCAAATCTT AACATTTTAT GACAGGTTGA TTTTTTATTA  31800

AATCAATGAT TTTAATAGTT ATAGGATTAT TAGGATTTTT TATTTCTTCT TTTGTTAATT  31860

TTAGTAAGTA GTGTTTTCCT AGGAATTTGT CTATTTTATC AAAATTTATA AATTAATTCA  31920

CAGAGTTGTT TATAATATCT TCTAATTATC TTTCTAATGT CTGCAACACA TGTAATAATG  31980

TTATTTTTGC TTATAAATTG ACAATTTATA ATTGCGTATA CTTATGGGGC ACAAAACAAT  32040

GTTATGATTT ATGAAAGCAA TGTGGAATAA TTAAATCTAG CAAATTAATA TATCCATCAC  32100

CTTAAATACT CATCATTTTT TGTGGTGAAA ACATTTGAAA TTCACTTTTT TTCACAATTT  32160

AAAAATGCAC AGTACACTAT TATTATCTAC AGGTGGTTCC TGACTTCTTA TGATGATTTG  32220

AATTATCACT TTTCAACTTT ACAATAATGT GAAAGGAATA TGCATTCAGT ATGCTCTATG  32280

ACTTATGTTG GGATTATGTC TGGATAAACC CATAGTAAGT TGAAAATATC AATGGGCTCA  32340

TCCAGATATA ACTCCATCAT AATTTGAGAA GCAGCTGTAT ATTTATCATG GTGTGCAATA  32400

AATCTCAAAA AAAGACTTAT TCCTCCCGTC TGAGATTTTG TACCCTTTGG CCATCACTCC  32460

TTCATTCCCC TCACCCACAG CCCCTGTAAC TACCATTCTA CTCTCTGCTT CTATGGATTT  32520

GATTGCTTGA GATTCCACAT GTAAGTGAGA ACATGTGGTG TTTGTCTTTC TGTGTCTGGC  32580

TTATTTTACT TAGCATGATG TTCTCCAGTT TCAGTGATGT TGTTGCAAAT GATAGAATTT  32640

CCTTCTGTTT AAAGGCTGAA TTATCCCATT GCATGTATAT ACTACATTTT ATTTATCCAT  32700

TCATCCATTG ATAGACACTT AGGTTGATTC CATAACTTGG CTAGTGTAAA TAGTGCTGCA  32760

GTGAACATGG GAGTAAGGAC ATGTCTTAGA CAATCTGATT TCAATATTTG GATAAACACC  32820

CAGAAGTGGA GTTACTTGGT CATATGATAA TCTAGTTTTA GTTTTTAAAG TAACTTTCAA  32880

ATAGTTTTTC ATGATGGCAG TACTAACATA CACTCCCAAC AGTGTACAAG GGTTCTCCTT  32940

TCTCCACAGA TGTTCTCTTT TTCATTACTG ACATGAGTTA TCTGTGCCTT TCCCATTTTT  33000

TGTCTTCATC TGTCTCAGCA GAGGTTTATC AATTTTATCA TTTAAAAGGT AAAAATTGTT  33060

ACCTTTTAAA TCTTGTCTAT TGTATTTTTT TGTTTCATTA ATTTTTGCTC TGATTTTTGT  33120

ACTTCCTTTT TTCCATATTT TTAGGAGATG ACTTTGCTGT TCTTCTAACT TCTCTTTCTA  33180

GGACTCCTAG AAATATGTTA AGTCTGCTCA TTGTATTTTT CTCACCTTTA TATTTTCCAT  33240

TGTTTTATCT CTTTCTTATT CATTCTGGGT AGTTTCTTCT AATCTACCTT CCAGTTCATT  33300

AATTATCTCT TTACCTGTGT TGAATTTGCT ATTAAACCTA TCTGAATGAC TTTTTCATTT  33360

TTTATTGGGT TTTTAAATGT TAAAATTCTC ATTCCTATTT GGTTCTTCCT CAAATTTGCA  33420

ATGATTTTGT TTCAGCTGAT TGCCAAAACG TTTTTAGTTC AAGTTCATCT CTTTGAGCAT  33480

AGTGAGCACT GTTGTTTTAC AGTCTTTATG TAAATACCTT CTCTTTTATT AATCTTTCCA  33540

CGTTTCTGGT GGAGGGACTG GCTATGAGAG ACAAAAACTT TCTTTCAGGT GCTTTTAGGA  33600

CTTACCCATA TTTCTTTCAT GGTGTCTATT ATTTTATTAT CTCATTATTT AGATACTTTT  33660

CTCCTCTACT AAACTAATGG TTCAAGGCTT ATCAAAGATA AATCCTCTGT CTTGTTCATC  33720

TCTGTGTCTC TCATGGTATC TAGCAGACTT CCACCCAAGA TATAAAGACA CTATGACTAA  33780

GTGAATGATT TTAGTCTTAC CTACCTGCCT GTTAACTTAC CTACTTGCAT CTCACTTATA  33840

CTTCAACTTT TGGCTTCTTC CTCAACCTCA ACTACCCCAT TCTTCCCATG GCTCACTGTG  33900

CTCACTGGCC TCCATACTGT CCCTTAAATA AGGAAAGCTG CCCTAGCCTC AGGGCCTTTG  33960

CACCTGCTCT GCCTGCTGTT TGGAATGCTC TTCTTCCCAT ATACCCATCT GTTTTAATCC  34020
```

```
CTCATCTTTT ATTCCCTCAT CCCATCTCTT CAAATGTGAT TTCTACAGAG GGTTCTCTGA  34080

CCACCTTATC CAATAACCAG CATTCCGTCT CCCCTCTGCC ATTCTCCATC ATCTCACCAT  34140

GCTTTATATC ACATATCACT AAGTGACAGT ATACTATAAA CGTACCCATT TGTTTACTGT  34200

CTGCCTCCCT AACTAATGTA TAAGCTCTCT GAGGGCAGGG ACTCTGTTTT ATTTGTACAC  34260

CACAATTATC TCCAGTGCCT TGAATAGTGT CTGGCATGTA GAAGGAATTC AAGAAATACT  34320

TGTCAAGCTA GGTGCTGTGA TAACTACTTT ATATGAAATT AAGTATTTCT CCTCCAGCAG  34380

CTCTAAAAGT TTAGTATGTT ATTATTGTCT CTGTTTTACT GATGAGTGAA CTGAGGTTCA  34440

GAGAGGTTAT TTAGCATACG TATGAAGACA GAATTAGTGA GTGATTGACC TGAGATTTGA  34500

ACTCAACCTG TGCTGTCTAA AGCTAGCCAG GCAGCCTCAC ATACATGGCA AATGCCTACT  34560

GAGACATGAA CATGCAGGTT GGGATCCCAA ACTGTTGGGA AGCATAAAAG AAAAACACTA  34620

AAGATGTGGG GAGTGTAGGA CTTTTTTTTT TAATAGGCCA GTGGCCCTCT CTGCAACCCT  34680

TTGAATGATC AGCTTGATCA GAGAATCCCC TACCCCTACC CCTGCCTCAG CCAGTTTCTA  34740

TCTGGCTGTG TCATCAGCTG GCTGATCCAA ACAGCAATGT CAACAAAAGA ATGGTGATCA  34800

GGCACGTAAA GCAATGTGTC AGAAAGAAAG AAAAGGCAGC TCAGATGATG CAAGATCATC  34860

CAGATGTCAA GCACTGTGTG GTGGCACACT TGCCCGTTCA TGTTGTTGAT TTTTTAAACA  34920

TTTGTGATAA GAACAAAAAC TTAGTTGCTT CCCTCAGGTC CTCCCTGTAT GGATTAGTGC  34980

AGACATCTGC CGCTTCAGGC TTTCTGATTG GTTCCCACTG GTTTGGGGCA AAACCGGAAA  35040

CTTCTGAGCC AAGTGCAGGG GCAGAAGAGC TCCCAAGAGC TCCTGGGAAA ACTAGGAAGG  35100

ACAATCAAGA AACCACCGGC AGCTCCATTT GCAGGATCTC ATCCCATCAG GGGCTGTCTC  35160

AGGAGGGGGA ATTGGAATAC CATTCACCTG TCCCCTTTGC AGATACACCA ATGTCTCGTT  35220

CAAGAACAAG CAGAAAGGAA ACACCAGATT GCCCAGAGCA CAGGATTAGG ACACACCACA  35280

CAGAGCCAAC TCAGCGTATC ATTGTTTGCA TTGATCATCT GGGGATGAAG CAGGCTCCGT  35340

TCTGGAAGGG GCAACCTGAA TAGAGAAGAG TCTGACATTG GAGTCAAGCA GAACTTGGTT  35400

GGAATTTGGC TCATTGCTGG GTGATCCAGA GACAGTTATT TAATCTGAGA ATCAGATATC  35460

TTGTCTGTTA AATGGAAATT ATAGTAGCCA CTTCACAGGA TTGCTGTAAA GAGTACATAA  35520

AACCAGGTAC CTGCAATGTA TAGTGCTAAG CCTGACACGT AGCAGGGTGT TAGTAAGTGG  35580

TACCTCTGAC TGGGGATGGA AGCCAGAGGA GCTGGACCTT TATTTGACTG GCCAGAAGCC  35640

AGCTCTCTAG TCACCTTCCT GATCCTTCCT TCTTCTGTGT GTACACGGAC AATGTTTTTC  35700

TACATAATGG AACAGTGGCC CTCAAAACTT GTTTTCATAA GAATTATCCA GGTTGCTAGT  35760

TATTAATACT AGTTATCCAG GTTGCTAGTT ATTAATACTA GTTATCTGTG TTGCTAGCTA  35820

AAAATACACT CAGTTCCCAT CCCCAGATTT TTCTATTTCA GTAGGTGGTA GTGGGTTCAG  35880

GAAATCTGTG TTTTTACCAA AGTATCCCCT ACTATAGAAT TAATTTTTGT GTTCCCCCCT  35940

CATTCATATG TTGACATTTA AACCTCCACT GTGATGATAC CAGGTGGCTT TGGGAGGTGA  36000

TTAGGTGATA ACGATGAAGC CCTCATAAAT GTGATTACTG ACCTAATAAA AGAGACCCCA  36060

GAATGCCCCC TTGTCCCTTC TGCCATGTGA GGTCACGGTG AGAAGATGGC ATCTATGAAC  36120

TAGGAAGTGG GCCCTCACCA GACGCTGAAT CTGCTGGTGC CTTGCTCTTG GACTTCCCAG  36180

CCTCTAGAAT TCTGAATAAT AAATTTCCGT TGCTTGTAGC CTAGTCTATG ACATTCTTTT  36240

GTGGCAGCGT AAATGGACTA AGATGTGCAC CCTCATGCCC TTTAGGGAAT TGTGACTTTG  36300

AGAAATGCTG CCCTAGGATT TACAGAATGC TGACAAAGCT TTGTTGACTC AAATGCAAAA  36360
```

```
TATTCTTATA AAGACCAAAA TAGAAATGAA TACTCCCTTG AACTCCTTTG GATGTGCACT   36420

TTGCGTAGTT ATAGCACCTT TTCATCATGT GCAAATGAGA CGCAAATGAA TCCTTAGTTT   36480

GACCCAGAAA GAATGTCTTT GCTGGTAGGG ACTACGGGAG AGAGAGAAGA GCCAGAATAC   36540

TGTAGGAAAA TTAACACCGG CCACGAGACA ACTGGTTGCT AGCTCGGTAG CTGTGCAACA   36600

TTGGCATGTT ACTTGAACTT CTAGAAATCT GTTCTTTCTT CTGTAAAATG AATATGGTCT   36660

GGAAAGTAAA GACCAGTCAC CTCCTCTATC AGTTGGAGTC TAATCAGGAA GAAACCTAAG   36720

TGTCTTCAAC AGAGGGAATT TAATGCAGGG AATGGGTCAC ACCAGTGTTA GAAAAGCTGC   36780

AATGCCAAAG AGGGGATAAA GAGATAGCTC AAAGGTTAAT AAGAGCAGAA AGTCACTAGT   36840

ATTCATAGGC TGAAAAGAGA AAGGGAGGAG ATAGTGTTCC CGGAATCCCT GATGGGCTTG   36900

TCTGGAGGGC GCTGGGGCCA TGGAGGAAAT GTAGTAGCTG CTGGAGGCAT GCTCAGGGCA   36960

GAGAGGGAGC AGAGAAATAC CCTGGCTTCT CATTTTCTTT CTCCAGTCCT TGCAGGCACC   37020

TCACTGGCTG AACTCAGGGG AGCATTTCTC CTCTACAGAA CAGAGTCTCC TTGCATACAA   37080

CAAGAGGGTC AAACAGAGGA TGGCTTAATT TTTCCTTCCA TTTCTCACTT CTATGATTCT   37140

CTCCCTTCAG GTTAAGTAAG TGAGGGTAAG TAAGCTGCCC AGTAAGTGAA CAGTTTTCCA   37200

AACAAGCCCA CAGCACCACC TCTATATACA GCAACTCTCT GTTTATCAGC ACTGCATTAA   37260

CCAGGACTCT CTATTAACTG GGACTTCCAG TTCCTTAAAT TTCTTCATGG TTCCTGTGTA   37320

CTCCCAAAGC ATCTTCATCA AACAAACATT AAGTTACGCT TAGAGACCAT TTCTCAATTG   37380

AATATAGATA AAAGATTCTA AGGCCTTGAA AAAAATTAAT ACATGCATAT TAGATATAGC   37440

TATAAAAGCC AGACTATCTG ATTAATTATG TGACTGGTGT TAAACTGTTT GGACAAAGGT   37500

TGGCTAAATT CCCTATGAAT ACTTACTTCC CTACTTCTGT GGACAAGGAA AAATAGACCA   37560

AAGGTTCAGA TAAAAGCTTG ATTCAATGTC ATCTCTTTTC TCACGAATCT TGGTCATGTG   37620

TGGGAAGTGA CCCAGATCTA GAACCTTAGC CTTTGGGACT TAAAAAAAAA ACAAAAAACT   37680

GTTGAGTTGA ATCATTAAGT GTTACTGAGG GACAGGAGAG AGGAGGGTAG CTTTCTTAGT   37740

TCCAAGACAA ATTTTGTTAA CAAAGATCTG TGGGTAGACT TGTGTCTGGG CAAAAGATCA   37800

GAAGATGTGC TGTTCTAGGC CTCTTTGCCC TCAGACCCAT TCCCTATCCT TTCCCCTTCA   37860

CTGTACCCCC TTATCTCCTC TTCTGCTGTC TTCCTCTGGG CCTGATGCTT GAGGATCCAG   37920

AAGTTTCTCA GGCTCCCATG TTCCAGCAAT CCAGGCCTCC TTCCCAGTAA GGGATGAGTA   37980

CAGGGGCCAC ACATAGCCCT GCAAGTTTTG TAATCCAACT TGAAATCCAA TGGCAGAATG   38040

AATGGTTATA TATGGTGTGA CCCAGGACCA CATGCAGTTG TATCACATGC ACTTACAAAA   38100

GAGCCCCATT TCTTGGACTC ATTCCCAGAC TCAATCTCTC TGAGGGTAGG ACCAGGAATT   38160

CGGCCCTTTT CACAATCTTC CCAGGTGATT CTCTACATAG TATAATAACA CAAACTCATG   38220

GAAATATATT TAATGAAAAA TGAATAAAAG AATAAATGAA ATAACAAATG GTGATGGCTG   38280

GCACAATGTG TGTATCCATT CTCCTACTGA GGTGCACTTA CTTTGCTTCC AAATGTTCAT   38340

TTGACAAGTA GTGATGCATT GAATATCCTT GTACATGTGA GCATGCAGTA AAGTTTCCAT   38400

GGGCTTATAT TTGCTGGATT ATGGGCACGT GCATCTTCCT CTTTTCTAGA TATTAACAAA   38460

TCACTCTCCA AAGTATTTAT AACAATCAAC ACTCCTGAAC AAGCAGTGGG TTGGAATTCC   38520

TTCCTCATCA CATCCTGGCC AACAATTATT ATCATCAGAT TTTTTAATTT TGCCAATTTG   38580

AAGGAAATGC AGTGGCTTCT CATGTGTTAG TGTTTCTGAT GATCAGTGAG TTGAGTGTC   38640

ATTTTTTTTT TTTTTTTTT TTTTTTTGA GATGGAGTTT TGCTCTTGTT GCCCAGGCTG   38700

GAGTGCAATG GTGCTATCTT GGCTCACTGC AACCTCCGCC TCCCGGGTTC AAGTGATTCT   38760
```

```
CCTGCTTCAG CCTCCCAAGT AGATGGGATT ACAGGCATGC ACCACCATGC CTGGCTAAGT   38820

TTTATATTTT TAGTAGAGAC AGGGTTTCAC CATGTTGGTC AGGCTGGTCT CAAACTCCTG   38880

ACCTCAAGTG ATCTGCCTGC CTCGGCCTCC CAAAGTGCTG GGATTACAGG CACGAGCCAC   38940

TGCACCTGGC CGATTGAGCA TCTTTTTATG TGTTTAATGA TGCTCATTTT TTATTGACTT   39000

CCTTCTGTGC TTTCTTTTTT TTAGCAGTGA ATTTGAGTTG TAAGAATATG TATTTCTTTC   39060

ACTCTGGGAT TCACCTACAT AAAGTAATTT TCACTTGAAT GAAAAGAAA TCAGTTGTAT    39120

AAACATCTGT TTTTTCTGAA TTTTACTGGT GTAAAAATGG CCACTCAGCC CTGGAAGAAA   39180

CAAAGGCACT TTGCCAACTG AAGTTGCAGA TGGGAAATTT TTAGAAAGGT CCTGTTCAAC   39240

CTCTGGAAGG GGAAGATCAT ATCTGAAAGT CAGGGTAATC CACCCAACCC AAATGTTTCT   39300

TCTACTATGG GTTCTGAGGA TTCGTCCATG TGCTTCTTCT GCATTGCTGC CATCTGATTT   39360

CCTTTGCTAG GCTCCTCTTG CAACTTGGGC TACAAAGAGG TGCTTCATAG TCCACAGTCT   39420

TTGCCTCACC TTCAGTCTTG AGGTGGTCCC CTAGGAGTTA TTGGTAGTTG CCGCTGGAAG   39480

CCATTCTAAC AAACCTGGCG AAGGCACAAA AGGATAGAAA GCCTTTAGCC AATATGGTGC   39540

CATCAAAAAC AAACAGAGCA CGCTGCCCAG TCCTCTTCTG GTTGCCTTTA CTAATGCATC   39600

AGTCATACTT CTTCTGCACT CGATCTTAGC CAAGAGGTCG AGAAGCCATA GTCATAATTC   39660

TTCTGAAATT AATCTCTTCC TGCCCCACCT CCCCATCATC TGTCTTTGAA TTCCCAGGGC   39720

TAGTACTCAT AAGATTATCT CTTTCTTCTC CTTTATGAGG AGACCCATTC TTTTTCACAA   39780

ACCAGCCACA AAAGCAAGTG TCATTACCCC CTACCGGAAA TACCAGACAG AGAGTTCATC   39840

TGGGGTTAGT TTCTAATCAA GCCTCCTGCC CGGGTTTTTC CTGCTCCTGT CTTGAAGCGA   39900

CCACAGGGGG AGAGCAGTTT CCAAATATGA TCCCTCCTTT CCACTGTCAC TTGTCCAACC   39960

CCGACCACTA TCATTCTTTT ATTTGCTTCT CCCCTGAGCC AGCCAAGAGC CTAGGTCAGT   40020

GACAGGGCAG GCAGAAGAGA GAGGGCTTC CAGGAAGGAG AGGGAGCAAC CCACAGAAGA    40080

GGCAGCAAGA CAGGAAGGCG GGCAGGGGCT GAAAATCCAA TACATATCTA AGTACATTTT   40140

TCTAGGATGG GCTTCTACAC TCAGCCAAAA CATATATTGC ATATTGTTTG TATTTTTTAG   40200

AGGTTTACAG GTCTCCCTGA AAGTCCCTCT GTGGAATTAT AAACCTCTAA TAAAAAATCC   40260

CAGGGTTAAA GAAAGGAAAA GATGAAGGAG AGGCCCACAC TCTGAAAGGA AAGGGTTCAG   40320

CGACTCCTGG AAGGTTCTGG ATGGTGCTTC CTTGACCAAG TCAGCTGCTT CTTCTACCTG   40380

GTCTCCTTTG TGGTTCAGCT GGGGTGGGGC TTACTAGAAA AAGCTGTGGG AGGTGGTTGC   40440

TCCAACGTAT GGGGGCTGTC TGTAAGTGTA GGTGTTATCT GATGAAAGCT GCCCCGGGTG   40500

AGGGTTTGTA CAGAAAGCTC CTGGTGGTGG GGAGATAATG TCAAGCTTCT CTCTCTCTCC   40560

CAGATCCTGG TTGTATCCTC TGTCCCTCTC CACCCCCACC CACTCACCCA CAGACTTCCA   40620

AGGAACCGGC GCCTGCAGAC ATGCCTCTCT GATGCCCTCC CAGTAACCCC TGGCAGGCAG   40680

CACAGCGCCA AACCTCTTGG CCTTACCCCA CTGGGCCCAT GACCCAGTGG CTGTGCCTCT   40740

GGGTCCTCCC TGTCCTGCAA AGAGAACTGG GCCCTCAGTC AGGTTCTTCT GCTCCAACCC   40800

AGTGGCCACC TGTGCTCTTG GGGAGCTCGG GGGAGGCTGG GAAACTTTCA AGAGCAGTT    40860

AATCACTAAC TAGCTGGAGA TAAGAGAGAG AGAATGAAAC AATTGAGAAA ATGCCCAACC   40920

CAGAGGTTAG TGCTTCCCTG CCTGCACACG CCAGAACCTG GCCCGCCCAG AGAAACTGGC   40980

GATCAAACTG AGTTTGTTCA CTGGAGAGAG CTGACATACA GTCTCTAAGG GGCTGCAGTA   41040

TCCCAGGCTG AGGTCCAGTG GCAGCCGCTG CCCCTTTCCT CCTAGGGCCC TTTCCTTCAG   41100
```

-continued

```
CCATGCCTCA GCCCTGAAGA CAAACAGGAG CAGTTTTCAA GGAGCCCTTC CCTTATCTCT 41160

AAGGTCTGGG CCTGGAATTC AGCTTGGCCC ATTTACTATG CCAGCTCTGT GCAGGGTGCA 41220

GAGATCCAAG ATAAATCAGA CAGGGTCTCT GCTGTCAGTG TGCTCAAGGA AAGAGGCTTT 41280

TAGGGGAAAC AAATCTAAAC GACTGCCAGC TGGAACTTCA ACTCTGTAAA GCAGCACCCT 41340

GCCACATCTG CCTGCTGGAA CATTTTCATC TGCTGGGCTC ACGTAGCTGT GCAACAGCTG 41400

GGGCTGGGGT CACATTCTGG GCTAATCTGA TGATTATTTT GGCTAGAGTG AGCTCATCCT 41460

TTTTGTTTTC AGGAGCTGTT CAAGGGTGGT CTGATGGTTT GGATCAAGAC TAGCTGTATC 41520

CCGGAGAAGA ATACGTTGAC TTTTCTGGGG TGGGGTCTGG GGCAGAAAGC AAGAAGGCTG 41580

CCTTACTTCA AGGAAGGCTC TCCTTCCACC TTCTGCCCTC TGAGTGCCTT GTATGCGCAA 41640

GTGACACTAG ACAAAGTGCT TAACACTTAT TACCTGACTT GAATCTCCCA ATGGCCCTGT 41700

AAAGCAGGTA CTCCATTATC ATCACCACCC TTCTTTTTAC AGGCAAGAAA ACCAAGGCAC 41760

AGTCAGTTTA ATAACTGGC TCAAGGCTGC ACGGCCGATA AGTAGCAAAT TTGGACTTCG 41820

AATCTGGGCG CTCTGGCTTC AAAGTGTGCT GTCCATTGTT CAGGTTCTGG TCTGGTACTG 41880

GCAATGTCAG CCACACCTGG AAGCTTGCTA GGACTATAGA ATCCCCAGCT GACCCCAAAC 41940

TCCCCAAATT AGCACCATGA TTTTAACAAG ATCTCAGGTG ATTGGTGTAC ACATTACAGT 42000

TAGAGAAACA CTGCCCTTTT CACATTATAT GGCTCTGTGC TCAGTACAGA TTTAATTTTC 42060

TTTTTTTTTT TTTTATTATA CTTTGAGTTC TGGGGTACAT GCGCAGAACA TGCAGGTTTG 42120

TTACATAGGT ATATATGTGC CATGGTGGCT TGCTGCACCC ATCAACAGGC CCCGGTGTGT 42180

GATATTCCCC TCCCTGTGTC CATGTGTTCT CATTGTTCAA CTCCCACTTA TGAGTGAGAA 42240

TGCGGTGTTT GGTTTTCTGT TCTTGTGTTA GTTTCACAAT CATTCTCAGA TTTAGCTTTC 42300

AAACTATTCA TTCCACCTGC CAACAATTAG CGAGCTCCAG ACATTGTGCC AGGTGAATGA 42360

TGGAGGTGAA GAGACAAATT TCCTTATAGA ACTTGGCCAT GCCCTTCATG CAGGCAGTGT 42420

GTGGAGTGCA AGTCAGGACA CTTGGATCTA AATCCAGTGC TACCACCTGC CGGCTGCGAG 42480

ACTGTGGCTG AGTCATTTCA CCTTCTTGGG TCCCAGGTTC CTAATCGGTA AAACCGGGAG 42540

GCAAGCCAGA GATGTCCGGC CCCAGCAGCA TATTCTATGT GAACAGGATG AGGTGCCCAG 42600

CAGGCAATCA GTGGGGATCT GCTGAATGAG GGAACCAGTA AATGAGTGAG TGAACCGATC 42660

ATCCACCACA AGGAAAGAGC CCTCCATTTC CAAATGAAGA AAAGAAGTAT GCTAGTGGAG 42720

GGGAGACGGG ATTATCTGCT GTGTGTCAGG AAGAGTAGG GCCTTCCCAA GCTCCCTTAA 42780

TACTAACATT ACACAGGGGT CCTCGCTTGC CCTTCTCAAT GGTCCACTCA GATGATTTCT 42840

CTTGGCGAAT GTCTGCCCCA CATCTGTGTG TCACTCAGCA ACTTTGGCCA CCTATCCAGT 42900

GTGAGATCTC TAGATCACAA GGTGGGAAA GGGGTGAGGA ATGACCTAGA ATCCTGGCCT 42960

CTGGCCTTAG AGCCTCACTT GTTAAAGGGA AAGGGGCAAA TAAGATCTGA ACATCAAAAA 43020

TTATTTCAGC TTGCCTTCCC TCTCACTTTT CTCTGTCCCC TTCTCCTCTT GTCTTCCCTG 43080

CAAACCACTT TGAGTCTCCT TTGGTTACCA AGATAAAACC AATCCACATT AACTATGGCT 43140

GGTATTTTTT TCGCTTTTAC TCCAAGCCAG TGCATAGTGC ATTTTGCTCA CATTAGATTA 43200

TGGAATCCTT CAAACAACCT GATGATGAGT GGGTGCCATT GATACCCCCA TTTTATAGCT 43260

GGGACAACTG AGGCACAGGG TTGTTAAGCA GCTAACCTGA GGCCACTCGG TCACTTCCTT 43320

GTGGTGGACC CAGGATTTGA ATCCAGGTTT GCTCAACTCC AAAGCCTGTG TACTAAACGA 43380

CACTTCCTGC CTTGATAAGA TAATTGTGGT TGTTACTTGG CCAAATAAAA AGCCTATGGA 43440

GAAGTTGTTT CCAATGAAGC ATATCAGCTT CTAAATCTGG CTGAACATTG GACTCTCCAA 43500
```

-continued

```
AGGGGCACAA AATACAGCTT TCCGGGCACC ATCTTGAAAT GACTGATTCA GCAAATTGGT 43560

CGTAGGCAGC GAGGCACCTG TAGTTTGGTA AAGCTCCCAG GTGATTCTGA TAATGAGCTT 43620

GTGCAGAACC CATTTACCTA AGGAGAACGC GGGTTCAAAG GGACTGGACG GCTCTTCCTT 43680

ATTTAGAGTA GGAGGCTGTT GGCTTCTGAG AATGAGGGCT AATTAACTTT GGGGAGCTTC 43740

CTGCAGTGAC CTTTGCCTTC GGGGAAAGTG TGGGGATTGA GATAAGAGAG AGAAATCCTT 43800

GGCGGCTAGG AGGAAGGGTA GGGTGTTTGC TGTCAGGCTC CAGGCTTAGC CCTCGTGGTG 43860

TCCCTCCTGG AGATGGTGTG CACTGAGTGC AGTGGCTGCT GGAGAGTGGG TGGAGAGATG 43920

AAGGTGATAG GGGTGGGATT AATTAAAATA TCAGGCAGTG TGGCTGGGCG CAGTGGTTCA 43980

CACCTGTAAT CCCAGCGCTT TAGGAGGCCA AGGCAGGTGG ATCACCTGAG ATTGGGAATT 44040

CGAGTTTAGC GTGGCCAACA TGACGAAACC CTGTCTCTAC TAAAAAAATG TAAAAATTAG 44100

CTGGGTGTGG TGGTGCACTG CAATCCCAGC TACTCGGGAG GGTGAGGTAT GAGAATTTCT 44160

CAAACCCAGG AGGCAGAGGC TGCAAGTGAG CGGAGATCAC ACCACTGCAC TCCGGCTGGG 44220

ACAACAGAGA GAGACTCTGT CTCAAAGAAA AGAAGCAGTG AACCTTTAGA TTATCCCACT 44280

CTAAAAGTGA GGCAACCTTA GTTTTTCTGG GTCTTTAGAA GCAGAAGTGC CCTTGGGTAT 44340

TTCTAGGCTG AGGGCCCCAC CTAGTTCAAG CCTTCTAAAC ATCCAGTGTT TTGCTATATT 44400

CATTTACCAC TTGTCCTATT AGACTCTTAG GTCTTTTTTT TTAATGACTC ACTTATTAAA 44460

GAATGTGCAT TTATTTACAA GGCAATAATA TCACTACCTT TAATGAAAAA TTAGCAACCC 44520

TGGCTACACC TAGAAGGTAA CTGTTAATAA ATAGGATGAA ACCCAAGGCT GGAATTAACT 44580

TCTCATTGGA TCCTGCAGCC TATGCTCCTT TCACTGAAGG GTGATATCAG CCAACTGAGA 44640

CCTCCTCTAA AGTCTGTGAA GGATTGAATT AAGAGAATTG GAAAGGGCAC ACATTTCTCA 44700

TGATGTGATT CAATATTGAT TAATTCCAGG TTCACCTATT ATCTAAAACC ATGTTACTGA 44760

AAGTGGCTTA TAAATACCGC AGCACCAGAA TGTAAACTCC ACAAGGGCAG AGTTTTTGGT 44820

TTTGTTTTGT CTTTTAAAAA TCTGTTCATT GCTTTATTCC TAGACTCTGG AACAGTACTT 44880

GGAATATAGT AGGTGTTCAC ATATTTATTG ACTACGTGGA CTCTTTTTAG ACTGAGAAGC 44940

GGAATATAAA GTCAGAGGGT CCGACTGGTG ATCGAATGCC TTCGTTCTGT ACTCAAGCCC 45000

ACTCACCCAC TTAGTTTTGA GAACTCTGGT GACCCAACCT ACAGCCTGTC CCACCTTCAA 45060

CTTATTCCCA TTCCTTGGGT GCACGTGTTG CTGTGAGGAT CAGATGAGGT CATGGATGGG 45120

CAGGACTCTG AACTGCGTGC CCTCTGCACA GGGAAACAGC TGGGCCGATT ATAAATTGCA 45180

AAGGGGATGC CTGATGGTGG CCCCATGACT TTTCATATGC TTTGGGCTGT TGTGAGAGAG 45240

AGTGCCCAAA GCCTGATTCT GGAACATTTT CTTTGCTGTC TTCTAAATGA GAACCTGCTT 45300

GCTTCAATTC TCCCACTGAG CAATCATGCT GACATGAGGG AGGCGGAGTC AGACCTTACA 45360

TTGTTGAGAC CAGATTCTGT GTTCTACGAG TATTGGGAAG GGTGATGCAG GCAGGCACCC 45420

ACCATGTTCC CTGTGAGTGC TTATTTTTAA TAAAAACCTT GGTATACTGC TATTAATGAA 45480

AATAATAATA ATAATAATAA TTACTCCTGC TAATAATATA AGGAAACACC CACTGGTCTG 45540

TGACTGAGCC AGCCTTGCCT GAAGGCAGGG GAATGAATTC AATGACCTCT TGACACTGGT 45600

CTCAGCCCTT TGGTTCTATT ACCACCTTGT AAACCTGAGG TTGTTCTGTT TTTATCCCTA 45660

GGGAGTTGTG GTTAGAACCT GCCAGAAATT TCTCACTATG AATCAATCTT CCATTGGTCA 45720

CTGCCCTTTT CAACATGCCT GTCATTCAAG ACTTACGATT TCCTAGGCAT TGACAGAGAG 45780

AAACTGGCCA TGTGGACCAA GGCAGTGGGA TTTACGTGAC ACCCGCCAAG CCGGTGGGGC 45840
```

```
TAAGTTCCAT TGCTGAAGTC TGATACCTGT CATCTGCTGT GGGGTGACAT CCACACCATG   45900

TCATTCTCCA TTCGTTCAAT ACATATTTGT GGATTCCTAA AATGCCCCTG CTGCTGTGAT   45960

AGTCCAGCTC AAGAGAGAGG AAGTACATGA GATGTTACCA CACAGTGTGG TATGTGCTGG   46020

AGAGGTGAAG ACTCTGGAGC AGAGAGGCAA CAACTCAGGT GGGGACTGAA TGGTGGCGGG   46080

GTGAGCTCAT CAGGAAAGGC CCCCCCAGGG AAGCTGTGTT TGGGCTGGGG TCTAAGGATG   46140

AGCAGCAGTT AGCCAGGGAA GACAAGGAGT AAATGTACCT AGGCATGTGG GGCAGTCTAT   46200

GCAATAATGT GGGGAGGAAG CAAAGAGAAA GAGAATGGGA GAATGGCCTG CCTGTTTGGG   46260

GAAATGAAAG GAGCCAGTAT GTAAAAATCA GGTGAGAGAC AGCTGGAGAT GAGGCTGCAG   46320

AAATAGGTAG GTGCCAGGTC ACAGAGGGCC TTGTGAATAG TATCATGGAC GCTGGACTTT   46380

ACTCCAAAGG GCATGGGAGC CATCAAAGGG TGTTGAACAA GGAGATGCAC ATTATAGAAA   46440

GGCCAGGAAG GCCTCTGGGA TCTCCTCTTC TCCAAACTGT GGCTCTGGGG ACAGCTCCT   46500

ATAGTGGTCT TGGGCAGCAC CAAACTGGTG TTTAGGCTCA GCTCACATGC AGCTCACAGC   46560

AAGATGGTGA CAAATGACTC ATCCTCAAAC AACAGAGCAG GCATAGGAAG GAGGCCCCAG   46620

TTAGGATCTT GCTTACCTGG TTTGCTGGTG GCCTATGCAT TTAATTGTAG AACAGAATGC   46680

CAAGCCACTT TTTAACCTTT CTTCTACACC ATGCCCTGCA CCTCCCCTTC TCTCTCTGCT   46740

CTTCTCCCTT CCACCCTCAA ATTTCTAAGC CATGTCCAGG TCTCGTTTTC ACCTGTGCCA   46800

GAGAAGATCT ATCTGACTTT GGCCATGGAA GAGGTATAGC AGGTATCAGT TGGAGAGGGC   46860

TGGAAAAGCT CCCTGGTGCT AGATATGGAC GACCTGAGCT TCCAGTCCTG GCTCTTGCAG   46920

CCACCAGGCA TTTGACATGG GCAGAAGCAC TTTTCCTCAC TGAGCCTCTG TTTCCTCATC   46980

TGTAAAATGG GAATCATGGT GATGGTGTGA TATTTGAACA AGTTTTTTTT TTTTTTTCAA   47040

AATTGCTTTG TAAACTGCAA AGCTCTGAAT AAGTGTTTAT TTGGGATTAT TAGGAACTGC   47100

TTTGCTGGAA CAGTCTACCA GAGGGATGGA AGGAGAGGAA CTGAGAAATC CATTCTTTGA   47160

AATATTTTTA TCATATGAGA TACAAATATG TATCTATATA AATATAGATA TAAATATGAA   47220

CAAATATATC TGTCATAAAA TTTAAAAAAG GATGAACCTT GCCCCAATC  TCACCCCTAG   47280

CAGCAACTAT TAATTTTTTG TTGTATATCT GCCCAGACAC ATATAAAATA TATATTCAAA   47340

CAAAAAATAT AATCATATTA TAAACTTTGT TTTTTAGCTT GTTTATTCAC ATTACATGGA   47400

AATCTTTCAG CATCATGGCA TATAGATCTG TCTTTTTAAT ATTACTTCAT GGTCTAGGTG   47460

AACCATAGTT TATTTAGCAT TTTCCTTTTG GTAAACATTA AAGTTAGTTG CAATTTTTCA   47520

TCATATATTT TTTCTGGTCT TTTGTACATA TATCTATGAG AGAAATTCCT AGAAATAGGG   47580

TTGCTGACTC AAAGGATACC AGCATTTTAA ATTTTGGTAG GTACTACCAA ATTGCTCTTC   47640

ATAAAGAGTG TACAAATACA CCCTCCCACA AACAGAGTGC CTGCCTTCCA TGCCTGGACC   47700

AACCACAGG ATTACCACCT CTGCTGAAGC TTTTTCATGA GACAAGGTCT TGCTCTGTTG   47760

CCCAGGCTGG AGTGCAGTGG CGTGATCTCT GCTCACTTCA ACCTCTGCCT CCCAGGTTCA   47820

AGTGACTGTC ATGTCTCAGC CTCTGGAGTA GCTGGGACTA CAGGTGCGTG CCACCAAACC   47880

TGGCTAATTT TTGTATTTTT GGTAGAGATG GGGTTTTGCC ATGTTGGCCA GGCTGGTCTC   47940

GAACTCCTGG CCTCAAGTGA TTTGACTGCC TTGGCCTCCC AAAGTGCTGG AATTACAGGC   48000

GTGAGCCACC ATGTCTGGAC TGCTGAGGTT TTTTTTTTTT TTTTGAGACC AAGTTTCACT   48060

CTTGTAGCCC AGGCTGCAGT GCAATGGCAT GATCTTGGCT CACTGCAACC TCCGCCTCCC   48120

AGGTTCAAGG GATTCTCCTG CCTCAGCCTT CCAAGTAGCT GGGATTATAG GCATGTGCCA   48180

CCATGCCCAG CTAATTTTGT ATTTTTAGTA GAGATGGGGT TTCTTCATGT TGGTTAGGCT   48240
```

```
GGTCTCGAAC TCCCAACCTC AGGTGATCTG CCCGCCTTGG CCTCTCAAAG TGCTGGGATT  48300

ACAGGCATGA ACCACTGCGC CCAGCCTTGC TGAGGCTTTT AAAACCATGA AACGCTCCTC  48360

CTCCCTCAAA TGGTCATGTG GCCACTGCCT GCTTCATCAC ACTGCTCCTC TGTCTGACAA  48420

GCCTGTTCTT ATATAACACC AGTAGGTAGG GCCATCCGAG ACATGGTTAT CCAATAAAAT  48480

GGTAAGAACC AGCCCTAGGG TATTTGGGAA ACTGGCTGTG AGGGTTCAAT GGAATATTCA  48540

CATTTCCAAA CATAAAATCT AGCAGCAATG GAGAAACGTA CTTTAAGCAG AGAGTTTTGC  48600

GCCTGACACA AGAAATTATT ATTATTGTTG TTATTGAAAG TTCTGACACA CAGATCTCGG  48660

TTGTGTTTGG AAGGAGGATA GTCAGAGAGA GGAGGAAGGT ATGAAGAGGT CGAGGTGTTA  48720

GTTTTAAAAA GTGTGTCTTT GTCATTGTCG AGCTGTGGCT GGTCCCACAA CCTGGTTCTA  48780

TCAGGCCTTT GGTGTTACAA AATGCAAAAC ACCAGGCAAC CAAATAGCGT TTCCATGGAA  48840

GTATCCCATG ACCTCTGGTG CTGTGTACAG GTGAGACAGT GAGCACTCAG AAAGGGATGG  48900

CCTGGGTGGG GAGGGCGAAA GGGGCCTCTC CAGCCTCTGC AACATAAAAC AAGGGGCCAA  48960

TGGAAAGTTC TGGAACTGGA TCACTAAGAA GACAGGCCCC ACTGCTGGCA TGAGTGGGAT  49020

GACCAAAGAA TTAGGAAACT GAGATTGGAG TTGGTCACCA ATTCAACTGG CCCATTTAAA  49080

AATTTTCATA GCAGGGACA GAGGATCAAG CCAAGAGCAC TAGGGAGATG GTGATGAATG  49140

GAAATTGTGT AAGGTAGATG GCTATGTGCC GGGGAAGGAG GAGAGAGGAT TCAGAATTAT  49200

AGGAATAATA CATGAAATGA CTGACAAAAG TAGCCTTTTA TGTGTGTTAT GTAATTTAAT  49260

CCTCTTAACC TTATAGAGTT AGCACTGTCA GGATCCACAT TAAAAAAAAA AAAGACGAAG  49320

CAGAAGCTCG GAGAAGTCAA ATTACTTGGC CAAGGTCAAG GTCACACAGC CACATGTGGC  49380

AAATCTGGAA TACAAACTTA GGTCTATCTG ACTTTAAACC AAAATGCTGC ATATAGCTTC  49440

GATTTCAGCA CAGCAGGGTT CAACTTGGAG ATAGAGGGTG GTGTTATAGA TTACCAGATA  49500

CGATAGTGGT AGGTTTTCTT CTGTCTTGAT GAAAGATGAG CTATTTTTAT CCTGTTGCAG  49560

GACAACGCGA AGGATCATGA CTTCCATTTT TGAACTGACA TTGTAGATTT GTGTATATTT  49620

GACAGCTCTA CCACATTCCC AACCCTATGC CCTCCTATCA CTCTTTTTGA GAATACTGGG  49680

CTAGTTGGGG GCAGTGTTGG GGGACTTGGG CCTGGGCGTA TGCTGGGAGG AAAGGCAAGG  49740

AGATTATGCA GTGTGGTAGT AGGGACTGGG GGAAGTTTTT TTGTTTTTTG TTTTTGTTTT  49800

TAAAATCCTA GTTGGTCCCC AGTGGAGCCT CCAGACCTCC TCAAAGTCTT TGAGGTTGTG  49860

ATTAATTACC ATATAAACTA GACAGTCCTT GGCCTTGGTG TTGCCATTCC AGCCTGTAAT  49920

TATCTTCATC ACAAGTTGCT GTCTGGCTTT GTTCTGTAGG TAGAGGCTCT TTCGTAGGTC  49980

CCTGCATGTC CCTGAGTCAC TAGCAGGCTC ACTTGTGCTT ATCCAAACTG GTGAATCATT  50040

AGCTGTCACC CTGGAGAGCA GTGCAGTTTG GGAAGGCGTG GGTGCGCCCA TGGAGAGGGT  50100

GATCCCCTCT CTCTTCTTTC CAGGCATGCG TAAGGAGCAG TGGCAGAGAA TTACGGAACA  50160

GAGGATGCTA TCATAGGTGA CCTATGAGCC AGGCACGTAC ATACGTGTCA TCTCAATGAA  50220

AGCTTTACAG CACAGGTTAT ACAAGTAGTA CACAGGGATA AACAGCAAGG TTCTTAGGTG  50280

GGTTTCAGAC CTGGCTCTGT CATTTATCTA GAGGTATGAC CTTGGCCCAA CCTTCCTAAC  50340

TTGTCTATGC CTTGATTTCC TCAACTATAA AATAGAGATA AAAATGGTAA CTGCATCCAA  50400

GAGCTTTTGA GAGGAATTGA TGCAAAGATG CAAGTACAGT GCCTAGCAAA CTGAAGCACT  50460

CCATGAGGAG TGGTGATGCG GATGCTAATG CTGATGCTGG GACAAACTTA CACCCACTTT  50520

ACAGATGGGA GAACTGAGCC TCAAGTTGTT TAAAGTGGCA TAGCTAGTAA GTGGTAGACT  50580
```

-continued

```
TGGGATGAAA ACCCCAGTCT GTTTCCAAGT CAGGAACCCT TTCCTCCATA ATGCCGTCTG    50640

CATAAATTAG ACTGTTGGAC TGAAAACAA TCCGTTCAAA CCACAAGGGT ACATTGGCCC    50700

AGGTTGCTTC TATGTTTTAT CCTCAATCTG AAGCAATATA ATGAGCAATG TAATGAGATT    50760

ATGTTAATAT TTACTCAGGG TTCTGGGAAA CCCAGAAGGG TTTCAGGGTA AACCATCTCC    50820

CAGCAAGCAA GGGCTCGCCC GCTAATTCCC CTTTCTTCCA AGACTGATCA GATTGCCCAG    50880

TGCCTAGTAA AATGCCAGTT TCCTTCTATG TGGAAGGGAG CAAAGCTGTC AGCTCCTGCT    50940

GGGGCACAGG GAGAGGATGT TTCTTGTGGA TAGGTAGGTG GTGCTTAGGG GTAGAGGCTC    51000

TGAGATCAGG CAGACATGGT TTCTATCTGT CCTCCCAGCA GTGTGTCCTT GGGTAAGTTA    51060

CTTAATGTTT CTCAGCTTCA ATGTCCTCAT CTTAAGATGA GGGATTATCA TGCTACTTTG    51120

TGGGGCCTTT GTGAGGATTA AATGAGATCT TAGTATCTGG CACATAGTAA GTGCTTAATA    51180

AAAATAATAA GGCAGAGCTG GGTAGATTGA GGGTTTGGTT TACAGCACTT TGACAGCAAG    51240

TTGCTTGTTT CCTGCCATTC AGAGACCCTG GCCAAACTAT GTCCATTGTG GCCACAAGAC    51300

CATTGGCATG TCAGCCTCCA AAAGAGAGAT GACTGCTCAG CAGGCATTAA CCAGATCAGA    51360

GGTTCTTTGA TTCAGCACAG TGCTCTCTTT TTGCACTGCT CTCAGTCTAC CAACAGTATC    51420

AATCACAGCA ACCATTCATG GTGCAAGGTG ATCTCCCTAA ACTTACATTA TATCTTTAAT    51480

CCTCACAGCA GCCTTGGGGG ATGGTATTAT TTCCATCTGT AGATGAGACA ATAGGGGCTC    51540

AGAGATGGTA GGTAATTGCC CAAGGACACA TAGCTGTTGG AGAAAGTAGT ATTGGAGCAA    51600

AATCTATGTG TGTGCATCTA GATTGACCAA CCTTCCTGGT TTGCCTGGGA ATATGGGGTT    51660

TTCTAGGATG TGGGGCATTC AGTGCTAAAA TCAGGAAAGT CTAAGATGAG TTGGTTACTC    51720

TATATGCGGC CTCTCCGTGG AGGGTTGGTT GGTGGGCCTG GAAAAGGGAT AGGGATAAGA    51780

GAGAGAAGAG GAGGACGCAG AGAGAATGGC AGAAGCAACT CTGCACTGTT TCTTTCTGCA    51840

AAGATGTCTT TTCAATTCAA CCTGCTTGTT CAGTTCAACA AGCAGGTTTG AATGCCCTCG    51900

TCCTTGGAGG GAGTCACGTC AGGACTTTCC GGGTATTTGA CCGTGATGAA GAGCGCTGTC    51960

TGCCAGGGTT CGCCAGGCTG GGTGTGGAAA AATGGTGCCC CAAACCAGCC CCACATGGCA    52020

GAATAGGAAA CATGCTGTCA TCTTGCTTCA TCTGAATCTC CATTCCATGA GGGCAGGAAT    52080

TGTTTTCTTT TTTACTTCTA TAGCTGAAGC CCCAGTGCCC AGAATATGGC AGAAACTCCA    52140

GAAACATTGG TGGAATGTAG ACTATTGAAT AATTCCAAGT ACAAACCAAT GGTCCAGGGA    52200

GATTTAGATT CTGATGAAGG CAATCTGGGG AAGACTGAAT GGAGAAATAG CATTGGAAAC    52260

GGTTTGGATA CCACGTGTTG GGATCAGGAA GCAGAGGAGC ACAGAATGCT TGTGCAGAAG    52320

TGACATGGGC CCACTGCACC TGGGGTGGAC CCTGTGAGGT AGAGTTGGAG ACCAAGGGC    52380

TGAGGACTGG ACATGTCGGT GGAGACCAGG TGGTGGAGGA TGGAGAATGC CATGCCCTCA    52440

GGGAGTTTGG ACTGCCTGTC GTTAAGCCAT TTTTTTCTCC AAATTTCAAT CCCCCTCATT    52500

CCATTGTCAC CATATTTGCC ATGTCTGTGT ACCTACCTAT ATTACTTATT TAACACTTTT    52560

CCTTCAAGTG ACTTACTTTT TAACTTTACA TTTGTTTTCA TATCAAACAC ACATGGCTGT    52620

TAAAATAAAA ATTACGATTT GAACTTAGAA TCATCTTGCC TACCACATGA GGTAGGTGTA    52680

CTTCCCTCTG AGGACCACAG CTCCAGCAAC TGGGGAACCG ACAAAGATTT TTGAAAGAAG    52740

AAATGATTCA GTTGCTTTTT GGGAAGACTA CACACGTGAG GAAGTACTGA GTGGAAGATA    52800

TGTGCATAAA ACATTGGCGC AATTGTGACT AACATGGTAA GAAATATTAT CAACGCAAGT    52860

TTGGGGGGCA TTTCAAAGTC TCTCAATGGT CATCCGGATG AAATATGCAA GAACTGCTCT    52920

CTCTCTCTCT CTCTCTGTCT TTTCTCTTCT TGGTCTCACT TTGCCCTCTT TCCCAGCAGC    52980
```

```
TCTGCCTTCT CCCCCATGCT TGCTGCCAAC AGCTCTGAGG AATGGGAGGG ATTGCAGTTC  53040

AAAGAGTAAA CAGGTCTACT CTGAGTAAGG CTGTGGGCTG TGCAGTGACC CCCAGTGGGT  53100

CTGGGTGCCT GGTAATGATG CCTGCACTGG CATGATGCTG TGGCTTTCCA GGCTTGTTTT  53160

ACCTGGTTGT GCAAAGAATG TTACCCCCAG CCAAGGCTCA AGTTCACAGA CCATTGGCCC  53220

ATCCCCTAAT AAGCATATTA TTCCCAGCTG GGCATTGAAC TTCCAAGTTA AGGTGACCTG  53280

CCAAACTGGA AGAAAATGG ATTTGCAAAA ATCAGATGTT TGCCAACAGC ACCATCCCCC  53340

ACCACAACCA TAGACAATTG TGAGATCTAA AGTTGGACTC CCTGAGGTTT TCTGCCCTGG  53400

TGGTTCTGGC AACTCCTGGA GAGCCACAGA CTGATGAATT TGAGGATCAT AAACCTTAAG  53460

AAGACTTTAA AGTATTTTTG GCATTAATTG ACAAAGTCCA CAGCAAGCCA GGCATGCTCT  53520

TCTCTCCCAC TCCCCTTGTC AGAGATGTCT CTTTCCCCTT GCTCTTCTTA CCCCATTCTT  53580

TCCAGCATAA CCAAGCTTAA TAGCTTCCAT GTTTCCACTG TAAGGAAGTG AGCCGAGTGT  53640

GGTTGGTCTG TTTCACAGCA GGGCTATCCT CACACGAAAA GTTTTCAGAT GCATTGACTA  53700

TGCAGATTTT TGGCTCAGTT TGCAGAAGAC TTCCTTATTT CAGTTTTACT GTACACCCAC  53760

CTACATAATA CTTTTTGGTT CTTAGAATTT CAGAGCTATT AACCTCTAAA CTTAAATCAA  53820

AATTCTCATC AAACTTTCCT AGGGCCTTGT CATAAAAGAA ACTAAGTCTC AAAATAGGAC  53880

TTTTTGGCCT AATTTCCTTG TCCAGGAAGA CAGATTGACT AATTCCAAAC CCTGGACTCA  53940

CATGTGATTG CTAAGAATAG GGGTGGGGGA GAGAGAGGGG ACAAAAGTCA TAGACATGCC  54000

ATGACACATA TTGGGAGATT TCATCTGAAT TTCCCCTGAG TATGAAATTA TTCAGAAATA  54060

ATTCCAAGGG CTTCTTTTCT GACATTCCAC CAGTGTGCAG GTGCATATGT TTTGAATGAA  54120

CTGAATGGAT AATTTATTTA TACAAATGAG TCTTTTTGAA TAGTTGCAAT GGATGTGCTG  54180

TCAACTCTCC AATATCACTT CCAGGGGGTT TGTAGATGCA TTCTTTCCAT GGGCATCAGC  54240

AGGTCTGGAT CTCCTGCTTT CTATCTGAAA GGCACTGGTC TGGATCTCCT GCTTTCTATC  54300

TGAAAGGCAT TATGGGCAGC AGTCTGGTTG ATTTTATACT ACTTTGATAC ACTCTCAATT  54360

GCATACTAAG AATGAGGATG GAGAAACTGA TAGTGACCCT CACCCCAATT AGGTTTCACT  54420

ACTGCCCTTG ACCTTCATAT TTAATGCCTT TGTTATCACA GCAACTCTTT GCTCTATTTC  54480

TGGATCCAAA TGCCTAAGGA TCTCCCTGGG GTGTTAAGCT TGCTCAGTGC TATTAAACCT  54540

GGTGGGTGGC AGAGTGACCT TTGTATCACA AGAGCCTCAT GACTTCCCAG GCAAGACCAA  54600

GTCACAACTT TTCCAATGGA TTTCCCCTCG ATTCTTATTC TGAGCATTTA GCTTTTTAAA  54660

TATTTGGCTC TGAAGGGCAG GGGCTAAACA TTGTTCTGTA AGATCCAAAC CTGCTTGTAT  54720

ATTTTATACT TTTGTTTTTT CATTTCAACT TTCCGATCTC GCTCTTCTGA GAAACATTCA  54780

CATTTCCAAT TGCATTCCAG AACTGAGCTT GACTTTCCAT GTCCATGTAA GATCTTGTAA  54840

TTCAAATTTC AGCCAGCTGC TAAGCTTCTC TTTTCTGGAG GGGATTGTGG TTAAGAGATC  54900

TTGTTTTGCA ATGACGCTGT CTGGTCTGAG CTCCAGCTAC TTGTCTTATT TACTGTGCAA  54960

CCTTGGCCAT GTTAACTTAT CAGGCTCATG AGGCTCGGTT TTCTCATCTA TAAAGTGAGA  55020

AAATGAATAG TACCTATCTG ATGGAGTTTT TCTAAGGCTT AAATGAAGTA ATGCAAATTA  55080

AATTCTTAGT CTAGTCACTG GGAAAAGATG AAAACTTAAC GAATATGAAT AGTCACTATT  55140

CTGTTTCTTT TTTTCTATGC CATTCCGGCT TCACCTCCTT CTCTTACTTT TTCCCTTTCT  55200

TTTTTCATTT GTTTTCTTTT TTTTTTTTT CTTTTTTGAG ATGGAGTTTC GCTCTTGTTG  55260

CCCAGACTGG AGTACAATGG CATGATCTTG GCTCGCTGCA ACCTCCACCT CCCAGGTTCA  55320
```

```
AGCGATTCTC CTGCCTCAGC CTCTCGAGTA CCTGGGATTA CAGGTGCCCA CCACCATGCC    55380

TGGCTAATTT TTGTATTTTT AGTAGAGATG GGGTTTCACC ATGTTGGCCA GGCTGGTCTT    55440

GAACTTCTGA CCTCAGGTGA TCCACCCACC TCAGCCTCCC AAAGTGCTGG GATAACAGGA    55500

TGCCGCACCA CTGTGCCTGG CCTCTTCTAC TTTTTCTTAG AAACATGGAG GGTTAGTTCT    55560

CTGGCCACTC ATATGAAACT TCATTCCCTG CTAAGGTGGA AGTATTGGAG TTCAAGCTCT    55620

ACACTTAGTG GAGGGAGTAA ATAAGCATTT CCAGAGAGCC CACCAAGTGC CATGCAATCT    55680

CCTAATGCTT TGTACTATTT CTCATTTAAC CCCCCAAACA GCTCACTGAG TATGTTAATA    55740

TCCCCAATAA ACAGATAGGG AAACTGAGAC CTAAAGTTTG AGCAAATATG GCAAAGTTTT    55800

CCTAGGCTGT CTGGCTTTAA AAACAATGTC CTTTCACCGC ATCAGGCTGC TTCTGAGGAG    55860

CAGAGCCACC TTGCTTTTGT AAGTCTGTTG GAATAGGCTC TGAGATGCCA CACGTTATCC    55920

CAAATAATTA GGCATCTGGA TGGAGATTTT ATACATTTTC TACTTGGACC TGAGTTTGCT    55980

GTCTCTCATG GTTCCTGGGT GAAAGAGGCC AGGCCCTGAG ACCTTTACCC AAGGTTGGCT    56040

CTACCAAAAT ATCTTCTTGA GTGAGTTCTC TGGTTGATCA TCTGTGGAAC AATGTGGGAG    56100

CCTACTAAAT ATGAATGGAA AATGAGGAAT GCAAAATGGA TGGTTTTCTC CACTATCACC    56160

TCACCCTTGG AGGTGTTTGC TGATTTGGTA GATGTGTGGA GGAACTCAGG AGTCTGAATT    56220

TGTAAAGGTA ATTTGGATGC TTCATTAGCT TAGAAAGGAC ACAGCAGGGA GAACTATATA    56280

GCAGAGAAGG CTGGATGCCT ATGAGGGTAG GGAAGGGAAA ACAAGGGGGT GGGGCTGTAG    56340

CTGCCCTACC TCCGGTCCAT ATATGGCTGC ATTTCTTTAA TCTCTTTTAC TTTTGGGATT    56400

CCATGGTAGT AAACAAAGAG TTCTTATGTT AAAACAATTG CTATCTAATT GTACAGCATG    56460

GTGAATATAG TCAATAACAA TGTATCATGT ATTTGCAAAT TGCTAAGAGA GTAGATTGTG    56520

TTTTCACCAC ACACAAAAAT GGCAAGTATG TGAGGTAATG CCCATGTTAA TTAGCTCAAT    56580

TTAGCCACTC CACAATGTGT GTGTGTGTGT GTGTGTGTGT GTATATATAT ATATATGTTT    56640

ATGTATATAT ACACACACAC ATATATATGA CATGTCAGAA TGTCATGTTT TATTCCATAA    56700

ATATATACAA ATTTTATTTG TCAATATAAA AAGAATAATA CCTGGAAAAA CAAAAAAAAA    56760

ATCCTAAGTG CTATACTTAT AAAGAAATCT TCCTCATACA AAAAGAAGA AATTCTGGCC     56820

ACAGGAAGGT TGCCTGAAAA TGGCCACCTT TTTCATGATT TTCCCTCCCT TTCTGAGACT    56880

GAGAAATGAG CCTTCTTGAA GACCCTGATG GAAATACTGT GAAGAAACTA AGACAGTTGG    56940

ATTCAAGAAC CAAAATGCTT ATCGTAGCAG TGAGGTTGGC TTGAAGTCAG GGAACAGTGT    57000

AAAGCTATTT GTGGGAAAG ATAAGGCCAG AAAGAGATTG ATAAAATACA GGCGAGACCA     57060

AAGGAACAGG GCAGGGCAA ATTAGTTTAG GCAAGAATAG AGGCGTCTTG ATATTAATTA     57120

AAATATGGAG GAGGAGTCCA GAAAATTCAT CCTTGGTGCT TGGGTAAGTT TAGCAACATG    57180

TTCAGATGCC TGAGTTTTGT GTGTGTATGT GTGTGGGCAT GCACGTGTGT GTGTACACAG    57240

TGGGTCATTC TTCTCAGGAA GAGTGAGCCA CTCTCCCCTC CTCCAGCACC AAAGTGGCCC    57300

CCACCTTGGC ACGCCAGTGG CACATGCCAT TGGGCCAGGA TTTGCTCAGA ATGCAGGCAC    57360

ACAGACATAA TGTCAGGAGG CATTGCTGGT GTGTGTCACA TCAACCTGTT AGAACAACTG    57420

TCAACGTGTG ACCTCCCAAA CAGAACTCAG GTGCCCCCTT CAGAGACCGT AAAGCTTGTC    57480

CTTAGAGGAT AATGAAGATC CCCAGGAACC TCATCTAATC CAAAACCAAA AGATTTGGGA    57540

AATGTGACCT TTAGAGGGGA GTAGCATTAA GAAGCAAAAT GATACTTATT AATTCTGTTG    57600

CTTATTTGAC TGTAACCAGT ATAATAAATG ATCATATTCT GCTCGATTTA ATTCCCCCTC    57660

CCCATAAGTT TCACAAGACC AGAAGGGAGTT TCTTCTTCCC ATTGGTCTTA CATTAATATT    57720
```

```
CTTGTACGGC TTTCACTAAA TAGATGCCGT GTTCTGCCCT GGAGGTAACA CCACGTCATT 57780

AGGAGGAGAT GATAGACAGA AATATATACA AACACACACT TGCTTTCAAA AATAAATATA 57840

GGCCCTCTAG TTAAAAGGTA TTGTGTAAAG TGTGTGAGCA TCCTCTTTCT TGCAAAGCAA 57900

GCACACAGCT TCCATTAATC TTGTAGCCAC AGCCTGTGTT GGTGTTAAGA CTCAGATTCC 57960

TTAACGCTTG ATACTTGGCT TAAAGAGATT CTTTGTCCTG GCCTTGATTT GGGAATTAAG 58020

ATCCCTAGGG TTTTTGGTTT TACAGTATGG ATCTTCTAGG AGACAACCCG ACTGACCTCC 58080

GGGTCTCCAG GCCACCACAC ACAACCTGGT TTGCTTTGCT CTGTTCCCCT TTTCCTCTGT 58140

GGGGACCAGC ACAGGACTCA ACTCAAGGGC TCTGTGTCTG TGCACAGGTT GGAGAGGGTG 58200

ATAGGGCCTT GACCTGTAGG GACAACCAGG AAGATTTCTA TGCAGAGTAA TTGGGTTTCT 58260

AGAGTTTGTT TCAGTTGATT TGAGGGCAAG CTGCTTGGCC TCTCTCTCTT GATTCTTCCC 58320

ATCCACAGAA TAAAGACAAT CAGCTTTGTT TATCACTCTG TTCATTTTGC TATGTCTTTA 58380

TCAGCCCCCC AGAGAATTCA GGAGCACAGA ACAAGTGCTG GAGGTCTCTC TTGCCAGAGT 58440

CCTCCTTGAG AACTTACAAT GTGTCCATAT TAAGGATCTG CTGTGTTTGA TGATTTTGTG 58500

ATTACACTTT AAACTTCTTA TCCATAAAGG ACATACTTGA TATATCTGAG ACTTGTAGTA 58560

GAAGGCCTTG AGACATCCAT CTCATCCCAT CATTATCTAT CTATCATCTA TCTATCTATC 58620

TATCTATCTA TCTATCTATC TATCTATCTA TCTATCATCT ATCTATCTAT CGCCAGTACT 58680

GTCTTGTTGA AGTTGGCAGT AGGGTGAAAG ACCTCAAACT CCAAAGGACT TTCCGTATGG 58740

ATGCAATATA CCTGCAATTC TAGCTTTTTT GTGTTTTTTT TTTTAGGTTG GGGGTGAGGG 58800

GTATTGTTTT CATTTTTGTT TTTCTTCTGG AAGGTTCAAC TAAGACCCAA GTAAAAAGAA 58860

GAATCAATAC TTAATAAGTA CCCAGCAAGT AGCAGGCACA CTTTTAGGTA CTTTATTTAC 58920

AAAAAAACCT CCACAAATAA AGTGGCTTGT GAGTATGAGG TGACATCTTT CCCTCCCCTC 58980

CCACCATCAC TACCCCAATA TGACTCGTCT CAATAGCCCT CCAATCTAAA ATGGACTAAA 59040

TACAAGTGGA TAAAGAAATG GAGATTTAAC CAGAATTCTT CAGCTATAAA TTACAGGGCC 59100

TATAATTAAA GGTGATTGGG ACTGGGTCAG AGAGCCACAT CACTTTTGTG GTTGCATTTG 59160

AAGTTCACTA TCTCTTGACC ACACAACCCT AGCCCTTCTA CTCCCACCCT GCTGTCTCAG 59220

GTTAATCTCA GGCAATGGTG TAAAGAAGGC CAAGTTTGTT TCCCTGGAGT CCCACGGGCT 59280

CTAGCAATAA TGCTTCCCTT TTCTCATGAG TGCCCCGCCA CCCACCCCCC TTCACCATCA 59340

CTACACACAA ATGCCCTGCA GTGGGTGGAA TGTAGTTACT TCAGGTTGTG CCTGATTTGT 59400

CTCTCAAGCA AAACTCCAGC AGGCCATTCC CTCAGGGCCC TGCTCTCAGA TCTGGAACTG 59460

ATAGACTAAT TGGGCTAAT GTGATAATGG GAAATAATGA AATTTGTTGT TTTTATCAGT 59520

GTGTATATGG GGCGGGGTTT ACATTTGCAT TTTCACAGGG CCCTTGGCAA GTTCACAGGG 59580

TTGAACAGTT GGGAAGGGTG GGAATGTCTG GGCAGGTTA GGGAGGCAGA GGGATTTATT 59640

AGAACTCCCC TAAACTGCAC TGACCAAAGC CTCAAGCCCT TCTTCAAGAC CTGCCCAGCT 59700

TCCAAGACCT TCCCAAGTCC ACCCTTGTTT TCCCACTGAG TCTTTTACAC TTTCAGAAAC 59760

CTCTGAATTT GTGTAGAAAC TAGAAAAAAT AAGTAAGAAA AGACTAATAC TACTGCACAC 59820

TCACTGTTCC CCCTTAATAT AATAACCAGT TTTTATTCTA TTCAGTCAGC CTTTGACCAT 59880

AAGCAGACCT TTTTTTTTTC TTTTTAACAC AAGTAACTTC TTGGTTTTGA TCACAAAATC 59940

TTTATCTCTG CCAAATCTCA ACTTCCCTTC CCTCTCCCAC AAAAGGGAGG CCCGTTGAGT 60000

CAAAGAAATC TGCTTAGACA CTTTGCTCAT GCCAGGCCAG TGTCCTGGAA GGTTCAACAG 60060
```

```
-continued

AGAGAGTTAA TGGTTGGGGG ATGGTATTTT TCTTTGCTAG GAGCAGTCAT TCACCCGTAT 60120

GGGAGAAGGT ACATTTGTGA CCCAGTGAAG CAGGTACAGG TAACTCCCCA TATGTCCCTT 60180

GGCCCAAGGG AATAGAGGTT GCCTGGGTAT TTGAATCCGT AGATCCTCCC TAATATTCCA 60240

CCTTCTTCTT GTCCAAACTG TGCTTTTTTA TTTCCAGTTT CAGCATTTTG GTCTTCTCAT 60300

CTCTAACTCT TATAGGGAGT GTCAATAAAC CTTTTAAAAA AGATCATGTA AGTGTCAAGA 60360

GGAAGTGAAG AACCTAGATA ATCCACCAAC CGGATAATCA GCTCTTGCAT ATTTGAGAGT 60420

TGACTGCTTG ACCTAAGCAT CTCCTCATAA GGTACCCTCC CTCCCAGGAC CTTCCCTTTC 60480

AAACCTCTCA AGGCTCTTAC CTGGGGCCAG GGAGATAGG CTTTTCAAAG TCCATTGAAT 60540

TGCCAAGAGT CTCTGTCAAG AAGGCAGTCA TGGTGCCTGG AGAGGAACT TGCTGGGAGC 60600

CCCTTCAGAG CCTGGTACTT ATAGAGCTAG GGAAAAGATC TTGATGCCAA AGCAGGGTGG 60660

ACTAAATACA GACTAATAAA TGAGACAGGT GCTCAAGAGG GCCCCTCCAT ACCATCATCT 60720

CCTCCAGATT TGGACTTCTA CTCACTTTGC TTTTACATTC CCTCTTCCCG ATGGTGTCTT 60780

TGGTGAGCAG GGTGCTTTTC ACCTGAAACA GCCTCTGAGC TGAAAAGAAC AGTCACCACC 60840

AAATCAATTC CTCATCCATT AACAGGTTGT CTCTCTGTTC TTGAGACACA GGCATTACCT 60900

GGTTAGACCT GTTTTGTTTG AACACTAACG TGTGAGTTGG CCAAATGCAA ATGAGCCAAT 60960

GTTTGTAATC CTTTATTTTA TTTTTTTAAA GGGCTGGGTA GCCAATCAGA AGAGGGGGAA 61020

GTGACTTAGG GAATTCCCGG TTGGTGGCTT ATTGCTTAAC ATCCTACAAA ATGATTTAAA 61080

ATTATTGTTA TATGCATTTA TCTTCACTCT GATGAGGGCT CAGACTTGAT AACGCCCGTG 61140

GTGCCCCATC CCTATAGGAG CTGGTGAGAT TGCAGCCTGC TGCCTCCCCT CCATCAGCCA 61200

CAGCTATTGG ATTTCCCACC CAGAATCTTT AGGTAAATGA GGTAAGTCCT GATTTTTAAA 61260

ACTTCTTTTG AATCTGGAAT CCAAACACTT GAGTGGAAAG AGAAGCCTGC TTTAAACTGG 61320

ACAGATGAAA CTAGAACAGA CTCTTGGAGA CGGCTGGCAG GAAGTGAAGC TCACCTTACC 61380

TGGGCTTACC TCACTGGGTC AAATCAGAAT TTTATTTTGG AGGGCAGGTT GGCTACTTTG 61440

GATATTATCT GTGAATTTCC TGCATTGTCT GGACTTCTAA TCTCTGTGAA TTTAAAAGCC 61500

CCCTCGTTTC CCTATGCCTG GGTGGCAAAA CCATTCCCCT GGGTTGAATT CTTCTGGAAC 61560

AAATAGGCAG CTAGAGATAG GTGGCTCTGA TATAGCTCAG AGAAGAAGTG GTTGGCTAAG 61620

TAGCTGTTAG GGCTCAGAGT ACACGGTCTC GCTTTCTAGA GATGTCTTCT GCTGGTAATT 61680

TTTCTGACTT ATGAGCTACA TGGAAAGGCC AATTTGTTTT TAATATGTTC CAGGACTGGA 61740

AAATGGCTAG AAATAGGCAA GAACATACAC AATCACACTG GAAAAAGTGG CCAGGCAGCC 61800

AAGGCAGGCA GAGGTATTGG GGAGAGCTGA ATATCTACAA AAACAAAAAT TCAGAAAAAA 61860

CAAAAATCAA TTTTGGCAAA GGGCTTCACT GTATAACAAG GGGACAAACT AACCCTTTGT 61920

TTACAAACTA ACCCTTTGTT TACTCCATTT TGTCCAGAAA ATACAACAAT CAGTTTTGGC 61980

AAAGGGCTTC ACTGTGTAAC AAGGGGACAA ACTAACCCTT TGTTTACTCC ATTTTGGGAG 62040

ACTATGATCA GACAGGCAGT TGTGACTCAG CAGCAACAAA TGCCTTCTGA GACAGGGATT 62100

CTTTTGATTT TGCTTGGACA TTGTGGAGAA GTGTTAGCCC CAATGTGGAC TGATCTGGGA 62160

ACAGTGGGAA ATTAACTTCT TGTTGGCAAA TATCAGGCTG AGGTGAGAAA GCGACATTTT 62220

CACCGTCCAT CTTTGCTGAT TTACCGTGCT CCCAGGATGG TGGGAGTGTG TGTTTTTAAG 62280

ATGGAGAGTG TATGCTTCTG GGTTCAAGTT CACAGGTGTC TCTGCTGGTT ATCTGCACTC 62340

ACCTTGGTAA CAGGGAGAAA GTGAGTGAAT GGATTCCAAG AACTTACTGA TGGAAGTCTA 62400

ATTCAGGAGT TGGTTCTGCA GCCATGGAGG TAAAGATGTG TTGATAGTCT TTCAATGTGT 62460
```

```
AAAAGGGCAA TTAGAGATTC TGTGTGACTG TGTGTTAATT CCACTGGGGT CAGGGGAAAA 62520

ATTTATTTCT AACAGAAAAG AAGAAGATAC GTTATTAGGA AGAATTTCAT GGCTAGGAGA 62580

TACTATCAGA AAAGGCTCTT AAGAGATTTT AAGGATGACT TTAATAGCCG CATTTGAAGT 62640

TTGCAGAGGA TCCACTTTTC CTCTTTTTGT GACCTAAAAT TCTGGGATGA TGAAATAACT 62700

CACCAATTCC ATCTTCTTAT AATATGGAGT CATGTAGACA ACACCATTTT CACACAAATG 62760

GCTAATGGTA TTTAAAAACC ATGATGGAAT GTGAATTGGG AGTCATTTGG AGGTCTGTAG 62820

TTGAACTTGA AAAAATAATA AATGTAATGG AGACAATACT TCACCGTGTT TCCAAAATAT 62880

TTTACAGAGG CATTTTAAAT GAAAGTCACT TTGAGGGAAC AGCTGTGCTG TAAGTTCTCT 62940

TACATGACTG CGCAAGATGG TAGCCTTCAT CAAGACCTCT CAAGGTAGTG TGGGTAGGGT 63000

GACGTGTTTG ATTCAGGCCT CGTTTGTTAT GAAAAGGCTC AAATTCAATT GTATTTGTTA 63060

TTTTTTTGGT TAAAAAGCAC CTATTTGTTC AATTCAAACA ATCCTTTTTG GTTTTTTTTT 63120

GAGATGAAGT CTCCGTCGCC CAGCCTGGAG TGCAGTGGCA TGATCTTGGC TGACTGCAAC 63180

CTCCGCCTCC CAGGTTCAAG TGATTCTCCC AACTCAGCCC CCCGAGTAGC TGGGATTACA 63240

TGTGCTCGCC ACTATGCCCA GTTAAGTTTT GTATTTTTAG TAGAGACGGG GTTTTGCCAT 63300

GTCAGCCAGG CTGGTTTTGA ACTCCTGACC TCAGGTGATC CACCTGCCTC AGCCTCCCAA 63360

AGTGCTGGGA TTATAGGCTT CAGCCACCGT GCCCAGCCAT ATTGTTTTCA TTTTTAATCT 63420

ATTAGTCTAT CGTGATCTCC CAGTGGAAGT ATCTTTGGCC TTTGTGGACG TCAGGAAAGC 63480

CCTACATTCC CACTCGCGAT TCCATGTTTA TGGGTACCCT AAATGCTCCC ATTAATTGAC 63540

CAACTTTACC CTGATCTTCT TTCAATATCT TTCTGACTCC TTGAAGGTAT GAGACAAAAT 63600

GGAAACTGAG AGGTTAAAAG GTTACTAGG TTGCATTCAA TTAGCGAATT GGAAACTGGA 63660

AGGAGCTCCT ATCGGGTCTC AGGTCAGAAC GTGAGTGCTT TTGGCCAAAG TTCACTTCTG 63720

AGGAAGTAGA ATTTCGCTTT CTGGAATCTT GCGATATTTT ATTTCCTCTA TATCTTTCCC 63780

ATGCCCCCGA CCCACCCAAT CTCCACAAAT TTGGGGATTT GAGCACTGGG TTGTGATCGT 63840

TAGACCATCT TGCTTTTCTG AAAGCCCAGG GCAAGACCCC TGCTTCATGT CACAGTATCA 63900

AACACAGACA TAGAAGCTTG TACAAATTAT TGAGAAGTTA TTGTCTTTTC TCCCTTCCTC 63960

CATATGGAGT CATCTCTATG CCCTTTCATA CAGATGTGAT TTACGAAGAC CTCTGGGTTA 64020

GGGGTGGGGT GGTGAGCAAG AATCCCGTGG CAGAATCTGC TAACACACTT GAGAAGCAAT 64080

GTTGTGGTTT TAAGGAACTC AATCTAAAGC TTGAACCTGA TTTTCAGGGA TACCATTTTG 64140

CTGCCGTTTC AGCCCATTTC TCTTGTTAAG ATCGCTCTCT GGTAGAGTTG ACGTGACACT 64200

CATTTCTGTT GTGGGTGGGG CCCTGGTTGG GAGGCATTGG CTCCACTGCA GCCTGGGTGT 64260

CTAGAGACCA CATTCTCACC CTGCCTTTGT TACTGGGAAA CCGAACGCGG CGCTGTGGCT 64320

TTCAGCTTGG GTAAGCCGGG TCTGCGGCGG GGATTGCCAT CTGAAGACAG AGGCAGGAGG 64380

GCAGCCACAC CTTGCCCAGG TTCTCTTAAA TCTCTTGCTC TATAACTGAA AGGAGGGCAT 64440

AGATAATTAA CTTTATTTGA CATTTTTCAT ATCTAATTTT TAAGAATATG ATTTTAAAAT 64500

AATAGATTTG TTCTAAAGAG CAAACAATCT TGCTGTTATT AAAAACGTGT TTACTTAAAT 64560

TGAACGGGGT TTCAAAGGGC CAAGCTACTA AGCTGTGCAG GAAACAAACA GTGCAGTGAG 64620

GAGAATGGCT CCTCACCACA GCTATTCTTA GGGTGGGACA TAGTTTCAAG CCAAATGACA 64680

TTGATGTCCG GAAACCAGGA TGTGCTGAAG TAGAAATTTC CAGGGATCCC TCAGAGTTAT 64740

TTGCTAAAAT GTTTATTATT CTTCAGAGGG GGGTGGAAAT ATTTCTTTAA GAGTCTTCCT 64800
```

```
TGAAGAATTT TGAACTCCAG CTTTGGAGTG ATGGGAGCAC AGTGCAGGGA AGGCGGGATG 64860

TGAGGTGGTG TGCTGGACGG CAGTCTAGGG ACCTGGTCTA GCACTGGCAG AGCTGTGTGT 64920

CCCAGAGCAC ACATTCCCCT TTGCCAGGCT TTAGTTTCCT CCTCTAGGCA AAAGGGTTTG 64980

AACCTGACCA TCTTTAAGAT CCATTTTAAC CCTCAGATTC TGTGGCTGTG GTGATTGGGG 65040

GTGGTGGGAG TACCTGGGGG TCAGCAGGAT AAGCACGAAT CTGTGAGAGC TGAGAACAGG 65100

TGGGAGAAGC CTTCTAAGGA TGAGGCAGGA AAGATTAGCA AGAGCCCTTA AATGGATTCT 65160

TTAGGGCCTT CAGAATTTTG GCTAAAGGCT ATACTAGTGG AGGTACTAAG ACCTGACACC 65220

TGGAGCCTTT ATTAAGGATG TTAGAATCCA CTCCCATGAC AACATCCCAG CTTTGCCAAT 65280

TTGCCTCATG TGTCTCAAGC TGGTGGGAAT GTAGAAGTGG ATGAAACAGA CTGTTTTGTG 65340

ATGGCAGGGA ACAGCCTATG CACAGGGGCA GGTGCTCTAC TGGTGTCTTC TATAAAACGC 65400

CAAAGCAGCC CGCCAGAAAA TGGACATTTA GGCACTCGTG GTGTCTACTG AGTTTGTATG 65460

GTACTGATGA GCTTGCTTGA CTGATTATCC ATGACTTACT GAGTAGATCG AACGTATGTG 65520

GACTCACTTC TCCTAGAGGA AGACCCTGTG GCTGCCCCAG CCACTGAGCA GCCTAACCTG 65580

GAGACCCTGA TGTGCCCAGA AAGCGTCAAC CTTGTATCTG GAGAAACCAG AACTTGCAAC 65640

AGGGCCAAGC AGGGTGGCCC ATTTAAAGAG GCTCCTAGGG TTTTAATTGA CCTTGTTTTA 65700

AAAGAGACAC CCTGTAAAAT ACTCCTATGA AAACTTATTT CACAAGCACC TAACCGCATT 65760

CTGTCTTTGG TTTGTTTTAC GGGGCCGGGC CCCTTGTTCT GGTCAATTGG TCTGCATTAT 65820

CTCTCCTCCT CCAATCTCAC CACACACCCT GGCCTCTGGG AGGCTTCCTC CCTTCTTTTT 65880

TTTTGTTTGT TTTGTTTTTT TAGCATCTTA GTTGTTACTA GGGGTACTTG CCTACTTATT 65940

TAAAATATGG CCAGTATAGG TGCATACAAA ATGTGCTTTC TGATTAAAAC AAAGCCAAAA 66000

ATAAAAAGAA ACCAAAATGC CTATTATAGT AGTTGGATTT TTAGACTAAC AGACCACCTC 66060

ATTAACCCTG TCATTTTACC ATAACAACTT ATTTTTATCT TTGTATGACC TTGTCTCAAT 66120

GTCCTTTTTC TTTGATGTTG TTGCAATTAT GAACATCAAA TTTCATAGCT GCTTTTCCAC 66180

CCCACTTTCT ATCACAGAAG CACAATAAAT AATCTTGGGG GCTGGGCTCT TGTTGGCCCA 66240

ACTGTGGCTT CAAAACATTT CAGTTGCCTG TCCAGCCCTT TCTTAGCCTG ATACAACATC 66300

CCCCAAAAGT CTGTTGAGCT TTTCCTGGAA TAAGAAGAGG GTCTTCTACT TTTTGAATAG 66360

AGCAATGGAG ATTGGAGAAT ATGGTCATCT TGTGGAGGTT ATTCCAGGCT TCTTCTTAGG 66420

AACCTTAAAA AAAATCTCCT CAGTAGGGCT GATGATATAT TCTGGACAAT AAGGTGAGCA 66480

GAGTCTGAAA GATGAGAGCA ATTTTCAATC TTGTCATGAT TTCATCTAGT CAGCCTCATT 66540

TCATCTAGTC ATGAGGCTGA CTAATGATAA GACTTGCTTT GTCTTTGCAG TGTACTCTAG 66600

ATTTGACTCT AAATTCAGCC TCTGTCTTGA TCATGCCCAC TTAGAAAATT AGAGTGCAGC 66660

TAGCTCACCT TTTAGTCATC TTAATTCCAC TAGGCAGAAG GCTGTGGGTC AAGGAATGTT 66720

GATGGAGTAA AATTTGACTG CATGTGTATC TGAAGGGGTA GGAGGCTAAG AGATTTTATG 66780

GCTTGGAAGC TGCTGAGATG TGGTGTAAAG AACACTGGAC TTAGAGTCCA GACACCTGAG 66840

TTTAAGCTGG ACTCTACCAC TGGGTAGTTG AATGACTTTG AGTGAGTTAT ATAAGCTCTA 66900

GCATCTAAGT TTTCTCATCT GGAAAATGGA GTTAATAACA TCTACTGCAT TGGGCTGTTG 66960

TAAAGATTAA ATTAACAAAG AATGTGAAAG CACCTGAACA AAAGCTTGTG AGTAAATAAT 67020

TAGTAATTTG TGGAATGAAC ATCAAGGGAA GTCTTCAATT TGGGTGTTTT CAGTGAGTTT 67080

CTGTTGGGTC AGAGTGAATG GATATTAAAT TCTGGGATTT TGGTTTGTGT GTGTGTGTGT 67140

GTGTGTGTGT GTGTGTGTGT GGCGATCAAC ATTGGTTCTT CACTGTGACC TTAGGAAAGA 67200
```

```
AATGCAATAG GGTTTTTATT GGGAAGGTGG GTAGCAGGGA GATGCATGAA CCATATTAAG  67260
GGGGGACCTC CAAATTGAAC CTTGTTTTGA GTCAACTGCA AACCACAACC AAGGAGGTCC  67320
TGGGAGACCT GGGGTGACTT GGGGTGATTG GGTATGCAGC ACATTCCTGT TCTTGTGTCC  67380
TGATGCCTGG CAAGTAGGGA CCTGCAGAAA ATACTGATTC TCCTCCAGGC AGTTCACATG  67440
ACTAGCTTTT AGGAGTGAGT ATACCGTTGC CCACCCCTAA AATTCTTGAT CATGTCTCCA  67500
GATGTCTACT GACCACTGAT GCTGAGGTCA TGAATCTTGG GCATTCTAGA GGCTTTGGGA  67560
AAAAAAATTC TACTTACTTC TTTTGCCCAG ACACTCTGGG GTCTACCTCT TGGTAAATTA  67620
TTCAAATGAG GTTTCTGGTC ATGCAAATGT GGTTTCTAGA GCCTATTTGA ATTGAACAAG  67680
TAGTTCTTAT TATTAGTAAA ACAGCAAGGA TCCCTAACTT GGGGTCCAAG GGTAAATTCA  67740
GGGTTTCTGT GAACTTGGAT GTAAAAAAAA ATTGTGTTTA TTTTCAATAA TCTCTAACTA  67800
GAATTTAACA TTTTCTTTCA ATATGAATGT AGGCAAAACT CCATGGTAGT ATTAGCTGCA  67860
ATTGTGACTA TCACCAGGAT AAATCACATT TTCATGTCTT ATTACACCTA TTACATATAT  67920
CACAAAAAGT GGGTATTTGA TATCAAGTTA GATCTGCACT AGGTAGATAT TCTTATTTAA  67980
TGTATTAACA AGGAAGCACA TATATTGTTA TCAGGTTGGT GCAAAAGTAA TTGTGGTTCT  68040
TGCCATTAAA AATAATTACA AAAACAGCCA GTCTGGCCAA CATGGCGAAA CCCCATCTCT  68100
ACTAAAAATA CAGGTGTGGT AGCACACACC TGTAATCCCA GCTACTTGGG AGGCTGAGGC  68160
AGGAGAATCA TTTGAACCTG GGAAGCAGAG GCTGCAGTGA GCCAAGATCA CACCACTGCA  68220
CTCTAGCCTG AGCAACAGAG TGAGACTCTG TCTCAAAAAA ATTAAAAAAT AAAAAAAAAC  68280
TCTGTAATTA CTTTTGCACC AACATAATAT GATATCACAC ATTTATTTTA AAAGTATTT   68340
TGACATTGTC TTTTAATATA AATTTTTTTA AATCTTATAA TATTTTAATT TGTCATGTAA  68400
AAATATTATT TTGAGAAGAG GCCTGTAGGC CTCACTAGAT TACAAAACAG ATCCATCGTA  68460
CAGATGAAAG GTTAAGAACA CCTCATTTAC AGCATTCTCT CACACACGAC TAACGAAATG  68520
ACTTCTGAAC AGCGCCAGTT GATAGATGTT CTCTGCCAAA AGGGGAATAT GATCTTCCCA  68580
TATGTTCCTG CCTATGGGTA GCCTTGGAGT TGTGAAGGGA CTTTGGCATA ATGAAGATGA  68640
TAATAAGAAT GATAATGGTA ATTTGTTGAG TGCCTGCTGT AAGCCAGGTG GTTACAGTCC  68700
TGTTCAATGT CATGTTTAGT TTAATCCTCC CAATGACCTC AGGAGGTAGT GCATGGAACA  68760
AAGACAGAAG AGATCCCCTG CCCACCCACG GTAATGAAAC ATGGGTACAG GTGAAGGCAA  68820
AAGTGGGGAC TGACCCTTTG GAGATGGCTG ATGTCACGAG TGTGCAACCT GTGCAGTTCC  68880
ACGGGGCCCC ATGCTTAGAA AGGTTCCATG TTTGGTTTAA GGCTCTGCTG TTGCCATCTT  68940
AAAATTCTTC GTAAGTTTTG AACAAAGGGC CCTGCATGTT CCTTTTACAC TGAGCTCTGC  69000
AAATGATGTA GCTGGTCCTG CCTCTGGTTA TGGTGAAATG GAATGTATGA CAACTCCTGA  69060
GACTGGGAGT CTGGGAAGCT GCTGCGGAGA GCCCTCTCCT CATTTTCATC AGGCTCAGCT  69120
ACGCAACCTC TGGTGGAAAG CTATGGCCTG TTGAGGAGGG AGGATGTCGT TTTTGAGTTA  69180
GTGAGTTTTC CAGTTTTGTT TGAGCTCCAA AGCTTTCCTC CAAACAACTG GAAAGATGGC  69240
TGAATAATTG GCTGAAAGGG ATTTAATCCC TTGAAAAACC TTTCTGGTAG GGAGTTGCTG  69300
GCAATACTGG TGGGTTTTTC ATGATTTTAT TTTACAGAGG GCTTGCTACG TAAACCAGTG  69360
AGCCAGGAGA AACAGAATAA AGTCTGTTCT GGAAGGAAAA ATGAGACCTG GTGTGCCACG  69420
AGTCTAGTGT TCTCATAGGA AGGCTCTAAA AACAAACTCA GCTTTCCTGC TATTGAATGA  69480
TTATCTCTAT AAAAGGAAAC TTTACTTCTT CTAAAGGAGA GGTCGTCTAA TTTGTGAGAA  69540
```

```
AATTCAGATG TTATTTGCTT CTTAAGCTGC AAGGATGCTA ATGAAATAAT TCTCATGAAG 69600

TTCTGTTGGT GTTTTAGGGC TAAGTTTTTA TAGACTGTTC CAAAATTCAA AACAGGGATG 69660

TGGACGTAGT GATGGTGGAA GAGGGGAAGA CTTTTCCTCG ATTTCTTTGC CTGAGGGATG 69720

GAATTCAGGC TCCCCCAATA ACATATTCAT GGTCTTTCTC TGGTCAGTCA GTGATGTTCA 69780

TAACACAAGC AAGCCTGTCA TCAGGACCAA TCTGTGATGG CTGAGACATC AGGTGCTCTT 69840

CCAAAAGAGC CATAATTCAC CCTTCATTTC CAAGGTTTT TTTTTTCTTG CTGTTATTAC 69900

TGCTCTTTTA TCATGGTTAA TAAGTCTGAG GTGGCTTCAG ACAGCCAGTC CTAACCCCTG 69960

AGTCAATCTG GGGCCTCTAA CAGGAAGCCA GACTGAAGTT CTGATAGATG GGTTTGAGTG 70020

GCTGTGAACT GTGTTTCTGT AGCATCCAGA CTGATTTGCA CTGAAAGGGA GCTTCCATAT 70080

TAGGGTACAA GGATGATCAA TATGTCTCCT GTTTATATTT GGTGGAAAAA GTTGTGGGAA 70140

TCGTGCTTAA AGGATCTCAA CTTTGAAATT AAAAGTATAA CGTCCTAACA GACATCCTCC 70200

TTCTCTTTAG AAACACAAGG ATCCATTTTC AAGTAATTTC AAAAGAACTA TGTTGCTTTC 70260

CCCACCCCTT CCCAAGTACA CTTATTATAA TATATCCAGT CCATTTGCTA GCTTTGTGTC 70320

TTTAGAAAAG TTGCTTAACC TCTCTCTGTA AAATGGTGCT TATATTAGTA CTAACATTCA 70380

GGGTTATTGT GAGGATTAAA TGAGGTAATT CATGTAATGA CTAGTTCTAT TTCTAGCACA 70440

ATTTAAACCC TCAACAAATA TGAACTATTA TCACTGTCAT AGTTTTTGTT GTTGTTTTCT 70500

AATTATATAA TCTTCAAGAT TCTGAGATGG GGGCTGTTGC TCTTTCCTTG ACTTGAACAT 70560

CTTGGTCTTT TCCTAGGAGG AAACTTGACT CTTGAAATGG TCAAATCCAT TGTCCTAGTT 70620

CATCCTGACC CCTCCCTGGC TCCAATCCCC ACCCCTTACC GTCCTCCACC CTTCCTACAT 70680

TCCTGCACAG TTGGTCTTAT TTATTTTCA GTCAACTAAG GGTGTTGTTA AATCTTTTAT 70740

TTTTCTGCTG CCCGATTTGG TTCTAAGCAC TCCACTCCCT ACGCTGCTCA TAACAAGAAT 70800

GCCTGGGAAC GCTCAGTCAG CCATATCCCT CCCCTGTCGG AACACCCAGT TCTTAATGCT 70860

CCTGGAGAGG CAACATTTCT GAGGCCCCAC TGCCATAAGC CCCCCTCCCC CATGAAGCCA 70920

GTGGTCTGGT AGTAATGAAC CCCCAACGGC CCGGAGAAAA CTGGGGCAAG GTGTTTGTCT 70980

GGGGAAATGT TGCATGTTGC CTTGACTGTG CTTTCTTCTA CAAAGCTTAA AAAGAGATAT 71040

TATATTATTT TATTTTTATT TTTATTTTTG AGATGGAGTC TTACTTGGTT GCCCAGGCTG 71100

GGTGTGCAGT GGCACAGTCA TGGCTCACTG CAACCTCCAC CTCCTGGGTT CAAGTGATTC 71160

TCCTGCCTCA GCCTCCCAAG TAGCTGGGAC TACAGGCACA TGCCACCATG CCTGGCTAAT 71220

TTGTATATTT TTAGTAGAGA CGGGGTTTCA CCATATTAAC TACATTGGTC TTGAACTCCT 71280

GACCTCAAGT GATATGCCCG CCTCGGACTC CCAAAGTGCT GGGATTAAAA GCATGAGCCA 71340

CTGCGCCCGG CCAAAAAGAG ATATTCAAAA GCTCCCTCTG ACTGTGTGTG CTGAAGGCTG 71400

AGTGCTGATG CCATTGCTTA ATTAATGTTG TTCATGATCT CCATTTGGGC GATTTGTTTA 71460

GCTCCTTGTG GCCCTTTTTG GACTTAGCTT ATCATGTGAC ATTGACAAAT TAATGAGAAG 71520

TGAGCATGTG ATGATGCTTG GATTAGGACA GAAATCACAT CTAGGACATC TCAGGCCCTT 71580

TCCACCTGGG ACCTGAGACC TCAAATCTCT TGGCAGGAGA TGAGTGGGTC TACACAGCCC 71640

GATTTTGAGG TAGGTGTGGC TAGCCTCATT TATGCGATGG GAAAACTGTG GTCCGGGAAC 71700

CAGGGGTTTT CAAATTATGC TTTTTGCCCA GGGCTGGATG TAGGATGTCT GGGGGAGAGG 71760

CTTGACTGAG ATCTGGGTAC ACTGAGCCTC CACTTTAGGA GGTAACCTAG AGACTACACC 71820

TACTCCCTAA ACTGTATTGA CTTTTGGAAG TCAACCATTT AGAAGAGTGT GGTTTTGGTT 71880

TCGATCGTAT CCCAGCAGTC TTTTCTCTGC CCTTGTTAAT CTGATTCATG ATCTGAACCT 71940
```

```
GGGCTGGCTG GAGGCTGGCC ATGTCACTTT GCAGACCATG GACACCCTG  AGTGCCCTCA    72000

CAGAACCAGC CAATGGAAAA GTACAACGTC TTCTGGCTTC TCAGCCTTGC CATCTCCCTC    72060

TGGCCTATTT GATACCCCCT TTTATATTGA GGGAGTGAAA ATGTAGCATC CAAACTGAAA    72120

ACGCAGGTTT TTCTTTGGTT TTTATAGGAA AAACAAATTG GCATGAACAC TCAGTCAAAC    72180

CAGCTCAGGC TGTTTGGGCA GATGCCTTTC TTTGCTTTTT TCTGTTTATT TTCCTACAAA    72240

TCAATGCTTA ACTGCGTTGT TATCGGAGCA GAGCAACAGG TGCAAAAAAA TAACTCTGCT    72300

GCCAACTCAA ATGAAAAGGT AGGGCTTATA CCCTCTGGGA GGTATTCAGA AGATAACAGA    72360

AGCCCCTGCC AGCAACTGAA TTAACAGCTC TGTTTACGGT GGGTTTTATG TTAACAACCT    72420

GCTCCTGACC CTCCTACACA TAAACACACC ATTGTCTCAG AGAGAGACAT TCAGCCATCC    72480

AGACAACCCA CTGCTTTATT CTGCCCTGAG TGGAGATTGG TTTTGGCTCA GGCTGCTTTG    72540

TGAAACTCAG AAGCATTATC CTCTCTGCCA ACTCCACGTC CTAGTCAGAG TTTTCTGTGA    72600

AGGCAAGGGC ATGGGGTTGC CGGAGAGAAG AGGATTGGTC CTGCTTTTAA GCCTAGCTGA    72660

AATTCTTTTC AAGGTTGGTC ATTCTCAAAT GCCAGAGAGG GTTGCCCGGC TCTCTCTGCT    72720

CTTGCCCCAT TCCATTCACA ACAGGAGGTG GGGAATGAGC TCAGATGACT TTGGAAGGAG    72780

CCACTATTAT TTTGGAAGCC GTGTCCTTGT GAATAGTCCA TCAGGGTAGG GCAGCGTCTA    72840

TGTTTTGTTA ACTATTGTAT CGCCAGCACC TAGCAAAGTG CCCAGCATCT AGTAGACACT    72900

TGGTAAATAT GTATGAATTA CAGAGGGT                                     72928

(2) INFORMATION FOR SEQ ID NO:2:

(i) SEQUENCE CHARACTERISTICS:
        (A) LENGTH: 5427 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

ATTTATCTTC ACTCTGATGA GGGCTCAGAC TTGATAACGC CCGTGGTGCC CCATCCCTAT      60

AGGAGCTGGT GAGATTGCAG CCTGCTGCCT CCCCTCCATC AGCCACAGCT ATTGGATTTC     120

CCACCCAGAA TCTTTAGGTA AATGAGATCA TGATTCTGGA AGGAGGTGGT GTAATGAATC     180

TCAACCCCGG CAACAACCTC CTTCACCAGC CGCCAGCCTG GACAGACAGC TACTCCACGT     240

GCAATGTTTC CAGTGGGTTT TTTGGAGGCC AGTGGCATGA AATTCATCCT CAGTACTGGA     300

CCAAGTACCA GGTGTGGGAG TGGCTCCAGC ACCTCCTGGA CACCAACCAG CTGGATGCCA     360

ATTGTATCCC TTTCCAAGAG TTCGACATCA ACGGCGAGCA CCTCTGCAGC ATGAGTTTGC     420

AGGAGTTCAC CCGGGCGGCA GGGACGGCGG GGCAGCTCCT CTACAGCAAC TTGCAGCATC     480

TGAAGTGGAA CGGCCAGTGC AGTAGTGACC TGTTCCAGTC CACACACAAT GTCATTGTCA     540

AGACTGAACA AACTGAGCCT TCCATCATGA ACACCTGGAA AGACGAGAAC TATTTATATG     600

ACACCAACTA TGGTAGCACA GTAGATTTGT TGGACAGCAA AACTTTCTGC CGGGCTCAGA     660

TCTCCATGAC AACCACCAGT CACCTTCCTG TTGCAGAGTC ACCTGATATG AAAAAGGAGC     720

AAGACCCCCC TGCCAAGTGC CACACCAAAA AGCACAACCC GAGAGGGACT CACTTATGGG     780

AATTCATCCG CGACATCCTC TTGAACCCAG ACAAGAACCC AGGATTAATA AAATGGGAAG     840

ACCGATCTGA GGGCGTCTTC AGGTTCTTGA AATCAGAGGC AGTGGCTCAG CTATGGGGTA     900

AAAAGAAGAA CAACAGCAGC ATGACCTATG AAAAGCTCAG CCGAGCTATG AGATATTACT     960
```

```
ACAAAAGAGA AATACTGGAG CGTGTGGATG GACGAAGACT GGTATATAAA TTTGGGAAGA    1020

ATGCCCGAGG ATGGAGAGAA AATGAAAACT GAAGCTGCCA ATACTTTGGA CACAAACCAA    1080

AACACACACC AAATAATCAG AAACAAAGAA CTCCTGGACG TAAATATTTC AAAGACTACT    1140

TTTCTCTGAT ATTTATGTAC CATGAGGGGA AAAAGAAACT ACTTCTAACG GGAAGAAGAA    1200

ACACTACAGT CGATTAAAAA AATTATTTTG TTACTTCGAA GTATGTCCTA TATGGGGAAA    1260

AAACGTACAC AGTTTTCTGT GAAATATGAT GCTGTATGTG GTTGTGATTT TTTTTCACCT    1320

CTATTGTGAA TTCTTTTTCA CTGCAAGAGT AACAGGATTT GTAGCCTTGT GCTTCTTGCT    1380

AAGAGAAAGA AAAACAAAAT CAGAGGGCAT TAAATGTTTT GTATGTGACA TGATTTAGAA    1440

AAAGGTGATG CATCCTCCTC ACATAAGCAT CCATATGGCT TCGTCAAGGG AGGTGAACAT    1500

TGTTGCTGAG TTAAATTCCA GGGTCTCAGA TGGTTAGGAC AAAGTGGATG GATGCCGGGA    1560

AGTTTAACCT GAGCCTTAGG ATCCAATGAG TGGAGAATGG GGACTTCCAA ACCCAAGGT     1620

TGGCTATAAT CTCTGCATAA CCACATGACT TGGAATGCTT AAATCAGCAA GAAGAATAAT    1680

GGTGGGGTCT TTATACTCAT TCAGGAATGG TTTATCTGAT GCCAGGGCTG TCTTCCTTTC    1740

TCCCCTTTGG ATGGTTGGTG AAATACTTTA ATTGCCCTGT CTGCTCACTT CTAGCTATTT    1800

AAGAGAGAAC CCAGCTTGGT TCTTTTTTGC TCCAAGTGCT TAAAAATAAG TTGGAAAAAG    1860

GAGACGGTGG TGTGGAAATG GCTGAAGAGT TTGCTCTTGT ATCCCTATAG TCCAAGGTTT    1920

CTCAATCTGC ACAATTGACA TTTTTGGCCG GAGTGTTCTT TGTGGTGAGG GCTTTCCTGT    1980

GCATTGTAAG ATGTTCAGCA GTATCCACTC ATGGTCTCTA ACCACTTGAC ACCAGAAACC    2040

CCCCAGCTGT GATAACGCAA AATGTCTCTA GACATCACCA AATGTTCCCT GGGGGTGGCA    2100

AATTTGCCCT TGATTGAGAA CCACCAGTTT AGCTAGTCAA TATGAGGATG GTGGTTTATT    2160

CTCAGAAGAA AAAGATATGT AAGGTCTTTT AGCTCCTTAG AGTGAAGCAA AAGCAAGACT    2220

TCAACCTCAA CCTATCTTTA TGTTTTAAAT ATTAGGGACA ATAAGTTGAA ATAGCTAGAG    2280

GAGCTTCTTT TCAGAACCCC AGATGAGAGC CAATGTCAGA TAAAGTAAGC ATAGCAATGT    2340

AGCAGGAACT ACAATAGAAG ACATTTTCAC TGGAATTACA AAGCAGAATT AAAATTATAT    2400

TGTAGAAGGA AACACCAAGA AAAGAATTTC CAGGGAAAAT CCTCTTTGCA GGTATTAATT    2460

CTTATAATTT TTTGTCTTTT GGATTATCTG TTTACTGTCT CATCTGAACT GATCCCAGGT    2520

GAACGGTTTA TTGCCTAGAT TTGTACTCAG AGGAATTTTT TTTGTTTTGT TTTGTCTTTT    2580

AAGAAAGGAA AGAAAGGATG AAAAAAATAA ACAGAAAACT CAGCTCAGGC ACAATTGTCA    2640

CCAAGGAGTT AAAAGCTTCT TCTTCAATAG AGGAATTGTT CTGGGGGTCC TGGAGACTTA    2700

CCATTGAGCC ATGCAATCTG GGAAGCACAG GAATAAGTAG ACACTTTGAA AATGGATTTG    2760

AATGTTCTCA TCCCTTTTGC AGCTTTTCTT TTTGGCTCTC TCATGTCCTT GGCTTGCTCC    2820

TCTATTCTAC CTCTCTTTCT CCAGCAATAA TATGCAAATG AAGACATGTA TCCATAAGAA    2880

GGAGTGCTCT TCATCAACTA ATAGAGCACC TACCACAGTG TCATACCTGG TAGAGGTGAG    2940

CAATTCATAT TCAAAGGTTG CAAAGTGTTT GTAATATATT CATGAGGCTG GAAGTAAGAA    3000

GAATTAAAAA TTTGTCCTAA TTACAATGAG AACCATTCTA GGTAGTGATC TTGGAGCACA    3060

CATGAATAAC TTTCTGAAGG TGCAACCAAA TCCATTTTTA TTTCTGCCTG GCTTGGTCAC    3120

CTCTGTAAAG GTTAACTTA GTGTTGTCAA GTAACAGTTA CTGAAAGAGC TGAGAAAAAG    3180

AACAATGAAC AGCAACGATC TTGACTGTGC AACTCAGACA TTCCTGCAGA AAAGACATAT    3240

GTTGCTTTAC AAGAAGGCCA AAGAACTATG GGGCCTTCCC AGCATTTGAC TGTTCATTGC    3300
```

```
ATAGAATGAA TTAAATATCC AGTTACTTGA ATGGGTATAA CGCATGAATA TTTGTGTGTC    3360

TGTGTGTGTG TCTGAGTTGT GTGATTTTAT TAGGGGCATC TGCCAATTCT CTCACTGTGG    3420

TTCCTTCTCT GACTTTGCCT GTTCATCATC TAAGGAGGCT AGATCCTTCG CTGACTTCAC    3480

CATTCCTCAA ACCTGTAAGT TTCTCACTTC TTCCAAATTG GCTTTGGCTC TTTCTTCAAC    3540

CTTTCCATTC AAGAGCAATC TTTGCTAAGG AGTAAGTGAA TGTGAAGAGT ACCAACTACA    3600

ACAATTCTAC AGATAATTAG TGGATTGTGT TGTTTGTTGA GAGTGAAGGT TTCTTGGCAT    3660

CTGGTGCCTG ATTAAGGCTT GAGTATTAAG TTCTCAGCAT ATCTCTCTAT TGTCTTGACT    3720

TGAGTTTGCT GCATTTTCTA TGTGCTGTTC GTGACTTGGA GAACTTAAAG TAATCGAGCT    3780

ATGCCAACTT GGGGTGGTAA CAGAGTACTT CCCACCACAG TGTTGAAAGG GAGAGCAAAG    3840

TCTTATGGAT AAACCCTCCT TTCTTTTGGG GACACATGGC TCTCACTTGA GAAGCTCACC    3900

TGTGCTGAAT GTCCACATGG TCACTAAACA TGTTATCCTT AAACCCCCCG TATGCCTGAG    3960

TTGAAAGGGC TCTCTCTTAT TAGGTTTTCA TGGGAACATG AGGCAGCAAA TCTATTGCTA    4020

AGACTTTACC AGGCTCAAAT CATCTGAGGC TGATAGATAT TTGACTTGGT AAGACTTAAG    4080

TAAGGCTCTG GCTCCCAGGG GCATAAGCAA CAGTTTCTTG AATGTGCCAT CTGAGAAGGG    4140

AGACCCAGGT TATGAGTTTT CCTTTGAACA CATTGGTCTT TTCTCAAAGT TCCTGCCTTG    4200

CTAGACTGTT AGCTCTTTGA GGACAGGGAC TATGTCTTAT CAATCACTAT TATTTTCCTG    4260

TTACCTAGCA TGGGACAAGT ACACAACACA TATTTGTTCA ATGAATGAAT GAATGTCTTC    4320

TAAAAGACTC CTCTGATTGG GAGACCATAT CTATAATTGG GATGTGAATC ATTTCTTCAG    4380

TGGAATAAGA GCACAACGGC ACAACCTTCA AGGACATATT ATCTACTATG AACATTTTAC    4440

TGTGAGACTC TTTATTTTGC CTTCTACTTG CGCTGAAATG AAACCAAAAC AGGCCGTTGG    4500

GTTCCACAAG TCAATATATG TTGGATGAGG ATTCTGTTGC CTTATTGGGA ACTGTGAGAC    4560

TTATCTGGTA TGAGAAGCCA GTAATAAACC TTTGACCTGT TTTAACCAAT GAAGATTATG    4620

AATATGTTAA TATGATGTAA ATTGCTATTT AAGTGTAAAG CAGTTCTAAG TTTTAGTATT    4680

TGGGGATTG GTTTTTATTA TTTTTTTCCT TTTTGAAAAA TACTGAGGGA TCTTTTGATA    4740

AAGTTAGTAA TGCATGTTAG ATTTTAGTTT TGCAAGCATG TTGTTTTTCA AATATATCAA    4800

GTATAGAAAA AGGTAAAACA GTTAAGAAGG AAGGCAATTA TATTATTCTT CTGTAGTTAA    4860

GCAAACACTT GTTGAGTGCC TGCTATGTGC ACGGCATGGG CCCATATGTG TGAGGAGCTT    4920

GTCTAATTAT GTAGGAAGCA ATAGATCTCG GTAGTTACGT ATTGGGCAGA TACTTACTGT    4980

ATGAATGAAA GAACATCACA GTAATCACAA TATCAGAGCT GAATTATCCT CAGTGTAGCT    5040

TCTTGGAATT CAGTTTCTGG AACTAGAGAT AGAGCATTTA TTAAAAAAAA CTCCTGTTGA    5100

GACTGTGTCT TATGAACCTC TGAAACGTAC AAGCCTTCAC AAGTTTAACT AAATTGGGAT    5160

TAATCTTTCT GTAGTTATCT GCATAATTCT TGTTTTTCTT TCCATCTGGC TCCTGGGTTG    5220

ACAATTTGTG GAAACAACTC TATTGCTACT ATTTAAAAAA AATCAGAAAT CTTTCCCTTT    5280

AAGCTATGTT AAATTCAAAC TATTCCTGCT ATTCCTGTTT TGTCAAAGAA TTATATTTTT    5340

CAAAATATGT TTATTTGTTT GATGGGTCCC AGGAAACACT AATAAAAACC ACAGAGACCA    5400

GCCTGGAAAA AAAAAAAAAA AAAAAAA                                      5427
```

(2) INFORMATION FOR SEQ ID NO:3:

(i) SEQUENCE CHARACTERISTICS:
        (A) LENGTH: 5510 base pairs
        (B) TYPE: nucleic acid
        (C) STRANDEDNESS: double (D) TOPOLOGY: linear (ii) MOLECULE TYPE: cDNA (xi) SEQUENCE DESCRIPTION: SEQ ID NO:3:

```
ATCGCTCTCT GGTAGAGTTG ACGTGACACT CATTTCTGTT GTGGGTGGGG CCCTGGTTGG      60
GAGGCATTGG CTCCACTGCA GCCTGGGTGT CTAGAGACCA CATTCTCACC CTGCCTTTGT     120
TACTGGGAAA CCGAACGCGG CGCTGTGGCT TTCAGCTTGG GTAAGCCGGG TCTGCGGCGG     180
GGATTGCCAT CTGAAGACAG AGGCAGGAGG GCAGCCACAC CTTGCCCAGA TCATGATTCT     240
GGAAGGAGGT GGTGTAATGA ATCTCAACCC CGGCAACAAC CTCCTTCACC AGCCGCCAGC     300
CTGGACAGAC AGCTACTCCA CGTGCAATGT TTCCAGTGGG TTTTTTGGAG GCCAGTGGCA     360
TGAAATTCAT CCTCAGTACT GGACCAAGTA CCAGGTGTGG GAGTGGCTCC AGCACCTCCT     420
GGACACCAAC CAGCTGGATG CCAATTGTAT CCCTTTCCAA GAGTTCGACA TCAACGGCGA     480
GCACCTCTGC AGCATGAGTT TGCAGGAGTT CACCCGGGCG GCAGGGACGG CGGGGCAGCT     540
CCTCTACAGC AACTTGCAGC ATCTGAAGTG GAACGGCCAG TGCAGTAGTG ACCTGTTCCA     600
GTCCACACAC AATGTCATTG TCAAGACTGA ACAAACTGAG CCTTCCATCA TGAACACCTG     660
GAAAGACGAG AACTATTTAT ATGACACCAA CTATGGTAGC ACAGTAGATT TGTTGGACAG     720
CAAAACTTTC TGCCGGGCTC AGATCTCCAT GACAACCACC AGTCACCTTC CTGTTGCAGA     780
GTCACCTGAT ATGAAAAAGG AGCAAGACCC CCCTGCCAAG TGCCACACCA AAAGCACAA      840
CCCGAGAGGG ACTCACTTAT GGGAATTCAT CCGCGACATC CTCTTGAACC CAGACAAGAA     900
CCCAGGATTA ATAAAATGGG AAGACCGATC TGAGGGCGTC TTCAGGTTCT TGAAATCAGA     960
GGCAGTGGCT CAGCTATGGG GTAAAAAGAA GAACAACAGC AGCATGACCT ATGAAAAGCT    1020
CAGCCGAGCT ATGAGATATT ACTACAAAAG AGAAATACTG GAGCGTGTGG ATGGACGAAG    1080
ACTGGTATAT AAATTTGGGA AGAATGCCCG AGGATGGAGA GAAAATGAAA ACTGAAGCTG    1140
CCAATACTTT GGACACAAAC CAAAACACAC ACCAAATAAT CAGAAACAAA GAACTCCTGG    1200
ACGTAAATAT TTCAAAGACT ACTTTTCTCT GATATTTATG TACCATGAGG GGAAAAAGAA    1260
ACTACTTCTA ACGGGAAGAA GAAACACTAC AGTCGATTAA AAAAATTATT TTGTTACTTC    1320
GAAGTATGTC CTATATGGGG AAAAAACGTA CACAGTTTTC TGTGAAATAT GATGCTGTAT    1380
GTGGTTGTGA TTTTTTTTCA CCTCTATTGT GAATTCTTTT TCACTGCAAG AGTAACAGGA    1440
TTTGTAGCCT TGTGCTTCTT GCTAAGAGAA AGAAAAACAA AATCAGAGGG CATTAAATGT    1500
TTTGTATGTG ACATGATTTA GAAAAGGTG ATGCATCCTC CTCACATAAG CATCCATATG     1560
GCTTCGTCAA GGGAGGTGAA CATTGTTGCT GAGTTAAATT CCAGGGTCTC AGATGGTTAG    1620
GACAAAGTGG ATGGATGCCG GGAAGTTTAA CCTGAGCCTT AGGATCCAAT GAGTGGAGAA    1680
TGGGACTTC CAAAACCCAA GGTTGGCTAT AATCTCTGCA TAACCACATG ACTTGGAATG     1740
CTTAAATCAG CAAGAAGAAT AATGGTGGGG TCTTTATACT CATTCAGGAA TGGTTTATCT    1800
GATGCCAGGG CTGTCTTCCT TTCTCCCCTT TGGATGGTTG GTGAAATACT TTAATTGCCC    1860
TGTCTGCTCA CTTCTAGCTA TTTAAGAGAG AACCCAGCTT GGTTCTTTTT TGCTCCAAGT    1920
GCTTAAAAAT AAGTTGGAAA AAGGAGACGG TGGTGTGGAA ATGGCTGAAG AGTTTGCTCT    1980
TGTATCCCTA TAGTCCAAGG TTTCTCAATC TGCACAATTG ACATTTTTGG CCGGAGTGTT    2040
CTTTGTGGTG AGGGCTTTCC TGTGCATTGT AAGATGTTCA GCAGTATCCA CTCATGGTCT    2100
CTAACCACTT GACACCAGAA ACCCCCCAGC TGTGATAACG CAAAATGTCT CTAGACATCA    2160
CCAAATGTTC CCTGGGGGTG GCAAATTTGC CCTTGATTGA GAACCACCAG TTTAGCTAGT    2220
```

-continued

| | |
|---|---|
| CAATATGAGG ATGGTGGTTT ATTCTCAGAA GAAAAAGATA TGTAAGGTCT TTTAGCTCCT | 2280 |
| TAGAGTGAAG CAAAAGCAAG ACTTCAACCT CAACCTATCT TTATGTTTTA AATATTAGGG | 2340 |
| ACAATAAGTT GAAATAGCTA GAGGAGCTTC TTTTCAGAAC CCCAGATGAG AGCCAATGTC | 2400 |
| AGATAAAGTA AGCATAGCAA TGTAGCAGGA ACTACAATAG AAGACATTTT CACTGGAATT | 2460 |
| ACAAAGCAGA ATTAAAATTA TATTGTAGAA GGAAACACCA AGAAAGAAT TTCCAGGGAA | 2520 |
| AATCCTCTTT GCAGGTATTA ATTCTTATAA TTTTTTGTCT TTTGGATTAT CTGTTTACTG | 2580 |
| TCTCATCTGA ACTGATCCCA GGTGAACGGT TTATTGCCTA GATTTGTACT CAGAGGAATT | 2640 |
| TTTTTTGTTT TGTTTTGTCT TTTAAGAAAG GAAAGAAAGG ATGAAAAAAA TAAACAGAAA | 2700 |
| ACTCAGCTCA GGCACAATTG TCACCAAGGA GTTAAAAGCT TCTTCTTCAA TAGAGGAATT | 2760 |
| GTTCTGGGGG TCCTGGAGAC TTACCATTGA GCCATGCAAT CTGGGAAGCA CAGGAATAAG | 2820 |
| TAGACACTTT GAAAATGGAT TTGAATGTTC TCATCCCTTT TGCAGCTTTT CTTTTTGGCT | 2880 |
| CTCTCATGTC CTTGGCTTGC TCCTCTATTC TACCTCTCTT TCTCCAGCAA TAATATGCAA | 2940 |
| ATGAAGACAT GTATCCATAA GAAGGAGTGC TCTTCATCAA CTAATAGAGC ACCTACCACA | 3000 |
| GTGTCATACC TGGTAGAGGT GAGCAATTCA TATTCAAAGG TTGCAAAGTG TTTGTAATAT | 3060 |
| ATTCATGAGG CTGGAAGTAA GAAGAATTAA AAATTTGTCC TAATTACAAT GAGAACCATT | 3120 |
| CTAGGTAGTG ATCTTGGAGC ACACATGAAT AACTTTCTGA AGGTGCAACC AAATCCATTT | 3180 |
| TTATTTCTGC CTGGCTTGGT CACCTCTGTA AAGGTTTAAC TTAGTGTTGT CAAGTAACAG | 3240 |
| TTACTGAAAG AGCTGAGAAA AAGAACAATG AACAGCAACG ATCTTGACTG TGCAACTCAG | 3300 |
| ACATTCCTGC AGAAAAGACA TATGTTGCTT TACAAGAAGG CCAAAGAACT ATGGGGCCTT | 3360 |
| CCCAGCATTT GACTGTTCAT TGCATAGAAT GAATTAAATA TCCAGTTACT TGAATGGGTA | 3420 |
| TAACGCATGA ATATTTGTGT GTCTGTGTGT GTGTCTGAGT TGTGTGATTT TATTAGGGGC | 3480 |
| ATCTGCCAAT TCTCTCACTG TGGTTCCTTC TCTGACTTTG CCTGTTCATC ATCTAAGGAG | 3540 |
| GCTAGATCCT TCGCTGACTT CACCATTCCT CAAACCTGTA AGTTTCTCAC TTCTTCCAAA | 3600 |
| TTGGCTTTGG CTCTTTCTTC AACCTTTCCA TTCAAGAGCA ATCTTTGCTA AGGAGTAAGT | 3660 |
| GAATGTGAAG AGTACCAACT ACAACAATTC TACAGATAAT TAGTGGATTG TGTTGTTTGT | 3720 |
| TGAGAGTGAA GGTTTCTTGG CATCTGGTGC CTGATTAAGG CTTGAGTATT AAGTTCTCAG | 3780 |
| CATATCTCTC TATTGTCTTG ACTTGAGTTT GCTGCATTTT CTATGTGCTG TTCGTGACTT | 3840 |
| GGAGAACTTA AAGTAATCGA GCTATGCCAA CTTGGGGTGG TAACAGAGTA CTTCCCACCA | 3900 |
| CAGTGTTGAA AGGGAGAGCA AAGTCTTATG GATAAACCCT CCTTTCTTTT GGGGACACAT | 3960 |
| GGCTCTCACT TGAGAAGCTC ACCTGTGCTG AATGTCCACA TGGTCACTAA ACATGTTATC | 4020 |
| CTTAAACCCC CCGTATGCCT GAGTTGAAAG GGCTCTCTCT TATTAGGTTT TCATGGGAAC | 4080 |
| ATGAGGCAGC AAATCTATTG CTAAGACTTT ACCAGGCTCA AATCATCTGA GGCTGATAGA | 4140 |
| TATTTGACTT GGTAAGACTT AAGTAAGGCT CTGGCTCCCA GGGGCATAAG CAACAGTTTC | 4200 |
| TTGAATGTGC CATCTGAGAA GGGAGACCCA GGTTATGAGT TTTCCTTTGA ACACATTGGT | 4260 |
| CTTTTCTCAA AGTTCCTGCC TTGCTAGACT GTTAGCTCTT TGAGGACAGG GACTATGTCT | 4320 |
| TATCAATCAC TATTATTTTC CTGTTACCTA GCATGGGACA AGTACACAAC ACATATTTGT | 4380 |
| TCAATGAATG AATGAATGTC TTCTAAAAGA CTCCTCTGAT TGGGAGACCA TATCTATAAT | 4440 |
| TGGGATGTGA ATCATTTCTT CAGTGGAATA AGAGCACAAC GGCACAACCT TCAAGGACAT | 4500 |
| ATTATCTACT ATGAACATTT TACTGTGAGA CTCTTTATTT TGCCTTCTAC TTGCGCTGAA | 4560 |

-continued

```
ATGAAACCAA AACAGGCCGT TGGGTTCCAC AAGTCAATAT ATGTTGGATG AGGATTCTGT    4620

TGCCTTATTG GGAACTGTGA GACTTATCTG GTATGAGAAG CCAGTAATAA ACCTTTGACC    4680

TGTTTTAACC AATGAAGATT ATGAATATGT TAATATGATG TAAATTGCTA TTTAAGTGTA    4740

AAGCAGTTCT AAGTTTTAGT ATTTGGGGA TTGGTTTTTA TTATTTTTTT CCTTTTTGAA     4800

AAATACTGAG GGATCTTTTG ATAAAGTTAG TAATGCATGT TAGATTTTAG TTTTGCAAGC    4860

ATGTTGTTTT TCAAATATAT CAAGTATAGA AAAGGTAAA ACAGTTAAGA AGGAAGGCAA     4920

TTATATTATT CTTCTGTAGT TAAGCAAACA CTTGTTGAGT GCCTGCTATG TGCACGGCAT    4980

GGGCCCATAT GTGTGAGGAG CTTGTCTAAT TATGTAGGAA GCAATAGATC TCGGTAGTTA    5040

CGTATTGGGC AGATACTTAC TGTATGAATG AAAGAACATC ACAGTAATCA CAATATCAGA    5100

GCTGAATTAT CCTCAGTGTA GCTTCTTGGA ATTCAGTTTC TGGAACTAGA GATAGAGCAT    5160

TTATTAAAAA AAACTCCTGT TGAGACTGTG TCTTATGAAC CTCTGAAACG TACAAGCCTT    5220

CACAAGTTTA ACTAAATTGG GATTAATCTT TCTGTAGTTA TCTGCATAAT TCTTGTTTTT    5280

CTTTCCATCT GGCTCCTGGG TTGACAATTT GTGGAAACAA CTCTATTGCT ACTATTTAAA    5340

AAAAATCAGA AATCTTTCCC TTTAAGCTAT GTTAAATTCA AACTATTCCT GCTATTCCTG    5400

TTTTGTCAAA GAATTATATT TTTCAAAATA TGTTTATTTG TTTGATGGGT CCCAGGAAAC    5460

ACTAATAAAA ACCACAGAGA CCAGCCTGGA AAAAAAAAA AAAAAAAAA                 5510

(2) INFORMATION FOR SEQ ID NO:4:

(i) SEQUENCE CHARACTERISTICS:
        (A) LENGTH: 5667 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

ATCGCTCTCT GGTAGAGTTG ACGTGACACT CATTTCTGTT GTGGGTGGGG CCCTGGTTGG      60

GAGGCATTGG CTCCACTGCA GCCTGGGTGT CTAGAGACCA CATTCTCACC CTGCCTTTGT    120

TACTGGGAAA CCGAACGCGG CGCTGTGGCT TTCAGCTTGG GTAAGCCGGG TCTGCGGCGG    180

GGATTGCCAT CTGAAGACAG AGGCAGGAGG GCAGCCACAC CTTGCCCAGC TGCACACCCA    240

GTAACAAGTT TCCTCAGTGC GGGTATCTGC CACAGGCTGG GCTGGTCATC AAAGGGCCTC    300

AGTCATATTT TAATAGAGCT CTTCAAGTAT CTGGCTTTGT GATAATATCA GGAATCAGTT    360

GGTTTCTCTG ACAGACACTG CCCATTATCA TGATTCTGGA AGGAGGTGGT GTAATGAATC    420

TCAACCCCGG CAACAACCTC CTTCACCAGC CGCCAGCCTG GACAGACAGC TACTCCACGT    480

GCAATGTTTC CAGTGGGTTT TTTGGAGGCC AGTGGCATGA AATTCATCCT CAGTACTGGA    540

CCAAGTACCA GGTGTGGGAG TGGCTCCAGC ACCTCCTGGA CACCAACCAG CTGGATGCCA    600

ATTGTATCCC TTTCCAAGAG TTCGACATCA ACGGCGAGCA CCTCTGCAGC ATGAGTTTGC    660

AGGAGTTCAC CCGGGCGGCA GGGACGGCGG GGCAGCTCCT CTACAGCAAC TTGCAGCATC    720

TGAAGTGGAA CGGCCAGTGC AGTAGTGACC TGTTCCAGTC CACACACAAT GTCATTGTCA    780

AGACTGAACA AACTGAGCCT TCCATCATGA ACACCTGGAA AGACGAGAAC TATTTATATG    840

ACACCAACTA TGGTAGCACA GTAGATTTGT TGGACAGCAA AACTTTCTGC CGGGCTCAGA    900

TCTCCATGAC AACCACCAGT CACCTTCCTG TTGCAGAGTC ACCTGATATG AAAAAGGAGC    960

AAGACCCCCC TGCCAAGTGC CACACCAAAA AGCACAACCC GAGAGGGACT CACTTATGGG   1020
```

-continued

```
AATTCATCCG CGACATCCTC TTGAACCCAG ACAAGAACCC AGGATTAATA AAATGGGAAG   1080

ACCGATCTGA GGGCGTCTTC AGGTTCTTGA AATCAGAGGC AGTGGCTCAG CTATGGGGTA   1140

AAAAGAAGAA CAACAGCAGC ATGACCTATG AAAAGCTCAG CCGAGCTATG AGATATTACT   1200

ACAAAAGAGA AATACTGGAG CGTGTGGATG GACGAAGACT GGTATATAAA TTTGGGAAGA   1260

ATGCCCGAGG ATGGAGAGAA AATGAAAACT GAAGCTGCCA ATACTTTGGA CACAAACCAA   1320

AACACACACC AAATAATCAG AAACAAAGAA CTCCTGGACG TAAATATTTC AAAGACTACT   1380

TTTCTCTGAT ATTTATGTAC CATGAGGGGA AAAAGAAACT ACTTCTAACG GGAAGAAGAA   1440

ACACTACAGT CGATTAAAAA AATTATTTTG TTACTTCGAA GTATGTCCTA TATGGGGAAA   1500

AAACGTACAC AGTTTTCTGT GAAATATGAT GCTGTATGTG GTTGTGATTT TTTTTCACCT   1560

CTATTGTGAA TTCTTTTTCA CTGCAAGAGT AACAGGATTT GTAGCCTTGT GCTTCTTGCT   1620

AAGAGAAAGA AAAACAAAAT CAGAGGGCAT TAAATGTTTT GTATGTGACA TGATTTAGAA   1680

AAAGGTGATG CATCCTCCTC ACATAAGCAT CCATATGGCT TCGTCAAGGG AGGTGAACAT   1740

TGTTGCTGAG TTAAATTCCA GGGTCTCAGA TGGTTAGGAC AAAGTGGATG GATGCCGGGA   1800

AGTTTAACCT GAGCCTTAGG ATCCAATGAG TGGAGAATGG GGACTTCCAA AACCCAAGGT   1860

TGGCTATAAT CTCTGCATAA CCACATGACT TGGAATGCTT AAATCAGCAA GAAGAATAAT   1920

GGTGGGGTCT TTATACTCAT TCAGGAATGG TTTATCTGAT GCCAGGGCTG TCTTCCTTTC   1980

TCCCCTTTGG ATGGTTGGTG AAATACTTTA ATTGCCCTGT CTGCTCACTT CTAGCTATTT   2040

AAGAGAGAAC CCAGCTTGGT TCTTTTTTGC TCCAAGTGCT TAAAAATAAG TTGGAAAAAG   2100

GAGACGGTGG TGTGGAAATG GCTGAAGAGT TTGCTCTTGT ATCCCTATAG TCCAAGGTTT   2160

CTCAATCTGC ACAATTGACA TTTTTGGCCG GAGTGTTCTT TGTGGTGAGG GCTTTCCTGT   2220

GCATTGTAAG ATGTTCAGCA GTATCCACTC ATGGTCTCTA ACCACTTGAC ACCAGAAACC   2280

CCCCAGCTGT GATAACGCAA AATGTCTCTA GACATCACCA AATGTTCCCT GGGGGTGGCA   2340

AATTTGCCCT TGATTGAGAA CCACCAGTTT AGCTAGTCAA TATGAGGATG GTGGTTTATT   2400

CTCAGAAGAA AAAGATATGT AAGGTCTTTT AGCTCCTTAG AGTGAAGCAA AAGCAAGACT   2460

TCAACCTCAA CCTATCTTTA TGTTTTAAAT ATTAGGGACA ATAAGTTGAA ATAGCTAGAG   2520

GAGCTTCTTT TCAGAACCCC AGATGAGAGC CAATGTCAGA TAAAGTAAGC ATAGCAATGT   2580

AGCAGGAACT ACAATAGAAG ACATTTTCAC TGGAATTACA AAGCAGAATT AAAATTATAT   2640

TGTAGAAGGA AACACCAAGA AAAGAATTTC CAGGGAAAAT CCTCTTTGCA GGTATTAATT   2700

CTTATAATTT TTTGTCTTTT GGATTATCTG TTTACTGTCT CATCTGAACT GATCCCAGGT   2760

GAACGGTTTA TTGCCTAGAT TTGTACTCAG AGGAATTTTT TTTGTTTTGT TTTGTCTTTT   2820

AAGAAAGGAA AGAAAGGATG AAAAAAATAA ACAGAAAACT CAGCTCAGGC ACAATTGTCA   2880

CCAAGGAGTT AAAAGCTTCT TCTTCAATAG AGGAATTGTT CTGGGGGTCC TGGAGACTTA   2940

CCATTGAGCC ATGCAATCTG GGAAGCACAG GAATAAGTAG ACACTTTGAA AATGGATTTG   3000

AATGTTCTCA TCCCTTTTGC AGCTTTTCTT TTTGGCTCTC TCATGTCCTT GGCTTGCTCC   3060

TCTATTCTAC CTCTCTTTCT CCAGCAATAA TATGCAAATG AAGACATGTA TCCATAAGAA   3120

GGAGTGCTCT TCATCAACTA ATAGAGCACC TACCACAGTG TCATACCTGG TAGAGGTGAG   3180

CAATTCATAT TCAAAGGTTG CAAAGTGTTT GTAATATATT CATGAGGCTG GAAGTAAGAA   3240

GAATTAAAAA TTTGTCCTAA TTACAATGAG AACCATTCTA GGTAGTGATC TTGGAGCACA   3300

CATGAATAAC TTTCTGAAGG TGCAACCAAA TCCATTTTTA TTTCTGCCTG GCTTGGTCAC   3360

CTCTGTAAAG GTTTAACTTA GTGTTGTCAA GTAACAGTTA CTGAAAGAGC TGAGAAAAAG   3420
```

```
AACAATGAAC AGCAACGATC TTGACTGTGC AACTCAGACA TTCCTGCAGA AAAGACATAT    3480

GTTGCTTTAC AAGAAGGCCA AAGAACTATG GGGCCTTCCC AGCATTTGAC TGTTCATTGC    3540

ATAGAATGAA TTAAATATCC AGTTACTTGA ATGGGTATAA CGCATGAATA TTTGTGTGTC    3600

TGTGTGTGTG TCTGAGTTGT GTGATTTTAT TAGGGGCATC TGCCAATTCT CTCACTGTGG    3660

TTCCTTCTCT GACTTTGCCT GTTCATCATC TAAGGAGGCT AGATCCTTCG CTGACTTCAC    3720

CATTCCTCAA ACCTGTAAGT TTCTCACTTC TTCCAAATTG GCTTTGGCTC TTTCTTCAAC    3780

CTTTCCATTC AAGAGCAATC TTTGCTAAGG AGTAAGTGAA TGTGAAGAGT ACCAACTACA    3840

ACAATTCTAC AGATAATTAG TGGATTGTGT TGTTTGTTGA GAGTGAAGGT TTCTTGGCAT    3900

CTGGTGCCTG ATTAAGGCTT GAGTATTAAG TTCTCAGCAT ATCTCTCTAT TGTCTTGACT    3960

TGAGTTTGCT GCATTTTCTA TGTGCTGTTC GTGACTTGGA GAACTTAAAG TAATCGAGCT    4020

ATGCCAACTT GGGGTGGTAA CAGAGTACTT CCCACCACAG TGTTGAAAGG GAGAGCAAAG    4080

TCTTATGGAT AAACCCTCCT TTCTTTTGGG GACACATGGC TCTCACTTGA GAAGCTCACC    4140

TGTGCTGAAT GTCCACATGG TCACTAAACA TGTTATCCTT AAACCCCCCG TATGCCTGAG    4200

TTGAAAGGGC TCTCTCTTAT TAGGTTTTCA TGGGAACATG AGGCAGCAAA TCTATTGCTA    4260

AGACTTTACC AGGCTCAAAT CATCTGAGGC TGATAGATAT TTGACTTGGT AAGACTTAAG    4320

TAAGGCTCTG GCTCCCAGGG GCATAAGCAA CAGTTTCTTG AATGTGCCAT CTGAGAAGGG    4380

AGACCCAGGT TATGAGTTTT CCTTTGAACA CATTGGTCTT TTCTCAAAGT TCCTGCCTTG    4440

CTAGACTGTT AGCTCTTTGA GGACAGGGAC TATGTCTTAT CAATCACTAT TATTTTCCTG    4500

TTACCTAGCA TGGGACAAGT ACACAACACA TATTTGTTCA ATGAATGAAT GAATGTCTTC    4560

TAAAAGACTC CTCTGATTGG GAGACCATAT CTATAATTGG GATGTGAATC ATTTCTTCAG    4620

TGGAATAAGA GCACAACGGC ACAACCTTCA AGGACATATT ATCTACTATG AACATTTTAC    4680

TGTGAGACTC TTTATTTTGC CTTCTACTTG CGCTGAAATG AAACCAAAAC AGGCCGTTGG    4740

GTTCCACAAG TCAATATATG TTGGATGAGG ATTCTGTTGC CTTATTGGGA ACTGTGAGAC    4800

TTATCTGGTA TGAGAAGCCA GTAATAAACC TTTGACCTGT TTTAACCAAT GAAGATTATG    4860

AATATGTTAA TATGATGTAA ATTGCTATTT AAGTGTAAAG CAGTTCTAAG TTTTAGTATT    4920

TGGGGATTG GTTTTTATTA TTTTTTTCCT TTTTGAAAAA TACTGAGGGA TCTTTTGATA    4980

AAGTTAGTAA TGCATGTTAG ATTTTAGTTT TGCAAGCATG TTGTTTTTCA AATATATCAA    5040

GTATAGAAAA AGGTAAAACA GTTAAGAAGG AAGGCAATTA TATTATTCTT CTGTAGTTAA    5100

GCAAACACTT GTTGAGTGCC TGCTATGTGC ACGGCATGGG CCCATATGTG TGAGGAGCTT    5160

GTCTAATTAT GTAGGAAGCA ATAGATCTCG GTAGTTACGT ATTGGGCAGA TACTTACTGT    5220

ATGAATGAAA GAACATCACA GTAATCACAA TATCAGAGCT GAATTATCCT CAGTGTAGCT    5280

TCTTGGAATT CAGTTTCTGG AACTAGAGAT AGAGCATTTA TTAAAAAAAA CTCCTGTTGA    5340

GACTGTGTCT TATGAACCTC TGAAACGTAC AAGCCTTCAC AAGTTTAACT AAATTGGGAT    5400

TAATCTTTCT GTAGTTATCT GCATAATTCT TGTTTTTCTT TCCATCTGGC TCCTGGGTTC    5460

ACAATTTGTG GAAACAACTC TATTGCTACT ATTTAAAAAA AATCAGAAAT CTTTCCCTTT    5520

AAGCTATGTT AAATTCAAAC TATTCCTGCT ATTCCTGTTT TGTCAAAGAA TTATATTTTT    5580

CAAAATATGT TTATTTGTTT GATGGGTCCC AGGAAACACT AATAAAAACC ACAGAGACCA    5640

GCCTGGAAAA AAAAAAAAA AAAAAAA                                       5667
```

(2) INFORMATION FOR SEQ ID NO:5:

(i) SEQUENCE CHARACTERISTICS:
        (A) LENGTH: 300 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Met Ile Leu Glu Gly Gly Val Met Asn Leu Asn Pro Gly Asn Asn
 1               5                  10                  15

Leu Leu His Gln Pro Pro Ala Trp Thr Asp Ser Tyr Ser Thr Cys Asn
                 20                  25                  30

Val Ser Ser Gly Phe Phe Gly Gly Gln Trp His Glu Ile His Pro Gln
             35                  40                  45

Tyr Trp Thr Lys Tyr Gln Val Trp Glu Trp Leu Gln His Leu Leu Asp
         50                  55                  60

Thr Asn Gln Leu Asp Ala Asn Cys Ile Pro Phe Gln Glu Phe Asp Ile
 65                  70                  75                  80

Asn Gly Glu His Leu Cys Ser Met Ser Leu Gln Glu Phe Thr Arg Ala
                 85                  90                  95

Ala Gly Thr Ala Gly Gln Leu Leu Tyr Ser Asn Leu Gln His Leu Lys
            100                 105                 110

Trp Asn Gly Gln Cys Ser Ser Asp Leu Phe Gln Ser Thr His Asn Val
        115                 120                 125

Ile Val Lys Thr Glu Gln Thr Glu Pro Ser Ile Met Asn Thr Trp Lys
        130                 135                 140

Asp Glu Asn Tyr Leu Tyr Asp Thr Asn Tyr Gly Ser Thr Val Asp Leu
145                 150                 155                 160

Leu Asp Ser Lys Thr Phe Cys Arg Ala Gln Ile Ser Met Thr Thr Thr
                165                 170                 175

Ser His Leu Pro Val Ala Glu Ser Pro Asp Met Lys Lys Glu Gln Asp
                180                 185                 190

Pro Pro Ala Lys Cys His Thr Lys Lys His Asn Pro Arg Gly Thr His
            195                 200                 205

Leu Trp Glu Phe Ile Arg Asp Ile Leu Leu Asn Pro Asp Lys Asn Pro
210                 215                 220

Gly Leu Ile Lys Trp Glu Asp Arg Ser Glu Gly Val Phe Arg Phe Leu
225                 230                 235                 240

Lys Ser Glu Ala Val Ala Gln Leu Trp Gly Lys Lys Asn Asn Ser
                245                 250                 255

Ser Met Thr Tyr Glu Lys Leu Ser Arg Ala Met Arg Tyr Tyr Tyr Lys
                260                 265                 270

Arg Glu Ile Leu Glu Arg Val Asp Gly Arg Arg Leu Val Tyr Lys Phe
            275                 280                 285

Gly Lys Asn Ala Arg Gly Trp Arg Glu Asn Glu Asn
            290                 295                 300

(2) INFORMATION FOR SEQ ID NO:6:

(i) SEQUENCE CHARACTERISTICS:
        (A) LENGTH: 2428 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:6:

```
CAGGGGTGCC GGGTTGCTCA GGCCATGGGA GCCACACCTG TTATTGCTGC CTCTGATTTG     60
TGTGACACTG AGAAGCCCAC AGGCCTGTCC CTCCAACTCG GTGGACCCTC TCTGTGTGCA    120
TTTGGTGTGT GAGCCAGCTC TGAGAAGGGT TCAGAAGCCA CTGGAGGCAT CTGGGGACCT    180
CAGCTTCCAT GCCATCTCTG CCTCACTCCC ACAGGGTAAT GTTGGACTCG GTGACACACA    240
GCACCTTCCT GCCTAATGCA TCCTTCTGCG ATCCCCTGAT GTCGTGGACT GATCTGTTCA    300
GCAATGAAGA GTACTACCCT GCCTTTGAGC ATCAGACAGC CTGTGACTCA TACTGGACAT    360
CAGTCCACCC TGAATACTGG ACTAAGCGCC ATGTGTGGGA GTGGCTCCAG TTCTGCTGCG    420
ACCAGTACAA GTTGGACACC AATTGCATCT CCTTCTGCAA CTTCAACATC AGTGGCCTGC    480
AGCTGTGCAG CATGACACAG GAGGAGTTCG TCGAGGCAGC TGGCCTCTGC GGCGAGTACC    540
TGTACTTCAT CCTCCAGAAC ATCCGCACAC AAGGTTACTC CTTTTTTAAT GACGCTGAAG    600
AAAGCAAGGC CACCATCAAA GACTATGCTG ATTCCAACTG CTTGAAAACA AGTGGCATCA    660
AAAGTCAAGA CTGTCACAGT CATAGTAGAA CAAGCCTCCA AAGTTCTCAT CTATGGGAAT    720
TTGTACGAGA CCTGCTTCTA TCTCCTGAAG AAAACTGTGG CATTCTGGAA TGGGAAGATA    780
GGGAACAAGG AATTTTTCGG GTGGTTAAAT CGGAAGCCCT GGCAAAGATG TGGGGACAAA    840
GGAAGAAAAA TGACAGAATG ACGTATGAAA AGTTGAGCAG AGCCCTGAGA TACTACTATA    900
AAACAGGAAT TTTGGAGCGG GTTGACCGAA GGTTAGTGTA CAAATTTGGA AAAAATGCAC    960
ACGGGTGGCA GGAAGACAAG CTATGATCTG CTCCAGGCAT CAAGCTCATT TTATGGATTT   1020
CTGTCTTTTA AAACAATCAG ATTGCAATAG ACATTCGAAA GGCTTCATTT TCTTCTCTTT   1080
TTTTTTAACC TGCAAACATG CTGATAAAAT TTCTCCACAT CTCAGCTTAC ATTTGGATTC   1140
AGAGTTGTTG TCTACGGAGG GTGAGAGCAG AAACTCTTAA GAAATCCTTT CTTCTCCCTA   1200
AGGGGATGAG GGGATGATCT TTTGTGGTGT CTTGATCAAA CTTTATTTTC CTAGAGTTGT   1260
GGAATGACAA CAGCCCATGC CATTGATGCT GATCAGAGAA AAACTATTCA ATTCTGCCAT   1320
TAGAGACACA TCCAATGCTC CCATCCCAAA GGTTCAAAAG TTTTCAAATA ACTGTGGCAG   1380
CTCACCAAAG GTGGGGGAAA GCATGATTAG TTTGCAGGTT ATGGTAGGAG AGGGTGAGAT   1440
ATAAGACATA CATACTTTAG ATTTTAAATT ATTAAAGTCA AAAATCCATA GAAAAGTATC   1500
CCTTTTTTTT TTTTTTGAGA CGGGTTCTCA CTATGTTGCC CAGGGCTGGT CTTGAACTCC   1560
TATGCTCAAG TGATCCTCCC ACCTCGGCCT CCCAAAGTAC TGTGATTACA AGCGTGAGCC   1620
ACGGCACCTG GGCAGAAAAG TATCTTAATT AATGAAAGAG CTAAGCCATC AAGCTGGGAC   1680
TTAATTGGAT TTAACATAGG TTCACAGAAA GTTTCCTAAC CAGAGCATCT TTTTGACCAC   1740
TCAGCAAAAC TTCCACAGAC ATCCTTCTGG ACTAAACAC  TTAACATTAA CCACATTATT   1800
AATTGTTGCT GAGTTTATTC CCCCTTCTAA CTGATGGCTG GCATCTGATA TGCAGAGTTA   1860
GTCAACAGAC ACTGGCATCA ATTACAAAAT CACTGCTGTT TCTGTGATTC AAGCTGTCAA   1920
CACAATAAAA TCGAAATTCA TTGATTCCAT CTCTGGTCCA GATGTTAAAC GTTTATAAAA   1980
CCGGAAATGT CCTAACAACT CTGTAATGGC AAATTAAATT GTGTGTCTTT TTTGTTTTGT   2040
CTTTCTACCT GATGTGTATT CAAGCGCTAT AACACGTATT TCCTTGACAA AAATAGTGAC   2100
AGTGAATTCA CACTAATAAA TGTTCATAGG TTAAAGTCTG CACTGACATT TTCTCATCAA   2160
TCACTGGTAT GTAAGTTATC AGTGACTGAC AGCTAGGTGG ACTGCCCCTA GGACTTCTGT   2220
TTCACCAGAG CAGGAATCAA GTGGTGAGGC ACTGAATCGC TGTACAGGCT GAAGACCTCC   2280
TTATTAGAGT TGAACTTCAA AGTAACTTGT TTTAAAAAAT GTGAATTACT GTAAAATAAT   2340
```

```
CTATTTTGGA TTCATGTGTT TTCCAGGTGG ATATAGTTTG TAAACAATGT GAATAAAGTA    2400

TTTAACATGT TCAAAAAAAA AAAAAAA                                        2428
```

(2) INFORMATION FOR SEQ ID NO:7:

(i) SEQUENCE CHARACTERISTICS:
        (A) LENGTH: 265 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Met Pro Ser Leu Pro His Ser His Arg Val Met Leu Asp Ser Val Thr
 1               5                  10                  15

His Ser Thr Phe Leu Pro Asn Ala Ser Phe Cys Asp Pro Leu Met Ser
            20                  25                  30

Trp Thr Asp Leu Phe Ser Asn Glu Glu Tyr Tyr Pro Ala Phe Glu His
        35                  40                  45

Gln Thr Ala Cys Asp Ser Tyr Trp Thr Ser Val His Pro Glu Tyr Trp
    50                  55                  60

Thr Lys Arg His Val Trp Glu Trp Leu Gln Phe Cys Cys Asp Gln Tyr
65                  70                  75                  80

Lys Leu Asp Thr Asn Cys Ile Ser Phe Cys Asn Phe Asn Ile Ser Gly
                85                  90                  95

Leu Gln Leu Cys Ser Met Thr Gln Glu Glu Phe Val Glu Ala Ala Gly
            100                 105                 110

Leu Cys Gly Glu Tyr Leu Tyr Phe Ile Leu Gln Asn Ile Arg Thr Gln
        115                 120                 125

Gly Tyr Ser Phe Phe Asn Asp Ala Glu Glu Ser Lys Ala Thr Ile Lys
    130                 135                 140

Asp Tyr Ala Asp Ser Asn Cys Leu Lys Thr Ser Gly Ile Lys Ser Gln
145                 150                 155                 160

Asp Cys His Ser His Ser Arg Thr Ser Leu Gln Ser Ser His Leu Trp
                165                 170                 175

Glu Phe Val Arg Asp Leu Leu Leu Ser Pro Glu Asn Cys Gly Ile
            180                 185                 190

Leu Glu Trp Glu Asp Arg Glu Gln Gly Ile Phe Arg Val Val Lys Ser
        195                 200                 205

Glu Ala Leu Ala Lys Met Trp Gly Gln Arg Lys Lys Asn Asp Arg Met
    210                 215                 220

Thr Tyr Glu Lys Leu Ser Arg Ala Leu Arg Tyr Tyr Lys Thr Gly
225                 230                 235                 240

Ile Leu Glu Arg Val Asp Arg Arg Leu Val Tyr Lys Phe Gly Lys Asn
                245                 250                 255

Ala His Gly Trp Gln Glu Asp Lys Leu
            260                 265
```

(2) INFORMATION FOR SEQ ID NO:8:

(i) SEQUENCE CHARACTERISTICS:
        (A) LENGTH: 2280 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:8:

```
CTGGGAGCGC CTGCCTTCTC TTGCCTTGAA AGCCTCCTCT TTGGACCTAG CCACCGCTGC    60

CCTCACGGTA ATGTTGGACT CGGTGACACA CAGCACCTTC CTGCCTAATG CATCCTTCTG   120

CGATCCCCTG ATGTCGTGGA CTGATCTGTT CAGCAATGAA GAGTACTACC CTGCCTTTGA   180

GCATCAGACA GCCTGTGACT CATACTGGAC ATCAGTCCAC CCTGAATACT GGACTAAGCG   240

CCATGTGTGG GAGTGGCTCC AGTTCTGCTG CGACCAGTAC AAGTTGGACA CCAATTGCAT   300

CTCCTTCTGC AACTTCAACA TCAGTGGCCT GCAGCTGTGC AGCATGACAC AGGAGGAGTT   360

CGTCGAGGCA GCTGGCCTCT GCGGCGAGTA CCTGTACTTC ATCCTCCAGA ACATCCGCAC   420

ACAAGGTTAC TCCTTTTTTA ATGACGCTGA AGAAAGCAAG GCCACCATCA AGACTATGC    480

TGATTCCAAC TGCTTGAAAA CAAGTGGCAT CAAAAGTCAA GACTGTCACA GTCATAGTAG   540

AACAAGCCTC CAAAGTTCTC ATCTATGGGA ATTTGTACGA GACCTGCTTC TATCTCCTGA   600

AGAAAACTGT GGCATTCTGG AATGGGAAGA TAGGGAACAA GGAATTTTTC GGGTGGTTAA   660

ATCGGAAGCC CTGGCAAAGA TGTGGGGACA AAGGAAGAAA AATGACAGAA TGACGTATGA   720

AAAGTTGAGC AGAGCCCTGA GATACTACTA TAAAACAGGA ATTTTGGAGC GGGTTGACCG   780

AAGGTTAGTG TACAAATTTG GAAAAAATGC ACACGGGTGG CAGGAAGACA AGCTATGATC   840

TGCTCCAGGC ATCAAGCTCA TTTTATGGAT TTCTGTCTTT TAAAACAATC AGATTGCAAT   900

AGACATTCGA AAGGCTTCAT TTTCTTCTCT TTTTTTTTAA CCTGCAAACA TGCTGATAAA   960

ATTTCTCCAC ATCTCAGCTT ACATTTGGAT TCAGAGTTGT TGTCTACGGA GGGTGAGAGC  1020

AGAAACTCTT AAGAAATCCT TTCTTCTCCC TAAGGGGATG AGGGGATGAT CTTTTGTGGT  1080

GTCTTGATCA AACTTTATTT TCCTAGAGTT GTGGAATGAC AACAGCCCAT GCCATTGATG  1140

CTGATCAGAG AAAAACTATT CAATTCTGCC ATTAGAGACA CATCCAATGC TCCCATCCCA  1200

AAGGTTCAAA AGTTTTCAAA TAACTGTGGC AGCTCACCAA AGGTGGGGGA AAGCATGATT  1260

AGTTTGCAGG TTATGGTAGG AGAGGGTGAG ATATAAGACA TACATACTTT AGATTTTAAA  1320

TTATTAAAGT CAAAAATCCA TAGAAAAGTA TCCCTTTTTT TTTTTTTTGA GACGGGTTCT  1380

CACTATGTTG CCCAGGGCTG GTCTTGAACT CCTATGCTCA AGTGATCCTC CCACCTCGGC  1440

CTCCCAAAGT ACTGTGATTA CAAGCGTGAG CCACGGCACC TGGGCAGAAA AGTATCTTAA  1500

TTAATGAAAG AGCTAAGCCA TCAAGCTGGG ACTTAATTGG ATTTAACATA GGTTCACAGA  1560

AAGTTTCCTA ACCAGAGCAT CTTTTTGACC ACTCAGCAAA ACTTCCACAG ACATCCTTCT  1620

GGACTTAAAC ACTTAACATT AACCACATTA TTAATTGTTG CTGAGTTTAT TCCCCCTTCT  1680

AACTGATGGC TGGCATCTGA TATGCAGAGT TAGTCAACAG ACACTGGCAT CAATTACAAA  1740

ATCACTGCTG TTTCTGTGAT TCAAGCTGTC AACACAATAA AATCGAAATT CATTGATTCC  1800

ATCTCTGGTC CAGATGTTAA ACGTTTATAA AACCGGAAAT GTCCTAACAA CTCTGTAATG  1860

GCAAATTAAA TTGTGTGTCT TTTTTGTTTT GTCTTTCTAC CTGATGTGTA TTCAAGCGCT  1920

ATAACACGTA TTTCCTTGAC AAAAATAGTG ACAGTGAATT CACACTAATA AATGTTCATA  1980

GGTTAAAGTC TGCACTGACA TTTTCTCATC AATCACTGGT ATGTAAGTTA TCAGTGACTG  2040

ACAGCTAGGT GGACTGCCCC TAGGACTTCT GTTTCACCAG AGCAGGAATC AAGTGGTGAG  2100

GCACTGAATC GCTGTACAGG CTGAAGACCT CCTTATTAGA GTTGAACTTC AAAGTAACTT  2160

GTTTTAAAAA ATGTGAATTA CTGTAAAATA ATCTATTTTG GATTCATGTG TTTTCCAGGT  2220

GGATATAGTT TGTAAACAAT GTGAATAAAG TATTTAACAT GTTCAAAAAA AAAAAAAAAA  2280
```

(2) INFORMATION FOR SEQ ID NO:9:

(i) SEQUENCE CHARACTERISTICS:
        (A) LENGTH: 255 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Met Leu Asp Ser Val Thr His Ser Thr Phe Leu Pro Asn Ala Ser Phe
 1               5                  10                  15

Cys Asp Pro Leu Met Ser Trp Thr Asp Leu Phe Ser Asn Glu Glu Tyr
            20                  25                  30

Tyr Pro Ala Phe Glu His Gln Thr Ala Cys Asp Ser Tyr Trp Thr Ser
        35                  40                  45

Val His Pro Glu Tyr Trp Thr Lys Arg His Val Trp Glu Trp Leu Gln
    50                  55                  60

Phe Cys Cys Asp Gln Tyr Lys Leu Asp Thr Asn Cys Ile Ser Phe Cys
65                  70                  75                  80

Asn Phe Asn Ile Ser Gly Leu Gln Leu Cys Ser Met Thr Gln Glu Glu
                85                  90                  95

Phe Val Glu Ala Ala Gly Leu Cys Gly Glu Tyr Leu Tyr Phe Ile Leu
            100                 105                 110

Gln Asn Ile Arg Thr Gln Gly Tyr Ser Phe Phe Asn Asp Ala Glu Glu
        115                 120                 125

Ser Lys Ala Thr Ile Lys Asp Tyr Ala Asp Ser Asn Cys Leu Lys Thr
    130                 135                 140

Ser Gly Ile Lys Ser Gln Asp Cys His Ser His Ser Arg Thr Ser Leu
145                 150                 155                 160

Gln Ser Ser His Leu Trp Glu Phe Val Arg Asp Leu Leu Leu Ser Pro
                165                 170                 175

Glu Glu Asn Cys Gly Ile Leu Glu Trp Glu Asp Arg Glu Gln Gly Ile
            180                 185                 190

Phe Arg Val Val Lys Ser Glu Ala Leu Ala Lys Met Trp Gly Gln Arg
        195                 200                 205

Lys Lys Asn Asp Arg Met Thr Tyr Glu Lys Leu Ser Arg Ala Leu Arg
    210                 215                 220

Tyr Tyr Tyr Lys Thr Gly Ile Leu Glu Arg Val Asp Arg Arg Leu Val
225                 230                 235                 240

Tyr Lys Phe Gly Lys Asn Ala His Gly Trp Gln Glu Asp Lys Leu
                245                 250                 255
```

(2) INFORMATION FOR SEQ ID NO:10:

(i) SEQUENCE CHARACTERISTICS:
        (A) LENGTH: 2498 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

```
GAGGGGCTGA CAGCGGCGTC CCTCGTCTGG GCAGCCTCCG CTCTGCCACT CTCCTCCCGT    60

CCTGAGGATG GGACCCCCGG AAAAGCGGCC TCTGGAGGCC TGCCATGGCA CCCAGAGCAG   120

CCATTTTCCT CCCAGTTCTG GGCTTTGGA AGGAGCTTGC GGATGAGGAG AGGGAGCCTC   180
```

```
CGCAGGGCTC TGGCTCCCCT CCAGGGGCCG AGGCCGCACA CAAAGCCGCT CTGTGGCCCA      240

ATTACACCTA CTGGATAGGA TTGTTGAGGG GACCTGAGAA ACTTGAGACG ACAAGAACGC      300

GTAGCGCCTC GGCTGGCTGA GGGTGCTGAG CCCTCGTGTT GTGTTCTCTC CAGCTTTCCC      360

CGTGCCTCAG CCACTCTTCA CGTTCCATCT GTGCTCTGTG CTGACCCGCC TGTGACTCAT      420

ACTGGACATC AGTCCACCCT GAATACTGGA CTAAGCGCCA TGTGTGGGAG TGGCTCCAGT      480

TCTGCTGCGA CCAGTACAAG TTGGACACCA ATTGCATCTC CTTCTGCAAC TTCAACATCA      540

GTGGCCTGCA GCTGTGCAGC ATGACACAGG AGGAGTTCGT CGAGGCAGCT GGCCTCTGCG      600

GCGAGTACCT GTACTTCATC CTCCAGAACA TCCGCACACA AGGTTACTCC TTTTTTAATG      660

ACGCTGAAGA AAGCAAGGCC ACCATCAAAG ACTATGCTGA TTCCAACTGC TTGAAAACAA      720

GTGGCATCAA AAGTCAAGAC TGTCACAGTC ATAGTAGAAC AAGCCTCCAA AGTTCTCATC      780

TATGGGAATT TGTACGAGAC CTGCTTCTAT CTCCTGAAGA AAACTGTGGC ATTCTGGAAT      840

GGGAAGATAG GGAACAAGGA ATTTTTCGGG TGGTTAAATC GGAAGCCCTG GCAAAGATGT      900

GGGGACAAAG GAAGAAAAAT GACAGAATGA CGTATGAAAA GTTGAGCAGA GCCCTGAGAT      960

ACTACTATAA AACAGGAATT TTGGAGCGGG TTGACCGAAG GTTAGTGTAC AAATTTGGAA     1020

AAAATGCACA CGGGTGGCAG GAAGACAAGC TATGATCTGC TCCAGGCATC AAGCTCATTT     1080

TATGGATTTC TGTCTTTTAA AACAATCAGA TTGCAATAGA CATTCGAAAG GCTTCATTTT     1140

CTTCTCTTTT TTTTTAACCT GCAAACATGC TGATAAAATT TCTCCACATC TCAGCTTACA     1200

TTTGGATTCA GAGTTGTTGT CTACGGAGGG TGAGAGCAGA AACTCTTAAG AAATCCTTTC     1260

TTCTCCCTAA GGGGATGAGG GGATGATCTT TTGTGGTGTC TTGATCAAAC TTTATTTTCC     1320

TAGAGTTGTG GAATGACAAC AGCCCATGCC ATTGATGCTG ATCAGAGAAA AACTATTCAA     1380

TTCTGCCATT AGAGACACAT CCAATGCTCC CATCCCAAAG GTTCAAAAGT TTTCAAATAA     1440

CTGTGGCAGC TCACCAAAGG TGGGGAAAG CATGATTAGT TTGCAGGTTA TGGTAGGAGA     1500

GGGTGAGATA TAAGACATAC ATACTTTAGA TTTTAAATTA TTAAAGTCAA AAATCCATAG     1560

AAAAGTATCC CTTTTTTTTT TTTTTGAGAC GGGTTCTCAC TATGTTGCCC AGGGCTGGTC     1620

TTGAACTCCT ATGCTCAAGT GATCCTCCCA CCTCGGCCTC CCAAAGTACT GTGATTACAA     1680

GCGTGAGCCA CGGCACCTGG GCAGAAAAGT ATCTTAATTA ATGAAAGAGC TAAGCCATCA     1740

AGCTGGGACT TAATTGGATT TAACATAGGT TCACAGAAAG TTTCCTAACC AGAGCATCTT     1800

TTTGACCACT CAGCAAAACT TCCACAGACA TCCTTCTGGA CTTAAACACT TAACATTAAC     1860

CACATTATTA ATTGTTGCTG AGTTTATTCC CCCTTCTAAC TGATGGCTGG CATCTGATAT     1920

GCAGAGTTAG TCAACAGACA CTGGCATCAA TTACAAAATC ACTGCTGTTT CTGTGATTCA     1980

AGCTGTCAAC ACAATAAAAT CGAAATTCAT TGATTCCATC TCTGGTCCCA GATGTTAAAC     2040

GTTTATAAAA CCGGAAATGT CCTAACAACT CTGTAATGGC AAATTAAATT GTGTGTCTTT     2100

TTTGTTTTGT CTTTCTACCT GATGTGTATT CAAGCGCTAT AACACGTATT TCCTTGACAA     2160

AAATAGTGAC AGTGAATTCA CACTAATAAA TGTTCATAGG TTAAAGTCTG CACTGACATT     2220

TTCTCATCAA TCACTGGTAT GTAAGTTATC AGTGACTGAC AGCTAGGTGG ACTGCCCCTA     2280

GGACTTCTGT TTCACCAGAG CAGGAATCAA GTGGTGAGGC ACTGAATCGC TGTACAGGCT     2340

GAAGACCTCC TTATTAGAGT TGAACTTCAA AGTAACTTGT TTTAAAAAAT GTGAATTACT     2400

GTAAAATAAT CTATTTTGGA TTCATGTGTT TTCCAGGTGG ATATAGTTTG TAAACAATGT     2460

GAATAAAGTA TTTAACATGT TCAAAAAAAA AAAAAAA                              2498
```

(2) INFORMATION FOR SEQ ID NO:11:

(i) SEQUENCE CHARACTERISTICS:
        (A) LENGTH: 164 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Met Thr Gln Glu Glu Phe Val Glu Ala Ala Gly Leu Cys Gly Glu Tyr
1               5                   10                15

Leu Tyr Phe Ile Leu Gln Asn Ile Arg Thr Gln Gly Tyr Ser Phe Phe
        20                   25                30

Asn Asp Ala Glu Glu Ser Lys Ala Thr Ile Lys Asp Tyr Ala Asp Ser
        35                   40                45

Asn Cys Leu Lys Thr Ser Gly Ile Lys Ser Gln Asp Cys His Ser His
    50                   55                 60

Ser Arg Thr Ser Leu Gln Ser Ser His Leu Trp Glu Phe Val Arg Asp
65              70                   75                80

Leu Leu Leu Ser Pro Glu Glu Asn Cys Gly Ile Leu Glu Trp Glu Asp
        85                   90                95

Arg Glu Gln Gly Ile Phe Arg Val Val Lys Ser Glu Ala Leu Ala Lys
        100                  105              110

Met Trp Gly Gln Arg Lys Lys Asn Asp Arg Met Thr Tyr Glu Lys Leu
        115                  120              125

Ser Arg Ala Leu Arg Tyr Tyr Tyr Lys Thr Gly Ile Leu Glu Arg Val
    130                  135                140

Asp Arg Arg Leu Val Tyr Lys Phe Gly Lys Asn Ala His Gly Trp Gln
145             150                 155              160

Glu Asp Lys Leu (2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:12:

AAATGAGCCA ATGTTTGTAA T                                       21

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:13:

AAATGAGCCA GTGTTTGTAA T                                       21

(2) INFORMATION FOR SEQ ID NO:14:

(i) SEQUENCE CHARACTERISTICS:

(A) LENGTH: 736 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:14:

```
AGGAAGTGAA GAACCTAGAT AATCCACCAA CCGGATAATC AGCTCTTGCA TATTTGAGAG      60

TTGACTGCTT GACCTAAGCA TCTCCTCATA AGGTACCCTC CCTCCCAGGA CCTTCCCTTT     120

CAAACCTCTC AAGGCTCTTA CCTGGGGCCA GGGGAGATAG GCTTTTCAAA GTCCATTGAA     180

TTGCCAAGAG TCTCTGTCAA GAAGGCAGTC ATGGTGCCTG GAGAGGGAAC TTGCTGGGAG     240

CCCCTTCAGA GCCTGGTACT TATAGAGCTA GGGAAAAGAT CTTGATGCCA AAGCAGGGTG     300

GACTAAATAC AGACTAATAA ATGAGACAGG TGCTCAAGAG GGCCCCTCCA TACCATCATC     360

TCCTCCAGAT TTGGACTTCT ACTCACTTTG CTTTTACATT CCCTCTTCCC GATGGTGTCT     420

TTGGTGAGCA GGGTGCTTTT CACCTGAAAC AGCCTCTGAG CTGAAAAGAA CAGTCACCAC     480

CAAATCAATT CCTCATCCAT TAACAGGTTG TCTCTCTGTT CTTGAGACAC AGGCATTACC     540

TGGTTAGACC TGTTTTGTTT GAACACTAAC GTGTGAGTTG GCCAAATGCA AATGAGCCAA     600

TGTTTGTAAT CCTTTATTTT ATTTTTTTAA AGGGCTGGGT AGCCAATCAG AAGAGGGGGA     660

AGTGACTTAG GGAATTCCCG GTTGGTGGCT TATTGCTTAA CATCCTACAA AATGATTTAA     720

AATTATTGTT ATATGC                                                    736
```

(2) INFORMATION FOR SEQ ID NO:15:

(i) SEQUENCE CHARACTERISTICS:
            (A) LENGTH: 333 base pairs
            (B) TYPE: nucleic acid
            (C) STRANDEDNESS: double
            (D) TOPOLOGY: linear (ii) MOLECULE TYPE: Genomic DNA (xi) SEQUENCE DESCRIPTION: SEQ ID NO:15:

```
GCCAGAGTCC TCCTTGAGAA CTTACAATGT GTCCATATTA AGGATCTGCT GTGTTTGATG      60

ATTTTGTGAT TACACTTTAA ACTTCTTATC CATAAAGGAC ATACTTGATA TATCTGAGAC     120

TTGTAGTAGA AGGCCTTGAG ACATCCATCT CATCCCATCA TTATCTATCT ATCATCTATC     180

TATCTATCTA TCTATCTATC TATCTATCTA TCTATCATCT ATCTATCTAT CGCCAGTACT     240

GTCTTGTTGA AGTTGGCAGT AGGGTGAAAG ACCTCAAACT CCAAAGGACT TTCCGTATGG     300

ATGCAATATA CCTGCAATTC TAGCTTTTCT GTG                                 333
```

(2) INFORMATION FOR SEQ ID NO:16:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:16:

```
ACAGAATGAC RTATGAAAAG T                                               21
```

(2) INFORMATION FOR SEQ ID NO:17:

(i) SEQUENCE CHARACTERISTICS:
            (A) LENGTH: 21 base pairs
            (B) TYPE: nucleic acid

```
        (C) STRANDEDNESS: single
        (D) TOPOLOGY: linear (xi) SEQUENCE DESCRIPTION: SEQ ID NO:17:

GTAACCAAGC KCAAGCCACC C                                         21

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:18:

AAGGAGCCCA YCTGAGTGCA G                                         21

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:19:

CGTTCCATCT STGCTCTGTG C                                         21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:20:

AGCGCCTCGG YTGGCTGAGG G                                         21

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:21:

TGTATTCAAG YGCTATAACA C                                         21

(2) INFORMATION FOR SEQ ID NO:22:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:22:

CACTGAGAAG CCNACAGGCC TGT                                       23

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
```

(D) TOPOLOGY: linear (xi) SEQUENCE DESCRIPTION: SEQ ID NO:23:

CCCACAGGCC WGTCCCTCCA A                                            21

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:24:

CGTCCATCTC YAGCTCCAGG G                                            21

(2) INFORMATION FOR SEQ ID NO:25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:25:

GACTTGATAA YGCCCGTGGT G                                            21

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:26:

ACTTGATAAC RCCCGTGGTG C                                            21

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:27:

CTCCCCTCCA WGAGCCACAG C                                            21

(2) INFORMATION FOR SEQ ID NO:28:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:28:

ATTTCCTGCA TNGTCTGGAC TT                                           22

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:29:

ATCCAAACAC YTGAGTGGAA A                                              21

(2) INFORMATION FOR SEQ ID NO:30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:30:

AGTTTCCTCA RTGCGGGAGC T                                              21

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:31:

GCGAGCACCT YTGCAGCATG A                                              21

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:32:

TTCACCCGGG YGGCAGGGAC G                                              21

(2) INFORMATION FOR SEQ ID NO:33:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:33:

CTGGGGAAAA NNGATCGCTG AC                                             22

(2) INFORMATION FOR SEQ ID NO:34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:34:

GTCAATTAAA YGGCTCTCAT T                                              21

(2) INFORMATION FOR SEQ ID NO:35:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:35:

TAGATCATTC RTAACCTGCC T                                                        21

(2) INFORMATION FOR SEQ ID NO:36:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:36:

AAAGAGAAAT WCTGGAGCGT G                                                        21

(2) INFORMATION FOR SEQ ID NO:37:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:37:

ATGAGGGGAA MAAGAAACTA C                                                        21

(2) INFORMATION FOR SEQ ID NO:38:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:38:

TTTTGTATGT KACATGATTT A                                                        21

(2) INFORMATION FOR SEQ ID NO:39:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:39:

AGCTTGGTTC YTTTTTGCTC C                                                        21

(2) INFORMATION FOR SEQ ID NO:40:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:40:

TTGACACCAG RAACCCCCCA G                                                        21

(2) INFORMATION FOR SEQ ID NO:41:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:41:

AAATGAGCCA RTGTTTGTAA T                                              21

(2) INFORMATION FOR SEQ ID NO:42:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:42:

ATCCATTTTG YATTCCTCAT T                                              21

(2) INFORMATION FOR SEQ ID NO:43:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:43:

CTGGAGCTCA RACCAGACAG C                                              21

(2) INFORMATION FOR SEQ ID NO:44:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:44:

GCCAGTGCAG SCATCATTAC C                                              21

(2) INFORMATION FOR SEQ ID NO:45:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:45:

AGTTCAAATC RTAATTTTTA T                                              21

(2) INFORMATION FOR SEQ ID NO:46:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:46:

TCATCAGAAT YTAAATCTCC C                                              21

(2) INFORMATION FOR SEQ ID NO:47:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:47:

GGAGATTCAG NTGAAGCAAG A                                          21

(2) INFORMATION FOR SEQ ID NO:48:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:48:

TTTTTCCACA YCCAGCCTGG C                                          21

(2) INFORMATION FOR SEQ ID NO:49:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:49:

CCCAGCCTGG YGAACCCTGG C                                          21

(2) INFORMATION FOR SEQ ID NO:50:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:50:

CTCTTCATCA YGGTCAAATA C                                          21

(2) INFORMATION FOR SEQ ID NO:51:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:51:

CAACTTGCTG YCAAAGTGCT G                                          21

(2) INFORMATION FOR SEQ ID NO:52:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:52:

TACTATGTGC YAGATACTAA G                                          21

(2) INFORMATION FOR SEQ ID NO:53:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:53:

ATGCCACTTT RRGACAACTT GAG                                        23

(2) INFORMATION FOR SEQ ID NO:54:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:54:

CGCATGCCTG KAAAGAAGAG A                                    21

(2) INFORMATION FOR SEQ ID NO:55:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:55:

GGATAAGCAC MAGTGAGCCT G                                    21

(2) INFORMATION FOR SEQ ID NO:56:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:56:

AAGCCAGAC RGCAACTTGT G                                    21

(2) INFORMATION FOR SEQ ID NO:57:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:57:

TCTCAAAAAG RGTGATAGGA G                                    21

(2) INFORMATION FOR SEQ ID NO:58:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:58:

TCTGAATCCT STCTCCTCCT T                                    21

(2) INFORMATION FOR SEQ ID NO:59:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:59:

TAGAACCAGG WTGTGGGACC A                                    21

(2) INFORMATION FOR SEQ ID NO:60:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:60:

TTCTTGTGTC RGGCGCAAAA C                                        21

(2) INFORMATION FOR SEQ ID NO:61:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:61:

AACCAACATG RAGAAACCCC A                                        21

(2) INFORMATION FOR SEQ ID NO:62:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:62:

AATAAACTAT RGTTCACCTA G                                        21

(2) INFORMATION FOR SEQ ID NO:63:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:63:

ACATATTTGT RTCTCATATG A                                        21

(2) INFORMATION FOR SEQ ID NO:64:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:64:

CAAAGCAGTT YCTAATAATC C                                        21

(2) INFORMATION FOR SEQ ID NO:65:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:65:

AGATCCTAAC YGGGGCCTCC T                                        21

(2) INFORMATION FOR SEQ ID NO:66:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:66:

CTCTTTCTCT YTGCTTCCTC C                               21

(2) INFORMATION FOR SEQ ID NO:67:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:67:

TTAGGAATCC WCAAATATGT A                               21

(2) INFORMATION FOR SEQ ID NO:68:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:68:

GTCTGACTCC RCCTCCCTCA T                               21

(2) INFORMATION FOR SEQ ID NO:69:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:69:

GAATCACATC RTGAGAAATG T                               21

(2) INFORMATION FOR SEQ ID NO:70:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:70:

AATTCAATCC YTCACAGACT T                               21

(2) INFORMATION FOR SEQ ID NO:71:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:71:

GTGTAGCCAG RGTTGCTAAT T                               21

(2) INFORMATION FOR SEQ ID NO:72:

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:72:

CCTAGAAATA SCCAAGGGCA C                                         21

(2) INFORMATION FOR SEQ ID NO:73:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:73:

AAATTCTCAT RCCTCACCCT C                                         21

(2) INFORMATION FOR SEQ ID NO:74:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:74:

TCCCACCCCT RTCACCTTCA T                                         21

(2) INFORMATION FOR SEQ ID NO:75:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:75:

CCTCATTCTC RGAAGCCAAC A                                         21

(2) INFORMATION FOR SEQ ID NO:76:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:76:

GAAGAGCCGT YCAGTCCCTT T                                         21

(2) INFORMATION FOR SEQ ID NO:77:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:77:

TCCATAGGCT YTTTATTTGG C                                         21

(2) INFORMATION FOR SEQ ID NO:78:
```

```
       (i) SEQUENCE CHARACTERISTICS:
           (A) LENGTH: 21 base pairs
           (B) TYPE: nucleic acid
           (C) STRANDEDNESS: single
           (D) TOPOLOGY: linear (xi) SEQUENCE DESCRIPTION: SEQ ID NO:78:

TCGTTTAGTA YACAGGCTTT G                                            21

(2) INFORMATION FOR SEQ ID NO:79:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (xi) SEQUENCE DESCRIPTION: SEQ ID NO:79:

GCCTCAGTTG YCCCAGCTAT A                                            21

(2) INFORMATION FOR SEQ ID NO:80:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (xi) SEQUENCE DESCRIPTION: SEQ ID NO:80:

AGCAAAATGC WCTATGCACT G                                            21

(2) INFORMATION FOR SEQ ID NO:81:

(i) SEQUENCE CHARACTERISTICS:
           (A) LENGTH: 31 base pairs
           (B) TYPE: nucleic acid
           (C) STRANDEDNESS: single
           (D) TOPOLOGY: linear (xi) SEQUENCE DESCRIPTION: SEQ ID NO:81:

GTGTCCTGAC NNNNNNNNNN NACACTGCCT G                                 31

(2) INFORMATION FOR SEQ ID NO:82:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (xi) SEQUENCE DESCRIPTION: SEQ ID NO:82:

ATCAGATAAC RCCTACACTT A                                            21

(2) INFORMATION FOR SEQ ID NO:83:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (xi) SEQUENCE DESCRIPTION: SEQ ID NO:83:

TCTCTCTTCT SCCTGCCCTG T                                            21

(2) INFORMATION FOR SEQ ID NO:84:

(i) SEQUENCE CHARACTERISTICS:
```

```
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:84:

TGGACACAGG KAGGGGAATA T                                              21

(2) INFORMATION FOR SEQ ID NO:85:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:85:

TGTCACTTGC RCATACAAGG C                                              21

(2) INFORMATION FOR SEQ ID NO:86:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:86:

ATCATCAGAT YAGCCCAGAA T                                              21

(2) INFORMATION FOR SEQ ID NO:87:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:87:

TCAACAGAGA RAGTTAATGG T                                              21

(2) INFORMATION FOR SEQ ID NO:88:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:88:

AGCAATAATG YTTCCCTTTT C                                              21

(2) INFORMATION FOR SEQ ID NO:89:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:89:

TCTAGCTTTT YTGTGTTTTT T                                              21

(2) INFORMATION FOR SEQ ID NO:90:

(i) SEQUENCE CHARACTERISTICS:
        (A) LENGTH: 21 base pairs
```

(B) TYPE: nucleic acid
        (C) STRANDEDNESS: single
        (D) TOPOLOGY: linear (xi) SEQUENCE DESCRIPTION: SEQ ID NO:90:

GATTCCTTAA YGCTTGATAC T                                            21

(2) INFORMATION FOR SEQ ID NO:91:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:91:

CCTCCTCCAG YACCAAAGTG G                                            21

(2) INFORMATION FOR SEQ ID NO:92:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:92:

ATGGCCACAG RTCAAATCCT G                                            21

(2) INFORMATION FOR SEQ ID NO:93:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:93:

ACTGAGTGTT YATGCCAATT T                                            21

(2) INFORMATION FOR SEQ ID NO:94:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:94:

GACAAGCCCT RTCTGACACA C                                            21

(2) INFORMATION FOR SEQ ID NO:95:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:95:

TGAAAAGCCT YCTTGCTGCC T                                            21

(2) INFORMATION FOR SEQ ID NO:96:

(i) SEQUENCE CHARACTERISTICS:
        (A) LENGTH: 21 base pairs
        (B) TYPE: nucleic acid

```
        (C) STRANDEDNESS: single
        (D) TOPOLOGY: linear (xi) SEQUENCE DESCRIPTION: SEQ ID NO:96:

TCCTGGAGTT YCTTTGCTCC C                                           21

(2) INFORMATION FOR SEQ ID NO:97:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:97:

GATTCCAAAT WAACTAAAGA T                                           21

(2) INFORMATION FOR SEQ ID NO:98:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:98:

GACCTCAAGT CRTCCACCCG CC                                          22

(2) INFORMATION FOR SEQ ID NO:99:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:99:

AACAAATACT MCCCCGCAAC CC                                          22

(2) INFORMATION FOR SEQ ID NO:100:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:100:

ATTTTTTTTT NAAGGAAAAT A                                           21

(2) INFORMATION FOR SEQ ID NO:101:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:101:

AAATTTCCCC MAAACAAGCA G                                           21

(2) INFORMATION FOR SEQ ID NO:102:

(i) SEQUENCE CHARACTERISTICS:
        (A) LENGTH: 21 base pairs
        (B) TYPE: nucleic acid
        (C) STRANDEDNESS: single
```

(D) TOPOLOGY: linear (xi) SEQUENCE DESCRIPTION: SEQ ID NO:102:

GAGAAAGGGT RTGTGTGTGT G                                              21

(2) INFORMATION FOR SEQ ID NO:103:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:103:

GTGTGTGTGT NNNNGTATGT GCGCGTG                                        27

(2) INFORMATION FOR SEQ ID NO:104:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:104:

ATCGGGAACC YCATACCCCA A                                              21

(2) INFORMATION FOR SEQ ID NO:105:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:105:

TTTGTTTCGC MATGAGGTAC G                                              21

(2) INFORMATION FOR SEQ ID NO:106:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:106:

TGAGGGTGTT STGGGCTGGA C                                              21

(2) INFORMATION FOR SEQ ID NO:107:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:107:

TCTTCATTGG YATCTGAATG T                                              21

(2) INFORMATION FOR SEQ ID NO:108:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:108:

GCGAGCACCT YTGCAGCATG A                                          21

(2) INFORMATION FOR SEQ ID NO:109:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:109:

AACCCCCCCC MCACACACAC A                                          21

(2) INFORMATION FOR SEQ ID NO:110:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:110:

TCAGTGCTCT STAATCAGTC A                                          21

(2) INFORMATION FOR SEQ ID NO:111:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:111:

TCTTTGTGAA ANNAATTAGT CTG                                        23

(2) INFORMATION FOR SEQ ID NO:112:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:112:

GCTGCCCTGA SAGCTGGGCC A                                          21

(2) INFORMATION FOR SEQ ID NO:113:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:113:

CCTTCTGATC YTTGTTTGCT G                                          21

(2) INFORMATION FOR SEQ ID NO:114:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:114:

GGAACACTGA KTCTTGATTA G                                              21

(2) INFORMATION FOR SEQ ID NO:115:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:115:

TAGGCTTCTC YTGATAATTG A                                              21

(2) INFORMATION FOR SEQ ID NO:116:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:116:

TCTTAAAATA MTTGGCTTGT A                                              21

(2) INFORMATION FOR SEQ ID NO:117:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:117:

TAGATCATTA RTAACCTGCC T                                              21

(2) INFORMATION FOR SEQ ID NO:118:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:118:

ATGAGGGGAA MAAGAAACTA C                                              21

(2) INFORMATION FOR SEQ ID NO:119:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:119:

TTGACACCAG RAACCCCCCA G                                              21

(2) INFORMATION FOR SEQ ID NO:120:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:120:

-continued

TGTTTTAAAT RTTAGGGACA A                     21

(2) INFORMATION FOR SEQ ID NO:121:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:121:

GTAAGCATAG YAATGTAGCA G                     21

(2) INFORMATION FOR SEQ ID NO:122:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:122:

GGCTCTTTCT KCAACCTTTC C                     21

(2) INFORMATION FOR SEQ ID NO:123:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:123:

GACCCAGGTT RTGAGTTTTC C                     21

(2) INFORMATION FOR SEQ ID NO:124:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:124:

GACAGAATGA YATATGAAAA G                     21

(2) INFORMATION FOR SEQ ID NO:125:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:125:

TGTGTGACAC YGAGAAGCCC A                     21

(2) INFORMATION FOR SEQ ID NO:126:

(i) SEQUENCE CHARACTERISTICS:
        (A) LENGTH: 21 base pairs
        (B) TYPE: nucleic acid
        (C) STRANDEDNESS: double (D) TOPOLOGY: linear (ii) MOLECULE TYPE: Other (xi) SEQUENCE DESCRIPTION: SEQ ID NO:126:

AGTACTGGAC MAAGTACCAG G                                               21

(2) INFORMATION FOR SEQ ID NO:127:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:127:

CCTGGGAGCA RGTATTGCAT T                                               21

(2) INFORMATION FOR SEQ ID NO:128:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:128:

AGATTTGAGG YCTCAGGTCC C                                               21

(2) INFORMATION FOR SEQ ID NO:129:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:129:

TGTCAATGTC RCATGATAAG C                                               21

(2) INFORMATION FOR SEQ ID NO:130:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:130:

TTGCCCCAGT KTTCTCCGGG C                                               21

(2) INFORMATION FOR SEQ ID NO:131:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:131:

TATGAGCAGC RTAGGGAGTG G                                              21

(2) INFORMATION FOR SEQ ID NO:132:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:132:

AGTTGACTGA AAAANTAAAT AAGAC                                          25

(2) INFORMATION FOR SEQ ID NO:133:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:133:

ATTCAAATAG SCTCTAGAAA C                                              21

(2) INFORMATION FOR SEQ ID NO:134:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:134:

CCCAGAATTT MATATCCATT C                                              21

(2) INFORMATION FOR SEQ ID NO:135:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:135:

TGACCCAACA RAAACTCACT G                                              21

(2) INFORMATION FOR SEQ ID NO:136:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:136:

CCAGAATATA WCATCAGCCC T                                              21

(2) INFORMATION FOR SEQ ID NO:137:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:137:

CATCAGCCCT WCTGAGGAGA T                                              21

(2) INFORMATION FOR SEQ ID NO:138:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:138:

CCAGAACAGA YTTTATTCTG T                                              21

(2) INFORMATION FOR SEQ ID NO:139:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:139:

TTCAGCCATC YTTCCAGTTG T                                              21

(2) INFORMATION FOR SEQ ID NO:140:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:140:

TCACTAACTC WAAAACGACA T                                              21

(2) INFORMATION FOR SEQ ID NO:141:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:141:

AACTCAAAAA YGACATCCTC C                                              21

(2) INFORMATION FOR SEQ ID NO:142:

(i) SEQUENCE CHARACTERISTICS:

(A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:142:

GAACTGCACA RGTTGCACAC T                                              21

(2) INFORMATION FOR SEQ ID NO:143:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:143:

TTGTTCCATG SACTACCTCC T                                              21

(2) INFORMATION FOR SEQ ID NO:144:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:144:

ACAGCAGGCA YTCAACAAAT T                                              21

(2) INFORMATION FOR SEQ ID NO:145:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:145:

TTATTTTTGG STTTGTTTTA A                                              21

(2) INFORMATION FOR SEQ ID NO:146:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:146:

TAGGCTGTTC YCTGCCATCA C                                              21

(2) INFORMATION FOR SEQ ID NO:147:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:147:

GTGCTCTGGG MCACACAGCT C                                              21

(2) INFORMATION FOR SEQ ID NO:148:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: Other (xi) SEQUENCE DESCRIPTION: SEQ ID NO:148:

AGACCCGATA RGAGCTCCTT C                                              21

(2) INFORMATION FOR SEQ ID NO:149:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: Other (xi) SEQUENCE DESCRIPTION: SEQ ID NO:149:

CATCTTGCGC RGTCATGTAA G                                              21

(2) INFORMATION FOR SEQ ID NO:150:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: Other (xi) SEQUENCE DESCRIPTION: SEQ ID NO:150:

CAGCACAGCT RTTCCCTCAA A                                              21

(2) INFORMATION FOR SEQ ID NO:151:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: Other (xi) SEQUENCE DESCRIPTION: SEQ ID NO:151:

TTTGGAAACA YGGTGAAGTA T                                              21

(2) INFORMATION FOR SEQ ID NO:152:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: Other (xi) SEQUENCE DESCRIPTION: SEQ ID NO:152:

```
ACACGGTGAA RTATTGTCTC C                                        21

(2) INFORMATION FOR SEQ ID NO:153:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:153:

AAAAGTGGAT MCTCTGCAAA C                                        21

(2) INFORMATION FOR SEQ ID NO:154:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:154:

CTTCAAATGC RGCTATTAAA G                                        21

(2) INFORMATION FOR SEQ ID NO:155:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:155:

CCTGGGAGCA YGGTAAATCA G                                        21

(2) INFORMATION FOR SEQ ID NO:156:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:156:

TGAAAATGTC RCTTTCTCAC CT                                       22

(2) INFORMATION FOR SEQ ID NO:157:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:157:

CCTGATATTT RCCAACAAGA A                                        21
```

(2) INFORMATION FOR SEQ ID NO:158:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:158:

AAAGGGTTAG YTTGTCCCCT T                                        21

(2) INFORMATION FOR SEQ ID NO:159:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:159:

TGAAAATAAA ASACAATTTT TT                                       22

(2) INFORMATION FOR SEQ ID NO:160:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:160:

CTGCTGTGGA CGAATAGG                                            18

(2) INFORMATION FOR SEQ ID NO:161:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:161:

TCAATATAAT CTTGCTTAAC TTGG                                     24

(2) INFORMATION FOR SEQ ID NO:162:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:162:

GACCTGTTTG GGTTGATTTC AG                                       22

(2) INFORMATION FOR SEQ ID NO:163:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:163:

```
GTTTCTTACA GTGTCTTGCT ATCACATCAC C                                              31

(2) INFORMATION FOR SEQ ID NO:164:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (xi) SEQUENCE DESCRIPTION: SEQ ID NO:164:

GAGGACTGGC AGTACCAAGT AAAC                                                      24

(2) INFORMATION FOR SEQ ID NO:165:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (xi) SEQUENCE DESCRIPTION: SEQ ID NO:165:

GTTTCTTTGG TTCATTCTAA GATGGCTGG                                                 29

(2) INFORMATION FOR SEQ ID NO:166:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (xi) SEQUENCE DESCRIPTION: SEQ ID NO:166:

GCTGAGGCAG GAGAAAAGAC AAG                                                       23

(2) INFORMATION FOR SEQ ID NO:167:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (xi) SEQUENCE DESCRIPTION: SEQ ID NO:167:

GTTTCTTCAT GCAAAGGTCA GGAGGTAGG                                                 29

(2) INFORMATION FOR SEQ ID NO:168:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (xi) SEQUENCE DESCRIPTION: SEQ ID NO:168:

GTTGCTTCCA GACGAGGTAC ATG                                                       23

(2) INFORMATION FOR SEQ ID NO:169:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (xi) SEQUENCE DESCRIPTION: SEQ ID NO:169:

GTTTCTTCAA TGGCTCCACA AACATCTCTG                                                30
```

(2) INFORMATION FOR SEQ ID NO:170:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:170:

AGGTTTAGGG GACAGGGTTT GG                                            22

(2) INFORMATION FOR SEQ ID NO:171:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:171:

GTTTCTTTCC TGGCTAACAC GGTGAAATC                                    29

(2) INFORMATION FOR SEQ ID NO:172:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:172:

GTTTCTTATT GCCTCCTCCC AAAATTC                                      27

(2) INFORMATION FOR SEQ ID NO:173:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:173:

AGAGGCCACT GGAAGACGAA                                              20

(2) INFORMATION FOR SEQ ID NO:174:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:174:

AACTGGAGTC AGGCAAAACG TG                                            22

(2) INFORMATION FOR SEQ ID NO:175:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:175:

GTTTCTTTGG CTGGTAAGGA AAGAAACCAC                                  30

(2) INFORMATION FOR SEQ ID NO:176:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:176:

GGCTAGGTTC ATAAACTCTG TGCTG                                              25

(2) INFORMATION FOR SEQ ID NO:177:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:177:

GTTTCTTGAT TGTTTGAGAT CCTTGACCCA G                                       31

(2) INFORMATION FOR SEQ ID NO:178:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:178:

GCCGAAATCA CAACACTGCA TC                                                 22

(2) INFORMATION FOR SEQ ID NO:179:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:179:

GTTTCTTGAT TCTGCTCTTA CTCTTGCCCC                                         30

(2) INFORMATION FOR SEQ ID NO:180:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:180:

GTAATAGAAC CAAAGGGCTG AGAC                                               24

(2) INFORMATION FOR SEQ ID NO:181:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:181:

GTTTCTTCGG AGTCAGACCT TACATTGTTG AG                                      32

(2) INFORMATION FOR SEQ ID NO:182:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:182:

```
ATCTCCCTGC TACCCACCTT                                           20
```

(2) INFORMATION FOR SEQ ID NO:183:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:183:

```
GTTTCTTGTT TTCAGTGAGT TTCTGTTGGG                                30
```

(2) INFORMATION FOR SEQ ID NO:184:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:184:

```
GTGTGCCAAA CAACATTTGC                                           20
```

(2) INFORMATION FOR SEQ ID NO:185:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:185:

```
GTTTCTTCAA GCCATCAAGC TAGAGTGG                                  28
```

(2) INFORMATION FOR SEQ ID NO:186:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:186:

```
GGGCTTTTAA ACCCTTATTT AACC                                      24
```

(2) INFORMATION FOR SEQ ID NO:187:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:187:

```
GTTTCTTAGG TGATCTCAGA GCCACTCA                                  28
```

(2) INFORMATION FOR SEQ ID NO:188:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:188:

AGGGCAGGTG GGAACTTACT                                                    20

(2) INFORMATION FOR SEQ ID NO:189:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:189:

GTTTCTTTGG AGTCAGTTGA GCTTTCTACC                                         30

(2) INFORMATION FOR SEQ ID NO:190:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:190:

TGAACTTGCC TACCTCCCAG                                                    20

(2) INFORMATION FOR SEQ ID NO:191:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:191:

GTTTCTTAGC ATATATCCTT ACACAAGCAC A                                       31

(2) INFORMATION FOR SEQ ID NO:192:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:192:

CATGGTTCCA AAGGCAAGTT                                                    20

(2) INFORMATION FOR SEQ ID NO:193:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:193:

GTTTCTTTTG AGGCTGAATG AGCTGTG                                            27

(2) INFORMATION FOR SEQ ID NO:194:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (xi) SEQUENCE DESCRIPTION: SEQ ID NO:194:

ACAGGTGGGA AGACTGAATG TC                                22

(2) INFORMATION FOR SEQ ID NO:195:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:195:

GTTTCTTGCA GTACACATCA CATGACCTTG                        30

(2) INFORMATION FOR SEQ ID NO:196:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:196:

GAAATAGGCG GAAACTGGTT C                                 21

(2) INFORMATION FOR SEQ ID NO:197:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:197:

GTTTCTTCGT TGTGGTTGTT CAGAAAGG                          28

(2) INFORMATION FOR SEQ ID NO:198:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:198:

GGTCAAGTGT TCAGAACGCA TC                                22

(2) INFORMATION FOR SEQ ID NO:199:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:199:

GTTTCTTGCA GGGATTATGC TAGGTCTGTA G                      31

(2) INFORMATION FOR SEQ ID NO:200:

(i) SEQUENCE CHARACTERISTICS:

(A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:200:

AGCACTTCTG AGGAAGGGAC AC                        22

(2) INFORMATION FOR SEQ ID NO:201:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:201:

GTTTCTTAGG GCAGGCAGAC ATACAAAC                  28

(2) INFORMATION FOR SEQ ID NO:202:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:202:

GCCAATGTGT TCCTAGAGCG AC                        22

(2) INFORMATION FOR SEQ ID NO:203:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:203:

GTTTCTTTTA AAGGGGTAG GGTGTCACC                  29

(2) INFORMATION FOR SEQ ID NO:204:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:204:

GGAAGGGAAA AGGACAAGGT TTTG                      24

(2) INFORMATION FOR SEQ ID NO:205:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:205:

GTTTCTTAGC AAGAGCACTG GTGTAGGAGT C              31

(2) INFORMATION FOR SEQ ID NO:206:

(i) SEQUENCE CHARACTERISTICS:
        (A) LENGTH: 20 base pairs (B) TYPE: nucleic acid
            (C) STRANDEDNESS: single
            (D) TOPOLOGY: linear (xi) SEQUENCE DESCRIPTION: SEQ ID NO:206:

GCTTTTCAAG CACTTGTCTC                                                     20

(2) INFORMATION FOR SEQ ID NO:207:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:207:

TGGGATTGTG ACTTACCATG                                                     20

(2) INFORMATION FOR SEQ ID NO:208:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:208:

ACTTGGTGTC TTATAGAAAG GTG                                                 23

(2) INFORMATION FOR SEQ ID NO:209:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:209:

GTTTCTTAGC TGTGTTTGCT GCATC                                               25

(2) INFORMATION FOR SEQ ID NO:210:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:210:

AGATGTGTGA TGAGATGCAG                                                     20

(2) INFORMATION FOR SEQ ID NO:211:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:211:

GTTTCTTCAA ATAGTGCAAC AAACCC                                              26

(2) INFORMATION FOR SEQ ID NO:212:

(i) SEQUENCE CHARACTERISTICS:
            (A) LENGTH: 21 base pairs
            (B) TYPE: nucleic acid

```
        (C) STRANDEDNESS: single
        (D) TOPOLOGY: linear (xi) SEQUENCE DESCRIPTION: SEQ ID NO:212:

TGTCATTCTG AAAGTGCTTC C                                              21

(2) INFORMATION FOR SEQ ID NO:213:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:213:

GTTTCTTCTG TAACTAACGA TCTGTAGTGG TG                                  32

(2) INFORMATION FOR SEQ ID NO:214:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:214:

TATCAAGGTA ATATAGTAGC CACGG                                          25

(2) INFORMATION FOR SEQ ID NO:215:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:215:

AGGTCTTTCA TGCAGAGTGG                                                20

(2) INFORMATION FOR SEQ ID NO:216:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:216:

ATTGCCAAAA CTTGGAAGC                                                 19

(2) INFORMATION FOR SEQ ID NO:217:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:217:

AGGTGACATA TCAAGACCCT G                                              21

(2) INFORMATION FOR SEQ ID NO:218:

(i) SEQUENCE CHARACTERISTICS:
        (A) LENGTH: 17 base pairs
        (B) TYPE: nucleic acid
        (C) STRANDEDNESS: single
```

(D) TOPOLOGY: linear (xi) SEQUENCE DESCRIPTION: SEQ ID NO:218:

TTGTCAACGA AGCCCAC                                                      17

(2) INFORMATION FOR SEQ ID NO:219:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (xi) SEQUENCE DESCRIPTION: SEQ ID NO:219:

GTTTCTTGCA AGATTGTGTG TATGGATG                                          28

(2) INFORMATION FOR SEQ ID NO:220:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:220:

GCTCTCTATG TGTTTGGGTG                                                   20

(2) INFORMATION FOR SEQ ID NO:221:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:221:

AAGAGTACGC TAGTGGATGG                                                   20

(2) INFORMATION FOR SEQ ID NO:222:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:222:

TCCATTAGAC CCAGAAAGG                                                    19

(2) INFORMATION FOR SEQ ID NO:223:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:223:

GTTTCTTCAC CAGGCTGAGA TGTTACT                                           27

(2) INFORMATION FOR SEQ ID NO:224:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:224:

AATCGTTCCT TATCAGGTAA TTTGG                                              25

(2) INFORMATION FOR SEQ ID NO:225:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (xi) SEQUENCE DESCRIPTION: SEQ ID NO:225:

GTTTCTTCAA AGAAAGCAAT TCCATCATAA CA                                      32

(2) INFORMATION FOR SEQ ID NO:226:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:226:

GCATTTGTTG AAGCAAGCGG                                                    20

(2) INFORMATION FOR SEQ ID NO:227:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:227:

CTTTGTTCCT TGGCTGATGG                                                    20

(2) INFORMATION FOR SEQ ID NO:228:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:228:

AATAGTACCA GACACACGTG                                                    20

(2) INFORMATION FOR SEQ ID NO:229:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:229:

CAATGGTTCA CAGCCCTTTT                                                    20

(2) INFORMATION FOR SEQ ID NO:230:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO:230:

AGCCTGGGAG ACAGAGTGAG                                                    20

(2) INFORMATION FOR SEQ ID NO:231:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:231:

GTTTCTTGCA CTTTTTGGGG AAGGTG                                             26

(2) INFORMATION FOR SEQ ID NO:232:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:232:

GTTCCTCCCT TCCCTCTCC                                                     19

(2) INFORMATION FOR SEQ ID NO:233:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:233:

GTTTCTTTCA GGGACTGGAT TGTAG                                              25

(2) INFORMATION FOR SEQ ID NO:234:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:234:

GTGTTCTTTA TGTGTAGTTC                                                    20

(2) INFORMATION FOR SEQ ID NO:235:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:235:

GTTTCTTGGC AACAGAGTGA GACTCA                                             26

(2) INFORMATION FOR SEQ ID NO:236:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:236:

```
GTGACATCCA GTGTTGGGAG                                                  20

(2) INFORMATION FOR SEQ ID NO:237:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (xi) SEQUENCE DESCRIPTION: SEQ ID NO:237:

GTTTCTTCCT AAGCAAGCAA GCAATCA                                          27

(2) INFORMATION FOR SEQ ID NO:238:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (xi) SEQUENCE DESCRIPTION: SEQ ID NO:238:

AAAGGCAATT GGTGGACA                                                    18

(2) INFORMATION FOR SEQ ID NO:239:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (xi) SEQUENCE DESCRIPTION: SEQ ID NO:239:

GTTTCTTTTC AATCCTTGAT GCAAAGT                                          27

(2) INFORMATION FOR SEQ ID NO:240:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (xi) SEQUENCE DESCRIPTION: SEQ ID NO:240:

GGTGACAGAG CAAGATTTCG                                                  20

(2) INFORMATION FOR SEQ ID NO:241:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (xi) SEQUENCE DESCRIPTION: SEQ ID NO:241:

GTTTCTTGTA GAGTTGAGGG AGCAGC                                           26

(2) INFORMATION FOR SEQ ID NO:242:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (xi) SEQUENCE DESCRIPTION: SEQ ID NO:242:

CATCCATCTC ATCCCATCAT                                                  20
```

(2) INFORMATION FOR SEQ ID NO:243:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:243:

GTTTCTTTTC ACCCTACTGC CAACTTC                              27

(2) INFORMATION FOR SEQ ID NO:244:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:244:

CCGCCATTTT AGAGAGCATA                                    20

(2) INFORMATION FOR SEQ ID NO:245:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:245:

GTTTCTTTTC TGGGACAATT GGTAGGA                              27

(2) INFORMATION FOR SEQ ID NO:246:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:246:

TTTGTGTTAT TATTTCAGGT GC                                   22

(2) INFORMATION FOR SEQ ID NO:247:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:247:

GTTTCTTGTT TTTTGTTTCA GTTTAGGAAC                          30

(2) INFORMATION FOR SEQ ID NO:248:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:248:

CATACCCAAA TCGTTCTCTT CCTC                                   24

(2) INFORMATION FOR SEQ ID NO:249:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:249:

GTTTCTTGGA AAAGCAAAGG CATCGTAGAG                30

(2) INFORMATION FOR SEQ ID NO:250:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:250:

TACTAACCAA AAGAGTTGGG G                         21

(2) INFORMATION FOR SEQ ID NO:251:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:251:

CTATCATTCA GAAAATGTTG GC                        22

(2) INFORMATION FOR SEQ ID NO:252:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:252:

GTATGGCAGT AGAGGGCATG                           20

(2) INFORMATION FOR SEQ ID NO:253:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:253:

AAGGTTACAT TTCAAGAAAT AAAGT                     25

(2) INFORMATION FOR SEQ ID NO:254:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:254:

CTGTTCAGGC CTCAATATAT ACC                       23

(2) INFORMATION FOR SEQ ID NO:255:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:255:

AAGAGGATAG GTGGGGTTTG                                               20

(2) INFORMATION FOR SEQ ID NO:256:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:256:

CCTCCCACCT AGACACAAT                                                19

(2) INFORMATION FOR SEQ ID NO:257:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:257:

ATATGATCTT TGCATCCCTG                                               20

(2) INFORMATION FOR SEQ ID NO:258:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:258:

AAGAAAGACC TGGAAGGAAT                                               20

(2) INFORMATION FOR SEQ ID NO:259:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:259:

AAACAGCAAA ACCTCATCTC                                               20

(2) INFORMATION FOR SEQ ID NO:260:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:260:

CCACCACTTA TTACCTGCAT                                               20

(2) INFORMATION FOR SEQ ID NO:261:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:261:

TGAATGAATG AATGAACGAA                                          20

(2) INFORMATION FOR SEQ ID NO:262:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:262:

AACTGTGATT GTGCCACTGC ACTC                                     24

(2) INFORMATION FOR SEQ ID NO:263:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:263:

GTTTCTTCAC CGCCTTTATC CCTCAAATG                                29

(2) INFORMATION FOR SEQ ID NO:264:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:264:

GATGGGTGGA GGGCAGTTAA AG                                       22

(2) INFORMATION FOR SEQ ID NO:265:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:265:

GTCAAGCAAC TTGTCCAAGG CTAC                                     24

(2) INFORMATION FOR SEQ ID NO:266:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:266:

CAGGCTATCA GTTTCCTTTG GAG                                      23

(2) INFORMATION FOR SEQ ID NO:267:
```

```
       (i) SEQUENCE CHARACTERISTICS:
           (A) LENGTH: 24 base pairs
           (B) TYPE: nucleic acid
           (C) STRANDEDNESS: single
           (D) TOPOLOGY: linear (xi) SEQUENCE DESCRIPTION: SEQ ID NO:267:

GGCAGGTAAT ACTGGAGAAT TAGG                                              24

(2) INFORMATION FOR SEQ ID NO:268:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:268:

GACGGATCTC AGAGCCACTC                                                   20

(2) INFORMATION FOR SEQ ID NO:269:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (xi) SEQUENCE DESCRIPTION: SEQ ID NO:269:

GTTTCTTAAA AGATAAGGGC TTTTAAACC                                         29

(2) INFORMATION FOR SEQ ID NO:270:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:270:

AGTTTCACAG CTTGTTATGG                                                   20

(2) INFORMATION FOR SEQ ID NO:271:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:271:

GGTTGATGAA GTGAGACTTT                                                   20

(2) INFORMATION FOR SEQ ID NO:272:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (xi) SEQUENCE DESCRIPTION: SEQ ID NO:272:

ATGGTGGATG CATCCTGTG                                                    19

(2) INFORMATION FOR SEQ ID NO:273:

(i) SEQUENCE CHARACTERISTICS:
```

```
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:273:

GTTTCTTGTA TTGACTCCTC CTCTGC                                            26

(2) INFORMATION FOR SEQ ID NO:274:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:274:

CAGTAAACAT                                                              10

(2) INFORMATION FOR SEQ ID NO:275:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:275:

TGTTGAGTGG                                                              10

(2) INFORMATION FOR SEQ ID NO:276:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:276:

TCTCCTCAAT GTGCATGT                                                     18

(2) INFORMATION FOR SEQ ID NO:277:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:277:

ATTCTACATA                                                              10

(2) INFORMATION FOR SEQ ID NO:278:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Other
```

(xi) SEQUENCE DESCRIPTION: SEQ ID NO:278:

GTGTTTGCAT                                                                    10

(2) INFORMATION FOR SEQ ID NO:279:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:279:

ACAAGTTGGC                                                                    10

(2) INFORMATION FOR SEQ ID NO:280:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:280:

TAGTACCAGA                                                                    10

(2) INFORMATION FOR SEQ ID NO:281:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:281:

TACATCCAAG AAAA                                                               14

(2) INFORMATION FOR SEQ ID NO:282:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:282:

GAGACTCTGA CAAATATATA TA                                                      22

(2) INFORMATION FOR SEQ ID NO:283:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:283:

TGTTGATCGC CAAACCAAAA TC                                                      22

(2) INFORMATION FOR SEQ ID NO:284:

(i) SEQUENCE CHARACTERISTICS:
           (A) LENGTH: 38 base pairs
           (B) TYPE: nucleic acid
           (C) STRANDEDNESS: single
           (D) TOPOLOGY: linear (xi) SEQUENCE DESCRIPTION: SEQ ID NO:284:

AATGCATGTA TGTATATGGT GTGGTATGTG TACATATG                                38

(2) INFORMATION FOR SEQ ID NO:285:

(i) SEQUENCE CHARACTERISTICS:
           (A) LENGTH: 22 base pairs
           (B) TYPE: nucleic acid
           (C) STRANDEDNESS: single
           (D) TOPOLOGY: linear (xi) SEQUENCE DESCRIPTION: SEQ ID NO:285:

CCTCCCAGAA CAATCATGAT AA                                                 22

(2) INFORMATION FOR SEQ ID NO:286:

(i) SEQUENCE CHARACTERISTICS:
           (A) LENGTH: 86 base pairs
           (B) TYPE: nucleic acid
           (C) STRANDEDNESS: single
           (D) TOPOLOGY: linear (xi) SEQUENCE DESCRIPTION: SEQ ID NO:286:

AGACAGTCTC AAAAAATATT TTAAAGAAAA AGCTGGATAA ATAACTAGCT TTAAGAAAAT         60

AAGAAGAAAA AGAAAGAAGA AAGTAA                                             86

(2) INFORMATION FOR SEQ ID NO:287:

(i) SEQUENCE CHARACTERISTICS:
           (A) LENGTH: 86 base pairs
           (B) TYPE: nucleic acid
           (C) STRANDEDNESS: single
           (D) TOPOLOGY: linear (xi) SEQUENCE DESCRIPTION: SEQ ID NO:287:

AACTAGCTTT AAGAAAATAA GAAGAAAAG AAAGAAGAAA GTAAGAAAGA GAAAGAAAAG          60

AAAGAAAAGA AAGAGGAATG ATTGAC                                             86

(2) INFORMATION FOR SEQ ID NO:288:

(i) SEQUENCE CHARACTERISTICS:
           (A) LENGTH: 22 base pairs
           (B) TYPE: nucleic acid
           (C) STRANDEDNESS: double
           (D) TOPOLOGY: linear (ii) MOLECULE TYPE: Other (xi) SEQUENCE DESCRIPTION: SEQ ID NO:288:

CGCGCACATA CACCCTTTCT CT                                                 22

(2) INFORMATION FOR SEQ ID NO:289:

(i) SEQUENCE CHARACTERISTICS:
           (A) LENGTH: 22 base pairs
           (B) TYPE: nucleic acid
           (C) STRANDEDNESS: double
           (D) TOPOLOGY: linear (ii) MOLECULE TYPE: Other (xi) SEQUENCE DESCRIPTION: SEQ ID NO:289:

CAGTAAACAT CATGTTGAGT GG                                    22

(2) INFORMATION FOR SEQ ID NO:290:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:290:

TCTCCTCAAT GTGCATGTGT GCATGAGTGC ACATTCTACA TA              42

(2) INFORMATION FOR SEQ ID NO:291:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:291:

GTGTTTGCAT GTTGTACAAG TTGGC                                 25

(2) INFORMATION FOR SEQ ID NO:292:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:292:

TAGTACCAGA CACGTGCAGG CAAGCGCACC ATACATCCAA GAAAA           45

(2) INFORMATION FOR SEQ ID NO:293:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:293:

GGAGGCTGAG CAGGGGTGCC                                       20

(2) INFORMATION FOR SEQ ID NO:294:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:294:

ACTCCCACAG GTACCTGCAG                                       20

(2) INFORMATION FOR SEQ ID NO:295:

(i) SEQUENCE CHARACTERISTICS:

(A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:295:

CTGCCCTCAC GTAAGCGCCT                                                    20

(2) INFORMATION FOR SEQ ID NO:296:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:296:

GCTGTTGCAG GGTAATGTTG                                                    20

(2) INFORMATION FOR SEQ ID NO:297:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:297:

CATCAGACAG GTGCGTACA                                                     19

(2) INFORMATION FOR SEQ ID NO:298:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:298:

GGCTGGTGAG GAGGGGCTGA                                                    20

(2) INFORMATION FOR SEQ ID NO:299:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:299:

CGCTCTGTGG GTGAGCTTCA                                                    20

(2) INFORMATION FOR SEQ ID NO:300:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:300:

TGTGGAATAG CCCAATTACA                                                    20

(2) INFORMATION FOR SEQ ID NO:301:

(i) SEQUENCE CHARACTERISTICS:
        (A) LENGTH: 20 base pairs

-continued

```
        (B) TYPE: nucleic acid
        (C) STRANDEDNESS: single
        (D) TOPOLOGY: linear (xi) SEQUENCE DESCRIPTION: SEQ ID NO:301:

AGGGTGCTGA GTGAGTAGTA                                                 20

(2) INFORMATION FOR SEQ ID NO:302:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:302:

TTCTTTTCAG GCCCTCGTGT                                                 20

(2) INFORMATION FOR SEQ ID NO:303:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:303:

TGCTGACCCG GTATGGTGGT                                                 20

(2) INFORMATION FOR SEQ ID NO:304:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:304:

TTTGGTGCAG CCTGTGACTC                                                 20

(2) INFORMATION FOR SEQ ID NO:305:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:305:

CGCACACAAG GTCAGTGTTC                                                 20

(2) INFORMATION FOR SEQ ID NO:306:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:306:

TCTTTCCCAG GTTACTCCTT                                                 20

(2) INFORMATION FOR SEQ ID NO:307:

(i) SEQUENCE CHARACTERISTICS:
        (A) LENGTH: 20 base pairs
        (B) TYPE: nucleic acid
```

```
        (C) STRANDEDNESS: single
        (D) TOPOLOGY: linear (xi) SEQUENCE DESCRIPTION: SEQ ID NO:307:

ATCAAAGACT GTAAGTAACC                                                20

(2) INFORMATION FOR SEQ ID NO:308:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:308:

TCTATTTCAG ATGCTGATTC                                                20

(2) INFORMATION FOR SEQ ID NO:309:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:309:

AGTAGAACAA GTAAGTGCAG                                                20

(2) INFORMATION FOR SEQ ID NO:310:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:310:

TTTTCAAAAG GCCTCCAAAG                                                20

(2) INFORMATION FOR SEQ ID NO:311:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:311:

GAGCCCTGAG GTAAGTTAAT                                                20

(2) INFORMATION FOR SEQ ID NO:312:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:312:

GCTTTTTCAG ATACTACTAT                                                20

(2) INFORMATION FOR SEQ ID NO:313:

(i) SEQUENCE CHARACTERISTICS:
        (A) LENGTH: 20 base pairs
        (B) TYPE: nucleic acid
        (C) STRANDEDNESS: single
```

(D) TOPOLOGY: linear (xi) SEQUENCE DESCRIPTION: SEQ ID NO:313:

TAACATGTTC AACTGTCTGT                                                    20

(2) INFORMATION FOR SEQ ID NO:314:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:314:

TGTTATATGC ATTTATCTTC                                                    20

(2) INFORMATION FOR SEQ ID NO:315:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:315:

GGTAAATGAG GTAAGTCCTG                                                    20

(2) INFORMATION FOR SEQ ID NO:316:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:316:

TCTTGTTAAG ATCGCTCTCT                                                    20

(2) INFORMATION FOR SEQ ID NO:317:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:317:

CCTTGCCCAG GTTCTCTTAA                                                    20

(2) INFORMATION FOR SEQ ID NO:318:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:318:

GCAATCGCAC CTGCACACCC                                                    20

(2) INFORMATION FOR SEQ ID NO:319:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:319:

ACTGCCCATT TCTGGTAAAG                    20

(2) INFORMATION FOR SEQ ID NO:320:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:320:

CCCCTAACAG ATCATGATTC                    20

(2) INFORMATION FOR SEQ ID NO:321:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:321:

ACGTGCAATG GTAAGAGGGC                    20

(2) INFORMATION FOR SEQ ID NO:322:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:322:

TGTTTTGCAG TTTCCAGTGG                    20

(2) INFORMATION FOR SEQ ID NO:323:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:323:

AAGTGGAACG GTGACTCTCT                    20

(2) INFORMATION FOR SEQ ID NO:324:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:324:

TCCTTCACAG GCCAGTGCAG                    20

(2) INFORMATION FOR SEQ ID NO:325:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:325:

GAACAAACTG GTGAGTAGTA 20

(2) INFORMATION FOR SEQ ID NO:326:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:326:

TTTTTTGTAG AGCCTTCCAT 20

(2) INFORMATION FOR SEQ ID NO:327:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:327:

AGCACAGTAG GTAACTAACT 20

(2) INFORMATION FOR SEQ ID NO:328:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:328:

ATGGCCACAG ATTTGTTGGA 20

(2) INFORMATION FOR SEQ ID NO:329:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:329:

CTTCCTGTTG GTAAGCTGTC 20

(2) INFORMATION FOR SEQ ID NO:330:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:330:

TTCTCCTTAG CAGAGTCACC 20

(2) INFORMATION FOR SEQ ID NO:331:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:331:

```
AAAAAGCACA GTAAGTTGGC                                                    20

(2) INFORMATION FOR SEQ ID NO:332:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:332:

TTTTCATCAG ACCCGAGAGG                                                    20

(2) INFORMATION FOR SEQ ID NO:333:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:333:

GAGCTATGAG GTGAGGAGTT                                                    20

(2) INFORMATION FOR SEQ ID NO:334:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:334:

TTTGTTACAG ATATTACTAC                                                    20

(2) INFORMATION FOR SEQ ID NO:335:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:335:

AGCCTGGAAA TGCGTGTTTC                                                    20

(2) INFORMATION FOR SEQ ID NO:336:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:336:

CGAGAATTCA CTCGAGCATC AGG                                                23

(2) INFORMATION FOR SEQ ID NO:337:

(i) SEQUENCE CHARACTERISTICS:
        (A) LENGTH: 21 base pairs
        (B) TYPE: nucleic acid
        (C) STRANDEDNESS: single
```

(D) TOPOLOGY: linear (ii) MOLECULE TYPE: Other (xi) SEQUENCE DESCRIPTION: SEQ ID NO:337:

CCTGATGCTC GAGTGAATTC T                                           21

(2) INFORMATION FOR SEQ ID NO:338:

(i) SEQUENCE CHARACTERISTICS:
        (A) LENGTH: 848 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 1...848
        (D) OTHER INFORMATION:

(xi) SEQUENCE DESCRIPTION: SEQ ID NO:338:

```
ATG ATT CTG GAA GGA AGT GGT GTA ATG AAT CTC AAC CCA GCC AAC AAC      48
Met Ile Leu Glu Gly Ser Gly Val Met Asn Leu Asn Pro Ala Asn Asn
 1               5                  10                  15

CTC CTT CAC CAG CAA CCA GCC TGG CCG GAC AGC TAC CCC ACA TGC AAT      96
Leu Leu His Gln Gln Pro Ala Trp Pro Asp Ser Tyr Pro Thr Cys Asn
             20                  25                  30

GTT TCC AGC GGT TTT TTT GGA AGC CAG TGG CAT GAA ATC CAC CCT CAG     144
Val Ser Ser Gly Phe Phe Gly Ser Gln Trp His Glu Ile His Pro Gln
         35                  40                  45

TAC TGG ACC AAA TAC CAG GTG TGG GAA TGG CTG CAG CAC CTC CTG GAC     192
Tyr Trp Thr Lys Tyr Gln Val Trp Glu Trp Leu Gln His Leu Leu Asp
     50                  55                  60

ACC AAC CAG CTA GAC GCT AGC TGC ATC CCT TTC AGG GAG TTC GAC ATT     240
Thr Asn Gln Leu Asp Ala Ser Cys Ile Pro Phe Gln Glu Phe Asp Ile
 65                  70                  75                  80

AGC GGA GAA CAC CTG TGC AGC ATG AGT CTG CAG GAG TTC ACG AGG GCA     288
Ser Gly Glu His Leu Cys Ser Met Ser Leu Gln Glu Phe Thr Arg Ala
                 85                  90                  95

GCA GGC TCA GCT GGG CAG CTG CTC TAC AGC AAC CTA CAG CAT CTC AAG     336
Ala Gly Ser Ala Gly Gln Leu Leu Tyr Ser Asn Leu Gln His Leu Lys
            100                 105                 110

TGG AAC GGC CAA TGC AGC AGT GAC CTT TTC CAG TCC GCA CAC AAT GTC     384
Trp Asn Gly Gln Cys Ser Ser Asp Leu Phe Gln Ser Ala His Asn Val
        115                 120                 125

ATT GTC AAG ACT GAA CAA ACC GAT CCT TCC ATC ATG AAC ACA TGG AAA     432
Ile Val Lys Thr Glu Gln Thr Asp Pro Ser Ile Met Asn Thr Trp Lys
    130                 135                 140

GAA GAA AAC TAT CTC TAT GAT CCC AGC TAT GGT AGC ACA GTA GAT CTG     480
Glu Glu Asn Tyr Leu Tyr Asp Pro Ser Tyr Gly Ser Thr Val Asp Leu
145                 150                 155                 160

TTG GAC AGT AAG ACT TTC TGC CGG GCT CAG ATC TCC ATG ACA ACC TCC     528
Leu Asp Ser Lys Thr Phe Cys Arg Ala Gln Ile Ser Met Thr Thr Ser
                165                 170                 175

AGT CAC CTT CCA GTT GCA GAG TCA CCT GAT ATG AAA AAG GAG CAA GAC     576
Ser His Leu Pro Val Ala Glu Ser Pro Asp Met Lys Lys Glu Gln Asp
            180                 185                 190

CAC CCT GTA AAG TCC CAC ACC AAA AAG CAC AAC CCA AGA GGC ACT CAC     624
His Pro Val Lys Ser His Thr Lys Lys His Asn Pro Arg Gly Thr His
        195                 200                 205

TTA TGG GAG TTC ATC CGA GAC ATT CTC TTG AGC CCA GAC AAG AAC CCA     672
```

```
Leu Trp Glu Phe Ile Arg Asp Ile Leu Leu Ser Pro Asp Lys Asn Pro
        210                 215                 220

GGG CTG ATC AAA TGG GAA GAC CGT TCG GAA GGC ATC TTC AGG TTC CTG          720
Gly Leu Ile Lys Trp Glu Asp Arg Ser Glu Gly Ile Phe Arg Phe Leu
225                 230                 235                 240

AAG TCA GAA GCT GTG GCT CAG CTG TGG GGG AAA AAG AAA AAT AAC AGT          768
Lys Ser Glu Ala Val Ala Gln Leu Trp Gly Lys Lys Lys Asn Asn Ser
                    245                 250                 255

AGC ATG ACA TAC GAG AAG CTC AGC CGG GCT ATG AGA TAT TAC TAC AAA          816
Ser Met Thr Tyr Glu Lys Leu Ser Arg Ala Met Arg Tyr Tyr Tyr Lys
                260                 265                 270

CGA GAA ATC CTG GAA CGT GTG GAT GGA CGA CG                               848
Arg Glu Ile Leu Glu Arg Val Asp Gly Arg Arg
            275                 280
```

(2) INFORMATION FOR SEQ ID NO:339:

(i) SEQUENCE CHARACTERISTICS:
        (A) LENGTH: 283 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:339:

```
Met Ile Leu Glu Gly Ser Gly Val Met Asn Leu Asn Pro Ala Asn Asn
1               5                   10                  15

Leu Leu His Gln Gln Pro Ala Trp Pro Asp Ser Tyr Pro Thr Cys Asn
                20                  25                  30

Val Ser Ser Gly Phe Phe Gly Ser Gln Trp His Glu Ile His Pro Gln
            35                  40                  45

Tyr Trp Thr Lys Tyr Gln Val Trp Glu Trp Leu Gln His Leu Leu Asp
        50                  55                  60

Thr Asn Gln Leu Asp Ala Ser Cys Ile Pro Phe Gln Glu Phe Asp Ile
65                  70                  75                  80

Ser Gly Glu His Leu Cys Ser Met Ser Leu Gln Glu Phe Thr Arg Ala
                85                  90                  95

Ala Gly Ser Ala Gly Gln Leu Leu Tyr Ser Asn Leu Gln His Leu Lys
                100                 105                 110

Trp Asn Gly Gln Cys Ser Ser Asp Leu Phe Gln Ser Ala His Asn Val
            115                 120                 125

Ile Val Lys Thr Glu Gln Thr Asp Pro Ser Ile Met Asn Thr Trp Lys
        130                 135                 140

Glu Glu Asn Tyr Leu Tyr Asp Pro Ser Tyr Gly Ser Thr Val Asp Leu
145                 150                 155                 160

Leu Asp Ser Lys Thr Phe Cys Arg Ala Gln Ile Ser Met Thr Thr Ser
                165                 170                 175

Ser His Leu Pro Val Ala Glu Ser Pro Asp Met Lys Lys Glu Gln Asp
                180                 185                 190

His Pro Val Lys Ser His Thr Lys Lys His Asn Pro Arg Gly Thr His
            195                 200                 205

Leu Trp Glu Phe Ile Arg Asp Ile Leu Leu Ser Pro Asp Lys Asn Pro
        210                 215                 220

Gly Leu Ile Lys Trp Glu Asp Arg Ser Glu Gly Ile Phe Arg Phe Leu
225                 230                 235                 240
```

```
Lys Ser Glu Ala Val Ala Gln Leu Trp Gly Lys Lys Lys Asn Asn Ser
                245                 250                 255

Ser Met Thr Tyr Glu Lys Leu Ser Arg Ala Met Arg Tyr Tyr Tyr Lys
                260                 265                 270

Arg Glu Ile Leu Glu Arg Val Asp Gly Arg Arg
            275                 280
```